US007541158B2

(12) United States Patent
Li et al.

(10) Patent No.: US 7,541,158 B2
(45) Date of Patent: Jun. 2, 2009

(54) TASTE RECEPTORS OF THE T1R FAMILY FROM DOMESTIC DOG

(75) Inventors: Xia Li, Havertown, PA (US); Weihua Li, Broomall, PA (US); Joseph G. Brand, Wayne, PA (US)

(73) Assignee: Monell Chemical Senses Center, Philadelphia, PA (US)

( * ) Notice: Subject to any disclaimer, the term of this patent is extended or adjusted under 35 U.S.C. 154(b) by 0 days.

(21) Appl. No.: 11/578,472

(22) PCT Filed: Apr. 14, 2005

(86) PCT No.: PCT/US2005/012765

§ 371 (c)(1),
(2), (4) Date: Aug. 2, 2007

(87) PCT Pub. No.: WO2005/116069

PCT Pub. Date: Dec. 8, 2005

(65) Prior Publication Data

US 2007/0287154 A1    Dec. 13, 2007

Related U.S. Application Data

(60) Provisional application No. 60/562,208, filed on Apr. 14, 2004.

(51) Int. Cl.
*C07K 14/705* (2006.01)
*C12N 15/12* (2006.01)
*G01N 33/566* (2006.01)
(52) U.S. Cl. ............... 435/7.21; 435/69.1; 435/252.3; 435/320.1; 530/350; 536/23.5
(58) Field of Classification Search ................ None
See application file for complete search history.

(56) References Cited

U.S. PATENT DOCUMENTS

| 4,399,216 A | 8/1983 | Axel et al. ................. 435/6 |
| 4,879,236 A | 11/1989 | Smith et al. ................. 435/235 |
| 5,585,277 A | 12/1996 | Bowie et al. ................. 436/518 |
| 2003/0232407 A1 | 12/2003 | Zoller et al. ................. 435/69.1 |

FOREIGN PATENT DOCUMENTS

| EP | 0 367 566 A1 | 3/1997 |
| WO | 91/09955 A1 | 7/1991 |
| WO | 91/18982 A1 | 12/1991 |
| WO | 92/20808 A1 | 11/1992 |
| WO | 94/12650 A2 | 6/1994 |
| WO | 97/09433 A1 | 3/1997 |
| WO | 01/72842 A2 | 10/2001 |
| WO | 02/064631 A2 | 8/2002 |

OTHER PUBLICATIONS

Anderson, W. F., "Human Gene Therapy," *Nature*, 1998, supplement to vol. 392, No. 6679, pp. 25-30.

Andersson, B. et al., "The Sweet Taste Fibres of the Dog," *Acta physiol scan*, 1950, 21, 105-119.

Bartoshuk, L. M. et al., "Taste of Water in the Cat: Effects on Sucrose Preference," *Science*, 1971, 171, 699-701.

Beauchamp, G. K. et al., "Flavor Preferences in Cats (*Felis catus* and *Panthera* sp.)," *J. Comp. Physiol. Phychol.*, 1977, 91(5), 1118-1127.

Bidlack, J. M. et al., "Assay of G Protein-Coupled Receptor Activation of G Proteins in Native Cell Membranes Using [$^{35}$S]GTPγS Binding," *Methods Mol Biol.*, 2004, 237, 135-143.

Boudreau, J. C. et al., "Neurophysiology of geniculate ganglion (facial nerve) taste systems: species comparisons," *Chem. Senses*, 1985, 10, 89-127.

Bradshaw, J. W. S., "Sensory and experimental factors in the design of foods for domestic dogs and cats," *Proc. Nutrition Soc.*, 1991, 50, 99-106.

Cane, D. E. et al., "Harnessing the Biosynthetic Code: Combinations, Permutations, and Mutations," *Science*, 1998, 282, 63-68.

Elbashir, S. M. et al., "RNA interference is mediated by 21-and 22-nucleotide RNAs," *Genes & Development*, 2001, 15, 188-200.

Friedmann, T., "Progress Toward Human Gene Therapy," *Science*, 1989, 244, 1275-1281.

Galés, C. et al., "Real-time monitoring of receptor and G-protein interactions in living cells," *Nat Methods*, 2005, 2(3), 177-184.

Grace, J. et al., "The Influence of Previous Experience on the Taste Behavior of Dogs Toward Sucrose and Saccharin," *Physiology and Behavior*, 1969, 4, 553-558.

Kitagawa, M. et al., "Molecular Genetic Identification Of A Candidate Receptor Gene For Sweet Taste," *Bioch. Bioph. Res. Comm.*, 2001, 283, 236-242.

Kurihara, K. et al., "Introductory Remarks on Umami Taste," *Ann. N. Y. Acad. Sci.*, 1998, 855, 393-397.

Li, X. et al., "Human receptors for sweet and umami taste," *Proc Natl Acad Sci USA*, 2002, 99, 4692-4696.

Li, X. et al., "Genetic, Physical, And Comparative Map Of The Subtelomeric Region Of Mouse Chromosome 4," *Mamm. Genome*, 2002, 13(1), 5-19.

Li, X. et al., "High-Resolution Genetic Mapping Of The Saccharin Preference Locus (Sac) And The Putative Sweet Taste Receptor (T1R1) Gene (Gpr70) To Mouse Distal Chromosome 4," *Mamm. Genome*, 2001, 12(1), 13-16.

(Continued)

*Primary Examiner*—John D Ulm
(74) *Attorney, Agent, or Firm*—Woodcock Washburn LLP

(57) ABSTRACT

The present invention relates to the discovery of several genes of the domestic dog (*Canine familiaris*) associated with taste perception. The invention provides, inter alia, the nucleotide sequence of the canine Tas1r1, Tas1r2, and Tas1r3 receptor genes, the amino acid sequences of the polypeptides encoded thereby, and antibodies to the polypeptides. The present invention also relates to methods for screening for compounds that modify the genes' function or activity, the compounds identified by such screens, and mimetics of the identified compounds. The invention further provides methods for modifying the taste preferences, ingestive responses, or general behavior of a mammal such as a dog by administering compounds that affect the function or activity of the gene or the polypeptide encoded thereby.

18 Claims, 20 Drawing Sheets

OTHER PUBLICATIONS

Li, X. et al., "Pseudogenization of a sweet-receptor gene accounts for cats' indifference toward sugar," *PLOS Genetics*, Jul. 2005, 11, 27-35.

Margolskee, R. F., "Molecular mechanisms of bitter and sweet taste transduction", *J. Biol. Chem.*, 2002, 277, 1-4.

Miller, A. D., "Human gene therapy comes of age," *Nature*, 1992, 357, 455-460.

Ming, D. et al. "Characterization and solubilization of bitter-responsive receptors that couple to gustducin," *Proc. Natl. Acad. Sci. USA*, 1998, 95, 8933-8938.

Montmayeur, J. P. et al., "Receptors For Bitter And Sweet Taste," *Curr. Opin. Neurobiol.*, 2002, 12(4), 366-371.

Nelson, G. et al., "An amino-acid taste receptor," *Nature*, 2002, 416, 199-202.

Nelson, G. et al., "Mammalian Sweet Taste Receptors," *Cell*, 2001, 106, 381-390.

Ruiz-Avila, L. et al., "An In Vitro Assay Useful to Determine the Potency of Several Bitter Compounds," *Chem. Senses*, 2000, 25, 361-368.

Verma, I. M., "Gene Therapy," *Scientific American*, 1990, 263(5) 68-72, 81-84.

Wahlestedt et al., "Potent and nontoxic antisense oligonucleotides containing locked nucleic acids," *Proc. Natl. Acad. Sci. USA*, 2000, 9710, 5633-5638.

Xu, H et al., "Different functional roles of T1R subunits in the heteromeric taste receptors," *Proc Natl Acad Sci USA*, 2004, 101, 14258-14263.

Yan, W. et al., "Bitter taste transduced by PLC-beta(2)-dependent rise in IP(3) and alpha-gustducin-dependent fall in cyclic nucleotides," *Am J Physiol Cell Physiol*, 2001, 280, C742-751.

FIG. 1A

```
mouseTas1r1   ATGCTTTTCTGGGCAGCTCACCTGCTGCTCAGCCTGCAGCTGGCCGTTGCTTACTGCTGG 60
ratTas1r1     ATGCTCTTCTGGGCTGCTCACCTGCTGCTCAGCCTGCAGTTGGTC------TACTGCTGG 54
catTas1r1     ATGTCACTCCCGGCGGCTCACCTGGT---CGGCCTGCAGCTCTCCCTCTCCTGCTGCTGG 57
dogTas1r1     ATGTCACTCCTGGCAGCTCACCTGGT---CAGCTTGCAGCTCTCCCTCTCCTGCTGCTGG 57
humanTAS1R1   ATGCTGCTCTGCACGGCTCGCCTGGT---CGGCCTGCAGCTTCTCATTTCCTGCTGCTGG 57
mouseTas1r2   ATGGGACCCCAGGCGAGGACACT------CCATTTGCTGTTTCTC-----CTGCTGCATG 49
ratTas1r2     ATGGGTCCCCAGGCAAGGACACT------CTGCTTGCTGTCTCTC-----CTGCTGCATG 49
humanTAS1R2   ATGGGGCCCAGGGCAAAGACCAT------CTGCTCCCTGTTCTTC-----CTCCTATGGG 49
dogTas1r2     ATGGGACCCCGGGCCAAGGCGGT------CTGCTCCCTATTCATC-----CTGCTGCAGG 49
catTas1r2     ATGGGACCCCGGGCCAGGGAAGT------CTGCTGCTTCATCATC-----CTGCCGCGGC 49
mouseTas1r3   ATGCCAGCTTTGGCTATCATGGGTCTCA-----------GCCTGG-CTGCTTTCCTGGA 47
ratTas1r3     ATGCCGGGTTTGGCTATCTTGGGCCTCA-----------GTCTGG-CTGCTTTCCTGGA 47
dogTas1r3     ATGGCAGGCCTGATGCTCCTGAGCCTCA--------------------TGGCTCTCTTGGG 41
catTas1r3     ATGCCCGGCCTCGCTCTCCTGGGCCTCACGGCTCTCCTGGGCCTCA-CGGCTCTCTTGGA 59
humanTAS1R3   ATGCTGGGCCCTGCTGTCCTGGGCCTCA-----------GCCTCT-GGGCTCTCCTGCA 47
                                                              ***                    *
```

```
mouseTas1r1   GCTTTCAGCTGCCA--AAGGACAGAATCCTCTCCAG-GTTTCAGCCTCCCTGGGGACTTC 117
ratTas1r1     GCTTTCAGCTGCCA--AAGGACAGAGTCCTCTCCAG-GCTTCAGCCTTCCTGGGGACTTC 111
catTas1r1     GCTCTCAGCTGCCA--CAGCACAGAGACGTCTGCCG-ACTTCAGCCTCCCTGGGGATTAC 114
dogTas1r1     GCCCTCAGCTGCCA--CAACACAGAGTCATCTCCTG-ATTTCAGCCTCCCTGGGGATTAC 114
humanTAS1R1   GCCTTTGCCTGCCA--TAGCACGGAGTCTTCTCCTG-ACTTCACCCTCCCCGGAGATTAC 114
mouseTas1r2   CTCTGCCTAAGCCAGTCATGCTGGTAGGGAACTCCG-ACTTTCACCTGGCTGGGGACTAC 108
ratTas1r2     TTCTGCCTAAGCCAGGCAAGCTGGTAGAGAACTCTG-ACTTCCACCTGGCCGGGGACTAC 108
humanTAS1R2   TCCTGGCTGAGCC---------GGCTGAGAACTCGG-ACTTCTACCTGCCTGGGGATTAC 99
dogTas1r2     TCCTGGCTGAACC---------GGCTGAGAACTCAG-ACTTCTACCTGCCTGGAGATTAC 99
catTas1r2     TCCTGGCTGAGCC---------GGCTGAGAACTCAG-ACTTCTACTTGGCTGGGGATTAC 99
mouseTas1r3   GCTTGGGATGGGGG--CCTCTTTGTGTCTGTCACAGCAATTCAAGGCACAAGGGGACTAC 105
ratTas1r3     GCTTGGGATGGGGT--CCTCTTTGTGTCTGTCACAGCAATTCAAGGCACAAGGGGACTAT 105
dogTas1r3     CCTTGGAGCAGGCG--CCCCATTGTGCTTATCCCGGCAGCTCAGGATGCAAGGGGACTAT 99
catTas1r3     CCACGGGAGGGCG--CAACGTCCTGCTTGTCACAGCAACTTAGGATGAAGGGGGACTAT 117
humanTAS1R3   CCCTGGGACGGGGG--CCCCATTGTGCCTGTCACAGCAACTTAGGATGAAGGGGGACTAC 105
                                      *   *      *                ** ** *
```

```
mouseTas1r1   CTCCTGGCAGGCCTGTTCTCCCTCCATGCTGACTGTCTGCAGGTGAGACAC---AGACCT 174
ratTas1r1     CTCCTTGCAGGTCTGTTCTCCCTCCATGGTGACTGTCTGCAGGTGAGACAC---AGACCT 168
catTas1r1     CTCCTCGCAGGTCTGTTCCCCTCTGCACTCTGACTGTCCGGGCGTGAGGCAC---CGGCCC 171
dogTas1r1     CTACTTGCAGGTCTGTTCCCCTCTGCACTCTGACTGTCCCGGGGTGAGACGC---AGGCCC 171
humanTAS1R1   CTCCTGGCAGGCCTGTTCCCCTCCATTCTGGCTGTCTGCAGGTGAGGCAC---AGACCC 171
mouseTas1r2   CTCCTGGGTGCCTCTTTACCCTCCATGCCAACGTGAAGAGCGTCTCTCACCCTCAGCTAC 168
ratTas1r2     CTCCTGGGTGGCCTCTTTACCCTCCATGCCAACGTGAAGAGCATCTCCCACCTCAGCTAC 168
humanTAS1R2   CTCCTGGGTGGCCTCTTCTCCCTCCATGCCAACATGAAGGGCATTGTTCACCTTAACTTC 159
dogTas1r2     CTCCTGGGTGGCCTCTTCACCCTCCATGCCAACGTGAAGGGCACCGTCCACCTCAGCTTC 159
catTas1r2     TTCCTCGGCGGCCTCTTCACCCTCCATGCCAACGTGAAGGGCATCGTCCACCTCAACCTC 159
mouseTas1r3   ATACTGGGCGGGCTATTTCCCTGGGCTCAACCG---AGGAGGCCACTCTCAACCAGAGA 162
ratTas1r3     ATATTGGGTGGACTATTTCCCTGGGCACAACTG---AGGAGGCCACTCTCAACCAGAGA 162
dogTas1r3     GTGCTGGGCGGGCTCTTCCCCCTGGGCACAGCTG---AGGACACAGGTCTCAGTGACAGG 156
catTas1r3     GTGCTGGGTGGGCTCTTCCCTCTGGGCTCTGCCG---AGGGTACAGGTCTTGGCGACGGG 174
humanTAS1R3   GTGCTGGGGGGCTGTTCCCCCTGGGCGAGGCCG---AGGAGGCTGGCCTCCGCAGCCGG 162
                  *  *  **  ** **  *  **                      *
```

```
mouseTas1r1   CTGGTGACAAGTTGTGACAGGTCTGACAGCTTCAACGGCCATGGCTATCACCTCTTCCAA 234
ratTas1r1     CTGGTGACAAGTTGTGACAGGCCCGACAGCTTCAACGGCCATGGCTACCACCTCTTCCAA 228
catTas1r1     ACGGTGACCCTCTGTGACAGGCCCGACAGCTTCAACGGTCACGGCTACCACCTCTTCCAG 231
dogTas1r1     ATGGTGACCCTCTGTGACAGGTCCAACAGCTTCAATGGCCATGGCTACCACCTCTTTCAG 231
humanTAS1R1   GAGGTGACCCTGTGTGACAGGTCTTGTAGCTTCAATGAGCATGGCTACCACCTCTTCCAG 231
mouseTas1r2   CTGCAGGTGCCCAAGTGCAATGAGTACAACATGAAGGTCTTGGGCTACAACCTCATGCAG 228
ratTas1r2     CTGCAGGTGCCCAAGTGCAAGTAGTTCAACATGAAGGTGTTGGGCTACAACCTCATGCAG 228
humanTAS1R2   CTGCAGGTGCCCATGTGCAAGGAGTATGAAGTGAAGGTGATAGGCTACAACCTCATGCAG 219
dogTas1r2     CTGCAGGTGCCCCAGTGCAAGAAGTATGAAATGAAGGTGTTGGGCTACAACCTGATGCAG 219
catTas1r2     CTGCAGGTGCCCCAGTGCAAGGAGTATGAAATAAAGGTGTTGGGCTACGATCTCATGCAG 219
mouseTas1r3   ACACAACCCAACAGCATCCCGTGCAACAGGTTCTCACCCCTTGGTTTGTTCCTGGCCATG 222
ratTas1r3     ACACAGCCCAACGGCATCCTATGTACCAGGTTCTCGCCCCTTGGTTTGTTCCTGGCCATG 222
dogTas1r3     ACACAGCCCAATGCCACTGTGTGCACCAGGTTCTCGTCCCTCGGCCTGCTCTGGGCGCTG 216
catTas1r3     CTGCAGCCCAATGCCACCGTGTGCACCAGGTTCTCGTCTCTGGGCCTGCTCTGGGCGCTG 234
humanTAS1R3   ACACGGCCCAGCAGCCCTGTGTGCACCAGGTTCTCCTCAAACGGCCTGCTCTGGGCACTG 222
                                                 .         **
                                                 .
```

FIG. 1B

```
mouseTas1r1  GCCATGCGGTTCACCGTTGAGGAGATAAACAACTCCACAGCTCTGCTTCCCAACATCACC 294
ratTas1r1    GCCATGCGGTTCACTGTTGAGGAGATAAACAACTCCTCGGCCCTGCTTCCCAACATCACC 288
catTas1r1    GCCATGCGGTTTGGCATCGAGGAGATAAACAACTCCACGGCCCTCCTGCCGAACGTCACC 291
dogTas1r1    GCCATGCGGTTTGGCATTGAGGAGATCAACAACTCCACAACACTGCTGCCTAATGTCACC 291
humanTAS1R1  GCTATGCGGCTTGGGGTTGAGGAGATAAACAACTCCACGGCCCTGCTGCCCAACATCACC 291
mouseTas1r2  GCCATGCGATTCGCCGTGGAGGAAATCAACAACTGTAGCTCTCTGCTGCCCGGCGTGCTG 288
ratTas1r2    GCCATGCGTTTCGCTGTGGAGGAGATCAACAACTGTAGCTCCCTGCTACCCGGCGTGCTG 288
humanTAS1R2  GCCATGCGCTTCGCGGTGGAGGAGATCAACAATGACAGCAGCCTGCTGCCTGGTGTGCTG 279
dogTas1r2    GCCATGCGCTTTGCGGTGGAAGAGATTAACAACCGCAGCGACCTGCTGCCCGGCGTGCTG 279
catTas1r2    GCCATGTGCTTTGCAGGGGAGGAGATCAATAGCCAGAGCAGCCTGCTGCCTGGCGTGCTG 279
mouseTas1r3   GCTATGAAGATGGCTGTGGAGGAGATCAACAATGGATCTGCCTTGCTCCCTGGGCTGCGG 282
ratTas1r3     GCTATGAAGATGGCTGTAGAGGAGATCAACAATGGATCTGCCTTGCTCCCTGGGCTGCGA 282
dogTas1r3     GCCATGAAGATGGCTGTGGAGGAGGTCAACAACAGGTCCACGCTGCTGCCAGGACTGCGC 276
catTas1r3     GCCGTGAAGATGGCCGTGGAGGAGATCAACAACGGGTCGCCCTGCTGCCCGGGCTGCAC 294
humanTAS1R3   GCCATGAAAATGGCCGTGGAGGAGATCAACAACAAGTCGGATCTGCTGCCCGGGCTGCGC 282
                       *     * **  *               *       * mouseTas1r1  CTGGGGTATGAACTGTATGACGTGTGCTCAGAGTCT---TCCAATGTCTATGCCACCCTG 351
ratTas1r1    CTGGGGTATGAGCTGTACGACGTGTGCTCAGAATCT---GCCAATGTGTATGCCACCCTG 345
catTas1r1    CTGGGATACCAGCTGTACGACGTGTGCTCGGAGTCT---GCCAACGTGTATGCCACACTA 348
dogTas1r1    CTGGGGTACCAGCTGTATGACGTGTGCTCAGAGTCA---GCCAATGTGTACGCCACACTC 348
humanTAS1R1  CTGGGGTACCAGCTGTATGATGTGTGTTCTGACTCT---GCCAATGTGTATGCCACGCTG 348
mouseTas1r2  CTCGGCTACGAGATGGTGGATGTCTGCTACCTCTCC---AACAATATCCAGCCTGGGCTC 345
ratTas1r2    CTCGGCTACGAGATGGTGGATGTCTGTTACCTCTCC---AACAATATCCACCCTGGGCTC 345
humanTAS1R2  CTGGGCTATGAGATCGTGGATGTGTGCTACATCTCC---AACAATGTCCAGCCGGTGCTC 336
dogTas1r2    CTGGGCTATGAGATAGTGGATGTCTGCTACATCTCC---AACAACGTCCAGCCCGTGCTC 336
catTas1r2    CTGGGCTACAAAATGGTGGATGTCAGCTACATCTCC---AACAATGTCCAGCCCGTGCTC 336
mouseTas1r3  CTGGGCTATGACCTATTTGACACATGCTCCGAGCCAGTGGTCACCATGAAATCCAGTCTC 342
ratTas1r3    CTGGGCTATGACCTGTTTGACACATGCTCAGAGCCAGTGGTCACCATGAAGCCCAGCCTC 342
dogTas1r3    CTGGGCTACGACCTCTTTGACACATGTTCGGAGCCTGTGGTGGCCATGAAGCCCAGCCTC 336
catTas1r3    CTGGGCTATGACCTCTTTGACACGTGTTCAGAGCCCATGGTGGCCATGAAGCCCAGCCTC 354
humanTAS1R3  CTGGGCTACGACCTCTTTGATACGTGCTCGGAGCCTGTGGTGGCCATGAAGCCCAGCCTC 342
                       *     **        *         *     *     ** mouseTas1r1  AGGGTGCTCGCCCAGCAAGGGACAGGCCACCTAGAGATGCAGAGAGATCTTCGCAACCAC 411
ratTas1r1    AGGGTGCTTGCCCTGCAAGGGCCCCGCCACATAGAGATACAGAAAGACCTTCGCAACCAC 405
catTas1r1    AACGTGCTCTCCCTGCTGGGGACACATCACGTAGAGATCCGAGCAGACCCTTCCCACTAT 408
dogTas1r1    AACGTACTCTCCACGCTGGGGACACATCACATAGAGATCCAAGCAGACCCTTCCCACTAT 408
humanTAS1R1  AGAGTGCTCTCCCTGCCAGGGCAACACCACATAGAGCTCCAAGGAGACCTTCTCCACTAT 408
mouseTas1r2  TACTTCCTGTC---ACAGATAGATGACTTCCTGCCCATCCTCAAAGACTACAGCCAGTAC 402
ratTas1r2    TACTTCCTGGC---ACAGGACGACGACCTCCTGCCCATCCTCAAAGACTACAGCCAGTAC 402
humanTAS1R2  TACTTCCTGGC---ACACGGACAACCTCCTTCCCATCCAAGAGGACTACAGTAACTAC 393
dogTas1r2    TACTTCTTGGC---ACGGGAGGACTACTCCCTGCCCATCCAGGAGGACTACAGCCACTAC 393
catTas1r2    CACTTCCCGGC---AAAGGAGGACTGTTCCTTGCCCATCCAGGAGGACTACAGCCACTGT 393
mouseTas1r3  ATGTTCCTGGCCAAGGTGGGCAGTCAAAGCATTGCTGCCTACTGCAACTACACACAGTAC 402
ratTas1r3    ATGTTCATGGCCAAGGTGGGAAGTCAAAGCATTGCTGCCTACTGCAACTACACACAGTAC 402
dogTas1r3    ATGTTCATGGCCAAAGCGGGCAGCTGCGACATCGCCGCCTACTGCAACTACACGCAGTAC 396
catTas1r3    GTGTTCATGGCCAAAGCAGGCAGCTGCAGCATTGCCGCCTACTGCAATTACACACAGTAC 414
humanTAS1R3  ATGTTCCTGGCCAAGGCAGGCAGCCGCGACATCGCCGCCTACTGCAACTACACGCAGTAC 402
                   *        *               * *           *         * mouseTas1r1  TCCTCCAAGGTGGTGGCACTCATTGGGCCTGATAACACTGACCACGCTGTCACCACTGCT 471
ratTas1r1    TCCTCCAAGGTGGTGGCCTTCATCGGGCCTGACAACACTGACCACGCTGTCACTACCGCT 465
catTas1r1    TCGCCTGCCGCCCTGGCTGTCATTGGGCCTGACACCACCAACCACGCAGCCACCACTGCA 468
dogTas1r1    TCCCCGGCCGCCCTGGCGGTGATTGGACCTGACACCACCAACCATGCTGCCACCGCTGCA 468
humanTAS1R1  TCCCCTACGGTGCTGGCAGTGATTGGGCCTGACAGCACCAACCGTGCTGCCACCACAGCC 468
mouseTas1r2  AGGCCCAAGTGGTGGCCGTCATTGGCCCAGACAACTCTGAGTCCGCCATCACCGTGTCC 462
ratTas1r2    ATGCCCACGTGGTGGCTGTCATTGGCCCCGACAACTCTGAGTCCGCCATTACCGTGTCC 462
humanTAS1R2  ATTTCCGTGTGTTGGCTGTCATTGGCCCTGACAACTCCGAGTCTGTCATGACTGTGGCC 453
dogTas1r2    GTGCCCGTGTGTTGGCGGTCATTGGCCCTGACAACTCCGAGTCCACTACTACTGTGGCC 453
catTas1r2    GTGCCCCGTGTGGTGGCTGTCATTGGTCCTGGCAACTCTGAGTCCACTGTGACTGTGGCC 453
mouseTas1r3  CAACCCGTGTGCTGGCTGTCATCGGCCCCCACTCATCAGAGCTTGCCCTCATTACAGGC 462
ratTas1r3    CAACCCGTGTGCTGGCTGTCATTGGTCCCCACTCATCAGAGCTTGCCCTCATTACAGGC 462
dogTas1r3    CAGCCCCGTGTGCTGGCAGTCATTGGGCCACACTCATCTGAGCTCGCCCTCATCACCGGC 456
catTas1r3    CAGCCCCGCGTGCTGGCCGTCATCGGGCCCCACTCGTCTGAGCTCGCCCTCGTCACCGGC 474
humanTAS1R3  CAGCCCCGTGTGCTGGCTGTCATCGGGCCCCACTCGTCAGAGCTCGCCATGGTCACCGGC 462
                 *        *     ****  *  *  * *        *     *        *
```

FIG. 1C

```
mouseTas1r1  GCCCTGCTGAGCCCTTTTCTGATGCCCCTGGTCAGCTATGAGGCGAGCAGCGTGATCCTC 531
ratTas1r1    GCCTTGCTGGGTCCTTTCCTGATGCCCCTGGTCAGCTATGAGGCAAGCAGCGTGGTACTC 525
catTas1r1    GCCCTGCTGAGCCCCTTCCTGGTGCCCCTGATCAGCTACGAGGCCAGCAGCGTGACGCTC 528
dogTas1r1    GCCCTGCTGAGCCCGTTTCTGGTGCCTGTGATCAGCTACGAGGCCAGCAGTGTGATGCTT 528
humanTAS1R1  GCCCTGCTGAGCCCTTTCCTGGTGCCCATGATTAGCTATGCGGCCAGCAGCGAGACGCTC 528
mouseTas1r2  AACATTCTCTCCTACTTCCTCGTGCCACAGGTCACATATAGCGCCATCACCGACAAGCTG 522
ratTas1r2    AACATTCTCTCTCATTTCCTCATCCCACAGATCACATACAGCGCCATCTCCGACAAGCTG 522
humanTAS1R2  AACTTCTCTCCCTATTTCTCCTTCCACAGATCACCTACAGCGCCATCAGCGATGAGCTG 513
dogTas1r2    CATTTCCTCTCACTCTTCCTCCTTCCACAGATCACCTACAGCGCCATCAGTGACGATCTG 513
catTas1r2    CGCTTCCTCTCTCTCTTCCTCCTTCCACAGATCACCTACAGCGCCATCAGTGACGAGCTA 513
mouseTas1r3  AAGTTCTTCAGCTTCTTCCTCATGCCACAGGTCAGCTATAGTGCCAGCATGGATCGGCTA 522
ratTas1r3    AAGTTCTTCAGCTTCTTCCTCATGCCACAGGTCAGCTATAGTGCCAGCATGGATCGGCTA 522
dogTas1r3    AAGTTCTTCAGCTTCTTCCTCATGCCTCAGGTCAGCTACGGGGCCAGCACCGACCGGCTG 516
catTas1r3    AAGTTCTTCAGCTTCTTCCTTGTGCCTCAGGTCAGCTACGGCGCCAGCACCGACCGGCTG 534
humanTAS1R3  AAGTTCTTCAGCTTCTTCCTCATGCCCCAGGTCAGCTACGGTGCTAGCATGGAGCTGCTG 522
                *  *          *  **     *          **  *       ** mouseTas1r1  AGTGGGAAGCGCAAGTTCCCGTCCTTCTTGCGCACCATCCCCAGCGATAAGTACCAGGTG 591
ratTas1r1    AGTGCCAAGCGCAAGTTCCCGTCTTTCCTTCGTACCGTCCCCAGTGACCGGCACCAGGTG 585
catTas1r1    GGAGTGAAGCGGCATTACCCCTCGTTTCTGCGCACCATCCCCAGCGACAAGCACCAGGTG 588
dogTas1r1    GGAGTGAAGCGGTATTACCCCTCGTTTCTGCGCACTATCCCCAGCGATAAGTACCAGGTG 588
humanTAS1R1  AGCGTGAAGCGGCAGTATCCCTCTTTCCTGCGCACCATCCCCAATGACAAGTACCAGGTG 588
mouseTas1r2  CGAGACAAGCGGCACTTCCCTGCCATGCTGCGCACCTGTGCCCAGCGCCACCCACCACATC 582
ratTas1r2    CGGGACAAGCGGCACTTCCCTAGCATGCTACGCACAGTGCCCAGCGCCACCCACCACATC 582
humanTAS1R2  CGAGACAAGGTGCGCTTCCCGGCTTTGCTGCGTACCACACCCAGCGCCGACCACCACGTC 573
dogTas1r2    CGGGACAAGCAGCACTTCCCGGCCCTGCTGCGCACAGTGGCGGGCGCGGACCACCAGATC 573
catTas1r2    CGGGACAAGCAGCGCTTCCCGGCCCTTCTGCCCACAGCGCCGGGCGCCGATCACCAGATC 573
mouseTas1r3  AGTGACCGGGAAACGTTTCCATCCTTCTTCCGCACAGTGCCCAGTGACCGGGTGCAGCTG 582
ratTas1r3    AGTGACCGGGAAACATTTCCATCCTTCTTCCGCACAGTGCCCAGTGACCGGGTGCAGCTG 582
dogTas1r3    AGCAACCGGGAGACGTTCCCATCCTTCTTCCGCACGGTGTCCAGCGACCGCGTACAGGCA 576
catTas1r3    AGCAACCGGGAGATCTTCCCGTCCTTCTTCCGCACGGTGCCCAGCGACCAGGTGCAGGTG 594
humanTAS1R3  AGCGCCCGGGAGACCTTCCCCTCCTTCTTCCGCACCGTGCCCAGCGACCGTGTGCAGCTG 582
                *        *    **        *     **      *    *           ** mouseTas1r1  GAAGTCATAGTGCGGCTGCTGCAGAGCTTCGGCTGGGTCTGGATCTCGCTCGTTGGCAGC 651
ratTas1r1    GAGGTCATGGTGCAGCTGCTGCAGAGTTTTGGGTGGGTGTGGATCTCGCTCATTGGCAGC 645
catTas1r1    GAGGCCATGGTGCTGCTGCTGCAGAGCTTCGGGTGGGTCTGGATCTCGGTGGTCGGCAGC 648
dogTas1r1    GAGATCATGGTGCTACTGCTGCAGAGGTTTGGGTGGGTCTGGATCTCATTGGTGGGCAGC 648
humanTAS1R1  GAGACCATGGTGCTGCTGCTGCAGAAGTTCGGGTGGACCTGGATCTCTCTGGTTGGCAGC 648
mouseTas1r2  GAGGCCATGGTGCAACTGATGGTTCACTTCCAGTGGAACTGGATCGTGGTGCTGGTGAGC 642
ratTas1r2    GAGGCCATGGTGCAGCTGATGGTTCACTTCCAATGGAACTGGATTGTGGTGCTGGTGAGC 642
humanTAS1R2  GAGGCCATGGTGCAGCTGATGCTGCACTTCCGCTGGAACTGGATCATTGTGCTGGTGAGC 633
dogTas1r2    GAGGCCATGGTGCAGCTCCTGCTCCACTTCAACTGGAACTGGATCATCGTGCTAGTGAGC 633
catTas1r2    GAGGCCATGGTGCAGCTGATGTTGTACTTCCGCCGGAACTGGATCATCGCGCTGGTGAGC 633
mouseTas1r3  CAGGCAGTTGTGACTCTGTTGCAGAACTTCAGCTGGAACTGGGTGGCCGCCTTAGGGAGT 642
ratTas1r3    CAGGCCGTTGTGACACTGTTGCAGAATTTCAGCTGGAACTGGGTGGCTGCCTTAGGTAGT 642
dogTas1r3    GTGGCCATGGTGGAGCTGCTGCAGGAGCTTGGCTGGAACTGGGTGGCTGCAGTGGGCAGC 636
catTas1r3    GCGGCCATGGTGGAGCTGCTGGAGGAGCTCGGCTGGAACTGGGTGGCGGCGGTGGGTAGT 654
humanTAS1R3  ACGGCCGCCGCGGAGCTGCTGCAGGAGTTCGGCTGGAACTGGGTGGCCGCCCTGGGCAGC 642
                *  *              *         * *         *  *    ** mouseTas1r1  TATGGTGACTACGGGCAGCTGGGCGTACAGGCGCTGGAGGAGC---TGGCCACTCCACGG 708
ratTas1r1    TACGGTGATTACGGGCAGCTGGGTGTGCAGGCGCTGGAGGAGC---TGGCCGTGCCCCGG 702
catTas1r1    GACGGCGACTACGGGCAGCTGGGGGTGCAGGCGCTGGAGGAGC---AGGCCACCCAGCAG 705
dogTas1r1    GACGGCGACTATGGGCAGCTGGGGGTGCAGGCACTGGAGGAGC---AGGCCACCCAGCAG 705
humanTAS1R1  AGTGACGACTATGGGCAGCTAGGGGTGCAGGCACTGGAGAACC---AGGCCACTGGTCAG 705
mouseTas1r2  GATGACGATTATGGCCGAGAGAACAGCCACCTGCTGAGCCAGCGTCTGACCAACACTGGC 702
ratTas1r2    GACGACGATTACGGCCGCGAGAACAGCCACCTGTTGAGCCAGCGTCTGACCAAAACGAGC 702
humanTAS1R2  AGCGACACCTATGGCCGCGACAATGGCCAGCTGCTTGGCGAGCGCGTGGCCCG---GCGC 690
dogTas1r2    AGCGACGACTACGGCCGCTACAACAGCCAGCTGCTCAACGATCGCCTGGCCA---CCGGC 690
catTas1r2    AGCGGCGACTGCGGCCGCGACGACAGCCAGCTGCTCAGCGATCGCCCGGCCGG---CGGC 690
mouseTas1r3  GATGATGACTATGGCCGGAAGGTCTGAGCATCTTTTCTAGTC---TGGCCAATGCACGA 699
ratTas1r3    GATGATGACTATGGCCGGAAGGTCTGAGCATCTTTTCTGGTC---TGGCCAACTCACGA 699
dogTas1r3    GATGACGAGTATGGCCGGCAGGGCCTGAGCCTCTTCTCCAGCC---TGGCCAATGCCAGG 693
catTas1r3    GACGACGAGTATGGCCGGCAGGGCCTGAGCCTCTTCTCCGGCC---TGGCCAGCGCCAGG 711
humanTAS1R3  GACGACGAGTACGGCCGGCAGGGCCTGAGCATCTTCTCGGCCC---TGGCCGCGGCACGC 699
                *     *  **  *                   *        *      *  **
```

FIG. 1D

```
mouseTas1r1   GGCATCTGCGTCGCCTTCAAGGACGTGGTGCCTCT--CTCCGCCCAGGCGGGTGACCC-- 764
ratTas1r1     GGCATCTGCGTCGCCTTCAAGGACATCGTGCCTTT--CTCTGCCCGGGTGGGTGACCC-- 758
catTas1r1     GGCATCTGCGTTGCCTTCAAGGACATCATCCCCTT--CTCTGCCCGGCCGGGCGACGA-- 761
dogTas1r1     GGCATCTGCATTGCCTTCAAGGACATCATACCCTT--CTCTGCCCAGCCGGGTAATGA-- 761
humanTAS1R1   GGGATCTGCATTGCTTTCAAGGACATCATGCCCTT--CTCTGCCCAGGTGGGCGATGA-- 761
mouseTas1r2   GATATCTGCATTGCCTTCCAGGAGGTTCTGCCTGTACCAGAACCCAACCAGGCCGTGAGG 762
ratTas1r2     GACATCTGCATTGCCTTCCAGGAGGTTCTGCCCATACCTGAGTCCAGCCAGGTCATGAGG 762
humanTAS1R2   GACATCTGCATCGCCTTCCAGGAGACGCTGCCCACACTGCAGCCCAACCAGAACATGACG 750
dogTas1r2     GACATCTGCATCGCCTTCCAGGAGACGCTGCCCATGCCGCAGCCCGACCAGGTGGTGACG 750
catTas1r2     GACACCTGCATCGCCTTCCGGGAGACGCTGCCCATGCCCCAGCCCAACCAGGCGGTGACG 750
mouseTas1r3   GGTATCTGCATCGCACATGAGGGCCTGGTGCCACAA-CATGACACTAGTGGCCAACAGTT 758
ratTas1r3     GGTATCTGCATTGCACACGAGGGCCTGGTGCCACAA-CATGACACTAGTGGCCAACAATT 758
dogTas1r3     GGCATCTGTATTGCGCATGAGGGCCTGGTGCCATTG-CCGCACACGAGTAGCCTGCGGCT 752
catTas1r3     GGCATCTGCACGCGCATGAGGGCCTGGTGCCACTG-CCGC---CAGGCAGCCTGCGGCT 767
humanTAS1R3   GGCATCTGCATCGCGCACGAGGGCCTGGTGCCGCTG-CCCCGTGCCGATGACTCGCGGCT 758
                *  * ***  *            * **           * mouseTas1r1   ---AAGGA-----------TGCAGCGCATGATGCTGCGTCTGGCTCGAGCCAGGACCACC 810
ratTas1r1     ---GAGGA-----------TGCAGAGCATGATGCAGCATCTGGCTCAGGCCAGGACCACC 804
catTas1r1     ---GAGGA-----------TGCAGAGCATCATGCACCACCTGGCCCGAGCGAGGACCACC 807
dogTas1r1     ---GAGGA-----------TGCAGAGCATGATGTACCACCTGGACCGAGCAAGGACCACT 807
humanTAS1R1   ---GAGGA-----------TGCAGTGCCTCATGCGCCACCTGGCCCAGGCCGGGGCCACC 807
mouseTas1r2   CCTGAGGAGCAGGACCAACTGGACAACATCCTGGACAAGCTGCGGCGG---ACCTCGGCG 819
ratTas1r2     TCCGAGGAGCAGAGACAACTGGACAACATCCTGGACAAGCTGCGGCGG---ACCTCGGCG 819
humanTAS1R2   TCAGAGGAGCGCCAGCGCCTGGTGACCATTGTGGACAAGCTGCAGCAG---AGCACAGCG 807
dogTas1r2     GAGTGGGAGCGCCAGCGCCTGGAGGCCATCGTGGGCAAGCTGCAGCAG---AGCTCGGCG 807
catTas1r2     CAGTGGGAGCGCCGGCGCCTGAAGGCCATCGTGGACGAGCAGCAGCGGCAGAGCTCTGCG 810
mouseTas1r3   GGGCAAGG-----------TGCTGGATGTACTACGCCAAGTGAACCAA---AGTAAAGTA 804
ratTas1r3     GGGCAAGG-----------TGGTGGATGTGCTACGCCAAGTGAACCAA---AGCAAAGTA 804
dogTas1r3     GGGCACTG-----------TCCAGGGCCTACTGCACCAGGTAAACCAG---AGCAGCGTG 798
catTas1r3     GGGCGCCC-----------TACAGGGCCTGCTGCGCCAGGTGAACCAG---AGCAGCGTG 813
humanTAS1R3   GGGGAAGG-----------TGCAGGACGTCCTGCACCAGGTGAACCAG---AGCAGCGTG 804
                              *    *  *               * mouseTas1r1   GTGGTCGTGGTCTT-CTCTAACCGGCACCTGGCTGGAGTG--TTCTTCAGGTCTGTGGTG 867
ratTas1r1     GTGGTTGTGGTCTT-CTCTAACCGGCACCTGGCTAGAGTG--TTCTTCAGGTCCGTGGTG 861
catTas1r1     GTTGTGGTCGTTTT-CTCCAGCAGGCAGCTGGCCAGGGTG--TTCTTTGAGTCGGTGGTG 864
dogTas1r1     GTTGTGGTCGTTTT-CTCCAGCAGGCAGCTGGCCAGGGTG--TTCTTCGAGTCCGTGGTC 864
humanTAS1R1   GTCGTGGTTGTTTT-TTCCAGCCGGCAGTTGGCCAGGGTG--TTTTTCGAGTCCGTGGTG 864
mouseTas1r2   CGTGTGGTGGTGATATTCTCGCCAGAGCTGAGCCTGCACAACTTCTTCCGCGAGGTGCTG 879
ratTas1r2     CGCGTCGTGGTGGTGTTCTCGCCCGAGCTGAGCCTGTATAGCTTCTTTCACGAGGTGCTC 879
humanTAS1R2   CGCGTCGTGGTCGTGTTCTCGCCCGACCTGACCCTGTACCACTTCTTCAATGAGGTGCTG 867
dogTas1r2     CGCGTCGTGGTGCTGTTCTCGCCAGACCTGATCCTGCACAACTTCTTCCGCGAGGTGCTC 867
catTas1r2     CGCGTCGTGGTCCTGCTGTCGCCAAAGCTGGTCCTGCACAACTTCTTCCGCGAGGTGCTC 870
mouseTas1r3   CAAGTGGTGGTGCTGTTTGCCTCTGCCCGTGCTGTCTACTCCCTTTTTAGTTACAGCATC 864
ratTas1r3     CAGGTGGTGGTGCTGTTTGCATCTGCCCGTGCTGTCTACTCCCTTTTTAGCTACAGCATC 864
dogTas1r3     CAGGTGGTGGTGCTTTTCTCTTCCACTCGTGCTGCCCGCACCCTCTTCAGCTACAGCATC 858
catTas1r3     CAGGTGGTGGTGCTGTTCTCCTCCGCCCACGCGGCCCGCACCCTCTTCAGCTACAGCATC 873
humanTAS1R3   CAGGTGGTGCTGCTGTTCGCCTCCGTGCACGCCGCCCACGCCCTCTTCAACTACAGCATC 864
                 *    * *                                 *  **     * mouseTas1r1   CTGGCCAACCTGACTGGCAAAGTGTGGATCGCCTCCGAAGACTGGGCCATCTCCACGTAC 927
ratTas1r1     CTGGCCAACCTGACTGGCAAAGTGTGGGTCGCCTCAGAAGACTGGGCCATCTCCACGTAC 921
catTas1r1     CTGGCCAACCTGACTGCCAAGGTGTGGATCGCCTCAGAAGACTGGGCCATCTCTAGACAC 924
dogTas1r1     CTGGCCAAGCTGACTGCCAAGGTGTGGATCGCTTCAGAAGACTGGGCCATCTCCAGACAT 924
humanTAS1R1   CTGACCAACCTGACTGGCAAGGTGTGGGTCGCCTCAGAAGCCTGGGCCCTCTCCAGGCAC 924
mouseTas1r2   CGCTGGAACTTCACAGGCTTTGTGTGGATTGCCTCTGAGTCTGGGCCATCGACCCTGTT 939
ratTas1r2     CGCTGGAACTTCACGGGTTTTGTGTGGATCGCCTCTGAGTCCTGGCTGTATCGACCCAGTT 939
humanTAS1R2   CGCCAGAACTTCACGGGCCGCGTGTGGATCGCCTCCGAGTCCTGGGCCATCGACCCGGTC 927
dogTas1r2     CGCCAGAACTTCACGGGCGCCGTGTGGATCGCCTCCGAGTCCTGGGCCATCGACCCGGTT 927
catTas1r2     CGCCAGAACCTCACGGGCGTCGTGCGGATCGCCTCCGAGTCCTGGGCCATCGACCCGGTC 930
mouseTas1r3   CATCATGGCCTCTCACCCAAGGTATGGGTGGCCAGTGAGTCTTGG-CTGACATCTGACCT 923
ratTas1r3     CTTCATGACCTCTCACCCAAGGTATGGGTGGCCAGTGAGTCCTGG-CTGACCTCTGACCT 923
dogTas1r3     CACTGCAGGCTCTCGCCCAAGGTTTGGGTGGCCAGTGAGGCCTGG-CTGACCTCGGACCT 917
catTas1r3     CGCTGCAAGCTCTCACCCAAGGTGTGGGTGGCCAGCGAGGCCTGG-CTGACCTCAGACCT 932
humanTAS1R3   AGCAGCAGGCTCTCGCCCAAGGTGTGGGTGGCCAGCGAGGCCTGG-CTGACCTCTGACCT 923
                *  *       **  ** * *       **       ***  *    *
```

FIG. 1E

```
mouseTas1r1   ATCACCAAT---GTGCCCGGGATCCAGGGCATTGGGACGGTGCTGGGGGTGGCCATCCAG 984
ratTas1r1     ATCACCAGC---GTGACTGGGATCCAAGGCATTGGGACGGTGCTCGGTGTGGCCGTCCAG 978
catTas1r1     ATCAGCAAT---GTGCCCGGGATCCAGGGCATTGGCGGTGCTGGGGTGTGGCCATCCAG 981
dogTas1r1     ATTAGCAGC---CTGCCCAGGATCTGGGGCATTGGCACAGTGTTGGGCGTGGCCATCCAG 981
humanTAS1R1   ATCACTGGG---GTGCCCGGGATCCAGCGCATTGGGATGGTGCTGGGCGTGGCCATCCAG 981
mouseTas1r2   CTACACAAC---CTCACAGAGCTGCGCCACACGGGCACTTTCCTGGGCGTCACCATCCAG 996
ratTas1r2     CTGCATAAC---CTCACGGAGCTGCGCCACACGGGTACTTTTCTGGGCGTCACCATCCAG 996
humanTAS1R2   CTGCACAAC---CTCACGGAGCTGGGCCACTTGGGCACCTTCCTGGGCATCACCATCCAG 984
dogTas1r2     CTGCACAAC---CTCACCGAGCTGCGCCAAACCGGCACCTTCCTGGGCGTCACCACCCAG 984
catTas1r2     CTGCACGACAGGCCCAC-GCGCTGCACAGCCTCCTGGGCTGCACCCAGACCAGCAGCTCC 989
mouseTas1r3   GGTCATGAC--ACTTCCCAATATTGCCCGTGTGGGCACTGTGCTTGGGTTTTTGCAGCGG 981
ratTas1r3     GGTCATGAC--ACTTCCCAATATTGCCCGTGTGGGCACTGTTCTTGGGTTTCTGCAGCGC 981
dogTas1r3     GGTCATGAC--GCTGCCTGGCATGGCTGAGGTGGGCACCGTGCTTGGGTTTCTGCAGCAG 975
catTas1r3     GGTCATGAC--GCTGCCCGGCATGCCTGGGGTGGGCACCGTGCTGGGCTTCCTGCAGCAG 990
humanTAS1R3   GGTCATGGG--GCTGCCCGGCATGGCCCAGATGGGCACGGTGCTTGGCTTCCTCCAGAGG 981
                             *         * mouseTas1r1   CAGAGACAAGTCCCTGGCCTGAAGGAGTTTGAAGAGTCCTATGT----CCAGGCAGTGAT 1040
ratTas1r1     CAGAGACAAGTCCCTGGGCTGAAGGAGTTTGAGGAGTCTTATGT----CAGGGCTGTAAC 1034
catTas1r1     CAGAGGCTTGTCCCTGGCCTGAAGGAGTTTGAAGAGGCCTATGT----CCAGGCAGATAA 1037
dogTas1r1     CAGAAGCTTGTCCCTGGTCTGAAGGAGTTTGAAGAGGCCTACGT----CCGGGCAAAGAA 1037
humanTAS1R1   AAGAGGGCTGTCCCTGGCCTGAAGGAGTTTGAAGAAGCCTATGC----CCGGGCAGACAA 1037
mouseTas1r2   AGGGTGTCCATCCCTGGCTTCAGCCAGTTCCGAGTGCGCCACGA----CAAGCC------ 1046
ratTas1r2     AGGGTGTCCATCCCTGGCTTCAGTCAGTTCCGAGTGCGCCGTGA----CAAGCC------ 1046
humanTAS1R2   AGCGTGCCCATCCCGGGCTTCAGTGAGTTCCGCGAGTGGGGCCC----ACAGGC------ 1034
dogTas1r2     AGTGTGCCCATCCCGGGCTTCAGCGAGTTCCGCATACGCCGCAC----CCCGGT------ 1034
catTas1r2     GGGTCGTCTATCCCTGGCA--GGTGAGGCCCCAC----CCACGG----AGAGTC------ 1033
mouseTas1r3   GGTGCCCTACTGCCTGAATTTTCCCATTATGTGGAGACTCACCTTGCCCTGGCCGCTGAC 1041
ratTas1r3     GGTGCCCTACTGCCTGAATTTTCCCATTATGTGGAGACTCGCCTTGCCCTAGCTGCTGAC 1041
dogTas1r3     GGCGCCCCAATACCCGAGTTCCCATCCTATGTGCAGACCTGCCTGGCCCTGGCTGCTGAC 1035
catTas1r3     GGCGCCCCGATGCCGGAGTTCCCATCCTACGTGCGGACCCGCCTGGCCCTGGCCGCTGAC 1050
humanTAS1R3   GGTGCCCAGCTGCACGAGTTCCCCCAGTACGTGAAGACGCACCTGGCCCTGGCCACCGAC 1041
                  * * *                                   * mouseTas1r1   GGGTGCTCCCAGAACTTGCCCAGAGG---------GGTCCTGGTGCGGCACTAACCAGCT 1091
ratTas1r1     AGCTGCTCCCAGCGCTTGCCCGGAGG---------GGTCCTGGTGCAGCACTAACCAGCT 1085
catTas1r1     GGGGGCCCCTGGGCCTTGCTCCAGGA---------CCTCCGAGTGCAGCAGCAACCAGCT 1088
dogTas1r1     GGCAGCCCATAGGCCTTGCTCCAGGG---------ACTCCTGGTGCAGCAGCAACCAACT 1088
humanTAS1R1   GAAGGCCCCTAGGCCTTGCCACAAGG---------GCTCCTGGTGCAGCAGCAATCAGCT 1088
mouseTas1r2   AGAGTATCCCATGCCTAACGAGACCA---------GCCTGAGGACTACCTGTAACCAGGA 1097
ratTas1r2     AGGGTATCCCGTGCCTAACGAGACCA---------ACCTGCGGACGACCTGCAACCAGGA 1097
humanTAS1R2   TGGGCCGCCACCCCTCAGCAGGACCA---------GCCAGGCTATACCTGCAACCAGGA 1085
dogTas1r2     CAGGCTGCCTGAGCCCAACAGGACCA---------GCCTGGAGGCCACCTGCAACCAGGA 1085
catTas1r2     GGGGCCACACACGCA-GGCGCCGCCA---------CAGCCCTGAGTGGTTGCCATGGAGA 1083
mouseTas1r3   CCAGCATTCTGTGCCTCACTGAATGCGGAGT---TGGATCTGGAGGAACATGTGATGGGG 1098
ratTas1r3     CCAACATTCTGTGCCTCCCTGAAAGCTGAGT---TGGATCTGGAGGAGCGCGTGATGGGG 1098
dogTas1r3     CCTGCCTTTTGCGCCTCACTGGATGCAGAGCAGCCGGGCCTGGAAGAGCACGTGGTGGGG 1095
catTas1r3     CCTGCCTTCTGCGCCTCGCTGGACGCTGAACAGCCAGGCCTGGAGGAGCACGTGGTGGGG 1110
humanTAS1R3   CCGGCCTTCTGCTCTGCCCTGGGCGAGAGGGAGCAGGGTCTGGAGGAGGACGTGGTGGGC 1101
                                             * mouseTas1r1   GTGCAGGGAGTGTCACGCTTTCACGACATGGAACATGCCC-------------------- 1131
ratTas1r1     GTGCCGGGAGTGCCACACGTTCACGACTCGTAACATGCCC-------------------- 1125
catTas1r1     CTGTAGAGAGTGTCGGGCTTTCACGGCAGAGCAGATGCCC-------------------- 1128
dogTas1r1     CTGCAGAGAGTGCCAAGCTTTCACAGTACAGCAGATGCCC-------------------- 1128
humanTAS1R1   CTGCAGAGAATGCCAAGCTTTCATGGCACACACGATGCCC-------------------- 1128
mouseTas1r2   CTGTGACGCCTGCATGAACATCACCGAGTCCTTTAACAAC-------------------- 1137
ratTas1r2     CTGTGACGCCTGCTTGAACACCACCAAGTCCTTCAACAAC-------------------- 1137
humanTAS1R2   GTGCGACAACTGCCTGAACGCCACCTTGTCCTTCAACACC-------------------- 1125
dogTas1r2     GTGCGACAACTGCCTGAACACCGTCCTTCAACAGC-------------------- 1125
catTas1r2     CCACTGC-CCTGCTCTAGCGTCCCCCTCTCTGGCCGGGTC-------------------- 1122
mouseTas1r3   CAACGCTGTCCACGGTGTGACGACATCATGCTGCAGAACCTATCATCTGGGCTGTTGCAG 1158
ratTas1r3     CCACGCTGTTCACAATGTGACTACATCATGCTACAGAACCTGTCATCTGGGCTGATGCAG 1158
dogTas1r3     CCCCGCTGTCCCCAGTGTGACCACGTCACTCTGGA-------------GGCTA------ 1135
catTas1r3     CCACGCTGCCCCCAATGTGACCACGTCACGCTAGAGAACC-------------------- 1150
humanTAS1R3   CAGCGCTGCCCGCAGTGTGACTGCATCACGCTGCAGAACG-------------------- 1141
```

FIG. 1F

```
mouseTas1r1   ---GAGCTTGGAGCCTTCTCCATGAGCGCTGCCTACAATGTGTATGAGGCTGTGTATGCT 1188
ratTas1r1     ---ACGCTTGGAGCCTTCTCCATGAGTGCCGCCTACAGAGTGTATGAGGCTGTGTACGCT 1182
catTas1r1     ---ACGCTCGGGGCATTCTCCATGAGCTCTGCTTATAACGCCTACCGGGCAGTCTACGCA 1185
dogTas1r1     ---ACACTCGGAGCATTCTCCATGAGCTCTGCCTACAATGCCTACCGGGCTGTCTACGCA 1185
humanTAS1R1   ---AAGCTCAAAGCCTTCTCCATGAGTTCTGCCTACAACGCATACCGGGCTGTGTATGCG 1185
mouseTas1r2   ---GTTCTCATGCTTTCGGGGGAGCGTGTGGTCTACAGTGTGTACTCGGCCGTCTACGCG 1194
ratTas1r2     ---ATCCTTATACTTTCGGGGGAGCGCGTGGTCTACAGCGTGTACTCGGCAGTTTACGCG 1194
humanTAS1R2   ---ATTCTCAGGCTCTCTGGGGAGCGTGTCGTCTACAGCGTGTACTCTGCGGTCTATGCT 1182
dogTas1r2     ---ATCCTCATGCTCTCCGGCGAGCGCGTGGTCTACAACGTGTACTCGGCTGTCTACGCC 1182
catTas1r2     ---CTGGGCAAACTGGCGGGAGAGGCCAGGGGACGTACCCTGTCCCAGACACATAA---  1176
mouseTas1r3   AACCTATCAGCTGGGCAATTGCACCACCAAATATTTGCAACCTATGCAGCTGTGTACAGT 1218
ratTas1r3     AACCTATCAGCTGGGCAGTTGCACCACCAAATATTTGCAACCTATGCAGCTGTGTACAGT 1218
dogTas1r3     ----TGTCTGCAGGGCTGCTGCACCACCAGACCTTCGCGGCCTACGCAGCCGTGTATGGC 1191
catTas1r3     ----TATCTGCGGGGCTGCTGCACCACCAGACCTTCGCTGCCTACGCGGCTGTGTATGGC 1206
humanTAS1R3   ----TGAGCGCAGGGCTAAATCACCACCAGACGTTCTCTGTCTACGCAGCTGTGTATAGC 1197
                                                            *      *   ** mouseTas1r1   GTGGCCCACGGCCTCCACCAGCTCCTGGGATGTACCTCTGGGACCTGTGCCA---GAGGC 1245
ratTas1r1     GTGGCCCACGGCCTCCACCAGCTCCTGGGATGTACTTCTGAGATCTGTTCCA---GAGGC 1239
catTas1r1     GTGGCCCATGGCCTCCACCAGCTCCTGGGCTGTGCCTCTGGAGCCTGTTCCA---GGGAC 1242
dogTas1r1     GCAGCCCATGGCCTCCACCAGCTCCTGGGCTGTGCCTCTGGAGCCTGTTCCA---GGGAC 1242
humanTAS1R1   GTGGCCCATGCCCTCCACCAGCTCCTGGGCTGTGCCTCTGGAGCTTGTTCCA---GGGGC 1242
mouseTas1r2   GTAGCCCACACCCTCCACAGACTCCTCCACTGCAACCAGGTCCGCTGCACCA---AGCAA 1251
ratTas1r2     GTGGCCCATGCCCTCCACAGACTCCTCGGCTGTAACCAGGTCCGCTGCACCA---AGCAA 1251
humanTAS1R2   GTGGCCCATGCCCTGCACAGCCTCCTCGGCTGTGACAAAAGCACCTGCACCA---AGAGG 1239
dogTas1r2     GTGGCCCATGCATTACACAGCCTTCTGGGCTGCACCCAGGCCTGCTCCA--A---GG-AG 1237
catTas1r2     ------------------------------------------------------------
mouseTas1r3   GTGGCTCAAGCCCTTCACAACACCCTACAGTGCAATGTCTCACATTGCCACGTATCAGAA 1278
ratTas1r3     GTGGCTCAGGCCCTTCACAACACCCTGCAGTGCAATGTCTCACATTGCCACACATCAGAG 1278
dogTas1r3     GTGGCCCAGGCCCTCCACAACACACTGCTCTGCAATGCCTCAGGCTGCCCCCACGGGAG  1251
catTas1r3     GTGGCCCAAGCCCTTCACAACACACTGCGCTGCAATGCCTCGGGCTGCCCCAGGCGGGAG 1266
humanTAS1R3   GTGGCCCAGGCCCTGCACAACACTCTTCAGTGCAACGCCTCAGGCTGCCCCGCGCAGGAC 1257 mouseTas1r1   CCAGTCTACCCCTGGCAGCTTCTTCAGCAGATCTACAAGGTGAATTTCCTTCTACATAAG 1305
ratTas1r1     CCAGTCTACCCCTGGCAGCTTCTTCAGCAGATCTACAAGGTGAATTTTCTTCTACATGAG 1299
catTas1r1     CGAGTCTACCCCTGGCAGCTTCTGGAGCAGATCCGCAAGGTGAATTTCCTCCTACACAAG 1302
dogTas1r1     CGAGTCTACCCCTGGCAGCTTCTAGAGCAGATCCGCAAGGTGAATTTCCTTCTACACGAG 1302
humanTAS1R1   CGAGTCTACCCCTGGCAGCTTTTGGAGCAGATCCACAAGGTGCATTTCCTTCTACACAAG 1302
mouseTas1r2   ATCGTCTATCCATGGCAGCTACTCAGGGAGATCTGGCATGTCAACTTCACGCTCCTGGGC 1311
ratTas1r2     AAGGTCTACCCGTGGCAGCTACTCAGGGAGATCTGGCACGTCAACTTCACGCTCCTGGGT 1311
humanTAS1R2   GTGGTCTACCCCTGGCAGCTGCTTGAGGAGATCTGGAAGGTCAACTTCACTCTCCTGGAC 1299
dogTas1r2     GTGGTCTACCCCTGGCAGCTCCTTAAGGAAATCTGGAAGGTCAACTTCACCCTTCTGGGC 1297
catTas1r2     ------------------------------------------------------------
mouseTas1r3   CATGTTCTACCCTGGCAGCTCCTGGAGAACATGTACAATATGAGTTTCCATGCTCGAGAC 1338
ratTas1r3     CCTGTTCAACCCTGGCAGCTCCTGGAGAACATGTACAATATGAGTTTCCGTGCTCGAGAC 1338
dogTas1r3     CCAGTGCGGCCCTGGCAGCTCCTAGAAAACATGTACAACTTGACCTTCCGTGTGCGCGGC 1311
catTas1r3     CCTGTGCGGCCCTGGCAGCTCCTAGAGAACATGTACAACGTGAGCTTCCGTGCTCGCGGC 1326
humanTAS1R3   CCCGTGAAGCCCTGGCAGCTCCTGGAGAACATGTACAACCTGACCTTCCACGTGGGCGGG 1317 mouseTas1r1   AAGACTGTAGCATTCGATGACAAGGGGGACCCTCTAGGTTATTATGACATCATCGCCTGG 1365
ratTas1r1     AATACTGTGGCATTTGATGACAACGGGGACCCTCTAGGTTACTACGACATCATCGCCTGG 1359
catTas1r1     GACACCGTGAGGTTTAATGACAACGGGGACCCTCTGAGTGGCTACGACATAATTGCCTGG 1362
dogTas1r1     GACACTGTGATATTTAATGACAACGGGGACCCTCTCAGTGGCTATGACATAATTGCCTGG 1362
humanTAS1R1   GACACTGTGGCGTTTAATGACAACAGAGATCCCCTCAGTAGCTATAACATAATTGCCTGG 1362
mouseTas1r2   AACCAGCTCTTCTTCGACGAACAAGGGGACATGCCGATGCTCCTGGACATCATCAGTGG  1371
ratTas1r2     AACCGGCTCTTCTTTGACCAACAAGGGGACATGCCGATGCTCTTGGACATCATCAGTGG  1371
humanTAS1R2   CACCAAATCTTCTTCGACCCGCAAGGGGACGTGGCTCTGCACTTGGAGATTGTCCAGTGG 1359
dogTas1r2     CACAATGTCTTTTTTGGGCAGCAAGGGGACGTGCTCATGCCCATGGAGGTCATCCAGTGG 1355
catTas1r2     ------------------------------------------------------------
mouseTas1r3   TTGACACTACAGTTTGATGCTGAAGGGAATGTAGACATGGAATATGACCTGAAGATGTGG 1398
ratTas1r3     TTGACACTGCAGTTTGATGCCAAAGGGAGTGTAGACATGGAATATGACCTGAAGATGTGG 1398
dogTas1r3     TTAGCACTGCAGTTCGATGCCGAGGGGAACGTGAATATGGATTATGACCTGAAACTGTGG 1371
catTas1r3     CTGGCACTGCAGTTCGACGCCAGCGGGAACGTGAACGTGGATTACGACCTGAAACTGTGG 1386
humanTAS1R3   CTGCCGCTGCGGTTCGACAGCAGCGGAAACGTGGACATGGAGTACGACCTGAAGCTGTGG 1377
```

FIG. 1G

```
mouseTas1r1  GACTGGAATGGACCTGAATGGACCTTTGAGGTCATTGGTTCTGCCTCACTGTCTCCAGTT 1425
ratTas1r1    GACTGGAATGGACCTGAATGGACCTTTGAGATCATTGGCTCTGCCTCACTGTCTCCAGTT 1419
catTas1r1    GACTGGAGTGGCCCCAAGTGGAACTTCAGGGTCATTGGCTCCTCCATGTGGCCTCCAGTT 1422
dogTas1r1    GACTGGAGTGGTCCCAAGTGGACCTTCAGGGTCATCGGCTCCTCCACGTGGCCTCCAGTT 1422
humanTAS1R1  GACTGGAATGGACCCAAGTGGACCTTCACGGTCCTCGGTTCCTCCACATGGTCTCCAGTT 1422
mouseTas1r2  CAATGGGCCTGAGCCAGAACCCCTTCCAAAGCATCGCCTCCTACTCCCCCACCGAGACG 1431
ratTas1r2    CAGTGGGACCTGAGCCAGAATCCCTTCCAAAGCATCGCCTCCTATTCTCCCACCAGCAAG 1431
humanTAS1R2  CAATGGGACCGGAGCCAGAATCCCTTCCAGAGCGTCGCCTCCTACTACCCCCTGCAGCGA 1419
dogTas1r2    CAGTGGGACCTGAGCCAGAACCCTTTCCAGAGCATCGCCTCCTACTACCCCAAGCTGCGG 1415
catTas1r2    ------------------------------------------------------------
mouseTas1r3  GTGTGGCAGAGCCCTACACCTGTATTACATACTGTGGGCACCTTCAACGGCACCCTTCAG 1458
ratTas1r3    GTGTGGCAGAGCCCTACACCTGTACTACATACTGTAGGCACCTTCAACGGCACCCTTCAG 1458
dogTas1r3    GTGTGGCGGGACCTGAAGCCCGAGTTGCGCACCGTAGGTGCCTTCAACGGCCGCCTGAAG 1431
catTas1r3    GTGTGGCAGGACCCGACGCCCGAGCTGCGCACCGTAGGCACCTTCAAGGGCCGCCTGGAG 1446
humanTAS1R3  GTGTGGCAGGGCTCAGTGCCCAGGCTCCACGACGTGGGCAGGTTCAACGGCAGCCTCAGG 1437 mouseTas1r1  CATCTAGACATAAATAAGACAAAAATCCAGTGGCACGGGAAGAACAATCAGGTGCCTGTG 1485
ratTas1r1    CATCTGGACATAAATAAGACAAAAATCCAGTGGCACGGGAAGAACAATCAGGTGCCTGTG 1479
catTas1r1    CAGCTGGACATAAATAAAACCAAAATCCGGTGGCACGGGAAGGACAACCAGGTGCCAAAG 1482
dogTas1r1    CAGCTGGACATAAATAAAACCAAAATCCGGTGGCACGGAGAGGACAACCAGGTGCCTGAG 1482
humanTAS1R1  CAGCTAAACATAAATGAGACCAAAATCCAGTGGCACGGAAAGGACAACCAGGTGCCTAAG 1482
mouseTas1r2  AGGCTGACCTACATTAG---CAATGTGTCCTGGTACACCCCCAACAACACGGTCCCCATA 1488
ratTas1r2    AGGCTAACCTACATTAA---CAATGTGTCCTGGTACACCCCCAACAACACGGTCCCTGTC 1488
humanTAS1R2  CAGCTGAAGAACATCCA---AGACATCTCCTGGCACACCGTCAACAACACGATCCCTATG 1476
dogTas1r2    CAGCTCAAGGCCATCCA---CAACATCTCCTGGCACACCGCCAACAACACGATCCCCGTG 1472
catTas1r2    ------------------------------------------------------------
mouseTas1r3  CTGCAGCAGTCTA---------AAATGTACTGGC------CAGGCAACCAGGTGCCAGTC 1503
ratTas1r3    CTGCAGCACTCGA---------AAATGTATTGGC------CAGGCAACCAGGTGCCAGTC 1503
dogTas1r3    GTCTGGCACTCCC---------AGATGTCCTGGCACACACCTGGGAACCAGCGGCCCGTG 1482
catTas1r3    CTCTGGCGCTCTC---------AGATGTGCTGGCACACGCCGGGGAAGCAGCAGCCCGTG 1497
humanTAS1R3  ACAGAGCGCCTGA---------AGATCCGCTGGCACACGTCTGACAACCAGAAGCCCGTG 1488 mouseTas1r1  TCAGTGTGTACCAGGGACTGTCTCGAAGGGCACCACAGGTTGGTCATGGGTTCCCACCAC 1545
ratTas1r1    TCAGTGTGTACCACGGACTGTCTGGCAGGGCACCACAGGGTGGTTGTGGGTTCCCACCAC 1539
catTas1r1    TCTGTGTGCTCCAGCGACTGCCTCGAAGGGCACCAGCGAGTGATTTCGGGTTTCTACCAC 1542
dogTas1r1    TCTGTGTGCTCCAGCAACTGTCTTGAAGGGCACCAGCGAGTAGTTGTGGGTTTCTACCAC 1542
humanTAS1R1  TCTGTGTGTTCCAGCGACTGTCTTGAAGGGCACCAGCGAGTGGTTACGGGTTTCCATCAC 1542
mouseTas1r2  TCCATGTGTTCTAAGAGTTGCCAGCCTGGGCAAATGAAAAAACCCATAGGCCTCCACCCG 1548
ratTas1r2    TCCATGTGTTCCAAGAGCTGCCAGCCAGGGCAAATGAAAAAGTCTGTGGGCCTCCACCCT 1548
humanTAS1R2  TCCATGTGTTCCAAGAGGTGCCAGTCAGGGCAAAAGAAGAAGCCTGTGGGCATCCACGTC 1536
dogTas1r2    TCCATGTGTTCCAAGGACTGCCATCCTGGCCAAAGGAAGAAGCCTGTGGGCATCCACTCC 1532
catTas1r2    ------------------------------------------------------------
mouseTas1r3  TCCCAGTGTTCCCGCCAGTGCAAAGATGGCCAGGTTCGCCGAGTAAAGGGCTTTCATTCC 1563
ratTas1r3    TCCCAGTGCTCCCGGCAGTGCAAAGATGGCCAGGTGCGCAGAGTAAAGGGCTTTCATTCC 1563
dogTas1r3    TCCCAGTGCTCCCGGCAGTGCGGGGAGGGCCAGGTGCGCCGTGTGAAGGGCTTCCACTCC 1542
catTas1r3    TCCCAGTGCTCCCGGCAGTGCAAGGAAGGCCAGGTGCGCCGCGTGAAGGGCTTCCACTCT 1557
humanTAS1R3  TCCCGGTGCTCGCGGCAGTGCCAGGAGGGCCAGGTGCGCCGGGTCAAGGGGTTCCACTCC 1548 mouseTas1r1  TGCTGCTTCGAGTGCATGCCCTGTGAAGCTGGGACATTTCTCAACACGAGTGAGCTTCA- 1604
ratTas1r1    TGCTGCTTTGAGTGTGTGCCCTGCGAAGCTGGGACCTTTCTCAACATGAGTGAGCTTCA- 1598
catTas1r1    TGTTGCTTTGAGTGTGTGCCCTGTGAGGCCGGGAGCTTCCTCAACAAGAGCGACCTCCA- 1601
dogTas1r1    TGTTGCTTTGAGTGTGTGCCCTGTGAGGCCGGCACCTTCCTCAACAAGAGTGACCTCCA- 1601
humanTAS1R1  TGCTGCTTTGAGTGTGTGCCCTGTGGGGCTGGGACCTTCCTCAACAAGAGTGACCTCTA- 1601
mouseTas1r2  TGCTGCTTCGAGTGTGTGGACTGTCCGCCGGGCACCTACCTCAACCGATCAGTAGATGAG 1608
ratTas1r2    TGTTGCTTCGAGTGCTTGGATTGTATGCCAGGCACCTACCTCAACCGCTCAGCAGATGAG 1608
humanTAS1R2  TGCTGCTTCGAGTGCATCGACTGCCTTCCCGGCACCTTCCTCAACCACACTGAAGATGAA 1596
dogTas1r2    TGCTGCTTCGAGTGTATTGACTGCCTTCCTGGCACCTTCCTCAACCGAACTGAAGACGAA 1592
catTas1r2    ------------------------------------------------------------
mouseTas1r3  TGCTGCTATGACTGCGTGGACTGCAAGGCGGGCAGCTACCGGAAGCATCCAGATGACTT- 1622
ratTas1r3    TGCTGCTATGACTGCGTGGACTGCAAGGCAGGGAGCTACCGGAAGCATCCAGATGACTT- 1622
dogTas1r3    TGCTGCTATGACTGCGTGGACTGCAAGGCGGGCACCTATCAGCGCAGCCCAGATGACCT- 1601
catTas1r3    TGCTGTTACAACTGCGTGGACTGCAAGGCGGGCAGTTATCAGCGCAACCCAGATGACCT- 1616
humanTAS1R3  TGCTGCTACGACTGTGTGGACTGCGAGGCGGGCAGCTACCGGCAAAACCCAGACGACAT- 1607
```

FIG. 1H

```
mouseTas1r1    --CACCTGCCAGCCTTGTGGAACAGAAGAATGGGCCCCTGAGGGGAGCTCAGCCTGCTTC 1662
ratTas1r1      --CATCTGCCAGCCTTGTGGAACAGAAGAATGGGCACCCAAGGAGAGCACTACTTGCTTC 1656
catTas1r1      --CAGCTGCCAGCCTTGTGGGAAAGAAAAGTGGGCACCCGCGGGAAGTGAAACCTGCTTT 1659
dogTas1r1      --CAGCTGCCAGCCTTGTGGGAAAGAAGAGTGGGCACCTGAGGGAAGTGAATCCTGCTTC 1659
humanTAS1R1    --CAGATGCCAGCCTTGTGGGAAAGAAGAGTGGGCACCTGAGGGAAGCCAGACCTGCTTC 1659
mouseTas1r2    TTTAACTGTCTGTCCTGCCCGGGTTCCATGTGGTCTTACAAGAACAACATCGCTTGCTTC 1668
ratTas1r2      TTTAACTGTCTGTCCTGCCCGGGTTCCATGTGGTCCTACAAGAACGACATCACTTGCTTC 1668
humanTAS1R2    TATGAATGCCAGGCCTGCCCGAATAACGAGTGGTCCTACCAGAGTGAGACCTCCTGCTTC 1656
dogTas1r2      TTTGACTGCCAGCCTTGCCCAAGTTACGAGTGGTCCCATAGGAACGACACCTCCTGCTTC 1652
catTas1r2      ------------------------------------------------------------
mouseTas1r3    --CACCTGTACTCCATGTAACCAGGACCAGTGGTCCCAGAGAAAAGCACAGCCTGCTTA 1680
ratTas1r3      --CACCTGTACTCCATGTGGCAAGGATCAGTGGTCCCCAGAAAAAAGCACAACCTGCTTA 1680
dogTas1r3      --CCTCTGCACCCAGTGTGACCAGAACCAGTGGTCCCCAGACCGGAGCACACGCTGCTTC 1659
catTas1r3      --CCTCTGCACCCAGTGTGACCAGGACCAGTGGTCCCCAGACCGGAGCACACGCTGCTTC 1674
humanTAS1R3    --CGCCTGCACCTTTTGTGGCCAGGATGAGTGGTCCCCGGAGCGAAGCACACGCTGCTTC 1665 mouseTas1r1    TCACGCACCGTGGAGTTCTTGGGGTGGCATGAACCCATCTCTTTGGTGCTATTAGCAGCT 1722
ratTas1r1      CCACGCACGGTGGAGTTCTTGGCTTGGCATGAACCCATCTCTTTGGTGCTAATAGCAGCT 1716
catTas1r1      CCACGCACCGTGGTGTTTTTGACTTGGCACGAGACCATCTCTTGGGTGCTGCTGGCAGCT 1719
dogTas1r1      CTACGCACTGTGGTGTTTTTGACTTGGCATGAGCCTATCTCTTGGGTGCTGCTGGCAGCT 1719
humanTAS1R1    CCGCGCACTGTGGTGTTTTTGGCTTTGCGTGAGCACACCTCTTGGGTGCTGCTGGCAGCT 1719
mouseTas1r2    AAGCGGCGGCTGGCCTTCCTGGAGTGGCACGAAGTGCCCACTATCGTGGTGACCATCCTG 1728
ratTas1r2      CAGCGGCGGCCTACCTTCCTGGAGTGGCACGAAGTGCCCACCATCGTGGTGGCCATACTG 1728
humanTAS1R2    AAGCGGCAGCTGGTCTTCCTGGAATGGCATGAGGCACCCACCATCGCTGTGGCCCTGCTG 1716
dogTas1r2      AAGCGGCGGCTGGCCTTCCTCGAATGGCACGAGCCCTCCACCATCTTTGTGGTTATGCTG 1712
catTas1r2      ------------------------------------------------------------
mouseTas1r3    CCTCGCAGGCCCAAGTTTCTGGCTTGGGGGGAGCCAGTTGTGCTGTCACTCCTCCTGCTG 1740
ratTas1r3      CCTCGCAGGCCCAAGTTTCTGGCTTGGGGGGAGCCAGCTGTGCTGTCACTTCTCCTGCTG 1740
dogTas1r3      CCCCGCAGGCTCACTTTCCTGGCATGGGGGCAGCCGGCTGTGCTGGTGCTGCTTATACTG 1719
catTas1r3      GCCCGCAAGCCCATGTTCCTGGCATGGGGGGAGCCAGCTGTGCTGCTACTGCTCGCGCTG 1734
humanTAS1R3    CGCCGCAGGTCTCGGTTCCTGGCATGGGGCGAGCCGGCTGTGCTGCTGCTGCTCCTGCTG 1725 mouseTas1r1    AACACGCTATTGCTGCTGCTGCTGATTGGGACTGCTGGCCTGTTTGCCTGGCGTCTTCAC 1782
ratTas1r1      AACACGCTATTGCTGCTGCTGCTGGTTGGGACTGCTGGCCTGTTTGCCTGGCATTTTCAC 1776
catTas1r1      AATACGTTGCTGCTGCTGCTGGTGACTGGGACTGCTGGCCTGTTTGCCTGGCACTTAGAC 1779
dogTas1r1      AATACGCTGCTGTTGCTGCTGGTGGCTGGGACTGCTGGCCTGTTTGCCTGGCACTTAGAC 1779
humanTAS1R1    AACACGCTGCTGCTGCTGCTGCTTGGGACTGCTGGCCTGTTTGCCTGGCACCTAGAC 1779
mouseTas1r2    GCCGCCCTGGGCTTCATCAGTACGCTGGCCATTCTGCTCATCTTCTGGAGACATTTCCAG 1788
ratTas1r2      GCTGCCCTGGGCTTCTTCAGTACACTGGCCATTCTTTTCATCTTCTGGAGACATTTCCAG 1788
humanTAS1R2    GCCGCCCTGGGCTTCCTCAGCACCCTGGCCATCCTGGTGATATTCTGGAGGCACTTCCAG 1776
dogTas1r2      ACCATCCTGGGCTTCCTCAGCACCCTGGCCATCATGGTGATCTTCTGGAGGCACCTCCAC 1772
catTas1r2      ------------------------------------------------------------
mouseTas1r3    CTTTGCCTGGTGCTGGGTCTAGCACTGGCTGCTCTGGGGCTCTCTGTCCACCACTGGGAC 1800
ratTas1r3      CTTTGCCTGGTGCTGGGCCTGACACTGGCTGCCCTGGGGCTCTTTGTCCACTACTGGGAC 1800
dogTas1r3      CTGGCTCTGGCGCTGGGCCTGGTGCTGGTGGCCCTGGGGCTCTTTATTAGGCACCGGGAC 1779
catTas1r3      CTGGCTCTGGCGCTGGGCCTGGCGCTGGCAGCCCTGGGGCTCTTCCTCTGGCACTCGGAC 1794
humanTAS1R3    CTGAGCCTGGCGCTGGGCCTTGTGCTGGCTGCTTTGGGGCTGTTCGTTCACCATCGGGAC 1785 mouseTas1r1    ACGCCTGTTGTGAGGTCAGCTGGGGGTAGGCTGTGCTTCCTCATGCTGGGTTCCTTGGTA 1842
ratTas1r1      ACACCTGTAGTGAGGTCAGCTGGGGGTAGGCTGTGCTTCCTCATGCTGGGTTCCCTGGTG 1836
catTas1r1      ACCCCTGTGGTGAAGTCCGCTGGGGGCCGACTGTGCTTCTTCATGCTAGGCTCCCTGGCA 1839
dogTas1r1      ACCCGGTGGTGAGGTCAGCTGGGGGCAGGCTGTGCTTCTTTATGCTGGGCTCCCTGGCA 1839
humanTAS1R1    ACCCCTGTGGTGAGGTCAGCAGGGGGCCGCCTGTGCTTTCTTATGCTGGGCTCCCTGGCA 1839
mouseTas1r2    ACGCCCATGGTGCGCTCGGCGGGCGGCCCCATGTGCTTCCTGATGCTGGTGCCCCTGCTG 1848
ratTas1r2      ACACCCATGGTGCGCTCGGCCGGTGGCCCCATGTGCTTCCTGATGCTCGTGCCCCTGCTG 1848
humanTAS1R2    ACACCCATAGTTCGCTCGGCTGGGGCCCCATGTGCTTCCTGATGCTGACACTGCTGCTG 1836
dogTas1r2      ACGCCCGTGGTTCGCTCGGCCGGGGGCCCCATGTGCTTCCTGATGCTGGTGCCGCTGCTG 1832
catTas1r2      ------------------------------------------------------------
mouseTas1r3    AGCCCTCTTGTCCAGGCCTCAGGTGGCTCACAGTTCTGCTTTGGCCTGATCTGCCTAGGC 1860
ratTas1r3      AGCCCTCTTGTTCAGGCCTCAGGTGGGTCACTGTTCTGCTTTGGCCTGATCTGCCTAGGC 1860
dogTas1r3      AGCCCACTGGTTCAGGCCTCAGGGGGCCACGGGCCTGCTTTGGCCTGGCCTCTGCCTGGGC 1839
catTas1r3      AGCCCGCTGGTTCAGGCCTCAGGTGGGCCACGGGCCTGCTTTGGCCTGGCTTGCCTGGGC 1854
humanTAS1R3    AGCCCACTGGTTCAGGCCTCGGGGGGGCCCCTGGCCTGCTTTGGCCTGGTGTGCCTGGGC 1845
```

FIG. 1I

```
mouseTas1r1    GCTGGGAGTTGCAGCCTCTACAGCTTCTTCGGGAAGCCCACGGTGCCCGCGTGCTTGCTG 1902
ratTas1r1      GCCGGAAGTTGCAGCTTCTATAGCTTCTTCGGGGAGCCCACGGTGCCCGCGTGCTTGCTG 1896
catTas1r1      GGGGGCAGCTGTGGGCTCTACGGCTTTTTTGGGGAGCCCACGCTGCCCACATGCTTGTTG 1899
dogTas1r1      GGGGGCAGCTGTGGGCTCTATGGCTTTTTTGGGGAGCCCACCCTGGCCACATGCTTGTTG 1899
humanTAS1R1    GCAGGTAGTGGCAGCCTCTATGGCTTCTTTGGGGAACCCACAAGGCCTGCGTGCTTGCTA 1899
mouseTas1r2    CTGGCGTTCGGGATGGTCCCCGTGTATGTGGGCCCCCCACGGTCTTCTCCTGTTTCTGC 1908
ratTas1r2      CTGGCGTTTGGGATGGTGCCCGTGTATGTGGGGCCCCCCACGGTCTTCTCATGCTTCTGC 1908
humanTAS1R2    GTGGCATACATGGTGGTCCCGGTGTACGTGGGGCCGCCCAAGGTCTCCACCTGCCTCTGC 1896
dogTas1r2      CTGGCGTACGCCATGGTCCCCATGTACATAGGGCAGCCCACGTTCTTCTCGTGCCTCTGG 1892
catTas1r2      ------------------------------------------------------------
mouseTas1r3    CTCTTCTGCCTCAGTGTCCTTCTGTTCCCAGGGCGGCCAAGCTCTGCCAGCTGCCTTGCA 1920
ratTas1r3      CTCTTCTGCCTCAGTGTCCTTCTGTTCCCAGGACGACCACGCTCTGCCAGCTGCCTTGCC 1920
dogTas1r3      CTTGTCTGCCTCAGTGTCCTTCTGTTCCCTGGCCAGCCGGGCCCTGCCAGCTGCCTGGCC 1899
catTas1r3      CTGGTCTGCCTCAGTGTCCTCCTGTTCCCTGGCCAGCCAGGCCCTGCCAGCTGCCTGGCC 1914
humanTAS1R3    CTGGTCTGCCTCAGCGTCCTCCTGTTCCCTGGCCAGCCCAGCCCTGCCCGATGCCTGGCC 1905 mouseTas1r1    CGTCAGCCCCTCTTTTCTCTCGGGTTTGCCATTTTCCTCTCCTGTCTGACAATCCGCTCC 1962
ratTas1r1      CGTCAGCCCCTCTTTTCTCTCGGGTTTGCCATCTTCCTCTCCTGCCTGACAATCCGCTCC 1956
catTas1r1      CGCCAAAGCCTCCTTGCCCTGGGTTTTGCCATCTTCCTGTCCTGCCTGACAATCCGCTCC 1959
dogTas1r1      CGCCAAGGCCTCTTTGCCCTCGGGTTTGCCATCTTCCTGTCCTGCCTGACAATCCGCTCC 1959
humanTAS1R1    CGCCAGGCCCTCTTTGCCCTTGGTTTCACCATCTTCCTGTCCTGCCTGACAGTTCGCTCA 1959
mouseTas1r2    CGCCAGGCTTTCTTCACCGTTTGCTTCTCCGTCTGCCTCTCCTGCATCACGGTGCGCTCC 1968
ratTas1r2      CGACAGGCTTTCTTCACCGTCTGCTTCTCCATCTGCCTATCCTGCATCACCGTGCGCTCC 1968
humanTAS1R2    CGCCAGGCCCTCTTTCCCTCTGCTTCACAATTTGCATCTCCTGTATCGCCGTGCGTTCT 1956
dogTas1r2      CGCCAGACCTTCTTCACCCTCTGCTTCACCATCTGCATCTCCTGCATCACCGTGCGCTCT 1952
catTas1r2      ------------------------------------------------------------
mouseTas1r3    CAACAACCAATGGCTCACCTCCCTCTCACAGGCTGCCTGAGCACACTCTTCCTGCAAGCA 1980
ratTas1r3      CAACAACCAATGGCTCACCTCCCTCTCACAGGCTGCCTGAGCACACTCTTCCTGCAAGCA 1980
dogTas1r3      CAGCAGCCACTGCTTCACCTTCCACTCACTGGCTGTCTGAGCACACTTTTCCTGCAAGCG 1959
catTas1r3      CAGCAGCCACTGTTCCACCTCCCACTCACTGGCTGCCTGAGCACGTTTTTCCTGCAAGCG 1974
humanTAS1R3    CAGCAGCCCTTGTCCCACCTCCCGCTCACGGGCTGCCTGAGCACACTCTTCCTGCAGGCG 1965 mouseTas1r1    TTCCAACTGGTCATCATCTTCAAGTTTTCTACCAAGGTACCCACATTCTACCACACTTGG 2022
ratTas1r1      TTCCAACTGGTCATCATCTTCAAGTTTTCTACCAAGGTGCCCACATTCTACCGTACCTGG 2016
catTas1r1      TTCCAACTGGTCTTCATCTTCAAGTTTTCTGCCAAGGTACCCACCTTCTACCGTGCCTGG 2019
dogTas1r1      TTCCAACTGGTCTTCATCTTCAAGTTTTCCGCCAAGGTACCCACCTTCTACCAGGCCTGG 2019
humanTAS1R1    TTCCAACTAATCATCATCTTCAAGTTTCACCAAGGTACCTACATTCTACCACGCCTGG 2019
mouseTas1r2    TTCCAGATTGTGTGCGTCTTCAAGATGGCCAGACGCCTGCCAAGCGCCTACGGTTTCTGG 2028
ratTas1r2      TTCCAGATCGTGTGTGTCTTCAAGATGGCCAGACGCCTGCCAAGTGCCTACAGTTTTTGG 2028
humanTAS1R2    TTCCAGATCGTCTGCGCCTTCAAGATGGCCAGCCGCTTCCCACGCGCCTACAGCTACTGG 2016
dogTas1r2      TTCCAGATCGTCTGCATCTTCAAGATGGCCAGGCGCCTCCCGCGCGCCTACGGCTACTGG 2012
catTas1r2      ------------------------------------------------------------
mouseTas1r3    GCTGAGACCTTTGTGGAGTCTGAGCTGCCACTGAGCTGGGCAAACTGGCTATGCAGCTAC 2040
ratTas1r3      GCCGAGATCTTTGTGGAGTCTGAGCTGCCACTGAGTTGGGCAAACTGGCTCTGCAGCTAC 2040
dogTas1r3      GCCCAGATATTTGTGGGTTCAGAGCTGCCATCAAGCTGGGCAGATCAGCTGCGTAGGTGC 2019
catTas1r3      GCCGAGATATTTGTGGGGTCGGAGCTGCCACCAAGCTGGGCTGAGAAGATGCGTGGCCGC 2034
humanTAS1R3    GCCGAGATCTTCGTGGAGTCAGAACTGCCTCTGAGCTGGGCAGACCGGCTGAGTGGCTGC 2025 mouseTas1r1    GCCCAAAACCATGGTGCCGGAATATTCGTCATTGTCAGCTCCACGGTCCATTTGTTCCTC 2082
ratTas1r1      GCCCAAAACCATGGTGCAGGTCTATTCGTCATTGTCAGCTCCACGGTCCATTTGCTCATC 2076
catTas1r1      GTCCAAAACCACGGTCCTGGCCTATTTGTGGTGATCAGCTCAATGGCCCAGCTGCTCATC 2079
dogTas1r1      GTCCAAAACCATGGTCCCCGCCTCTTTGTGGTGATCAGCTCCATGGCCCAGCTGCTCATC 2079
humanTAS1R1    GTCCAAAACCACGGTGCTGGCCTGTTTGTGATGATCAGCTCAGCGGCCCAGCTGCTTATC 2079
mouseTas1r2    ATGCGTTACCACGGGCCCTACGTCTTTGTGGCCTTCATCACGGCCGTCAAGGTGGCCCTG 2088
ratTas1r2      ATGCGTTACCACGGGCCCTATGTCTTCGTGGCCTTCATCACGGCCATCAAGGTGGCCCTG 2088
humanTAS1R2    GTCCGCTACCAGGGGCCCTACGTCTCTATGGCATTTATCACGGTACTCAAAATGGTCATT 2076
dogTas1r2      GTGCGCTGCCACGGGCCCTACGTCTTCGTGGCGTCCTTCATGGTGCTCAAGGTGGTCATC 2072
catTas1r2      ------------------------------------------------------------
mouseTas1r3    CTTCGGGGACTCTGGGCCTGGCTAGTGGTACTGTTGGCCACTTTTGTGGAGGCAGCACTA 2100
ratTas1r3      CTTCGGGGCCCCTGGGCTTGGCTGGTGGTACTGCTGGCCACTCTTGTGGAGGCTGCACTA 2100
dogTas1r3      CTGCAGGGGCCCTGGGCCTGGTTGCTGGTGCTGCTTGCTTTGCTGGCGGAAGCGGCATTA 2079
catTas1r3      CTGCGGGGGCCCTGGGCCTGGCTGGTGGTGCTGCTTGCTATGCTGGCAGAAGCCGCATTG 2094
humanTAS1R3    CTGCGGGGGCCCTGGGCCTGGCTGGTGGTGCTGCTGGCCATGCTGGTGGAGGTCGCACTG 2085
```

FIG. 1J

```
mouseTas1r1  TGTCTCACGTGGCTTGCAATGTGGACCCCACGGCCCACCA---GGGAGTACCAGCGCTTC 2139
ratTas1r1    TGTCTCACATGGCTTGTAATGTGGACCCCACGACCCACCA---GGGAATACCAGCGCTTC 2133
catTas1r1    TGTCTAACTTGGCTGGCGGTGTGGACCCCACTGCCCACCA---GGGAGTACCAGCGCTTC 2136
dogTas1r1    TGTGTAACTTGGCTTGCGGTGTGCCCGTTGCCCACCA---GGGAGTACCAGCGCTTC 2136
humanTAS1R1  TGTCTAACTTGGCTGGTGGTGTGGACCCCACTGCCTGCTA---GGGAATACCAGCGCTTC 2136
mouseTas1r2  GTGGCAGGCAACATGCTGGCCACCACCATCAACCCCATTGGCCGGACCGACCCCGATGAC 2148
ratTas1r2    GTGGTGGGCAACATGCTGGCCACCACCATCAACCCCATTGGCCGGACCGACCCGGATGAC 2148
humanTAS1R2  GTGGTAATTGGCATGCTGGCCACGGGCCTCAGTCCCACCACCCGTACTGACCCCGATGAC 2136
dogTas1r2    GTGGCAGGCAACGTGCTGGCCACGACCGCCAACCCTACTGCCCGCCCCGACCCCGATGAC 2132
catTas1r2    ------------------------------------------------------------
mouseTas1r3   TGTGCCTGGTATTTGATCGCTTTCCCACCAGAGGTGGTGA--CAGACTGGTCAGTGCTGC 2158
ratTas1r3    TGTGCCTGGTACTTGATGGCTTTCCCTCCAGAGGTGGTGA--CAGATTGGCAGGTGCTGC 2158
dogTas1r3    TGTGCCTGGTACCTGGTGGCCTTTCCACCAGAGGTGGTGA--CAGACTGGTGGGTGCTAC 2137
catTas1r3    TGTGCCTGGTACCTGGTAGCCTTCCCGCCAGAGGTGGTGA--CGGACTGGCGGGTACTGC 2152
humanTAS1R3  TGCACCTGGTACCTGGTGGCCTTCCCGCCGGAGGTGGTGA--CGGACTGGCACATGCTGC 2143 mouseTas1r1  CCCCATCTGGTGATTCTTGAGTGCACAGAGGTCAACTCTGTGGGCTTCCTGGTGGCTTTC 2199
ratTas1r1    CCCCATCTGGTGATTCTCGAGTGCACAGAGGTCAACTCTGTAGGCTTCCTGTTGGCTTTC 2193
catTas1r1    CCTCAGCTGGTGGTGCTTGATTGCACAGAGGCCAACTCACCGGGCTTCATGTTGGCTTTC 2196
dogTas1r1    CCTCAGCTGGTGGTGCTTGACTGCACGGAGGCCAACTCCCCGGGCTTCATGGTGGCCTTT 2196
humanTAS1R1  CCCCATCTGGTGATGCTTGAGTGCACAGAGACCAACTCCCTGGGCTTCATACTTGGCCTTC 2196
mouseTas1r2  CCCAATATCATAATCCTCTCCTGCCACCCTAACTACCGCAACGGGCTACTCTTCAACACC 2208
ratTas1r2    CCCAACATCATGATCCTCTCGTGCCACCCCTAACTACCGCAACGGGCTACTGTTCAACACC 2208
humanTAS1R2  CCCAAGATCACAATTGTCTCCTGTAACCCCAACTACCGCAACAGCCTGCTGTTCAACACC 2196
dogTas1r2    CCCAATATCATGGTCCTGTCCTGC------AACTACCGCAGGGCGCTGCTGTTCAACACC 2186
catTas1r2    ------------------------------------------------------------
mouseTas1r3   CCACAGA-GGTACTGGAGCACTGCCACGTGCGTTCCTGGGTCAGCCTGGGCTTGGTGCAC 2217
ratTas1r3    CCACGGA-GGTACTGGAACACTGCCGCATGCGTTCCTGGGTCAGCCTGGGCTTGGTGCAC 2217
dogTas1r3    CCACGCA-AGTGCTGGTGCACTGCCGAATGCGCTCCTGGATCAGCTTTGGCCTAGTGCAT 2195
catTas1r3    CCACAGA-GGCGCTGGTGCACTGCCACGTGCACTCCTGGATCAGCTTCGGCCTGGTGCAT 2211
humanTAS1R3  CCACGGA-GGCGCTGGTGCACTGCCGCACACGCTCCTGGGTCAGCTTCGGCCTAGCGCAC 2202 mouseTas1r1  GCACACAACATCCTCCTCTCCATCAGCACCTTTGTCTGCAGCTACCTGGGTAAGGAACTG 2259
ratTas1r1    ACCCACAACATTCTCCTCTCCATCAGTACCTTCGTCTGCAGCTACCTGGGTAAGGAACTG 2253
catTas1r1    GCCTACAATGGCCTCCTGTCCGTCAGCGCCTTTGCCTGCAGCTACCTGGGCAAGGACCTG 2256
dogTas1r1    GCCTACAATGGCCTGCTGTCCGTCAGCGCCTTTGCCTGCAGCTACCTGGGTAAGGACCTG 2256
humanTAS1R1  CTCTACAATGGCCTCCTCTCCATCAGTGCCTTTGCCTGCAGCTACCTGGGTAAGGACTTG 2256
mouseTas1r2  AGCATGGACTTGCTGCTGTCCGTGCTGGGTTTCAGCTTCGCGTACGTGGGCAAGGAACTG 2268
ratTas1r2    AGCATGGACTTGCTGCTGTCTGTGCTGGGTTTCAGCTTCGCTTACATGGGCAAGGAGCTG 2268
humanTAS1R2  AGCCTGGACCTGCTGCTCTCAGTGGTGGGTTTCAGCTTCGCCTACATGGGCAAAGAGCTG 2256
dogTas1r2    AGCCTGGACCTGCTCCTGTCCGTGGCGGGCTTCAGCTTCGCCTACATGGGCAAGGAGCTG 2246
catTas1r2    ------------------------------------------------------------
mouseTas1r3  ATCACCAATGCAATGTTAGCTTTCCTCTGCTTTCTGGGCACTTTCCTGGTACAGAGCCAG 2277
ratTas1r3    ATCACCAATGCAGTGTTAGCTTTCCTCTGCTTTCTGGGCACTTTCCTGGTACAGAGCCAG 2277
dogTas1r3    GCCATCAATGCCATGCTGGCCTTCCTCTGCTTCCTGGGCACGTTCTTGGTGCAGAGCCGG 2255
catTas1r3    GCCACTAACGCCATGCTGGCCTTCCTCTGCTTCCTGGGCACTTTCCTGGTGCAGAGCCGG 2271
humanTAS1R3  GCCACCAATGCCACGCTGGCCTTTCTCTGCTTCCTGGGCACTTTCCTGGTGCGGAGCCAG 2262 mouseTas1r1  CCGGAGAACTATAACGAAGCCAAATGTGTCACCTTCAGCCTGCTCCTCCACTTCGTATCC 2319
ratTas1r1    CCAGAGAACTATAATGAAGCCAAATGTGTCACCTTCAGCCTGCTCCTCAACTTCGTATCC 2313
catTas1r1    CCAGAGAACTACAACGAGGCCAAATGTGTCACTTTTAGTCTGCTGCTCAACTTCGTGTCC 2316
dogTas1r1    CCGGAGAACTACAACGAGGCCAAATGCGTCACCTTCAGTCTGCTCCTCAACTTCGTGTCC 2316
humanTAS1R1  CCAGAGAACTACAACGAGGCCAAATGTGTCACCTTCAGCCTGCTCTTCAACTTCGTGTCC 2316
mouseTas1r2  CCCACCAACTACAACGAAGCCAAGTTCATCACCCTCAGCATGACCTTCTCCTTCACCTCC 2328
ratTas1r2    CCCACCAACTACAACGAAGCCAAGTTCATCACTCTCAGCATGACCTTCTCCTTCACCTCC 2328
humanTAS1R2  CCCACCAACTACAACGAGGCCAAGTTCATCACCCTCAGCATGACCTTCTATTTCACCTCA 2316
dogTas1r2    CCCACCAACTACAACGAGGCCAAGTTCATCACCCTCTGCATGACCTTCTACTTCACCTCC 2306
catTas1r2    ------------------------------------------------------------
mouseTas1r3  CCTGGCCGCTACAACCGTGCCCGTGGTCTCACCTTCGCCATGCTAGCTTATTTCATCACC 2337
ratTas1r3    CCTGGTCGCTATAACCGTGCCCGTGGCCTCACCTTCGCCATGCTAGCTTATTTCATCATC 2337
dogTas1r3    CCAGGCCGCTACAATGGCGCCCGGGGTCTCACTTTTGCCATGCTGGCCTACTTCATCACC 2315
catTas1r3    CCAGGCCGCTACAATGGTGCCCGCGGCCTCACCTTTGCCATGCTGGCCTACTTCATCACC 2331
humanTAS1R3  CCGGGCCGCTACAACCGTGCCCGTGGCCTCACCTTTGCCATGCTGGCCTACTTCATCACC 2322
```

FIG. 1K

```
mouseTas1r1   TGGATCGCTTTCTTCACCATGTCCAGCATTTACCAGGGCAGCTACCTACCCGCGGTCAAT 2379
ratTas1r1     TGGATCGCCTTCTTCACCATGGCCAGCATTTACCAGGGCAGCTACCTGCCTGCGGTCAAT 2373
catTas1r1     TGGATTGCCTTCTTCACCACGGCCAGCGTCTACCAGGGCAAGTACTTGCCCGCGGTCAAC 2376
dogTas1r1     TGGATTGGCTTTTTCACCACAGCCAGCGTCTACCAGGGCAAATACCTGCCCGCGGTCAAC 2376
humanTAS1R1   TGGATCGCCTTCTTCACCACGGCCAGCGTCTACGACGGCAAGTACCTGCCTGCGCCAAC  2376
mouseTas1r2   TCCATCTCCCTCTGCACGTTCATGTCTGTCCACGATGGCGTGCTGGTCACCATCATGGAT 2388
ratTas1r2     TCCATCTCCCTCTGCACCTTCATGTCTGTGCACGACGGCGTGCTGGTCACCATCATGGAC 2388
humanTAS1R2   TCCGTCTCCCTCTGCACCTTCATGTCTGCCTACAGCGGGGTGCTGGTCACCATCATGGAC 2376
dogTas1r2     TCCGTCTCCCTCTGCACCTTCATGTCCGTCTATGATGGGGTCCTGGTCACCATCCTGGAC 2366
catTas1r2     ------------------------------------------------------------
mouseTas1r3   TGGGTCTCTTTTGTGCCCCTCCTGGCCAATGTGCAGGTGGCCTACCAGCCAGCTGTGCAG 2397
ratTas1r3     TGGGTCTCTTTTGTGCCCCTCCTGGCTAATGTGCAGGTGGCCTACCAGCCAGCTGTGCAG 2397
dogTas1r3     TGGATCTCCTTTGTCCCTCTCTTTGCCAATGTGCATGTGGCCTACCAGCCCACTGTGCAG 2375
catTas1r3     TGGATCTCCTTTGTGCCCCTCTTTGCCAATGTGCACGTGGCCTACCAGCCTGCCGTGCAG 2391
humanTAS1R3   TGGGTCTCCTTTGTGCCCCTCCTGGCCAATGTGCAGGTGGTCCTCAGGCCCGCCGTGCAG 2382 mouseTas1r1   GTGCTGGCAGGGCTGGCCACTCTGAGTGGCGGCTTCAGCGGCTATTTCCTCCCCTAAATGC 2439
ratTas1r1     GTGCTGGCAGGGCTGACCACACTGAGCGGCGGCTTCAGCGGTTACTTCCTCCCCAAGTGC 2433
catTas1r1     GTGCTGGCGGCGCTGAGCAGCCTGAGTGGCGGCTTCAGCGGTTATTTCCTCCCCAAGTGC 2436
dogTas1r1     GTGCTGGCGGCGCTGAGCAGCCTGAGCAGCGGCTTCAGCGGTTACTTCCTCCCCAAGTGC 2436
humanTAS1R1   ATGATGGCTGGGCTGAGCAGCCTGAGCAGCGGCTTCGGTGGGTATTTTCTGCCTAAGTGC 2436
mouseTas1r2   CTCCTGGTCACTGTGCTCAACTTTCTGGCCATCGGCTTGGGGTACTTTGGCCCCAAGTGT 2448
ratTas1r2     CTCCTGGTCACTGTGCTCAACTTCCTGGCCATCGGCTTGGGATACTTTGGCCCCAAGTGT 2448
humanTAS1R2   CTCTTGGTCACTGTGCTCAACCTCCTGGCCATCGGCCTGGGCTACTTCGGCCCCAAGTGC 2436
dogTas1r2     CTCTTGATCACCGTGCTCAACCTTCTGGGGCATCAGCTTTGGCTACTTTGGTCCCAAATGC 2426
catTas1r2     ------------------------------------------------------------
mouseTas1r3   ATGGGTGCTATCCTAGTCTGTGCCCTGGGCATCCTGGTCACCTTCCACCTGCCCAAGTGC 2457
ratTas1r3     ATGGGTGCTATCTTATTCTGTGCCCTGGGCATCCTGGCCACCTTCCACCTGCCCAAATGC 2457
dogTas1r3     ATGGCCGCCATCCTCCTCTGTGCCCTGGGCATCCTGGCCACCTTCCACCTGCCCAAGTGC 2435
catTas1r3     ATGGGCACCATCCTCCTCTGTGCCCTGGGTATCCTAGCCACCTTCCACCTGCCCAAGTGC 2451
humanTAS1R3   ATGGGCGCCCTCCTGCTCTGTGTCCTGGGCATCCTGGCTGCCTTCCACCTGCCCAGGTGT 2442 mouseTas1r1   TACGTGATTCTCTGCCGTCCAGAACTCAACAACACAGAACACTTTCAGGCCTCCATCCAG 2499
ratTas1r1     TATGTGATTCTCTGCCGTCCAGAACTCAACAATACAGAACACTTTCAGGCCTCCATCCAG 2493
catTas1r1     TACGTGATCCTGTGCCGCCCAAAATTTAACAGCACACAGCACTTCCAGGCCTCCATCCAG 2496
dogTas1r1     TATGTGATCCTGTGCCGCCCAGATCTCAACAGCACCGAGCACTTCCAGGCCTCCATCCAG 2496
humanTAS1R1   TACGTGATCCTCTGCCGCCCAGACCTCAACAGCACAGAGCACTTCCAGGCCTCCATTCAG 2496
mouseTas1r2   TACATGATCCTTTTCTACCCGGAGCGCAACACTTCAGCTTATTTCAATAGCATGATTCAG 2508
ratTas1r2     TACATGATCCTTTTCTACCCGGAGCGCAACACCTCAGCCTATTTCAATAGCATGATCCAG 2508
humanTAS1R2   TACATGATCCTCTTCTACCCGGAGCGCAACACGCCCGCCTACTTCAACAGCATGATCCAG 2496
dogTas1r2     TACATGGTCCTCTTCTACCCAGAGCGCAACACGCAGGTCTACTTCAGCAGCATGATTCAG 2486
catTas1r2     ------------------------------------------------------------
mouseTas1r3   TATGTGCTTCTTTGGCTGCCAAAGCTCAACACCCAGGAGTTCTTCCTGGGAAGGAATGCC 2517
ratTas1r3     TATGTACTTCTGTGGCTGCCAGAGCTCAACACCCAGGAGTTCTTCCTGGGAAGGAGCCCC 2517
dogTas1r3     TACCTGCTGCTGCAGCAGCTGGAGCTCAACAACCCGGAGTTCTTCCTAGGAGATGATGCC 2495
catTas1r3     TACCTGCTGCTGCAGCGGCCGGAGCTCAACACCCCTGAGTTCTTCCTGGAAGACAATGCC 2511
humanTAS1R3   TACCTGCTCATGCGGCAGCCAGGGCTCAACACCCCCGAGTTCTTCCTGGGAGGGGGCCCT 2502 mouseTas1r1   GACTACACGAGGCGCTGCGGCACTACCTGA------------------------------ 2529
ratTas1r1     GACTACACGAGGCGCTGCGGCACTACC--------------------------------- 2520
catTas1r1     GAGTACACGAGGCGCTGCGGCTCCACCTGA------------------------------ 2526
dogTas1r1     GACTACACGAGGCGCTGCGGCTCCACCTGA------------------------------ 2526
humanTAS1R1   GACTACACGAGGCGCTGCGGCTCCACCTGA------------------------------ 2526
mouseTas1r2   GGCTACACGATGAGGAAGAGCTAG------------------------------------ 2532
ratTas1r2     GGCTACACCATGAGGAAGAGC--------------------------------------- 2529
humanTAS1R2   GGCTACACCATGAGGAGGGACTAG------------------------------------ 2520
dogTas1r2     GGCTACACCATGGGGAAGGACTAG------------------------------------ 2510
catTas1r2     ------------------------------------------------------------
mouseTas1r3   AAGAAAGCAGCAGATGAGAAC-AGTGGCGGTGGTGAGGCAGCTCAGGGACACAATGAATG 2576
ratTas1r3     AAGGAAGCATCAGATGGGAAT-AGTGGTAGTAGTGAGGCAACTCGGGGACACAGTGAATG 2576
dogTas1r3     A---GAGGACAGGGCAGCAGT-GGTAGTGGGGGGAAGGAGACTTAGGGCAAAAACAAGTG 2551
catTas1r3     A---GAGCACAGGGCAGCAGTTGGGGGCAGGGGAGGGGAGAATCGGGGCAAAAACAAGTG 2568
humanTAS1R3   GGGGATGCCCAAGGCCAGAAT----GACGGGAACACAGGAAATCAGGGGAAACATGAGTG 2558
```

FIG. 1L

```
mouseTas1r1         -
ratTas1r1           -
catTas1r1           -
dogTas1r1           -
humanTAS1R1         -
mouseTas1r2         -
ratTas1r2           -
humanTAS1R2         -
dogTas1r2           -
catTas1r2           -
mouseTas1r3         A 2577
ratTas1r3           A 2577
dogTas1r3           A 2552
catTas1r3           A 2569
humanTAS1R3         A 2559
```

Fig. 2A

```
mouseT1R2   MGPQARTLHLLFLLLHALPKPV---MLVGNSDFHLAGDYLLGGLFTLHANVKSVSHLSYL 57
ratT1R2     MGPQARTLCLLSLLLHVLPKPG---KLVENSDFHLAGDYLLGGLFTLHANVKSISHLSYL 57
humanT1R2   MGPRAKTICSLFFLLWVLAEP------AENSDFYLPGDYLLGGLFSLHANMKGIVHLNFL 54
dogT1R2     MGPRAKAVCSLFILLQVLAEP------AENSDFYLPGDYLLGGLFTLHANVKGTVHLSFL 54
catT1R2     MGPRAREVCCFIILPRLLAEP------AENSDFYLAGDYFLGGLFTLHANVKGIVHLNLL 54
mouseT1R1   MLFWAAHLLLSLQLAVAYCWAFSCQRTESSPGFSLPGDFLLAGLFSLHADCLQVRHR--P 58
ratT1R1     MLFWAAHLLLSLQL--VYCWAFSCQRTESSPGFSLPGDFLLAGLFSLHGDCLQVRHR--P 56
dogT1R1     MSLLAAHLVS-LQLSLSCCWALSCHNTESSPDFSLPGDYLLAGLFPLHSDCPGVRRR--P 57
catT1R1     MSLPAAHLVG-LQLSLSCCWALSCHSTETSADFSLPGDYLLAGLFPLHSDCPGVRHR--P 57
humanT1R1   MLLCTARLVG-LQLLISCCWAFACHSTESSPDFTLPGDYLLAGLFPLHSGCLQVRHR--P 57
mouseT1R3   MPALAIMGLSLAAFLEL----GMGASLCLSQQFKAQGDYILGGLFPLGSTEEATLNQR-- 54
ratT1R3     MPGLAILGLSLAAFLEL----GMGSSLCLSQQFKAQGDYILGGLFPLGTTEEATLNQR-- 54
humanT1R3   MLGPAVLGLSLWALLHP----GTGAPLCLSQQLRMKGDYVLGGLFPLGEAEEAGLRSR-- 54
dogT1R3     MAGLMLLSLMALLGL------GAGAPLCLSRQLRMQGDYVLGGLFPLGTAEDTGLSDR-- 52
catT1R3     MPGLALLGLTALLGLTALLDHGEGATSCLSQQLRMQGDYVLGGLFPLGSAEGTGLGDG-- 58
            *                      . :    **:.*.***.* mouseT1R2   QVPKCN-EYNMKVLGYNLMQAMRFAVEEINNCSSLLPGVLLGYEMVDVCYL-SNNIQPGL 115
ratT1R2     QVPKCN-EFTMKVLGYNLMQAMRFAVEEINNCSSLLPGVLLGYEMVDVCYL-SNNIHPGL 115
humanT1R2   QVPMCK-EYEVKVIGYNLMQAMRFAVEEINNDSSLLPGVLLGYEIVDVCYI-SNNVQPVL 112
dogT1R2     QVPQCK-KYEMKVLGYNLMQAMRFAVEEINNRSDLLPGVLLGYEIVDVCYI-SNNVQPVL 112
catT1R2     QVPQCK-EYEIKVLGYDLMQAMCFAGEEINSQSSLLPGVLLGYKMVDVSYI-SNNVQPVL 112
mouseT1R1   LVTSCDRSDSFNGHGYHLFQAMRFTVEEINNSTALLPNITLGYELYDVCSE-SSNVYATL 117
ratT1R1     LVTSCDRPDSFNGHGYHLFQAMRFTVEEINNSSALLPNITLGYELYDVCSE-SANVYATL 115
dogT1R1     MVTLCDRSNSFNGHGYHLFQAMRFGIEEINNSTTLLPNVTLGYQLYDVCSE-SANVYATL 116
catT1R1     TVTLCDRPDSFNGHGYHLFQAMRFGIEEINNSTALLPNVTLGYQLYDVCSE-SANVYATL 116
humanT1R1   EVTLCDRSCSFNEHGYHLFQAMRLGVEEINNSTALLPNITLGYQLYDVCSD-SANVYATL 116
mouseT1R3   TQPNSIPCNRFSPLGLFLAMAMKMAVEEINNGSALLPGLRLGYDLFDTCSEPVVTMKSSL 114
ratT1R3     TQPNGILCTRFSPLGLFLAMAMKMAVEEINNGSALLPGLRLGYDLFDTCSEPVVTMKPSL 114
humanT1R3   TRPSSPVCTRFSSNGLLWALAMKMAVEEINNKSDLLPGLRLGYDLFDTCSEPVVAMKPSL 114
dogT1R3     TQPNATVCTRFSSLGLLWALAMKMAVEEVNNRSTLLPGLRLGYDLFDTCSEPVVAMKPSL 112
catT1R3     LQPNATVCTRFSSLGLLWALAVKMAVEEINNGSALLPGLHLGYDLFDTCSEPMVAMKPSL 118
            .           ..  *       *: :   **:*. : *.: *.: *..   : .* mouseT1R2   YFLSQID-DFLPILKDYSQYRPQVVAVIGPDNSESAITVSNILSYFLVPQVTYSAITDKL 174
ratT1R2     YFLAQDD-DLLPILKDYSQYMPHVVAVIGPDNSESAITVSNILSHFLIPQITYSAISDKL 174
humanT1R2   YFLAHED-NLLPIQEDYSNYISRVVAVIGPDNSESVMTVANFLSLFLLPQITYSAISDEL 171
dogT1R2     YFLARED-YSLPIQEDYSHYVPRVLAVIGPDNSESTTTVAHFLSLFLLPQITYSAISDDL 171
catT1R2     HFPAKED-CSLPIQEDYSHCVPRVVAVIGPGNSESTVTVARFLSLFLLPQITYSAISDEL 171
mouseT1R1   RVLAQQGTGHLEMQRDLRNHSSKVVALIGPDNTDHAVTTAALLSPFLMPLVSYEASSVIL 177
ratT1R1     RVLALQGPRHIEIQKDLRNHSSKVVAFIGPDNTDHAVTTAALLGPFLMPLVSYEASSVVL 175
dogT1R1     NVLSTLGTHHIEIQADPSHYSPAALAVIGPDTTNHAATAAALLSPFLVPVISYEASSVML 176
catT1R1     NVLSLLGTHHVEIRADPSHYSPAALAVIGPDTTNHAATTAALLSPFLVPLISYEASSVTL 176
humanT1R1   RVLSLPGQHHIELQGDLLHYSPTVLAVIGPDSTNRAATTAALLSPFLVPMISYAASSETL 176
mouseT1R3   MFLAKVGSQSIAAYCNYTQYQPRVLAVIGPHSSELALITGKFFSFFLMPQVSYSASMDRL 174
ratT1R3     MFMAKVGSQSIAAYCNYTQYQPRVLAVIGPHSSELALITGKFFSFFLMPQVSYSASMDRL 174
humanT1R3   MFLAKAGSRDIAAYCNYTQYQPRVLAVIGPHSSELAMVTGKFFSFFLMPQVSYGASMELL 174
dogT1R3     MFMAKAGSCDIAAYCNYTQYQPRVLAVIGPHSSELALITGKFFSFFLMPQVSYGASTDRL 172
catT1R3     VFMAKAGSCSIAAYCNYTQYQPRVLAVIGPHSSELALVTGKFFSFFLVPQVSYGASTDRL 178
            .  :   .  :    :       . .:*.*  .:: .   ::. :*  ::*  *        * mouseT1R2   RDKRRFPAMLRTVPSATHHIEAMVQLMVHFQWNWIVVLVSDDDYGRENSHLLSQRLTNTG 234
ratT1R2     RDKRHFPSMLRTVPSATHHIEAMVQLMVHFQWNWIVVLVSDDDYGRENSHLLSQRLTKTS 234
humanT1R2   RDKVRFPALLRTTPSADHHVEAMVQLMLHFRWNWIIVLVSSDTYGRDNGQLLGERVARR- 230
dogT1R2     RDKQHFPALLRTVAGADHQIEAMVQLLLHFNWNWIIVLVSSDDYGRYNSQLLNDRLATG- 230
catT1R2     RDKQRFPALLPTAPGADHQIEAMVQLMLYFRRNWIIALVSSGDCGRDDSQLLSDRPAGG- 230
mouseT1R1   SGKRRFPSFLRTIPSDKYQVEVIVRLLQSFGWVWISLVGSYGDYGQLGVQALEELATPR- 236
ratT1R1     SAKRRFPSFLRTVPSDRHQVEVVMVQLQSFGWVWISLIGSYGDYGQLGVQALEELAVPR- 234
dogT1R1     GVKRYYPSFLRTIPSDKYQVEIMVLLLQRFGWVWISLVGSDGDYGQLGVQALEEQATQQ- 235
catT1R1     GVKRHYPSFLRTIPSDKHQVEAMVLLLQSFGWVWISVVGSDGDYGQLGVQALEEQATQQ- 235
humanT1R1   SVKRQYPSFLRTIPNDKYQVETMVLLLQKFGWTWISLVGSSDDYGQLGVQALENQATGQ- 235
mouseT1R3   SDRETFPSFFRTVPSDRVQLAVVTLLQNFSWNWVAALGSDDDYGREGLSIFSSLANAR- 233
ratT1R3     SDRETFPSFFRTVPSDRVQLAVVTLLQNFSWNWVAALGSDDDYGREGLSIFSGLANSR- 233
humanT1R3   SARETFPSFFRTVPSDRVQLTAAAELLQEFGWNWVAALGSDDEYGRQGLSIFSALAAAR- 233
dogT1R3     SNRETFPSFFRTVSSDRVQAVAMVELLQELGWNWVAAVGSDDDYGRQGLSLFSSLANAR- 231
catT1R3     SNREIFPSFFRTVPSDQVQVAAMVELLEELGWNWVAAVGSDDDYGRQGLSLFSGLASAR- 237
            :   :*::: *   ..    :     . *:   *:  *: *  . *:   :
```

Fig. 2B

```
mouseT1R2   DICIAFQEVLPVPEPNQAVRPEEQDQLDNILDKLR-RTSARVVVIFSPELSLHNFFREVL 293
ratT1R2     DICIAFQEVLPIPESSQVMRSEEQRQLDNILDKLR-RTSARVVVFSPELSLYSFFHEVL 293
humanT1R2   DICIAFQETLPTLQPNQNMTSEERQRLVTIVDKLQ-QSTARVVVFSPDLTLYHFFNEVL 289
dogT1R2     DICIAFQETLPMPQPDQVVTEWERQRLEAIVGKLQ-QSSARVVVLFSPDLILHNFFREVL 289
catT1R2     DTCIAFRETLPMPQPNQAVTQWERRRLKAIVDEQQRQSSARVVVLLSPKLVLHNFFREVL 290
mouseT1R1   GICVAFKDVVPLS------AQAGDPRMQRMMLRLA-RARTTVVVVFSNRHLAGVFFRSVV 289
ratT1R1     GICVAFKDIVPFS------ARVGDPRMQSMMQHLA-QARTTVVVVFSNRHLARVFFRSVV 287
dogT1R1     GICIAFKDIIPFS------AQPGNERMQSMMYHLD-RARTTVVVVFSSRQLARVFFESVV 288
catT1R1     GICVAFKDIIPFS------ARPGDERMQSIMHHLA-RARTTVVVVFSSRQLARVFFESVV 288
humanT1R1   GICIAFKDIMPFS------AQVGDERMQCLMRHLA-QAGATVVVVFSSRQLARVFFESVV 288
mouseT1R3   GICIAHEGLVPQHD----TSGQQLGKVLDVLRQVN-QSKVQVVVLFASARAVYSLFSYSI 288
ratT1R3     GICIAHEGLVPQHD----TSGQQLGKVVDVLRQVN-QSKVQVVVLFASARAVYSLFSYSI 288
humanT1R3   GICIAHEGLVPLPR----ADDSRLGKVQDVLHQVN-QSSVQVVLLFASVHAAHALFNYSI 288
dogT1R3     GICIAHEGLVPLPH----TSSLRLGTVQGLLHQVN-QSSVQVVVLFSSTRAARTLFSYSI 286
catT1R3     GICIAHEGLVPLP-----PGSLRLGALQGLLRQVN-QSSVQVVVLFSSAHAARTLFSYSI 291
            . *:*..   :*              :  ::  . **:::         :*    :

mouseT1R2   RWNFTGFVWIASESWAIDPVLHNLTELRHTGTFLGVTIQRVSIPGFSQFRVRHDKPEYPM 353
ratT1R2     RWNFTGFVWIASESWAIDPVLHNLTELRHTGTFLGVTIQRVSIPGFSQFRVRRDKPGYPV 353
humanT1R2   RQNFTGAVWIASESWAIDPVLHNLTELGHLGTFLGITIQSVPIPGFSEFREWGPQAGPPP 349
dogT1R2     RQNFTGAVWIASESWAIDPVLHNLTELRQTGTFLGVTTQSVPIPGFSEFRIRRTPVRLPE 349
catT1R2     RQNLTGVVWRIASESWAIDPVLH------------------------------------ 312
mouseT1R1   LANLTGKVWIASEDWAISTYITNVPGIQGIGTVLGVAIQQRQVPGLKEFEESYVQAVMGA 349
ratT1R1     LANLTGKVWVASEDWAISTYITSVTGIQGIGTVLGVAVQQRQVPGLKEFEESYVRAVTAA 347
dogT1R1     LAKLTAKVWIASEDWAISRHISSLPRIWGIGTVLGVAIQQKLVPGLKEFEEAYVRAKKAA 348
catT1R1     LANLTAKVWIASEDWAISRHISNVPGIQGIGTVLGVAIQQRLVPGLKEFEEAYVQADKGA 348
humanT1R1   LTNLTGKVWVASEAWALSRHITGVPGIQRIGMVLGVAIQKRAVPGLKAFEEAYARADKKA 348
mouseT1R3   HHGLSPKVWVASESWLTSDLVMTLPNIARVGTVLGFLQRGALLPEFSHYVETHLALAADP 348
ratT1R3     LHDLSPKVWVASESWLTSDLVMTLPNIARVGTVLGFLQRGALLPEFSHYVETRLALAADP 348
humanT1R3   SSRLSPKVWVASEAWLTSDLVMGLPGMAQMGTVLGFLQRGAQLHEFPQYVKTHLALATDP 348
dogT1R3     HCRLSPKVWVASEAWLTSDLVMTLPGMAEVGTVLGFLQQGAPIPEFPSYVQTCLALAADP 346
catT1R3     RCKLSPKVWVASEAWLTSDLVMTLPGMPGVGTVLGFLQQGAPMPEFPSYVRTRLALAADP 351
            ::    *  :*** *   . :

mouseT1R2   PNETSLRTTC--NQDCDACMNITESFNNVLMLSGERVV------------YSVYSAVYAV 399
ratT1R2     PNTTNLRTTC--NQDCDACLNTTKSFNNILILSGERVV------------YSVYSAVYAV 399
humanT1R2   LSRTSQSYTC--NQECDNCLNATLSFNTILRLSGERVV------------YSVYSAVYAV 395
dogT1R2     PNRTSLEATC--NQECDTCQDTTASFNSILMLSGERVV------------YNVYSAVYAV 395
catT1R2     ------------------------------------------------------------
mouseT1R1   PRTCPEGSWCGTNQLCRECHAFTTWNMPELGAFSMSAA------------YNVYEAVYAV 397
ratT1R1     PSACPEGSWCSTNQLCRECHTFTTRNMPTLGAFSMSAA------------YRVYEAVYAV 395
dogT1R1     HRPCSRDSWCSSNQLCRECQAFTVQQMPTLGAFSMSSA------------YNAYRAVYAA 396
catT1R1     PGPCSRTSECSSNQLCRECRAFTAEQMPTLGAFSMSSA------------YNAYRAVYAV 348
humanT1R1   PRPCHKGSWCSSNQLCRECQAFMAHTMPKLKAFSMSSA------------YNAYRAVYAV 396
mouseT1R3   AFCASLN-AELDLEEHVMGQRCPRCDDIMLQNLSSGLLQNLSAGQLHHQIFATYAAVYSV 407
ratT1R3     TFCASLK-AELDLEERVMGPRCSQCDYIMLQNLSSGLMQNLSAGQLHHQIFATYAAVYSV 407
humanT1R3   AFCSALGEREQGLEEDVVGQRCPQCDCITLQNVSAGLN--------HHQTFSVYAAVYSV 400
dogT1R3     AFCASLDAEQPGLEEHVVGPRCPQCDHVTLEAMSAGLL--------HHQTFAAYAAVYGV 398
catT1R3     AFCASLDAEQPGLEEHVVGPRCPQCDHVTLENLSAGLL--------HHQTFAAYAAVYGV 403 mouseT1R2   AHTLHRLLHCNQVRCT-KQIVYPWQLLREIWHVNFTLLGNQLFFDEQGDMPMLLDIIQWQ 458
ratT1R2     AHALHRLLGCNRVRCT-KQKVYPWQLLREIWHVNFTLLGNRLFFDQQGDMPMLLDIIQWQ 458
humanT1R2   AHALHSLLGCDKSTCT-KRVVYPWQLLEEIWKVNFTLLDHQIFFDPQGDVALHLEIVQWQ 454
dogT1R2     AHALHSLLGCTQ-ACS-KEVVYPWQLLKEIWKVNFTLLGHNVFFGQQGDVLMPMEVIQWQ 453
catT1R2     ------------------------------------------------------------
mouseT1R1   AHGLHQLLGCTSGTCA-RGPVYPWQLLQQIYKVNFLLHKKTVAFDDKGDPLGYYDIIAWD 456
ratT1R1     AHGLHQLLGCTSEICS-RGPVYPWQLLQQIYKVNFLLHENTVAFDDNGDTLGYYDIIAWD 454
dogT1R1     AHGLHQLLGCASGACS-RDRVYPWQLLEQIRKVNFLLHEDTVIFNDNGDPLSGYDIIAWD 455
catT1R1     AHGLHQLLGCASGACS-RDRVYPWQLLEQIRKVNFLLHKDTVRFNDNGDPLSGYDIIAWD 455
humanT1R1   AHGLHQLLGCASGACS-RGRVYPWQLLEQIHKVHFLLHKDTVAFNDNRDPLSSYNIIAWD 455
mouseT1R3   AQALHNTLQCNVSHCHVSEHVLPWQLLENMYNMSFHARDLTLQFDAEGNVDMEYDLKMWV 467
ratT1R3     AQALHNTLQCNVSHCHTSEPVQPWQLLENMYNMSFRARDLTLQFDAKGSVDMEYDLKMWV 467
humanT1R3   AQALHNTLQCNASGCPAQDPVKPWQLLENMYNLTFHVGGLPLRFDSSGNVDMEYDLKLWV 460
dogT1R3     AQALHNTLLCNASGCPPREPVRPWQLLENMYNLTFRVRGLALQFDARGNVNMDYDLKLWV 458
catT1R3     AQALHNTLRCNASGCPRREPVRPWQLLENMYNVSFRARGLALQFDASGNVNVDYDLKLWV 463
```

Fig. 2C

```
mouseT1R2   WGLSQNPFQSIASYSPTETRLTY-ISNVSWYTPNNTVPISMCSKSCQPGQMKKPIGLHPC 517
ratT1R2     WDLSQNPFQSIASYSPTSKRLTY-INNVSWYTPNNTVPVSMCSKSCQPGQMKKSVGLHPC 517
humanT1R2   WDRSQNPFQSVASYYPLQRQLKN-IQDISWHTVNNTIPMSMCSKRCQSGQKKKPVGIHVC 513
dogT1R2     WDLSQNPFQSIASYYPKLRQLKA-IHNISWHTANNTIPVSMCSKDCHPGQRKKPVGIHSC 512
catT1R2     ----DRPTRCTAS---------------WAAP----------RPAAPGRLS-------- 334
mouseT1R1   WNGPEWTFEVIGSASLSPVHLDINKTKIQWHGKNNQVPVSVCTRDCLEGHHRLVMGSHHC 516
ratT1R1     WNGPEWTFEIIGSASLSPVHLDINKTKIQWHGKNNQVPVSVCTTDCLAGHHRVVVGSHHC 514
dogT1R1     WSGPKWTFRVIGSSTWPPVQLDINKTKIRWHGEDNQVPESVCSSNCLEGHQRVVVGFYHC 515
catT1R1     WSGPKWNFRVIGSSMWPPVQLDINKTKIRWHGKDNQVPKSVCSSDCLEGHQRVISGFYHC 515
humanT1R1   WNGPKWTFTVLGSSTWSPVQLNINETKIQWHGKDNQVPKSVCSSDCLEGHQRVVTGFHHC 515
mouseT1R3   WQSPTPVLHTVGTFNG---TLQLQQSKMYWPG--NQVPVSQCSRQCKDGQVRRVKGFHSC 522
ratT1R3     WQSPTPVLHTVGTFNG---TLQLQHSKMYWPG--NQVPVSQCSRQCKDGQVRRVKGFHSC 522
humanT1R3   WQGSVPRLHDVGRFNG---SLRTERLKIRWHTSDNQKPVSRCSRQCQEGQVRRVKGFHSC 517
dogT1R3     WRDLKPELRTVGAFNG---RLKVWHSQMSWHTPGNQRPVSQCSRQCGEGQVRRVKGFHSC 515
catT1R3     WQDPTPELRTVGTFKG---RLELWRSQMCWHTPGKQQPVSQCSRQCKEGQVRRVKGFHSC 520
                .                        *                  . *:

mouseT1R2   CFECVDCPPGTYLNRSVDEFNCLSCPGSMWSYKNNIACFKRRLAFLEWHEVPTIVVTILA 577
ratT1R2     CFECLDCMPGTYLNRSADEFNCLSCPGSMWSYKNDITCFQRRPTFLEWHEVPTIVVAILA 577
humanT1R2   CFECIDCLPGTFLNHTEDEYECQACPNNEWSYQSETSCFKRQLVFLEWHEAPTIAVALLA 573
dogT1R2     CFECIDCLPGTFLNRTADEFDCQPCPSYEWSHRNDTSCFKRRLAFLEWHEPSTIFVVMLT 572
catT1R2     -------LAG------------EAPPTESRGHT------RRRRHSPEWLP---------- 359
mouseT1R1   CFECMPCEAGTFLNTS-ELHTCQPCGTEEWAPEGSSACFSRTVEFLGWHEPISLVLLAAN 575
ratT1R1     CFECVPCEAGTFLNMS-ELHICQPCGTEEWAPKESTTCFPRTVEFLAWHEPISLVLIAAN 573
dogT1R1     CFECVPCEAGTFLNKS-DLHSCQPCGKEEWAPEGSESCFLRTVVFLTWHEPISWVLLAAN 574
catT1R1     CFECVPCEAGSFLNKS-DLHSCQPCGKEKWAPAGSETCFPRTVVFLTWHETISWVLLAAN 574
humanT1R1   CFECVPCGAGTFLNKS-DLYRCQPCGKEEWAPEGSQTCFPRTVVFLALREHTSWVLLAAN 574
mouseT1R3   CYDCVDCKAGSYRKHP-DDFTCTPCNQDQWSPEKSTACLPRRPKFLAWGEPVVLSLLLLL 581
ratT1R3     CYDCVDCKAGSYRKHP-DDFTCTPCGKDQWSPEKSTTCFPRRPKFLAWGEPAVLSLLLLL 581
humanT1R3   CYDCVDCEAGSYRQNP-DDIACTCFGQDEWSPERSTRCFRRRSRFLAWGEPAVLLLLLLL 576
dogT1R3     CYDCVDCKAGTYQRSP-DDLLCTQCDQNQWSPDRSTRCFPRRLTFLAWGQPAVLVLLILL 574
catT1R3     CYNCVDCKAGSYQRNP-DDLLCTQCDQDQWSPDRSTRCFARKPMFLAWGEPAVLLLLALL 579
                .*               .                * mouseT1R2   ALGFISTLAILLIFWRHFQTPMVRSAGGPMCFLMLVPLLLAFGMVPVYVGPPTVFSCFCR 637
ratT1R2     ALGFFSTLAILFIFWRHFQTPMVRSAGGPMCFLMLVPLLLAFGMVPVYVGPPTVFSCFCR 637
humanT1R2   ALGFLSTLAILVIFWRHFQTPIVRSAGGPMCFLMLTLLLVAYMVVPVYVGPPKVSTCLCR 633
dogT1R2     ILGFLSTLAIMVIFWRHLHTPVVRSAGGPMCFLMLVPLLLAYAMVPMYIGQPTFFSCLWR 632
catT1R2     --------------WRPLPCSSVPLSG--------------------------------- 372
mouseT1R1   TLLLLLLIGTAGLFAWRLHTPVVRSAGGRLCFLMLGSLVAGSCSLYSFFGKPTVPACLLR 635
ratT1R1     TLLLLLLVGTAGLFAWHFHTPVVRSAGGRLCFLMLGSLVAGSCSFYSFFGEPTVPACLLR 633
dogT1R1     TLLLLLVAGTAGLFAWHLDTPVVRSAGGRLCFFMLGSLAGGSCGLYGFFGEPTLATCLLR 634
catT1R1     TLLLLLVTGTAGLFAWHLDTPVVKSAGGRLCFFMLGSLAGGSCGLYGFFGEPTLPTCLLR 634
humanT1R1   TLLLLLLLGTAGLFAWHLDTPVVRSAGGRLCFLMLGSLAAGSGSLYGFFGEPTRPACLLR 634
mouseT1R3   CLVLGLALAALGLSVHHWDSPLVQASGGSQFCFGLICLGLFCLSVLLFPGRPSSASCLAQ 641
ratT1R3     CLVLGLTLAALGLFVHYWDSPLVQASGGSLFCFGLICLGLFCLSVLLFPGRPRSASCLAQ 641
humanT1R3   SLALGLVLAALGLFVHHRDSPLVQASGGPLACFGLVCLGLVCLSVLLFPGQPSPARCLAQ 636
dogT1R3     ALALGLVLVALGLFIRHRDSPLVQASGGPRACFGLACLGLVCLSVLLFPGQPGPASCLAQ 634
catT1R3     ALALGLALAALGLFLWHSDSPLVQASGGPRACFGLACLGLVCLSVLLFPGQPGPASCLAQ 639
                    .   *    :* mouseT1R2   QAFFTVCFSVCLSCITVRSFQIVCVFKMARRLPSAYGFWMRYHGPYVFVAFITAVKVALV 697
ratT1R2     QAFFTVCFSICLSCITVRSFQIVCVFKMARRLPSAYSFWMRYHGPYVFVAFITAIKVALV 697
humanT1R2   QALFPLCFTICISCIAVRSFQIVCAFKMASRFPRAYSYWVRYQGPYVSMAFITVLKMVIV 693
dogT1R2     QTFFTLCFTICISCITVRSFQIVCIFKMARRLPRAYGYWVRCHGPYVFVASFMVLKVVIV 692
catT1R2     -------------------------------RVLG--------------KL 378
mouseT1R1   QPLFSLGFAIFLSCLTIRSFQLVIIFKFSTKVPTFYHTWAQNHGAGIFVIVSSTVHLFLC 695
ratT1R1     QPLFSLGFAIFLSCLTIRSFQLVIIFKFSTKVPTFYRTWAQNHGAGLFVIVSSTVHLLIC 693
dogT1R1     QGLFALGFAIFLSCLTIRSFQLVFIFKFSAKVPTFYQAWVQNHGPRLFVVISSMAQLLIC 694
catT1R1     QSLLALGFAIFLSCLTIRSFQLVFIFKFSAKVPTFYRAWVQNHGPGLFVVISSMAQLLIC 694
humanT1R1   QALFALGFTIFLSCLTVRSFQLIIIFKFSTKVPTFYHAWVQNHGAGLFVMISSAAQLLIC 694
mouseT1R3   QPMAHLPLTGCLSTLFLQAAETFVESELPLSWANWLCSYLRGLWAWLVVLLATFVEAALC 701
ratT1R3     QPMAHLPLTGCLSTLFLQAAEIFVESELPLSWANWLCSYLRGPWAWLVVLLATLVEAALC 701
humanT1R3   QPLSHLPLTGCLSTLFLQAAEIFVESELPLSWADRLSGCLRGPWAWLVVLLAMLVEVALC 696
dogT1R3     QPLLHLPLTGCLSTLFLQAAQIFVGSELPSSWADQLRRCLQGPWAWLLVLLALLAEAALC 694
catT1R3     QPLFHLPLTGCLSTFFLQAAEIFVGSELPPSWAEKMRGRLRGPWAWLVVLLAMLAEAALC 699
                                        :
```

Fig. 2D

```
mouseT1R2    AGNMLATTINPIGRTDPDDPNIIILSCHPNYRNGLLFNTSMDLLLSVLGFSFAYVGKELP 757
ratT1R2      VGNMLATTINPIGRTDPDDPNIMILSCHPNYRNGLLFNTSMDLLLSVLGFSFAYMGKELP 757
humanT1R2    VIGMLATGLSPTTRTDPDDPKITIVSCNPNYRNSLLFNTSLDLLLSVVGFSFAYMGKELP 753
dogT1R2      AGNVLATTANPTARPDPDDPNIMVLSCN--YRRALLFNTSLDLLLSVAGFSFAYMGKELP 750
catT1R2      AGEARGRTLSPDT----------------------------------------------- 391
mouseT1R1    LTWLAMWTPRPTREYQR-FPHLVILECTEVNSVGFLVAFAHNILLSISTFVCSYLGKELP 754
ratT1R1      LTWLVMWTPRPTREYQR-FPHLVILECTEVNSVGFLLAFTHNILLSISTFVCSYLGKELP 752
dogT1R1      VTWLAVWTPLPTREYQR-FPQLVVLDCTEANSPGFMVAFAYNGLLSVSAFACSYLGKDLP 753
catT1R1      LTWLAVWTPLPTREYQR-FPQLVVLDCTEANSPGFMLAFAYNGLLSVSAFACSYLGKDLP 753
humanT1R1    LTWLVVWTPLPAREYQR-FPHLVMLECTETNSLGFILAFLYNGLLSISAFACSYLGKDLP 753
mouseT1R3    AWYLIAFPPEVVTDWSV-LPTEVLEHCHVRSWVSLGLVHITNAMLAFLCFLGTFLVQSQP 760
ratT1R3      AWYLMAFPPEVVTDWQV-LPTEVLEHCRMRSWVSLGLVHITNAVLAFLCFLGTFLVQSQP 760
humanT1R3    TWYLVAFPPEVVTDWHM-LPTEALVHCRTRSWVSFGLAHATNATLAFLCFLGTFLVRSQP 755
dogT1R3      AWYLVAFPPEVVTDWWV-LPTQVLVHCRMRSWISFGLVHAINAMLAFLCFLGTFLVQSRP 753
catT1R3      AWYLVAFPPEVVTDWRV-LPTEALVHCHVHSWISFGLVHATNAMLAFLCFLGTFLVQSRP 758 mouseT1R2    TNYNEAKFITLSMTFSFTSSISLCTFMSVHDGVLVTIMDLLVTVLNFLAIGLGYFGPKCY 817
ratT1R2      TNYNEAKFITLSMTFSFTSSISLCTFMSVHDGVLVTIMDLLVTVLNFLAIGLGYFGPKCY 817
humanT1R2    TNYNEAKFITLSMTFYFTSSVSLCTFMSAYSGVLVTIVDLLVTVLNLLAISLGYFGPKCY 813
dogT1R2      TNYNEAKFITLCMTFYFTSSVSLCTFMSVYDGVLVTILDLLITVLNLLGISFGYFGPKCY 810
catT1R2      ------------------------------------------------------------ 391
mouseT1R1    ENYNEAKCVTFSLLLHFVSWIAFFTMSSIYQGSYLPAVNVLAGLATLSGGFSGYFLPKCY 814
ratT1R1      ENYNEAKCVTFSLLLNFVSWIAFFTMASIYQGSYLPAVNVLAGLTTLSGGFSGYFLPKCY 812
dogT1R1      ENYNEAKCVTFSLLLNFVSWIGFFTTASVYQGKYLPAVNVLAALSSLSSGFSGYFLPKCY 813
catT1R1      ENYNEAKCVTFSLLLNFVSWIAFFTTASVYQGKYLPAVNVLAALSSLSSGGFSGYFLPKCY 813
humanT1R1    ENYNEAKCVTFSLLFNFVSWIAFFTTASVYDGKYLPAANMMAGLSSLSSGFGGYFLPKCY 813
mouseT1R3    GRYNRARGLTFAMLAYFITWVSFVPLLANVQVAYQPAVQMGAILVCALGILVTFHLPKCY 820
ratT1R3      GRYNRARGLTFAMLAYFIIWVSFVPLLANVQVAYQPAVQMGAILFCALGILATFHLPKCY 820
humanT1R3    GRYNRARGLTFAMLAYFITWVSFVPLLANVQVVLRPAVQMGALLLCVLGILAAFHLPRCY 815
dogT1R3      GRYNGARGLTFAMLAYFITWISFVPLFANVHVAYQPTVQMAAILLCALGILATFHLPKCY 813
catT1R3      GRYNGARGLTFAMLAYFITWISFVPLFANVHVAYQPAVQMGTILLCALGILATFHLPKCY 818 mouseT1R2    MILFYPERNTSAYFNSMIQGYTMRKS--------------------- 843
ratT1R2      MILFYPERNTSAYFNSMIQGYTMRKS--------------------- 843
humanT1R2    MILFYPERNTPAYFNSMIQGYTMRRD--------------------- 839
dogT1R2      MVLFYPERNTQVYFSSMIQGYTMGKD--------------------- 836
catT1R2      ----------------------------------------------- 391
mouseT1R1    VILCRPELNNTEHFQASIQDYTRRCGTT------------------- 842
ratT1R1      VILCRPELNNTEHFQASIQDYTRRCGTT------------------- 840
dogT1R1      VILCRPDLNSTEHFQASIQDYTRRCGST------------------- 841
catT1R1      VILCRPKFNSTQHFQASIQEYTRRCGST------------------- 841
humanT1R1    VILCRPDLNSTEHFQASIQDYTRRCGST------------------- 841
mouseT1R3    VLLWLPKLNTQEFFLGRNAKKAADENSGGGEAAQGHNE--------- 858
ratT1R3      VLLWLPELNTQEFFLGRSPKEASDGNSGSSEATRGHSE--------- 858
humanT1R3    LLMRQPGLNTPEFFLGGGPGDAQGQNDGN-TGNQGKHE--------- 852
dogT1R3      LLLQQLELNNPEFFLGDDARGQGSSGSGGKET--------------- 845
catT1R3      LLLQRPELNTPEFFLEDNARAQGSSWGQGRGESGQKQVTPDPVTSPQ 865
```

TASTE RECEPTORS OF THE T1R FAMILY FROM DOMESTIC DOG

CROSS-REFERENCE TO RELATED APPLICATION

This application is the U.S. National Phase of international patent application PCT/US2005/012765, filed in English on Apr. 14, 2005, designating the United States. PCT/US2005/012765 claims the benefit of U.S. Provisional Application 60/562,208, filed Apr. 14, 2004. The entire contents of each of these applications are incorporated herein by reference.

FIELD OF THE INVENTION

The present invention relates to the field of sensory mechanisms of the domestic dog, *Canis familiaris*. The invention relates, for example, to the discovery of several genes of *Canis familiaris* encoding taste receptors of the T1R family, T1R1 (Ta1r1), T1R2 (Tas1r2), and T1R3 (Tas1r3). The invention further relates to the polypeptides encoded by the canine T1R1, T1R2, and T1R3 genes and to methods and uses of the same.

BACKGROUND OF THE INVENTION

The sense of taste is important for determining food choice, for regulating food intake, and for ensuring efficient use of ingested nutrients. Taste can act as a warning system for the presence of potentially harmful foods, by, for example, the aversive sensations of sourness or bitterness, and as an attractant to potentially nutrient-rich foods, by, for example, the appealing sensations of sweetness, saltiness, and umami.

Taste stimuli are received by taste receptor cells assembled into taste buds that are located in the epithelium of taste papillae of the tongue (Kitagawa et al., *Bioch. Bioph. Res. Comm.*, 283:236-242 (2001)). The stimuli are believed to be transduced by taste receptors at the surface of the taste receptor cells (Id.). The taste receptors encoded by the genes of a given species are reflective of that species' food choices. For example, the "sweet receptors" of an herbivorous species are expected to be different from those of a carnivorous species, since the two consume completely different diets whose foods contain different primary stimuli. Since taste receptor specificity likely reflects food choice, it follows that receptor sequence homology among species may be as predictive or more predictive of food preferences of a given species as phylogenetic relatedness among species.

Evolution has provided that each species' genes code for taste receptors unique to that species' food choices. For example, the "sweet receptors" of an herbivore are expected to be different from those of a carnivore, since the two consume completely different diets whose foods contain different primary stimuli. Even within the Order Carnivora, Feliformia (cat branch) and Caniformia (dog and bear branch) have different diets and show different taste responses to various sweeteners. Since taste receptor specificity must reflect food choice, it may follow that receptor sequence homology among species might be dependent more upon the types of foods consumed by individual species rather than by the phylogenetic relatedness of species. The behavior of carnivores, such as the domestic cat, towards stimuli such as sweet carbohydrates, which it cannot taste (Beauchamp, et al., *J. Comp. Physiol. Psychol.*, 91(5):1118-1127 (1977)), and towards L-amino acids, which it can taste, should be explainable based on the specificity of the taste receptors of carnivores in general. The behavior of the domestic cat (*Felis catus*), a carnivore, towards stimuli such as sweet carbohydrates, which it generally cannot taste, and towards L-amino acids, which it generally can taste, should be explicable by the specificity of taste receptors of other carnivores.

The domestic dog and the domestic cat are two readily accessible and popular members of the Order Carnivora. Neurophysiological studies with dog show that it responds to chemicals representative of each of the five basic taste modalities: sweet, sour, bitter, salty, and umami. However, the spectrum of compounds within each taste group to which the dog responses are different from those to which the human, rodent, and cat respond (Bradshaw, *Proc. Nutrition Soc.*, 50:99-106 (1991)). For example, while the dog responds to a range of mono- and d-saccharides and to some high intensity sweeteners, the cat does not. Particularly active in the dog are D-fructose, β-D-fructose, and sucrose. (Beauchamp et al., *J. Comp. Physiol. Psychol.*, 91(5):1118-1127 (1977); Boudreau et al., *Chem. Senses*, 10:89-127 (1985); Boudreau (ed.), Neurophysiology and stimulus chemistry of mammalian taste systems. IN FLAVOR CHEMISTRY TRENDS AND DEVELOPMENTS. Washington D.C.: American Chemical Society (1989); Bartoshuk et al., *Science*, 171:699-701 (1971)).

Early studies suggest that domestic dog shows a preference for sucrose and that this behavior is congenital. (Grace & Russek, *Physiology and Behavior*, 4:553-558 (1968)). Additionally, domestic dog is believed to taste saccharin as bitter. (Grace & Russek, *Physiology and Behavior*, 4:553-558 (1968)). Electrophysiological studies showed that dog taste nerve fibers that responded to sucrose exhibited no response to saccharin and that the fibers fired by saccharin respond to the bitter alkaloid, strychnine. (Anderson et al., *Acta physiol scan*, 21:105-119 (1950)). Experiments using amiloride show that the umami component of the canine chorda tympani nerve response is independent of the sodium component. (Kurihara & Kashiwayanagi, *Ann. N. Y. Acad. Sci.*, 855:393-397 (1998)). Direct knowledge of taste receptor genes of the domestic dog will allow insight into an animal's sensory world and may be useful for identifying modulators of the taste receptors encoded thereby to influence an animal's taste preferences.

Molecular receptors for the taste element of sweetness have recently been identified from human, mouse, and rat. Thus far, there are three known members of the T1R taste receptor family: T1R1, T1R2, and T1R3 (Montmayeur & Matsunami, *Curr. Opin. Neurobiol.*, 12(4):366-371 (2002)). The T1R3 receptor gene is located within the Sac locus, the primary genetic locus controlling preference for sweet-tasting stimuli in mice (Li et al., *Mamm. Genome*, 12(1):13-16 (2001); Li et al., *Mamm. Genome*, 13(1):5-19 (2002)). The human syntenic region for the mouse T1R3 gene is on 1p36.33 (1162-1186 kb). The gene for T1R1 is located on human 1p36.23 (6324-6349 kb), which is ~5 Mb from T1R3, and that for T1R2 is located on human 1p36.13 (18483-18729 kb), which is ~12 Mb from T1R1.

Most of the T1Rs are G-protein coupled receptors with long N-terminal extracellular domains believed to be involved in ligand binding (Montmayeur & Matsunami, *Curr. Opin. Neurobiol.*, 12(4):366-371 (2002)). Within the cell, the taste receptors heterodimerize, with T1R3 coupling separately with T1R1 and T1R2. In mouse, the T1R1/T1R3 heterodimer functions as a receptor for selected amino acids. The T1R2/T1R3 heterodimer functions as a receptor for stimuli considered sweet by humans. Current data indicate that the T1R3 component of the T1R heterodimer couples the taste receptor to cellular signal transduction processes, thereby ensuring that the stimulus-binding event is transduced to a neural signal. Thus, knowledge of the T1R receptors will lead to better understanding of species-specific reactions to sapid stimuli.

Currently, mechanisms for identifying novel taste stimuli for the domestic dog are limited, for example, to exhaustive and difficult feeding studies in which a novel ingredient is paired with a control ingredient and intake of the two are compared. Considerable time, effort, and expense can be expended in the discovery of a single stimulus. Furthermore, canine illnesses often are exacerbated by the animal's refusal to eat. Additionally, the molecular features that define acceptable taste stimuli for domestic dog remain largely unknown, making rational computational design approaches for taste stimuli difficult. As a result, knowledge of the canine taste receptor and its ligands may lead to a better understanding of dog taste perception and modulation thereof.

The present invention provides novel canine taste receptors, T1R1, T1R2, and T1R3, (also interchangeably referred to herein as Ta1r1, Tas1r2, and Tas1r3, respectively) methods of use thereof to identify compounds that can stimulate, inhibit, or modify the ingestive responses or general behavior of a dog. The screening methods of the invention allow the rapid screening of binding partners, agonists, antagonists, and modulators of the T1R receptors of the domestic dog. The results of the canine T1R receptor studies reflect the unique taste profile of the domestic dog.

SUMMARY OF THE INVENTION

Certain embodiments of the present invention relate to polynucleotides encoding a T1R receptor, including, but not limited to polynucleotides having the nucleotide sequence of SEQ ID NO:1, SEQ ID NO:2, SEQ ID NO:4, SEQ ID NO:5, SEQ ID NO:7, and SEQ ID NO:8, fragments of the polynucleotide of SEQ ID NO:1, SEQ ID NO:2, SEQ ID NO:4, SEQ ID NO:5, SEQ ID NO:7, and SEQ ID NO:8 encoding a polypeptide having substantially the same biological activity as a polypeptide encoded by the nucleotide sequence of SEQ ID NO:1, SEQ ID NO:2, SEQ ID NO:4, SEQ ID NO:5, SEQ ID NO:7, and SEQ ID NO:8, respectively; variants of the polynucleotide of SEQ ID NO:1, SEQ ID NO:2, SEQ ID NO:4, SEQ ID NO:5, SEQ ID NO:7, or SEQ ID NO:8 having at least 80% homology to the polynucleotide of SEQ ID NO:1, SEQ ID NO:2, SEQ ID NO:4, SEQ ID NO:5, SEQ ID NO:7, or SEQ ID NO:8; polynucleotide variants of SEQ ID NO:1, SEQ ID NO:2, SEQ ID NO:4, SEQ ID NO:5, SEQ ID NO:7, and SEQ ID NO:8 encoding a polypeptide having substantially the same biological activity as a polypeptide encoded by the nucleotide sequence of SEQ ID NO:1, SEQ ID NO:2, SEQ ID NO:4, SEQ ID NO:5, SEQ ID NO:7, and SEQ ID NO:8, respectively; variants of the polynucleotide of SEQ ID NO:1, SEQ ID NO:2, SEQ ID NO:4, SEQ ID NO:5, SEQ ID NO:7, and SEQ ID NO:8 encoding a polypeptide conferring modified taste perception to one or more taste stimuli relative to a polypeptide encoded by the polynucleotide of SEQ ID NO:1, SEQ ID NO:2, SEQ ID NO:4, SEQ ID NO:5, SEQ ID NO:7, and SEQ ID NO:8, respectively; nucleotide sequences encoding the amino acid sequence of SEQ ID NO:3, SEQ ID NO:6, or SEQ ID NO:9; nucleotide sequences substantially complementary to the nucleotide sequence of SEQ ID NO:1, SEQ ID NO:2, SEQ ID NO:4, SEQ ID NO:5, SEQ ID NO:7, and SEQ ID NO:8; and nucleotide sequences that hybridize to the complement of the polynucleotide having SEQ ID NO:1, SEQ ID NO:2, SEQ ID NO:4, SEQ ID NO:5, SEQ ID NO:7, and SEQ ID NO:8 under high stringency conditions. The polynucleotides of the invention may be DNA or RNA and may be single- or double-stranded. In some embodiments of the invention, the polynucleotide fragments have at least about 45 nucleotides. The polynucleotide fragments of the invention encode, for example, an extracellular domain of the polypeptide of SEQ ID NO:3, SEQ ID NO:6, or SEQ ID NO:9; a transmembrane domain of the polypeptide of SEQ ID NO:3, SEQ ID NO:6, or SEQ ID NO:9; or an intracellular domain of the polypeptide of SEQ ID NO:3, SEQ ID NO:6, or SEQ ID NO:9.

The invention also encompasses expression vectors containing the polynucleotides of the invention operably linked to a promoter. Another embodiment of the invention provides host cells containing the expression vector. The host cells may be prokaryotic, such as bacterial cells, or eukaryotic, such as yeast or mammalian cells, including human, murine, porcine, bovine, canine, or feline cells. The invention further encompasses cell cultures of the host cells. The invention also encompasses methods of producing a canine T1R receptor by culturing the host cells and recovering receptor therefrom.

Another embodiment of the invention includes T1R receptor polypeptides, including polypeptides encoded by the polynucleotides of the invention. The polypeptides of the invention include, for example, those having the amino acid sequence of SEQ ID NO:3, SEQ ID NO:6, or SEQ ID NO:9, fragments of at least 30 contiguous amino acids of SEQ ID NO:3, SEQ ID NO:6, or SEQ ID NO:9, and variants thereof having substantially the same biological activity as the polypeptide of SEQ ID NO:3, SEQ ID NO:6, or SEQ ID NO:9, respectively. The biological activity of the polypeptides of the invention may be determined, for example, by an in vitro binding assay, such as but not limited to assessing the level of binding of the polypeptide to its respective T1R heterodimerization partner. Biological activity of the polypeptides of the invention also may be determined by measuring ion conductance; ion flow; calcium imaging including with fura-2, green dextran activity, or aquorin activity; voltage measurement and/or voltage imaging with dyes or reporter genes such as β-luciferase, alkaline phosphatase, β-galactosidase, or β-lactamase; second messenger measurement, for example, $IP_3$, cAMP, G-protein activation-based assays; or receptor phosphorylation. The variant polypeptides of the invention may have an amino acid sequence having at least one sequence variation of SEQ ID NO:3, SEQ ID NO:6, or SEQ ID NO:9 that confers modified taste perception to one or more taste stimuli relative to a polypeptide of SEQ ID NO:3, SEQ ID NO:6, or SEQ ID NO:9, respectively.

The invention provides methods of identifying a canine T1R receptor variant that confers modified taste perception by expressing a variant of the polynucleotide of SEQ ID NO:1, SEQ ID NO:2, SEQ ID NO:4, SEQ ID NO:5, SEQ ID NO:7, or SEQ ID NO:8 homologous to the polynucleotide of SEQ ID NO:1, SEQ ID NO:2, SEQ ID NO:4, SEQ ID NO:5, SEQ ID NO:7, or SEQ ID NO:8, respectively, and detecting an increase or a decrease in the biological activity of the polypeptide encoded by the variant relative to the biological activity of the polypeptide encoded by SEQ ID NO:1, SEQ ID NO:2, SEQ ID NO:4, SEQ ID NO:5, SEQ ID NO:7, or SEQ ID NO:8, respectively.

The invention further provides kits for the detection of polynucleotides encoding a canine T1R receptor including a polynucleotide that specifically hybridizes to a polynucleotide encoding a polypeptide having an amino acid sequence of SEQ ID NO:3, SEQ ID NO:6, or SEQ ID NO:9, and instructions relating to detection thereof.

Also provided by the invention are antibodies that immunoreact specifically with at least one epitope of a polypeptide of the invention. The invention also includes kits for the detection of polypeptides encoding a canine T1R receptor including antibodies of the invention and instructions relating to detection.

Further provided by the invention are methods for identifying a compound that interacts with a canine T1R receptor by expressing a polynucleotide of the invention in the presence of a test compound, and detecting direct or indirect interaction between a polypeptide produced by the expression step with the compound. Also provided are methods for identifying compounds that interact with a canine T1R receptor by contacting a canine T1R receptor with a test compound, and detecting interaction between the receptor and the compound. The methods for detecting such interaction may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a canine-specific electronic tongue or biosensor.

The invention also provides methods for identifying agonists and antagonists of a canine T1R receptor. For example, the methods of the invention include identification of an agonist of a canine T1R receptor by expressing a polynucleotide of the invention in the presence of a test compound, and detecting increased transcription of said polynucleotide or increased biological activity of a polypeptide produced by the expression step in the presence of the compound relative to the rate of transcription or biological activity of the polypeptide in the absence of the compound. The biological activity detected may be an increase or decrease in the interaction between the T1R receptor and its T1R heterodimerization partner. For example, the T1R heterodimerization partner of a T1R1 or a T1R2 receptor may be T1R3 and vice versa. Also included are methods for identifying agonists of a canine T1R receptor by contacting a polypeptide of the invention with a test compound, and detecting an increase in biological activity of the polypeptide in the presence of the compound relative to biological activity of the polypeptide in the absence of the compound. The methods for identifying agonists of the dog T1R receptors may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a canine-specific electronic tongue or biosensor.

Methods for identifying antagonists of the polypeptides of the invention also are provided. For example, the invention provides methods for identifying antagonists of a canine T1R receptor by expressing a polynucleotide of the invention in the presence of a test compound, and detecting decreased transcription of said polynucleotide or decreased biological activity of a polypeptide produced by the expression step in the presence of the compound relative to the rate of transcription or biological activity of the polypeptide in the absence of the compound. Another example of methods for identifying an antagonist of a canine T1R receptor involves contacting a polypeptide of the invention with a test compound, and detecting a decrease in biological activity of the polypeptide in the presence of the compound relative to biological activity of the polypeptide in the absence of the compound. The methods for identifying the antagonists may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a canine-specific electronic tongue or biosensor.

Also encompassed by the invention are methods for predicting the taste perception of an organism such as a mammal. The methods may involve detection of a nucleotide sequence or amino acid sequence of the invention in a biological sample of the organism. For example, an organism in which a nucleotide sequence of the invention has been identified may perceive saccharin as bitter and/or D-fructose, β-D-fructose, or sucrose as sweet.

Another embodiment of the invention includes compounds and compositions for modifying, for example, stimulating, the taste perception of a mammal, such as a dog. The compounds and compositions may contain at least one of the polynucleotides of the invention, polypeptides of the invention, or compounds identified by the methods of the invention. Examples of the compositions of the invention include veterinary foods and drinks and pharmaceutical compositions. The compositions of the invention may include a pharmaceutically acceptable excipient. The compositions of the invention may be breed-specific. Methods for modifying the taste perception of a mammal (e.g., a dog) by administering to the mammal a polynucleotide of the invention, a polypeptide of the invention, and/or a compound identified according to the methods of the invention also are provided.

The invention further provides transgenic animals comprising a polynucleotide of the invention.

The materials, methods, and examples provided herein are illustrative only and are not intended to be limiting. Other features and advantages of the invention will be apparent from the following detailed description and claims.

BRIEF DESCRIPTION OF THE DRAWINGS

FIGS. 1A-L show the multiple cDNA sequence alignment of the T1R receptors of domestic dog (T1R1, SEQ ID NO:2; T1R2, SEQ ID NO:5; and T1R3, SEQ ID NO:8) with known cDNA nucleotide sequences of receptors of the T1R family from human (T1R1, SEQ ID NO:15; T1R2, SEQ ID NO:12; T1R3, SEQ ID NO:18), cat (T1R1, SEQ ID NO:133; T1R2, SEQ ID NO:135; T1R3, SEQ ID NO:137), mouse (T1R1, SEQ ID NO:13; T1R2, SEQ ID NO:10; T1R3, SEQ ID NO:16), and rat (T1R1, SEQ ID NO:14; T1R2, SEQ ID NO:11; T1R3, SEQ ID NO:17). An asterisk (*) indicates a conserved nucleotide position among the sequences.

FIGS. 2A-D show the deduced amino acid sequences of the canine T1R taste receptors (T1R1, SEQ ID NO:3; T1R2, SEQ ID NO:6; and T1R3, SEQ ID NO:9) aligned with the amino acid sequences of members of the T1R receptor family from human (T1R1, SEQ ID NO:24; T1R2, SEQ ID NO:21; T1R3, SEQ ID NO:27), cat (T1R1, SEQ ID NO:134; T1R2, SEQ ID NO:136; T1R3, SEQ ID NO:138), rat (T1R1, SEQ ID NO:23; T1R2, SEQ ID NO:20; T1R3, SEQ ID NO:26), and mouse (T1R1, SEQ ID NO:22; T1R2, SEQ ID NO:19; T1R3, SEQ ID NO:25). An asterisk (*) indicates a conserved nucleotide position among the sequences. A colon (:) indicates an observed conserved amino acid substitution. A period (.) indicates an observed semi-conserved amino acid substitution.

FIG. 4A shows that the canine T1R1 receptor (SEQ ID NO:3) is a seven-transmembrane domain receptor. The structure of the canine T1R1 receptor was generated through use of the protein modeling programs available online through the European Bioinformatics Institute and the Sequence Analysis and Consulting Service of the University of California, San Francisco. FIG. 4B illustrates the predicted conformation of dog T1R2 receptor (SEQ ID NO:6) as a seven-transmembrane-domain receptor. FIG. 4C illustrates the predicted conformation of canine T1R3 receptor (SEQ ID NO:9) to be a seven-transmembrane domain structure. The dog T1R receptors T1R1, T1R2, and T1R3 are each predicted to have a seven transmembrane domain-structure, which is typical structure for G protein-coupled receptors involved in taste transduction.

DETAILED DESCRIPTION OF ILLUSTRATIVE EMBODIMENTS

Figure 3:
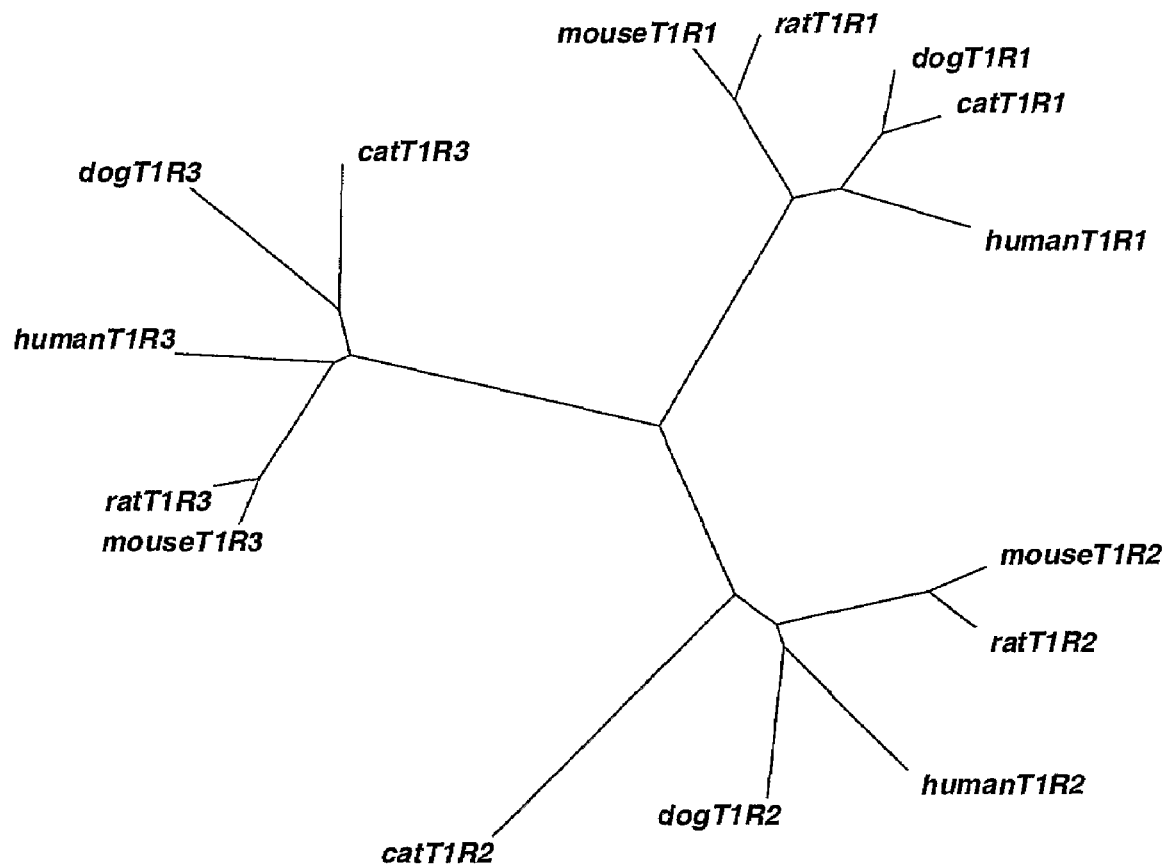
FIG. 3 illustrates a phylogenetic tree showing the relatedness of canine T1R receptor family to the T1R family of receptors including human, cat, rat, and mouse T1R1, T1R2, and T1R3. The T1R receptors of the rat and mouse are closely related, while the T1R receptors of human and dog diverge from rat and mouse. Interestingly, the sweet stimuli to which the rat and mouse respond are very similar, whereas those that stimulate human and those that stimulate dog differ from one another and from those for rat and mouse. For example, humans are unique in their ability to taste most high-intensity sweeteners, while dogs find saccharin bitter.

The reference works, patents, patent applications, and scientific literature that are referred to herein reflect in part the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology are known to those of skill in the art (Ausubel et al., CURRENT PROTOCOLS IN MOLECULAR BIOLOGY, John Wiley & Sons, New York, 1998; Sambrook et al., MOLECULAR CLONING: A LABORATORY MANUAL, 2D ED., Cold Spring Harbor Laboratory Press, Plainview, N.Y., 1989; Kaufman et al., Eds., HANDBOOK OF MOLECULAR AND CELLULAR METHODS IN BIOLOGY AND MEDICINE, CRC Press, Boca Raton, 1995; McPherson, Ed., DIRECTED MUTAGENESIS: A PRACTICAL APPROACH, IRL Press, Oxford, 1991).

As used herein, "T1R receptor" encompasses the taste receptors of the T1R1, T1R2, and T1R3 types.

As used herein, "taste perception" refers to a response (e.g., biochemical, behavioral) or sensitivity of a T1R receptor of the invention to a taste stimulus. "Taste stimulus" as used herein refers to any compound that elicits, for example at the biochemical level (e.g., activation or inhibition of a taste receptor) or behavioral level (e.g., preference, indifference, or distaste), a taste response which would be perceived by a mammal as at least one of the five taste elements, including sweet, salty, sour, bitter, and umami. "Taste perception" or "taste stimulus," or variants thereof, does not require, though it does include, transmission of a neural signal resulting in in vivo sensation of taste by a mammal. Modification of taste perception includes an alteration of (enhancement of, reduction to, or change to) a biochemical response, an ingestive response, a taste preference, or general behavior of a mammal in response to a compound.

As used herein "polynucleotide" refers to a nucleic acid molecule and includes genomic DNA, cDNA, RNA, mRNA, mixed polymers, recombinant nucleic acids, fragments and variants thereof, and the like. Polynucleotide fragments of the invention comprise at least 10, and preferably at least 12, 14, 16, 18, 20, 25, 30, 35, 40, 45, 50, 75, 80, 90 or 100 consecutive nucleotides of a reference polynucleotide. Polynucleotide fragments of the invention may also comprise at least about 110, 120, 130, 140, 150, 160, 170, 180, 190, 200, 210, 220, 230, 240, 250, 275, 300, 325, 250, 275, 400, 425, 450, 475, 500, 525, 550, 575, 600, 625, 650, 675, 700, 725, 750, 775, 800, 825, 850, 875, 900, 925, 950, 975, or 1000 consecutive nucleotides of a reference polynucleotide. The polynucleotides of the invention include sense and antisense strands. The polynucleotides of the invention may be naturally occurring or non-naturally occurring polynucleotides. A "synthesized polynucleotide" as used herein refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. The polynucleotides of the invention may be single- or double-stranded. The polynucleotides of the invention may be chemically modified and may contain non-natural or derivatized nucleotide bases as will be readily appreciated by those skilled in the art. Such modifications include, for example, labels, methylation, substitution of one or more nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides, etc.), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Recombinant nucleic acid" is a nucleic acid generated by combination of two segments of nucleotide sequence. The combination may be, for example, by chemical means or by genetic engineering.

As used herein, "polynucleotide amplification" refers to a broad range of techniques for increasing the number of copies of specific polynucleotide sequences. Typically, amplification of either or both strand(s) of the target nucleic acid comprises the use of one or more nucleic acid-modifying enzymes, such as a DNA polymerase, ligase, RNA polymerase, or RNA-dependent reverse transcriptase. Examples of polynucleotide amplification include, but are not limited to, polymerase chain reaction (PCR), nucleic acid sequence based amplification (NASB), self-sustained sequence replication (3SR), strand displacement activation (SDA), ligase chain reaction, Qβ replicase system, and the like. A wide variety of alternative cloning and in vitro amplification methodologies are well known to those skilled in the art. Examples of these techniques are found in, for example, Berger et al., *Guide to Molecular Cloning Techniques*, METHODS IN ENZYMOLOGY 152, Academic Press, Inc., San Diego, Calif. (Berger), which is incorporated herein by reference in its entirety.

As used herein, the term "oligonucleotide" or "primer" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar, or complementary DNA or RNA in a particular cell or tissue. Oligonucleotides comprise portions of a nucleic acid sequence having at least about 10 nucleotides and as many as about 50 nucleotides, often about 12 or 15 to about 40 or 45 nucleotides. They are chemically synthesized and may be used as probes. "Primer pair" refers to a set of primers including a 5' upstream primer that hybridizes with the 5' end of a target sequence to be amplified and a 3' downstream primer that hybridizes with the complement of the 3' end of the target sequence to be amplified.

As used herein, the term "probe" refers to nucleic acid sequences of variable length, for example between at least about 10 and as many as about 8,500 nucleotides, depending on use. Probes are used in the detection of identical, similar, or complementary target nucleic acid sequences, which target sequences may be single- or double-stranded. Longer probes are usually obtained from a natural or recombinant source, are highly specific, and are much slower to hybridize than oligomers, or shorter probes. They may be single- or double-stranded and are carefully designed to have specificity in PCR, hybridization membrane-based, or ELISA-like technologies. An "overgo probe" is a DNA probe comprising two short, overlapping DNA sequences (e.g., 10-50 nucleotides each) with a complementary overlapping region (e.g., 5-15 nucleotides) that is used in an overgo hybridization strategy. For example, an overgo probe may be two 22mers with an 8 bp complementary overlap, resulting in a 36mer overgo probe. As another example, an overgo probe may be two 24mers with an 8 bp complementary overlap, resulting in a 40mer overgo probe.

As used herein, the phrase "stringent hybridization conditions" or "stringent conditions" refers to conditions under which a probe, primer, or oligonucleotide will hybridize to its target sequence, but to a minimal number of or no other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Stringent temperature conditions will generally include temperatures in excess of 30° C., typically in excess of 37° C., and may be in excess of 45° C. Stringent salt conditions will ordinarily be less than 1.0 M, typically less than 0.5 M, and may be less than 0.2 M. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers, or oligonucleotides (e.g., 10 to 50 nucleotides) and at least about 60° C. for longer probes, primers, or oligonucleotides. Stringent conditions may also be achieved with the addition of destabilizing agents, such as formamide.

As used herein "antisense oligonucleotide" refers to a nucleic acid molecule that is complementary to at least a portion of a target nucleotide sequence of interest and specifically hybridizes to the target nucleotide sequence under physiological conditions. The term "double stranded RNA" or "dsRNA" as used herein refers to a double-stranded RNA molecule capable of RNA interference, including short interfering RNA (siRNA) (see for example, Bass, Nature, 411, 428-429 (2001); Elbashir et al., Nature, 411, 494-498 (2001)).

As used herein, the term "complementary" refers to Watson-Crick basepairing between nucleotide units of a nucleic acid molecule.

The term "marker gene" or "reporter gene" refers to a gene encoding a product that, when expressed, confers a phenotype at the physical, morphologic, or biochemical level on a transformed cell that is easily identifiable, either directly or indirectly, by standard techniques and includes, but is not limited to, genes encoding proteins that confer resistance to toxins or antibiotics such as ampicillin, neomycin, and methotroxate; genes encoding proteins that complement auxotrophic deficiencies; and genes encoding proteins that supply critical components not available from complex media. Examples of marker genes include green fluorescent protein (GFP), red fluorescent protein (DsRed), cyan fluorescent protein (CFP), yellow fluorescent protein (YFP), cerianthus orange fluorescent protein (cOFP), alkaline phosphatase (AP), β-lactamase, chloramphenicol acetyltransferase (CAT), adenosine deaminase (ADA), aminoglycoside phosphotransferase (neor, G418r) dihydrofolate reductase (DHFR), hygromycin-B-phosphotransferase (HPH), thymidine kinase (TK), lacZ (encoding β-galactosidase), β-lactamase, luciferase (luc), and xanthine guanine phosphoribosyltransferase (XGPRT). As with many of the standard procedures associated with the practice of the invention, skilled artisans will be aware of additional sequences that can serve the function of a marker or reporter. Thus, this list is merely meant to show examples of what can be used and is not meant to limit the invention.

As used herein, the term "promoter" refers to a regulatory element that regulates, controls, or drives expression of a nucleic acid molecule of interest and can be derived from sources such as from adenovirus, SV40, parvoviruses, vaccinia virus, cytomegalovirus, or mammalian genomic DNA. Examples of suitable promoters include, but are not limited to, CMV, MSH2, trp, lac, phage, and TRNA promoters. Suitable promoters that can be used in yeast include, but are not limited to, such constitutive promoters as 3-phosphoglycerate kinase and various other glycolytic enzyme gene promoters such as enolase or glyceraldehyde-3-phosphate dehydrogenase, or such inducible promoters as the alcohol dehydrogenase 2 promoter or metallothionine promoter. Again, as with many of the standard procedures associated with the practice of the invention, skilled artisans will be aware of additional promoters that can serve the function of directing the expression of a marker or reporter. Thus, the list is merely meant to show examples of what can be used and is not meant to limit the invention.

"Operably linked" refers to juxtaposition wherein the components are in a functional relationship. For example, a promoter is operably linked or connected to a coding sequence if it controls the transcription or expression of the sequence.

The terms "polypeptide," "peptide," and "protein" are used interchangeably herein. "Polypeptide" refers to a polymer of amino acids without referring to a specific length. Polypeptides of the invention include peptide fragments, derivatives, and fusion proteins. Peptide fragments preferably have at least about 10, 15, 20, 25, 30, 35, 40, 45, 50, 60, 70, 80, 90, or 100 amino acids. Some peptide fragments of the invention are biologically active. Biological activities include immunogenicity, ligand binding, and activity associated with the reference peptide. Immunogenic peptides and fragments of the invention generate an epitope-specific immune response, wherein "epitope" refers to an immunogenic determinant of a peptide and preferably contains at least three, five, eight, nine, ten, fifteen, twenty, thirty, forty, forty-five, or fifty amino acids. Some immunogenic peptides of the invention generate an immune response specific to that peptide. Polypeptides of the invention include naturally occurring and non-naturally occurring peptides. The term includes modified polypeptides (wherein examples of such modifications include glycosylation, acetylation, phosphorylation, carboxylation, ubiquitination, labeling, etc.), analogs (such as non-naturally occurring amino acids, substituted linkages, etc.), and functional mimetics. A variety of methods for labeling polypeptides are well known in the art and include radioactive isotopes such as $^{32}P$ or $^{35}S$, ligands that bind to labeled antiligands (e.g., antibodies), fluorophores, chemiluminescent agents, enzymes, and antiligands.

As used herein, the term "amino acid" denotes a molecule containing both an amino group and a carboxyl group. In some embodiments, the amino acids are $\alpha$-, $\beta$-, $\gamma$- or $\delta$-amino acids, including their stereoisomers and racemates. As used herein the term "L-amino acid" denotes an $\alpha$-amino acid having the L configuration around the $\alpha$-carbon, that is, a carboxylic acid of general formula CH(COOH)(NH2)-(side chain), having the L-configuration. The term "D-amino acid" similarly denotes a carboxylic acid of general formula CH(COOH)(NH2)-(side chain), having the D-configuration around the $\alpha$-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. Amino acid substituents may be attached, for example, through their carbonyl groups through the oxygen or carbonyl carbon thereof, or through their amino groups, or through functionalities residing on their side chain portions.

The amino acid sequences are presented in the amino (N) to carboxy (C) direction, from left to right. The N-terminal $\alpha$-amino group and the C-terminal $\beta$-carboxy groups are not depicted in the sequence. The nucleotide sequences are presented by single strands only, in the 5' to 3' direction, from left to right. Nucleotides and amino acids are represented in the manner recommended by the IUPAC-IUB Biochemical Nomenclature Commission, or amino acids are represented by their three letters code designations.

As used herein, the term "antibody" is meant to refer to complete, intact antibodies, and Fab, Fab', F(ab)$_2$, F$_v$, and other fragments thereof. Complete, intact antibodies include antibodies such as polyclonal antibodies, monoclonal antibodies, chimeric antibodies, and humanized antibodies, felinized antibodies, and immunologic binding equivalents thereof. The antibodies of the invention may be labeled or unlabeled. Examples of labels of antibodies include, but are not limited to, radionuclides, enzymes, substrates, cofactors, inhibitors, fluorescent agents, chemiluminescent agents, magnetic particles, and the like. Recombinant immunoglobulins are included in the invention.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates. Binding may be detected in many different manners. As a non-limiting example, the physical binding interaction between two molecules can be detected using a labeled compound. Other methods of detecting binding are well-known to those of skill in the art.

As used herein, the term "contacting" means bringing together, either directly or indirectly, a compound into physical proximity to a molecule of interest. Contacting may occur, for example, in any number of buffers, salts, solutions, or in a cell or cell extract.

As used herein, the terms "modulates" or "modifies" means an increase or decrease in the amount, quality, or effect of a particular activity or protein. "Modulators" refer to any inhibitory or activating molecules identified using in vitro and in vivo assays for, e.g., agonists, antagonists, and their homologs, including fragments, variants, and mimetics, as defined herein, that exert substantially the same biological activity as the molecule. "Inhibitors" or "antagonists" are modulating compounds that reduce, decrease, block, prevent, delay activation, inactivate, desensitize, or downregulate the biological activity or expression of a molecule or pathway of interest. "Inducers," "activators," or "agonists" are modulating compounds that increase, induce, stimulate, open, activate, facilitate, enhance activation, sensitize, or upregulate a molecule or pathway of interest. In some preferred embodiments of the invention, the level of inhibition or upregulation of the expression or biological activity of a molecule or pathway of interest refers to a decrease (inhibition or downregulation) or increase (upregulation) of greater than about 50%, 60%, 70%, 75%, 80%, 85%, 90%, 91%, 92%, 93%, 94%, 95%, 96%, 97%, 98%, or 99%. The inhibition or upregulation may be direct, i.e., operate on the molecule or pathway of interest itself, or indirect, i.e., operate on a molecule or pathway that affects the molecule or pathway of interest.

A "purified" or "substantially purified" polynucleotide or polypeptide is substantially separated from other cellular components that naturally accompany a native (or wild-type) nucleic acid or polypeptide and/or from other impurities (e.g., agarose gel). A purified polypeptide or protein will comprise about 60% to more than 99% w/w of a sample, and may be about 90%, about 95%, about 98%, about 99% or preferably about 100% pure. As used herein, the term "isolated" refers to a molecule that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

"About" as used herein refers to +/−10% of the reference value.

As used herein, "variant" nucleotide or amino acid sequences refer to homologs, including, for example, isoforms, species variants, allelic variants, and fragments of the sequence of interest. "Homologous nucleotide sequence" or "homologous amino acid sequence," or variations thereof, refers to sequences characterized by a homology, at the nucleotide level or amino acid level, of at least about 60%, at least about 70%, at least about 75%, at least about 80%, at least about 81%, at least about 82%, at least about 83%, at least about 84%, at least about 85%, preferably at least about 90%, at least about 95%, at least about 98%, or at least about 99%, and more preferably 100%, to a reference sequence, or portion or fragment thereof encoding or having a functional domain. The reference sequence may include, for example, but is not limited to the nucleic acid sequence of SEQ ID NO:1, SEQ ID NO:2, SEQ ID NO:4, SEQ ID NO:5, SEQ ID NO:7, and SEQ ID NO:8, or portions thereof which encode a functional domain of the encoded polypeptide, SEQ ID NO:3, SEQ ID NO:6, or SEQ ID NO:9, or the polypeptide having amino acid sequence SEQ ID NO:3, SEQ ID NO:6, or SEQ ID NO:9. Functional domains of the T1R receptors of the invention include extracellular domains, transmembrane domains, and intracellular domains. Examples of functional domains of the T1R1 polypeptide of SEQ ID NO:3 include extracellular domains corresponding to residues 1-565, 624-637, 704-725, and 784-786; transmembrane domains corresponding to residues 566-588, 601-623, 638-660, 681-703, 726-748, 761-783, and 787-809; and intracellular domains corresponding to residues 589-600, 661-680, 749-760, and 810-841. Examples of functional domains of the T1R2 receptor of SEQ ID NO:6 include extracellular domains corresponding to residues 1-565, 622-634, 699-723, and 778-782; transmembrane domains corresponding to residues 566-587, 602-621, 635-658, 678-698, 724-744, 758-777, and 783-802; and intracellular domains corresponding to residues 588-601, 659-677, 745-757, and 803-836. Examples of functional domains of the T1R3 polypeptide of SEQ ID NO:9 include the extracellular domains corresponding to residues 1-566, 623-636, 702-725, or 780-793; transmembrane domains corresponding to residues 567-589, 600-622, 637-659, 679-701, 726-748, 761-779, or 794-816; and intracellular domains corresponding to residues 590-599, 660-678, 749-760, or 817-845. Isoforms can be expressed in different tissues of the same organism as a result of, for example, alternative splicing of RNA. Alternatively, isoforms can be encoded by different genes. Homologous nucleotide sequences include nucleotide sequences encoding for a species variant of a protein. Homologous nucleotide sequences also include, but are not limited to, naturally occurring allelic variations and mutations of the nucleotide sequences set forth herein. Study of mutations and polymorphisms of the T1R receptor polynucleotide sequences may explain breed-specific and/or individual taste preferences of a mammal such as a dog. Additionally, sequence variants of the T1R receptors may be associated with specific disease states, such that knowledge of the genes allows diagnosis and treatment of T1R-associated disorders (e.g., obesity, diabetes). Homologous amino acid sequences include those amino acid sequences which encode conservative amino acid substitutions in polypeptides having an amino acid sequence of SEQ ID NO:3, SEQ ID NO:6, or SEQ ID NO:9, as well as in polypeptides identified according to the methods of the invention. Percent homology may be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Smith and Waterman, *Adv. Appl. Math.*, 2: 482-489, 1981). Nucleic acid fragments of the invention preferably have at least about 5, at least about 10, at least about 15, at least about 20, at least about 25, at least about 50, or at least about 100 nucleotides of the reference nucleotide sequence. The nucleic acid fragments of the invention may encode a polypeptide having at least one biological property, or function, that is substantially similar to a biological property of the polypeptide encoded by the full-length nucleic acid sequence.

As is well known in the art, because of the degeneracy of the genetic code, there are numerous DNA and RNA molecules that can code for the same polypeptide as that encoded by a nucleotide sequence of interest. The present invention, therefore, contemplates those other DNA and RNA molecules which, on expression, encode a polypeptide encoded by the nucleic acid molecule of interest. DNA and RNA molecules other than those specifically disclosed herein characterized simply by a change in a codon for a particular amino acid, are within the scope of this invention.

Amino acid "insertions", "substitutions" or "deletions" are changes to or within an amino acid sequence. The variation allowed in a particular amino acid sequence may be experimentally determined by producing the peptide synthetically or by systematically making insertions, deletions, or substitutions of nucleotides in the nucleic acid sequence using recombinant DNA techniques. Alterations of the naturally occurring amino acid sequence can be accomplished by any of a number of known techniques. For example, mutations can be introduced into the polynucleotide encoding a polypeptide at particular locations by procedures well known to the skilled artisan, such as oligonucleotide-directed mutagenesis.

A polypeptide variant of the present invention may exhibit substantially the biological activity of a naturally occurring reference polypeptide. "Biological activity" as used herein refers to the level of a particular function (for example, enzymatic activity) of a molecule or pathway of interest in a biological system. "Wild-type biological activity" refers to the normal level of function of a molecule or pathway of interest. "Reduced biological activity" refers to a decreased level of function of a molecule or pathway of interest relative to a reference level of biological activity of that molecule or pathway. For example, reduced biological activity may refer to a decreased level of biological activity relative to the wild-type biological activity of a molecule or pathway of interest. "Increased biological activity" refers to an increased level of function of a molecule or pathway of interest relative to a reference level of biological activity of that molecule or pathway. For example, increased biological activity may refer to an increased level of biological activity relative to the wild-type biological activity of a molecule or pathway of interest.

With respect to the polypeptides of the present invention, "biological activity" is deemed to encompass, among other things, heterodimerization of the polypeptide to its cognate heterodimerization partner, the ability to elicit an adaptive immune response, and the ability to activate or inhibit a specific biochemical or signal transduction pathway. Heterodimerization may be measured by any means known in the art, such as size exclusion chromatography, or an electrophoretic mobility shift assay. Immunogenicity may be measured by means that are well known and practiced in the art. The activation or inhibition of a biochemical or signal transduction pathway may also be determined by any means known in the art. For example, any number of assays that measure the interaction of a G protein-coupled receptor with the G protein, or assays that measure taste transduction may be utilized. See e.g., Ruiz-Avila, L. et al. *Chem. Senses* 25:361-368 (2000); Ming, D. et al. *Proc. Natl. Acad. Sci. USA* 95:8933-8938 (1998); Margolskee, R F *J. Biol. Chem.* 277: 1-4 (2002), Bidlack J M *Methods Mol Biol.* 237:135-43 (2004); Gale, C, et al. *Nat Methods* 2:177-184 (2005), Nelson G, et al. *Cell* 106: 381-390 (2001), Nelson G, et al. *Nature* 416: 199-202 (2002), Li X, et al. *Proc Natl Acad Sci USA* 99:4692-4696 (2002), Xu, H et al. Proc Natl Acad Sci USA 101: 14258-14263 (2004), and Yan W, et al. *Am J Physiol Cell Physiol* 280: C742-751 (2001), each of which is hereby incorporated by reference in its entirety. Biological activity of the polypeptides of the invention also may be determined by measuring ion conductance; ion flow; calcium imaging including with fura-2, green dextran activity, or aquorin activity; voltage measurement and/or voltage imaging with dyes or reporter genes such as β-luciferase, alkaline phosphatase, β-galactosidase, or β-lactamase; second messenger measurement, for example, IP₃, cAMP, G-protein activation-based assays; or receptor phosphorylation.

"Substantially the same" biological activity refers to a polypeptide fragment, derivative, homolog, analog, or variant retaining at least about 50%, 55%, 60%, 65%, 70%, preferably at least about 75%, 80%, 85%, 90%, more preferably at least about 91%, 92%, 93%, 94%, 95%, and most preferably at least about 96%, 97%, 98%, 99% or greater biological activity of the parent polypeptide. The extent to which a polypeptide fragment, derivative, homolog, analog, or variant retains the biological activity of the parent polypeptide may be assessed by any means available in the art, including, but not limited to, the assays listed or described herein.

Reference to exhibiting "substantially the biological activity of a naturally occurring polypeptide" indicates that variants within the scope of the invention can comprise conservatively substituted sequences, meaning that one or more amino acid residues of a polypeptide are replaced by different residues that do not alter the secondary and/or tertiary structure of the polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges are known in the art (Bowie et al., *Science*, 247: 1306-1310, 1990). Other polypeptide homologs which might retain substantially the biological activities of the reference polypeptide are those where amino acid substitutions have been made in areas outside functional regions of the protein.

A nucleotide and/or amino acid sequence of a nucleic acid molecule or polypeptide employed in the invention or of a compound identified by the screening method of the invention may be used to search a nucleotide and amino acid sequence databank for regions of similarity using Gapped BLAST (Altschul et al., *Nuc. Acids Res.*, 25: 3389, 1997). Briefly, the BLAST algorithm, which stands for Basic Local Alignment Search Tool is suitable for determining sequence similarity (Altschul et al., *J Mol. Biol.*, 215: 403-410, 1990). Software or performing BLAST analyses is publicly available online through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., *J Mol. Biol.*, 215: 403-410, 1990). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The BLAST algorithm parameters W, T, and X determine the sensitivity and speed of the alignment. The BLAST program uses as defaults a word length (W) of 11, the BLOSUM62 scoring matrix (Henikoff et al., *Proc. Natl. Acad. Sci. USA*, 89: 10915-10919, 1992) alignments (B) of 50, expectation (E) of 10, M=5, N=4, and a comparison of both strands. The BLAST algorithm (Karlin et al., *Proc. Natl. Acad. Sci. USA*, 90: 5873-5787, 1993) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a gene or cDNA if the smallest sum probability in comparison of the test nucleic acid to the reference nucleic acid is less than about 1, preferably less than about 0.1, more preferably less than about 0.01, and most preferably less than about 0.001.

The term "mimetic" as used herein refers to a compound that is sterically similar to a reference compound. Mimetics are structural and functional equivalents to the reference compounds.

The terms "patient" and "subject" are used interchangeably herein and include, but are not limited to, avians, felines, canines, bovines, ovines, porcines, equines, rodents, simians, and humans. "Host cell" includes, for example, a prokaryotic cell, such as a bacterial cell, or eukaryotic cell, such as a mammalian cell (e.g., human, rodent, canine, feline), a yeast cell, or a plant cell. "Rodents" include, for example, rats and mice.

The term "treatment" as used herein refers to any indicia of success of prevention, treatment, or amelioration of a disease or condition. Treatment includes any objective or subjective parameter, such as, but not limited to, abatement, remission, normalization of receptor activity, reduction in the number or severity of symptoms or side effects, or slowing of the rate of degeneration or decline of the patient. Treatment also includes a prevention of the onset of symptoms in a patient that may be at increased risk for or is suspected of having a disease or condition but does not yet experience or exhibit symptoms thereof.

As used herein, the term "compound" means any identifiable chemical or molecule, including, but not limited to a small molecule, peptide, protein, sugar, nucleotide, or nucleic acid. Such compound can be natural or synthetic.

Polynucleotides

The invention provides purified and isolated polynucleotides (e.g., cDNA, genomic DNA, synthetic DNA, RNA, or combinations thereof, whether single- or double-stranded) that comprise a nucleotide sequence encoding the amino acid sequence of the polypeptides of the invention. Such polynucleotides are useful for recombinantly expressing the receptor and also for detecting expression of the receptor in cells (e.g., using Northern hybridization and in situ hybridization assays). Such polynucleotides also are useful in the design of antisense and other molecules for the suppression of the expression of a T1R receptor in a cultured cell, a tissue, or an animal; for therapeutic purposes; or to provide a model for diseases or conditions characterized by aberrant T1R expression. Specifically excluded from the definition of polynucleotides of the invention are entire isolated, non-recombinant native chromosomes of host cells. Polynucleotides of the invention include the nucleotide sequences of SEQ ID NO:1, SEQ ID NO:2, SEQ ID NO:4, SEQ ID NO:5, SEQ ID NO:7, and SEQ ID NO:8. It will be appreciated that numerous other polynucleotide sequences exist that also encode the T1R receptors of the invention due to the well-known degeneracy of the universal genetic code.

The invention also provides a purified and isolated polynucleotide comprising a nucleotide sequence that encodes a canine polypeptide, wherein the polynucleotide hybridizes to a polynucleotide having a sequence of SEQ ID NO:1, SEQ ID NO:2, SEQ ID NO:4, SEQ ID NO:5, SEQ ID NO:7, or SEQ ID NO:8, or the non-coding strand complementary thereto, under stringent hybridization conditions.

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode a T1R polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants that arise from in vitro manipulation).

The invention also comprehends cDNA that is obtained through reverse transcription of an RNA polynucleotide encoding a T1R receptor (conventionally followed by second strand synthesis of a complementary strand to provide a double-stranded DNA).

One embodiment of the DNA of the invention comprises a double-stranded molecule along with the complementary molecule (the "non-coding strand" or "complement") having a sequence unambiguously deducible from the coding strand according to Watson-Crick base-pairing rules for DNA.

The present invention includes fragments of nucleotide sequences encoding a T1R receptor comprising at least 10, and preferably at least 12, 14, 16, 18, 20, 25, 30, 35, 40, 45, 50, 75, 80, 90, 100, 110, 120, 130, 140, 150, 160, 170, 180, 190, 200, 210, 220, 230, 240, 250, 275, 300, 325, 250, 275, 400, 425, 450, 475, 500, 525, 550, 575, 600, 625, 650, 675, 700, 725, 750, 775, 800, 825, 850, 875, 900, 925, 950, 975, or 1000 consecutive nucleotides of a polynucleotide encoding a T1R receptor. Fragment polynucleotides of the invention may comprise sequences unique to the T1R-encoding polynucleotide sequence, and therefore hybridize under highly stringent or moderately stringent conditions only (i.e., "specifically") to polynucleotides encoding a T1R receptor (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

Fragment polynucleotides are particularly useful as probes for detection of full-length or fragments of T1R polynucleotides. One or more polynucleotides can be included in kits that are used to detect the presence of a polynucleotide encoding a T1R receptor, or used to detect variations in a polynucleotide sequence encoding a T1R receptor.

The invention also embraces DNAs encoding T1R polypeptides that hybridize under high stringency conditions to the non-coding strand, or complement, of the polynucleotides.

Exemplary highly stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described, for example, in Ausubel et al. (Eds.), PROTOCOLS IN MOLECULAR BIOLOGY, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described, for example, in Sambrook et al., (Eds.), MOLECULAR CLONING: A LABORATORY MANUAL, Cold Spring Harbor Laboratory Press: Cold Spring Harbor, N.Y. (1989), pp. 9.47 to 9.51.

With the knowledge of the nucleotide sequence information disclosed in the present invention, one skilled in the art can identify and obtain nucleotide sequences which encode T1R receptors from different sources (i.e., different tissues or different organisms) through a variety of means well known to the skilled artisan and as disclosed by, for example, Sambrook et al., MOLECULAR CLONING: A LABORATORY MANUAL, Second Edition, Cold Spring Harbor Press, Cold Spring Harbor, N.Y. (1989).

For example, DNA that encodes a T1R receptor may be obtained by screening mRNA, cDNA, or genomic DNA with oligonucleotide probes generated from the T1R gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising a T1R nucleotide sequence can alternatively be synthesized by use of the polymerase chain reaction (PCR) procedure, with the PCR oligonucleotide primers produced from the nucleotide sequences provided herein. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, METHODS IN ENZYMOLOGY 152, Academic Press, Inc., San Diego, Calif. (Berger), which is incorporated herein by reference in its entirety.

The polynucleotides of the invention may be used in hybridization techniques known to those skilled in the art, including but not limited to, Northern and Southern blotting and overgo hybridization (see infra). For example, polynucleotide probes of the invention may be used in tissue distribution studies and diagnostic assays.

Automated sequencing methods can be used to obtain or verify the T1R receptor-encoding nucleotide sequence. The nucleotide sequences of the present invention are believed to be accurate. However, as is known in the art, nucleotide sequences obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

The nucleic acid molecules of the present invention, and fragments derived therefrom, are useful for screening for restriction fragment length polymorphism (RFLP) associated with certain disorders, for genetic mapping, and for methods for predicting the taste perception of an organism such as a mammal involving detection of a nucleotide sequence of the invention in a biological sample of the organism. For example, an organism in which a nucleotide sequence of the invention has been identified may perceive saccharin as bitter and/or D-fructose, β-D-fructose, or sucrose as sweet.

The polynucleotide sequence information provided by the invention makes possible large-scale expression of the encoded polypeptide by techniques well known and routinely practiced in the art.

Vectors

Another aspect of the present invention is directed to vectors, or recombinant expression vectors, comprising any of the nucleic acid molecules described above. Vectors are used herein either to amplify DNA or RNA encoding a T1R receptor and/or to express DNA which encodes a T1R receptor. Examples of vectors include, but are not limited to, plasmids, phages, cosmids, episomes, viral particles or viruses, and integratable DNA fragments (i.e., fragments integratable into the host genome by homologous recombination). Examples of viral particles include, but are not limited to, adenoviruses, baculoviruses, parvoviruses, herpesviruses, poxviruses, adeno-associated viruses, Semliki Forest viruses, vaccinia viruses, and retroviruses. Examples of expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE™ vectors (Qiagen), pSE420™ (Invitrogen), and pYES2™(Invitrogen).

Expression constructs may comprise T1R-encoding polynucleotides operably linked to an endogenous or exogenous expression control DNA sequence and a transcription terminator. Expression control DNA sequences include promoters, enhancers, operators, and regulatory element binding sites generally, and are typically selected based on the expression systems in which the expression construct is to be utilized. Promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, or promote, homologous recombination in a host cell. Constructs of the invention also may include sequences necessary for replication in a host cell.

Expression constructs may be utilized for production of an encoded protein, but may also be utilized simply to amplify a T1R-encoding polynucleotide sequence. In some embodiments, the vector is an expression vector wherein a polynucleotide of the invention is operably linked to a polynucleotide comprising an expression control sequence. Autonomously replicating recombinant expression constructs such as plasmid and viral DNA vectors incorporating polynucleotides of the invention are also provided. Some expression vectors are replicable DNA constructs in which a DNA sequence encoding a T1R receptor is operably linked or connected to suitable control sequence(s) capable of effecting the expression of the receptor in a suitable host. Amplification vectors do not require expression control domains, but rather need only the ability to replicate in a host, such as conferred by an origin of replication, and a selection gene to facilitate recognition of transformants. The need for control sequences in the expression vector will vary depending upon the host selected and the transformation method chosen. Control sequences include a transcriptional promoter, an optional operator sequence to control transcription, a sequence encoding suitable mRNA ribosomal binding, and sequences which control the termination of transcription and translation.

Vectors of the invention may contain a promoter that is recognized by the host organism. The promoter sequences of the present invention may be prokaryotic, eukaryotic, or viral. Examples of suitable prokaryotic sequences include the $P_R$ and $P_L$ promoters of bacteriophage lambda (THE BACTERIOPHAGE LAMBDA, Hershey, A. D., Ed., Cold Spring Harbor Press, Cold Spring Harbor, N.Y. (1973), which is incorporated herein by reference in its entirety; LAMBDA II, Hendrix, R. W., Ed., Cold Spring Harbor Press, Cold Spring Harbor, N.Y. (1980), which is incorporated herein by reference in its entirety), the trp, recA, heat shock, and lacZ promoters of E. coli, and the SV40 early promoter (Benoist et al. Nature, 1981, 290, 304-310), which is incorporated herein by reference in its entirety. Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metallothionein.

Additional regulatory sequences can also be included in vectors of the invention. Examples of suitable regulatory sequences are represented by the Shine-Dalgarno of the replicase gene of the phage MS-2 and of the gene cII of bacteriophage lambda. The Shine-Dalgarno sequence may be directly followed by DNA encoding a T1R receptor, resulting in the expression of the mature protein.

Moreover, suitable expression vectors can include an appropriate marker that allows the screening of transformed host cells. The transformation of the selected host is carried out using any one of the various techniques well known to the expert in the art and described in Sambrook et al., supra.

An origin of replication or autonomously replicating sequence (ARS) can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and T1R DNA. An example of a suitable marker is dihydrofolate reductase (DHFR) or thymidine kinase (see, U.S. Pat. No. 4,399,216).

Additional regulatory sequences that may be included in the polynucleotides of the invention include secretion signals which allow the encoded polypeptide to cross and/or lodge in cell membranes, or be secreted from the cell.

Nucleotide sequences encoding a T1R receptor may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al, *Mol. Cell. Biol.*, 1983, 3, 280, Cosman et al., *Mol. Immunol.*, 1986, 23, 935, Cosman et al., *Nature*, 1984, 312, 768, EP-A-0367566, and WO 91/18982, each of which is incorporated herein by reference in its entirety.

Host Cells

According to another aspect of the invention, host cells are provided, including prokaryotic and eukaryotic cells, comprising a polynucleotide of the invention (or vector of the invention) in a manner that permits expression of the encoded T1R polypeptide. Polynucleotides of the invention may be introduced into the host cell as part of a circular plasmid, or as linear DNA comprising an isolated protein-coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cell systems.

The invention provides host cells that are transformed or transfected (stably or transiently) with polynucleotides of the invention or vectors of the invention. As stated above, such host cells are useful for amplifying the polynucleotides and also for expressing a T1R polypeptide or fragment thereof encoded by the polynucleotide.

In still another related embodiment, the invention provides a method for producing a T1R polypeptide (or fragment thereof) comprising the steps of growing a host cell of the invention in a nutrient medium and isolating the polypeptide or variant thereof from the cell or the medium. Because the T1R receptor is a membrane-spanning polypeptide, it will be appreciated that, for some applications, such as certain activity assays, the preferable isolation may involve isolation of cell membranes containing the polypeptide embedded therein, whereas for other applications a more complete isolation may be preferable.

According to some aspects of the present invention, transformed host cells having an expression vector comprising any of the nucleic acid molecules described above are provided. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces*, and *Staphylococcus*.

If a eukaryotic expression vector is employed, then the appropriate host cell would be any eukaryotic cell capable of expressing the cloned sequence. Eukaryotic cells may be cells of higher eukaryotes. Suitable eukaryotic cells include, but are not limited to, non-human mammalian tissue culture cells and human tissue culture cells. Host cells include, but are not limited to, insect cells, HeLa cells, Chinese hamster ovary cells (CHO cells), African green monkey kidney cells (COS cells), human HEK-293 cells, and murine 3T3 fibroblasts. Propagation of such cells in cell culture has become a routine procedure (see, TISSUE CULTURE, Academic Press, Kruse and Patterson, eds. (1973), which is incorporated herein by reference in its entirety).

In addition, a yeast host may be employed as a host cell. Yeast cells include, but are not limited to, the genera *Saccharomyces, Pichia*, and *Kluveromyces*. Yeast hosts may be *S. cerevisiae* and *P. pastoris*. Yeast vectors may contain an origin of replication sequence from a 2T yeast plasmid, an autonomous replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In some embodiments, the polypeptides of the invention are expressed using a baculovirus expression system (see, Luckow et al., *Bio/Technology*, 1988, 6, 47; BACULOVIRUS EXPRESSION VECTORS: A LABORATORY MANUAL, O'Reilly et al. (Eds.), W.H. Freeman and Company, New York, 1992; and U.S. Pat. No. 4,879,236, each of which is incorporated herein by reference in its entirety). In addition, the MAXBAC™ complete baculovirus expression system (Invitrogen) can, for example, be used for production in insect cells.

Host cells of the invention are a valuable source of immunogen for development of antibodies specifically immunoreactive with the T1R receptor. Host cells of the invention also are useful in methods for the large-scale production of T1R polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of the canine T1R receptor-encoding nucleotide sequence allows for modification of cells to permit, or increase, expression of endogenous receptor. Cells can be modified (e.g., by homologous recombination) to provide increased expression by replacing, in whole or in part, the naturally occurring T1R promoter with all or part of a heterologous promoter so that the cells express the receptor at higher or lower levels. The heterologous promoter is inserted in such a manner that it is operably linked to endogenous T1R coding sequence. (See, for example, PCT International Publication No. WO 94/12650, PCT International Publication No. WO 92/20808, and PCT International Publication No. WO 91/09955.) It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA. If linked to the T1R coding sequence, amplification of the marker DNA by standard selection methods results in co-amplification of the T1R coding sequences in the cells.

Knock-Out and Transplacement Animals

The DNA sequence information provided by the present invention also makes possible the development (e.g., by homologous recombination strategies; see Capecchi, *Science* 244:1288-1292 (1989), which is incorporated herein by reference) of transgenic or gene-targeted animals, including, for example, animals that fail to express functional T1R ("knockout") or that express a variant thereof ("transplacement"). Such animals (especially small laboratory animals such as rats, rabbits, mice, and cats) are useful as models for studying the in vivo activities of T1R receptors and modulators of T1R receptors.

Antisense and siRNA

Also encompassed by the invention are antisense and short interfering polynucleotides that recognize and hybridize to polynucleotides encoding T1R receptors. Full-length and fragment antisense polynucleotides are provided. Fragment antisense molecules of the invention include those that specifically recognize and hybridize to T1R RNA (as determined by sequence comparison of DNA encoding T1R receptor to DNA encoding other known molecules). Identification of sequences unique to T1R-encoding polynucleotides can be deduced through use of any publicly available sequence database, and/or through use of commercially available sequence comparison programs. After identification of the desired sequences, isolation through restriction digestion or amplification using any of the various polymerase chain reaction techniques well known in the art can be performed. Antisense polynucleotides are particularly relevant to regulation of expression of T1R receptor by those cells expressing T1R mRNA.

Antisense nucleic acids (preferably 10 to 30 base-pair oligonucleotides) capable of specifically binding to T1R expression control sequences or T1R RNA are introduced into cells (e.g., by a viral vector or colloidal dispersion system such as a liposome). The antisense nucleic acid binds to the target nucleotide sequence in the cell and prevents transcription and/or translation of the target sequence. Phosphorothioate and methylphosphonate antisense oligonucleotides are specifically contemplated for therapeutic use by the invention. Locked nucleic acids are also specifically contemplated for therapeutic use by the present invention. (See, for example, Wahlestedt et al., *Proc. Natl. Acad. Sci. USA,* 97(10), 5633-5638 (2000), which is incorporated by reference in its entirety.) The antisense oligonucleotides may be further modified by adding poly-L-lysine, transferrin polylysine, or cholesterol moieties at their 5' end. Suppression of T1R expression at either the transcriptional or translational level is useful to generate cellular or animal models for diseases/conditions characterized by aberrant T1R expression.

Antisense oligonucleotides, or fragments of nucleotide sequence of SEQ ID NO:1, SEQ ID NO:2, SEQ ID NO:4, SEQ ID NO:5, SEQ ID NO:7, or SEQ ID NO:8, or sequences complementary or homologous thereto, derived from the nucleotide sequences of the present invention encoding T1R receptors are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides may be directed to regulatory regions of a T1R nucleotide sequence, or mRNA corresponding thereto, including, but not limited to, the initiation codon, TATA box, enhancer sequences, and the like.

Those of skill in the art recognize that the antisense oligonucleotides that inhibit the expression and/or biological activity of a T1R receptor may be predicted using any gene encoding a T1R receptor. Specifically, antisense nucleic acid molecules comprise a sequence preferably complementary to at least about 5, 10, 15, 20, 25, 30, 35, 40, 45, 50, 100, 250 or 500 nucleotides or an entire T1R receptor gene sequence. The antisense oligonucleotides may comprise a sequence complementary to about 15 consecutive nucleotides of the coding strand of the T1R receptor-encoding sequence.

In one embodiment, an antisense nucleic acid molecule is antisense to a "coding region" of the coding strand of a nucleotide sequence encoding a T1R protein. The coding strand may also include regulatory regions of the T1R sequence. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding a T1R protein. The term "noncoding region" refers to 5' and 3' sequences which flank the coding region that are not translated into amino acids (i.e., also referred to as 5' and 3' untranslated regions (UTR)).

Antisense oligonucleotides may be directed to regulatory regions of a nucleotide sequence encoding a T1R protein, or mRNA corresponding thereto, including, but not limited to, the initiation codon, TATA box, enhancer sequences, and the like. Given the coding strand sequences provided herein, antisense nucleic acids of the invention can be designed according to the rules of Watson and Crick or Hoogsteen base pairing. The antisense nucleic acid molecule can be complementary to the entire coding region of a T1R mRNA, but also may be an oligonucleotide that is antisense to only a portion of the coding or noncoding region of the mRNA. For example, the antisense oligonucleotide can be complementary to the region surrounding the translation start site of an mRNA. An antisense oligonucleotide can be, for example, about 5, 10, 15, 20, 25, 30, 35, 40, 45 or 50 nucleotides in length.

Another means to inhibit the activity of a T1R receptor according to the invention is via RNA interference (RNAi) (see e.g., Elbashir et al., *Nature,* 411:494-498 (2001); Elbashir et al., *Genes Development,* 15:188-200 (2001)). RNAi is the process of sequence-specific, post-transcriptional gene silencing, initiated by double-stranded RNA (dsRNA) that is homologous in sequence to the silenced gene (e.g., is homologous in sequence to the sequence encoding a T1R receptor, for example but not limited to the sequence as set forth in SEQ ID NO:1, SEQ ID NO:2, SEQ ID NO:4, SEQ ID NO:5, SEQ ID NO:7, or SEQ ID NO:8). siRNA-mediated silencing is thought to occur post-transcriptionally and/or transcriptionally. For example, siRNA duplexes may mediate post-transcriptional gene silencing by reconstitution of siRNA-protein complexes (siRNPs), which guide mRNA recognition and targeted cleavage.

Accordingly, another form of a T1R inhibitory compound of the invention is a short interfering RNA (siRNA) directed against a T1R-encoding sequence. Exemplary siRNAs are siRNA duplexes (for example, 10-25, preferably 20, 21, 22, 23, 24, or 25 residues in length) having a sequence homologous or identical to a fragment of the T1R sequence set forth as SEQ ID NO:1, SEQ ID NO:2, SEQ ID NO:4, SEQ ID NO:5, SEQ ID NO:7, or SEQ ID NO:8 and having a symmetric 2-nucleotide 3'-overhang. The 2-nucleotide 3' overhang may be composed of (2'-deoxy) thymidine because it reduces costs of RNA synthesis and may enhance nuclease resistance of siRNAs in the cell culture medium and within transfected cells. Substitution of uridine by thymidine in the 3' overhang is also well tolerated in mammalian cells, and the sequence of the overhang appears not to contribute to target recognition.

Polypeptides

The invention also provides purified and isolated mammalian T1R receptor polypeptides encoded by a polynucleotide of the invention. Some embodiments include a canine T1R polypeptide comprising the amino acid sequence of SEQ ID NO:3, SEQ ID NO:6, or SEQ ID NO:9, or fragments thereof comprising an epitope specific to the polypeptide. A reference to "epitope specific to" or "polypeptide-specific epitope," or variations thereof, indicates that a portion of the T1R receptor or amino acid sequence is recognizable by an antibody that is specific for the T1R or amino acid sequence.

Included within the scope of the invention are polypeptides encoded by canine allelic variants of T1R. The allelic variants of the T1R receptor of the invention may modify the taste perception of a mammal, such as a dog, to a taste stimulus. Such functional amino acid sequence modifications may account for differences in intraspecies (e.g., breed-specific) taste perception.

Extracellular epitopes are useful for generating and screening for antibodies and other binding compounds that bind to a T1R receptor. Thus, in another embodiment, the invention provides a purified and isolated polypeptide comprising at least one extracellular domain of the T1R receptor. Examples of extracellular domains of the T1R polypeptides of the invention include residues 1-565, 624-637, 704-725, and 784-786 of SEQ ID NO:3; residues 1-565, 622-634, 699-723, and 778-782 of SEQ ID NO:6; and residues 1-566, 623-636, 702-725, or 780-793 of SEQ ID NO:9. Polypeptide fragments of the invention may be continuous portions of the native receptor. However, it will also be appreciated that knowledge of the T1R genes and protein sequences as provided herein permits recombination of various domains that are not contiguous in the native protein.

The invention embraces polypeptides that preferably have at least about 99%, at least about 95%, at least about 90%, at least about 85%, at least about 80%, at least about 75%, at least about 74%, at least about 73%, at least about 72%, at least about 71%, at least about 70%, at least about 65%, at least about 60%, at least about 55%, or at least about 50% identity and/or homology to the polypeptides of the invention.

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention.

The invention also embraces variant T1R polypeptides. Insertions may be located at either or both termini of the protein, or may be positioned within internal regions of the amino acid sequence. Insertional variants with additional residues at either or both termini can include, for example, fusion proteins and proteins including amino acid tags or labels.

Insertion variants include T1R polypeptides wherein one or more amino acid residues are added to a biologically active fragment thereof. For example, the insertion variants of the invention include chimeric T1R receptors wherein at least one functional domain of a canine T1R receptor of the invention is present.

The invention also embraces T1R variants having additional amino acid residues that result from use of specific expression systems. For example, use of commercially available vectors that express a desired polypeptide as part of a glutathione-S-transferase (GST) fusion product provides the desired polypeptide having an additional glycine residue at position −1 after cleavage of the GST component from the desired polypeptide. Variants that result from expression in other vector systems are also contemplated.

In another aspect, the invention provides deletion variants wherein one or more amino acid residues in a T1R polypeptide are removed. Deletions can be effected at one or both termini of the T1R polypeptide, or with removal of one or more non-terminal amino acid residues of T1R. Deletion variants, therefore, include all fragments of a T1R polypeptide.

The invention also embraces polypeptide fragments that maintain biological (e.g., ligand binding, heterodimerization, receptor activity) and/or immunological properties of a T1R polypeptide.

As used in the present invention, polypeptide fragments preferably comprise at least 10, 15, 20, 25, 30, 35, 40, 45, or 50 consecutive amino acids of SEQ ID NO:3, SEQ ID NO:6, or SEQ ID NO:9. Some polypeptide fragments display antigenic properties unique to, or specific for, a canine T1R receptor. Fragments of the invention having the desired biological and immunological properties can be prepared by any of the methods well known and routinely practiced in the art.

In still another aspect, the invention provides substitution variants of T1R polypeptides. Substitution variants include those polypeptides wherein one or more amino acid residues of a T1R polypeptide are removed and replaced with alternative residues. In one aspect, the substitutions are conservative in nature; however, the invention embraces substitutions that are also non-conservative. Conservative substitutions for this purpose may be defined as set out in Tables 1, 2, or 3 below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 1 (from WO 97/09433, page 10, published Mar. 13, 1997 (PCT/GB96/02197, filed Sep. 6, 1996), immediately below.

TABLE 1

| Conservative Substitutions I | |
|---|---|
| SIDE CHAIN CHARACTERISTIC | AMINO ACID |
| Aliphatic | |
| Non-polar | G A P<br>I L V |
| Polar - uncharged | C S T M<br>N Q |
| Polar - charged | D E<br>K R |
| Aromatic | H F W Y |
| Other | N Q D E |

Alternatively, conservative amino acids can be grouped as described in Lehninger, [BIOCHEMISTRY, Second Edition; Worth Publishers, Inc. NY, N.Y. (1975), pp. 71-77] as set out in Table 2, below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, below.

TABLE 3

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve the targeting capacity of the polypeptide for desired cells, tissues, or organs. Similarly, the invention further embraces T1R polypeptides that have been covalently modified to include one or more water-soluble polymer attachments such as polyethylene glycol, polyoxyethylene glycol, or polypropylene glycol. Variants that display ligand binding properties of native T1R and are expressed at higher levels, as well as variants that provide for constitutively active receptors, are particularly useful in assays of the invention; the variants are also useful in providing cellular, tissue and animal models of diseases/conditions characterized by aberrant T1R activity.

In a related embodiment, the present invention provides compositions comprising purified polypeptides of the invention. Some compositions comprise, in addition to the polypeptide of the invention, a pharmaceutically acceptable (i.e., sterile and non-toxic) liquid, semisolid, or solid diluent that serves as a pharmaceutical vehicle, excipient, or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter.

Variants that display ligand-binding properties of native T1R and are expressed at higher levels, as well as variants that provide for constitutively active receptors, are particularly useful in assays of the invention; the variants are also useful in assays of the invention and in providing cellular, tissue and animal models of diseases/conditions characterized by aberrant T1R activity.

Antibodies

Also included in the present invention are antibodies (e.g., monoclonal and polyclonal antibodies, single chain antibodies, chimeric antibodies, bifunctional/bispecific antibodies, humanized antibodies, human antibodies, caninized antibodies, canine antibodies, and complementary determining region (CDR)-grafted antibodies, including compounds which include CDR sequences which specifically recognize a polypeptide of the invention) specific for a T1R receptor of the invention or fragments thereof. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind T1R polypeptides, preferably exclusively (i.e., are able to distinguish T1R polypeptides of the invention from other known polypeptides by virtue of measurable differences in binding affinity, despite the possible existence of localized sequence identity, homology, or similarity between T1R and such polypeptides). It will be understood that specific antibodies may also interact with other proteins (for example, S. aureus protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6. Antibodies that recognize and bind fragments of the T1R polypeptides of the invention are also contemplated, provided that the antibodies are specific for T1R polypeptides. Antibodies of the invention can be produced using any method well known and routinely practiced in the art.

The invention provides an antibody that is specific for the canine T1R receptors of the invention. Antibodies that can be generated from polypeptides that have previously been described in the literature and that are capable of fortuitously cross-reacting with canine T1R receptor (e.g., due to the fortuitous existence of a similar epitope in both polypeptides) are considered "cross-reactive" antibodies. Such cross-reactive antibodies are not antibodies that are "specific" for a canine T1R receptor. The determination of whether an antibody is specific for a canine T1R receptor or is cross-reactive with another known receptor is made using any of several assays, such as Western blotting assays, that are well known in the art. For identifying cells that express a T1R receptor and also for modulating T1R-ligand binding activity, antibodies that specifically bind to an extracellular epitope of the T1R receptor may be used.

In some variations, the invention provides monoclonal antibodies. Hybridomas that produce such antibodies also are intended as aspects of the invention. In yet another variation, the invention provides a caninized antibody. Caninized antibodies are useful for in vivo therapeutic indications.

In another variation, the invention provides a cell-free composition comprising polyclonal antibodies, wherein at least one of the antibodies is an antibody of the invention specific for T1R receptor. Antisera isolated from an animal is an exemplary composition, as is a composition comprising an antibody fraction of an antisera that has been resuspended in water or in another diluent, excipient, or carrier.

In still another related embodiment, the invention provides an anti-idiotypic antibody specific for an antibody that is specific for T1R receptor of the invention.

It is well known that antibodies contain relatively small antigen binding domains that can be isolated chemically or by recombinant techniques. Such domains are useful T1R receptor binding molecules themselves, and also may be reintroduced into other antibodies or fused to toxins or other polypeptides. Thus, in still another embodiment, the invention provides a polypeptide comprising a fragment of a T1R-specific antibody, wherein the fragment and the polypeptide bind to the T1R receptor. By way of non-limiting example, the invention provides polypeptides that are single chain antibodies and CDR-grafted antibodies.

Non-canine antibodies may be caninized by any of the methods known in the art for humanization of antibodies, for example. In one method, the non-canine CDRs are inserted into a canine antibody or consensus antibody framework sequence. Similarly, non-human antibodies may be humanized by methods known in the art. In one embodiment, non-human CDRs are inserted into a human antibody or consensus antibody framework sequence. Further changes can then be introduced into the antibody framework to modulate affinity or immunogenicity.

Antibodies of the invention are useful for, e.g., therapeutic purposes (such as by modulating activity of T1R receptor), diagnostic purposes (such as detecting or quantitating T1R receptor activity), and also for purification of T1R receptor. Kits comprising an antibody of the invention for any of the purposes described herein are also included within the scope of the invention. In general, a kit of the invention preferably includes a control antigen for which the antibody is immunospecific.

Compositions

Mutations in the T1R gene that result in loss of normal function of the T1R gene product underlie some T1R-related disease states. The invention comprehends gene and peptide therapy, for example, to restore T1R activity to treat those disease states. Delivery of a functional T1R gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature*, supplement to vol. 392, No. 6679, pp. 25-20 (1998). For additional reviews of gene therapy technology see Friedmann, *Science,* 244: 1275-1281 (1989); Verma, *Scientific American:* 68-84 (1990); and Miller, *Nature,* 357: 455-460 (1992). Alternatively, it is contemplated that in other disease states, preventing the expression of, or inhibiting the activity of, T1R receptor will be useful in treatment. It is contemplated that antisense therapy or gene therapy could be applied to negatively regulate the expression of T1R receptor.

Another aspect of the present invention is directed to compositions, including pharmaceutical compositions, comprising any of the nucleic acid molecules or recombinant expression vectors described above and an acceptable carrier or diluent. The carrier or diluent may be pharmaceutically acceptable. Suitable carriers are described in the most recent edition of *Remington's Pharmaceutical Sciences*, A. Osol, a standard reference text in this field, which is incorporated herein by reference in its entirety. Examples of such carriers or diluents include, but are not limited to, water, saline, Ringer's solution, dextrose solution, and 5% serum albumin. Liposomes and nonaqueous vehicles such as fixed oils may also be used. The formulations may be sterilized by commonly used techniques.

Also within the scope of the invention are compositions comprising polypeptides, polynucleotides, or antibodies of the invention that have been formulated with, e.g., a pharmaceutically acceptable carrier.

The invention also provides methods of using antibodies of the invention. For example, the invention provides a method for modulating ligand-binding of a T1R receptor comprising the step of contacting the receptor with an antibody specific for the T1R polypeptide, under conditions wherein the antibody binds the receptor.

Methods of Identifying Ligands and Modulators

The invention also provides assays to identify compounds that bind and/or modulate T1R receptor. A "T1R binding partner" is a compound that directly or indirectly binds a T1R polypeptide of the invention. One assay of the invention comprises the steps of: (a) contacting T1R receptor with a compound suspected of binding T1R receptor (the test compound); and (b) measuring binding between the compound and the T1R receptor. In one variation, the composition comprises a cell expressing T1R receptor on its surface. In another variation, isolated T1R receptor or cell membranes comprising T1R receptor are employed. The binding may be measured directly, e.g., by using a labeled compound, or may be measured indirectly. Compounds identified as binding T1R receptor may be further tested in other assays including, but not limited to, T1R activity assays and/or in vivo models, in order to confirm or quantitate their activity.

Specific binding molecules, including natural ligands and synthetic compounds, can be identified or developed using isolated or recombinant T1R products, T1R variants, or preferably, cells expressing such products. Binding partners are useful for purifying T1R products and detection or quantification of T1R products in fluid and tissue samples using known immunological procedures. Binding molecules are also manifestly useful in modulating (i.e., blocking, inhibiting or stimulating) biological activities of T1R, especially those activities involved in signal transduction. Binding molecules also are useful in methods for predicting the taste perception of an organism such as a mammal by detecting a polypeptide of the invention in a biological sample of the organism. For example, an organism in which a polypeptide of the invention has been identified may perceive saccharin as bitter and/or D-fructose, β-D-fructose, or sucrose as sweet.

The DNA and amino acid sequence information provided by the present invention also makes possible identification of binding partner compounds with which a T1R polypeptide or polynucleotide will interact. Methods to identify binding partner compounds include solution assays, in vitro assays wherein T1R polypeptides are immobilized, and cell-based assays. Identification of binding partner compounds of T1R polypeptides provides candidates for therapeutic or prophylactic intervention in pathologies associated with T1R normal and aberrant biological activity.

The invention includes several assay systems for identifying T1R-binding partners. In solution assays, methods of the invention comprise the steps of (a) contacting a T1R polypeptide with one or more candidate binding partner compounds and (b) identifying the compounds that bind to the T1R polypeptide. Identification of the compounds that bind the T1R polypeptide can be achieved by isolating the T1R polypeptide/binding partner complex, and separating the binding partner compound from the T1R polypeptide. An additional step of characterizing the physical, biological, and/or biochemical properties of the binding partner compound is also comprehended in another embodiment of the invention. In one aspect, the T1R polypeptide/binding partner complex is isolated using an antibody immunospecific for either the T1R polypeptide or the candidate binding partner compound.

In still other embodiments, either the T1R polypeptide or the candidate binding partner compound comprises a label or tag that facilitates its isolation, and methods of the invention to identify binding partner compounds include a step of isolating the T1R polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

In one variation of an in vitro assay, the invention provides a method comprising the steps of (a) contacting an immobilized T1R polypeptide with a candidate binding partner compound and (b) detecting binding of the candidate compound to the T1R polypeptide. In an alternative embodiment, the candidate binding partner compound is immobilized and binding of T1R receptor is detected. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. The support may, for example, be formulated into a canine-specific electronic tongue or biosensor. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

The invention also provides cell-based assays to identify binding partner compounds of a T1R polypeptide. In one embodiment, the invention provides a method comprising the steps of contacting a T1R polypeptide expressed on the surface of a cell with a candidate binding partner compound and detecting binding of the candidate binding partner compound to the T1R polypeptide. In some embodiments, the detection comprises detecting physiological event in the cell caused by the binding of the molecule.

Another aspect of the present invention is directed to methods of identifying compounds that bind to either T1R receptor or nucleic acid molecules encoding T1R receptor, comprising contacting T1R receptor, or a nucleic acid molecule encoding the same, with a compound, and determining whether the compound binds T1R receptor or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross-linking, interaction trap/two-hybrid analysis, southwestern analysis, ELISA, and the like, which are described in, for example, CURRENT PROTOCOLS IN MOLECULAR BIOLOGY, 1999, John Wiley & Sons, NY, which is incorporated herein by reference in its entirety. The compounds to be screened include (which may include compounds which are suspected to bind T1R receptor, or a nucleic acid molecule encoding the same), but are not limited to, extracellular, intracellular, biological, or chemical origin. The methods of the invention also embrace ligands, especially neuropeptides, that are attached to a label, such as a radiolabel (e.g., $^{125}$I, $^{35}$S, $^{32}$P, $^{33}$P, $^{3}$H), a fluorescence label, a chemiluminescent label, an enzymic label, and an immunogenic label. Modulators falling within the scope of the invention include, but are not limited to, non-peptide molecules such as non-peptide mimetics, non-peptide allosteric effectors, and peptides. The T1R polypeptide or polynucleotide employed in such a test may either be free in solution, attached to a solid support, borne on a cell surface or located intracellularly, or associated with a portion of a cell. One skilled in the art can, for example, measure the formation of complexes between T1R receptor and the compound being tested. Alternatively, one skilled in the art can examine the diminution in complex formation between T1R receptor and its substrate caused by the compound being tested. In some embodiments of the invention, the recognition sites of the T1R receptor are coupled with a monitoring system, either electrical or optical. An appropriate chemical stimulus can bind to the receptor's ligand binding domain, changing the receptor conformation to a degree that the coupled electronics or optical changes can be observed on a read-out. Such a device could be developed into a canine-specific electronic tongue, for example.

In another embodiment of the invention, high throughput screening for compounds having suitable binding affinity to T1R receptor is employed. Briefly, large numbers of different small peptide test compounds are synthesized on a solid substrate. The peptide test compounds are contacted with T1R receptor and washed. Bound T1R receptor is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed T1R receptor can be used for HTS binding assays in conjunction with a ligand, such as an amino acid or carbohydrate. The identified peptide is labeled with a suitable radioisotope, including, but not limited to, $^{125}$I, $^{3}$H, $^{35}$S or $^{32}$P, by methods that are well known to those skilled in the art. Alternatively, the peptides may be labeled by well-known methods with a suitable fluorescent derivative (Baindur et al., *Drug Dev. Res.*, 1994, 33, 373-398; Rogers, *Drug Discovery Today*, 1997, 2, 156-160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams, *Med. Res. Rev.*, 1991, 11, 147-184; Sweetnam et al., *J. Natural Products*, 1993, 56, 441-455). Alternative methods include a scintillation proximity assay (SPA) or a FlashPlate format in which such separation is unnecessary (Nakayama, *Cur. Opinion Drug Disc. Dev.,* 1998, 1, 85-91; Bossé et al., *J. Biomolecular Screening,* 1998, 3, 285-292.). Binding of fluorescent ligands can be detected in various ways, including fluorescence energy transfer (FRET), direct spectrophotofluorometric analysis of bound ligand, or fluorescence polarization (Rogers, *Drug Discovery Today,* 1997, 2, 156-160; Hill, *Cur. Opinion Drug Disc. Dev.,* 1998, 1, 92-97).

Other assays may be used to identify specific ligands of a T1R receptor, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al., *Nature,* 340:245-246 (1989), and Fields et al., *Trends in Genetics,* 10:286-292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is a receptor, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal.

The yeast two-hybrid assay can also be used to identify proteins that bind to the gene product. In an assay to identify proteins that bind to a T1R receptor, or fragment thereof, a fusion polynucleotide encoding both a T1R receptor (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method that distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., *Anal. Chem.,* 69:1683-1691 (1997), incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with T1R receptor. Radiolabeled competitive binding studies are described in A. H. Lin et al., *Antimicrobial Agents and Chemotherapy,* 1997, 41(10): 2127-2131, the disclosure of which is incorporated herein by reference in its entirety.

Another aspect of the present invention is directed to methods of identifying compounds that modulate (i.e., increase or decrease) activity of T1R receptor comprising contacting T1R receptor with a compound, and determining whether the compound modifies activity of T1R receptor. The activity in the presence of the test compound is compared to the activity in the absence of the test compound. Where the activity of the sample containing the test compound is higher than the activity in the sample lacking the test compound, the compound is an agonist. Similarly, where the activity of the sample containing the test compound is lower than the activity in the sample lacking the test compound, the compound is an antagonist.

Agents that modulate (i.e., increase, decrease, or block) T1R receptor activity or expression also may be identified, for example, by incubating a putative modulator with a cell containing a T1R polypeptide or polynucleotide and determining the effect of the putative modulator on T1R receptor activity or expression. The selectivity of a compound that modulates the activity of T1R receptor can be evaluated by comparing its effects on T1R receptor to its effect on other T1R receptors. Selective modulators may include, for example, antibodies and other proteins, peptides, or organic molecules that specifically bind to a T1R polypeptide or a T1R receptor-encoding nucleic acid. Modulators of T1R receptor activity will be therapeutically useful in treatment of diseases and physiological conditions in which normal or aberrant T1R receptor activity is involved. Compounds identified as modulating T1R receptor activity may be further tested in other assays including, but not limited to, in vivo models, in order to confirm or quantitate their activity.

The invention also provides methods for identifying a T1R receptor modulator by: (a) contacting a T1R receptor binding partner and a composition comprising a T1R receptor in the presence and in the absence of a putative modulator compound; (b) detecting binding between the binding partner and the T1R receptor; and (c) identifying a putative modulator compound or a modulator compound in view of decreased or increased binding between the binding partner and the T1R receptor in the presence of the putative modulator, as compared to binding in the absence of the putative modulator. Compounds identified as modulators of binding between T1R receptor and a T1R binding partner may be further tested in other assays including, but not limited to, in vivo models, in order to confirm or quantitate their activity.

The invention also includes within its scope high-throughput screening (HTS) assays to identify compounds that interact with, enhance, or inhibit biological activity (i.e., affect enzymatic activity, binding activity, etc.) of a T1R polypeptide. HTS assays permit screening of large numbers of compounds in an efficient manner. Cell-based HTS systems are contemplated to investigate T1R receptor-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the T1R polypeptide.

For example, modulators of T1R receptor activity may be identified by expressing the T1R receptor in a heterologous cultured mammalian cell line, such as HEK cells, and detecting receptor activity in the presence and absence of a test compound by monitoring changes in intracellular calcium using a calcium-specific intracellular dye. In another embodiment, this process may be automated using a high-throughput screening device.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides, or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms that are used to create mixtures for screening by: (1) fermentation and extraction of broths from soil, plant, or marine microorganisms or (2) extraction of plants or marine organisms. Natural product libraries include polyketides, non-ribosomal peptides, and variants (non-naturally occurring) thereof. For a review, see *Science* 282:63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are nonpeptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701-707 (1997). Identification of modulators through use of the various libraries described herein permits modification of the candidate "hit" (or "lead") to optimize the capacity of the "hit" to modulate activity.

T1R receptor binding partners that stimulate T1R receptor activity are useful as agonists in disease states or conditions characterized by insufficient T1R receptor signaling (e.g., as a result of insufficient activity of a T1R receptor ligand). T1R receptor binding partners that block ligand-mediated T1R receptor signaling are useful as T1R receptor antagonists to treat disease states or conditions characterized by excessive T1R receptor signaling. Thus, in another aspect, the invention provides methods for treating a disease or abnormal condition by administering to a patient in need of such treatment a substance that modulates the activity or expression of a polypeptide having a sequence of SEQ ID NO:3, SEQ ID NO:6, or SEQ ID NO:9, or exhibiting substantially the same biological activity as a polypeptide having a sequence of SEQ ID NO:3, SEQ ID NO:6, or SEQ ID NO:9.

In addition T1R receptor modulators in general, as well as T1R receptor encoding polynucleotides and polypeptides, are useful in diagnostic assays for such diseases or conditions.

Mimetics

Mimetics or mimics of compounds identified herein (sterically similar compounds formulated to mimic the key portions of the structure) may be designed for pharmaceutical use. Mimetics may be used in the same manner as the compounds identified by the present invention that modulate the T1R receptor and hence are also functional equivalents. The generation of a structural-functional equivalent may be achieved by the techniques of modeling and chemical design known to those of skill in the art. It will be understood that all such sterically similar constructs fall within the scope of the present invention.

The design of mimetics to a known pharmaceutically active compound is a known approach to the development of pharmaceuticals based on a "lead" compound. This is desirable where, for example, the active compound is difficult or expensive to synthesize, or where it is unsuitable for a particular method of administration, e.g., some peptides may be unsuitable active agents for oral compositions as they tend to be quickly degraded by proteases in the alimentary canal.

There are several steps commonly taken in the design of a mimetic. First, the particular parts of the compound that are critical and/or important in determining its T1R-modulating properties are determined. In the case of a polypeptide, this can be done by systematically varying the amino acid residues in the peptide, e.g. by substituting each residue in turn. Alanine scans of peptides are commonly used to refine such peptide motifs.

Once the active region of the compound has been identified, its structure is modeled according to its physical properties, e.g. stereochemistry, bonding, size, and/or charge, using data from a range of sources, such as, but not limited to, spectroscopic techniques, X-ray diffraction data, and NMR. Computational analysis, similarity mapping (which models the charge and/or volume of the active region, rather than the bonding between atoms), and other techniques known to those of skill in the art can be used in this modeling process.

In a variant of this approach, the three-dimensional structure of the compound that modulates a T1R receptor and the active region of the T1R receptor are modeled. This can be especially useful where either or both of these compounds change conformation upon binding. Knowledge of the structure of the ligand-binding domain the receptor also allows the design of high potency ligands and/or modulators.

A template molecule is then selected onto which chemical groups that mimic the T1R modulator can be grafted. The template molecule and the chemical groups grafted onto it can conveniently be selected so that the mimetic is easy to synthesize, is pharmacologically acceptable, and does not degrade in vivo, while retaining the biological activity of the lead compound. Alternatively, where the mimetic is peptide-based, further stability can be achieved by cyclizing the peptide, thereby increasing its rigidity. The mimetic or mimetics found by this approach can then be screened by the methods of the present invention to see whether they have the ability to modulate the T1R receptor. Further optimization or modification can then be performed to arrive at one or more final mimetics for in vivo or clinical testing.

Compositions of Binding and/or Modulating Compounds

Following identification of a compound that binds and/or or modulates a T1R receptor, the compound may be manufactured and/or used in preparation of compositions including, but not limited to, foods, drinks, and pharmaceutical compositions. The compositions are provided or administered to patients, including, but not limited to, avians, felines, canines, bovines, ovines, porcines, equines, rodents, simians, and humans.

Thus, the present invention extends, in various aspects, not only to compounds identified in accordance with the methods disclosed herein but also foods, drinks, pharmaceutical compositions, drugs, or other compositions comprising such a compound; methods comprising administration of such a composition to a patient, e.g. for treatment (which includes prophylactic treatment) of a T1R receptor-associated disorder (e.g., obesity, diabetes); uses of such a compound in the manufacture of a composition for administration to a patient; and methods of making a composition comprising admixing such a compound with a pharmaceutically acceptable excipient, vehicle or carrier, and optionally other ingredients.

Some compositions of the invention comprise a taste-modifying amount of at least one or more binding or modulating compounds. A "taste-modifying amount" is a quantity sufficient to increase or decrease the perception of a taste stimulus by a given mammal. The food and drink compositions of the invention are formulated by the addition of a binding or modulating compound to a food or drink of the mammal. Such compositions may be individualized or breed-specific. For example, canine veterinary specialty diets may thus be made more palatable.

The pharmaceutical compositions of the invention comprise a therapeutically effective amount of a compound identified according to the methods disclosed herein, or a pharmaceutically acceptable salt thereof, and a pharmaceutically acceptable carrier or excipient.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Pharmaceutically acceptable carriers include but are not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc.

The pharmaceutical compositions of the invention may further comprise a secondary compound for the treatment of a disorder unrelated to the T1R receptor, such as an antibiotic or other therapeutic agent, to improve the palatability of the pharmaceutical composition, thereby improving the ease of administration.

In one embodiment, the composition is formulated in accordance with routine procedures as a pharmaceutical composition adapted for oral (e.g., tablets, granules, syrups) or non-oral (e.g., ointments, injections) administration to the subject. Various delivery systems are known and can be used to administer a compound that modulates a T1R receptor, e.g., encapsulation in liposomes, microparticles, microcapsules, expression by recombinant cells, receptor-mediated endocytosis, construction of a therapeutic nucleic acid as part of a retroviral or other vector, etc. Methods of introduction include but are not limited to intradermal, intramuscular, intraperitoneal, intravenous, subcutaneous, intranasal, topical, and oral routes.

The compounds of the invention may be administered by any convenient route, for example by infusion or bolus injection, by absorption through epithelial or mucocutaneous linings (e.g., oral mucosa, rectal and intestinal mucosa, etc.), and may be administered together with other biologically active agents, for example in HAART therapy. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery; topical application, e.g., in conjunction with a wound dressing after surgery; by injection; by means of a catheter; by means of a suppository; or by means of an implant, said implant being of a porous, non-porous, or gelatinous material, including membranes, such as sialastic membranes, or fibers.

The composition can be administered in unit dosage form and may be prepared by any of the methods well known in the pharmaceutical art, for example, as described in REMINGTON'S PHARMACEUTICAL SCIENCES (Mack Publishing Co., Easton, Pa.). The amount of the compound of the invention that modulates a T1R receptor that is effective in the treatment of a particular disorder or condition will depend on factors including but not limited to the chemical characteristics of the compounds employed, the route of administration, the age, body weight, and symptoms of a patient, the nature of the disorder or condition, and can be determined by standard clinical techniques. Typically therapy is initiated at low levels of the compound and is increased until the desired therapeutic effect is achieved. In addition, in vitro assays may optionally be employed to help identify optimal dosage ranges. Suitable dosage ranges for intravenous administration are preferably generally about 20-500 micrograms of active compound per kilogram body weight. Suitable dosage ranges for intranasal administration are preferably generally about 0.01 pg/kg body weight to 1 mg/kg body weight. Suppositories preferably generally contain active ingredient in the range of 0.5% to 10% by weight; oral formulations preferably may contain 10% to 95% active ingredient. Effective doses may be extrapolated from dose-response curves derived from in vitro or animal model test systems.

Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry-lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline.

Where the composition is administered by injection, an ampoule of sterile water for injection or saline can be provided so that the ingredients may be mixed prior to administration.

Treatment Methods

The invention provides methods of treatment of T1R receptor-associated disorders by administering to a subject or patient an effective amount of a compound that modulates the T1R receptor. In some aspects of the invention, the compounds or pharmaceutical compositions of the invention are administered to a patient having an increased risk of or having a disorder associated with the T1R receptor. The patient may be, for example, avian, feline, canine, bovine, ovine, porcine, equine, rodent, simian, or human.

Kits

A kit of the invention comprises a carrier means being compartmentalized to receive in close confinement one or more container means such as vials, tubes, and the like, each of the container means comprising an element to be used in the methods of the invention. For example, one of the container means may comprise the a polynucleotide encoding a T1R receptor of the invention, a T1R receptor of the invention, or an antibody thereto. The kit may also have one or more conventional kit components, including, but not limited to, instructions, test tubes, Eppendorf™ tubes, labels, reagents helpful for quantification of marker gene expression, etc.

EXAMPLES

The following examples are meant to be illustrative of the present invention and are not intended to limit the scope thereof.

Cloning and Characterization of the Canine T1R Receptors

The discovery of canine taste receptors, T1R1, T1R2, and T1R3, was achieved by using a molecular strategy termed "overgo" (Thomas, et al., *Genome Res.*, 12:1277-1285 (2002); Vollrath, D., *DNA markers for physical mapping* In GENOME ANALYSIS: A LABORATORY MANUAL, Vol. 4, ed. B. Birren, et al., pp. 187-215, 1999). Cold Spring Harbor Laboratory Press, Cold Spring Harbor, N.Y.). This strategy involves the use of the shortest DNA probes among the many kinds of probes used in bacterial artificial chromosome (BAC) library screening. These probes are comprised of two DNA sequences (e.g., 22mers) with a complementary 8 base overlap. They can be designed by computer program (available online through the Genome Sequencing Center of the Washington University School of Medicine) and are readily synthesized.

Overgo probes were designed from conserved coding regions of Tas1R1, Tas1R2, and Tas1R3 gene sequences from human, mouse, rat, cow, and pig. The overlapping sequences of the seven DVL1 overgo probes used in the present invention were as follows:

```
t1r1_1-OVa
TAAACAACTCCACGGCCCTGCTGC            (SEQ ID NO:28)
t1r1_1-OVb
CCCAGGGTGATGTTGGGCAGCAGG            (SEQ ID NO:29)

t1r1_2-OVa
GCTGTGTATGCGGTGGCCCATGGC            (SEQ ID NO:30)
t1r1_2-OVb
CCAGGAGCTGGTGGAGGCCATGGG            (SEQ ID NO:31)

t1r1_3-OVa
TGCTGACCAACCTGACTGGCAAGG            (SEQ ID NO:32)
t1r1_3-OVb
TCTGAGGCGACCCACACCTTGCCA            (SEQ ID NO:33)

t1r1_4-OVa
CCAGTTCAGCTAAACATAAATGAG            (SEQ ID NO:34)
t1r1_4-OVb
GCCACTGGATTTTGGTCTCATTTA            (SEQ ID NO:35)

t1r1_5-OVa
AGCTAACACGCTGCTGCTGCTGCT            (SEQ ID NO:36)
t1r1_5-OVb
AGCAGTCCCAAGCAGCAGCAGCAG            (SEQ ID NO:37)

t1r1_6-OVa
TGTGTCACCTTCAGCCTGCTCTTC            (SEQ ID NO:38)
t1r1_6-OVb
TCCAGGACACGAAGTTGAAGAGCA            (SEQ ID NO:39)

t1r2_1-OVa
TACTTCGGCCCCAAGTGCTACATG            (SEQ ID NO:40)
t1r2_1-OVb
CCGGGTAGAAGAGGATCATGTAGC            (SEQ ID NO:41)

t1r2_2-OVa
TGGTCACCATCGTGGACCTCTTGG            (SEQ ID NO:42)
t1r2_2-OVb
AGGTTGAGCACAGTGACCAAGAGG            (SEQ ID NO:43)

t1r2_3-OVa
ACCAACTACAACGAGGCCAAGTTC            (SEQ ID NO:44)
t1r2_3-OVb
TCATGCTGAGGGTGATGAACTTGG            (SEQ ID NO:45)

t1r2_4-OVa
TCCGAGTCCTGGGCCATCGACCCG            (SEQ ID NO:46)
t1r2_4-OVb
TGAGGTTGTGCAGGACCGGGTCGA            (SEQ ID NO:47)

t1r2_5-OVa
TACAACCTCATGCAGGCCATGCGC            (SEQ ID NO:48)
t1r2_5-OVb
TCTCCTCCACCGCGAAGCGCATGG            (SEQ ID NO:49)

t1r2_6-OVa
ATCACCATCCAGAGCGTGCCCATC            (SEQ ID NO:50)
```

-continued

| Name | Sequence | ID |
|------|----------|-----|
| t1r2_6-OVb | ACTCACTGAAGCCCGGGATGGGCA | (SEQ ID NO:51) |
| t1r2_7-OVa | ACCACCACGTCGAGGCCATGGTGC | (SEQ ID NO:52) |
| t1r2_7-OVb | AAGTGCAGCATCAGCTGCACCATG | (SEQ ID NO:53) |
| t1r3-OV1a | CTTCCACTCCTGCTGCTACGACTG | (SEQ ID NO:54) |
| t1r3-OV1b | TGCCTCGCAGTCCACGCAGTCGTA | (SEQ ID NO:55) |
| t1r3-OV2a | AGGTGCGCCGCGTCAAGGGCTTCC | (SEQ ID NO:56) |
| t1r3-OV2b | TCGTAGCAGCAGGAGTGGAAGCCC | (SEQ ID NO:57) |
| t1r3-OV3a | GTTCCTGGCATGGGGGGAGCCGGC | (SEQ ID NO:58) |
| t1r3-OV3b | GAGCAGCACAAGCACAGCCGGCTC | (SEQ ID NO:59) |
| t1r3-OV4a | ACAGCCCACTAGTTCAGGCCGCAG | (SEQ ID NO:60) |
| t1r3-OV4b | CAGGCCCGGGGTCCCCCTGCGGCC | (SEQ ID NO:61) |
| t1r3-OV5a | CCCACTGGTTCAGGCCTCGGGGGG | (SEQ ID NO:62) |
| t1r3-OV5b | AAAGCAGGCCAGGGGCCCCCCCGA | (SEQ ID NO:63) |
| t1r3-OV6a | AGGCGCTGGTGCACTGCCGCACAC | (SEQ ID NO:64) |
| t1r3-OV6b | AAGCTGACCCAGGAGCGTGTGCGG | (SEQ ID NO:65) |
| t1r3-OV7a | ACAGAGGCACTGGTGCACTGCCGC | (SEQ ID NO:66) |
| t1r3-OV7b | TGATCCAGGAGTGCACGCGGCAGT | (SEQ ID NO:67) |
| t1r3-OV8a | ACCAATGCCACGCTGGCCTTTCTC | (SEQ ID NO:68) |
| t1r3-OV8b | AAGTGCCCAGGAAGCAGAGAAAGG | (SEQ ID NO:69) |
| t1r3-OV9a | TGGTACATGCTGCCAATGCCACGC | (SEQ ID NO:70) |
| t1r3-OV9b | AAGCAGAGGAAAGCCAGCGTGGCA | (SEQ ID NO:71) |
| t1r3-OV10a | TACAACCGTGCCCGTGGCCTCACC | (SEQ ID NO:72) |
| t1r3-OV10b | AGGCCAGCATGGCGAAGGTGAGGC | (SEQ ID NO:73) |
| t1r3-OV11a | TCATCACCTGGGTCTCCTTTGTGC | (SEQ ID NO:74) |
| t1r3-OV11b | ACATTGGCCAGGAGGGGCACAAAG | (SEQ ID NO:75) |
| t1r3-OV12a | TGCAGATGGGTGCCCTCCTGCTCT | (SEQ ID NO:76) |
| t1r3-OV12b | AGGATGCCCAGCACACAGAGCAGG. | (SEQ ID NO:77) |

The 14-base single-stranded overhangs were filled in with $^{32}$P labeled dATP and dCTP, and the overgo probes hybridized with BAC libraries.

The overgo strategy is considered to be more versatile than a PCR-based strategy by those skilled in the art of comparative physical mapping for the following reasons: (1) overgo probes are short (e.g., 36mers or 40mers), making the probability of good alignment from among many species more favorable; (2) overgo probes are more specific to the target genes compared with traditional cDNA and genomic DNA probes used by PCR; and (3) although overgo probes are short, they are not as restricted as traditional PCR probes, which cannot tolerate even a few mismatches, because they can be used in hybridization approaches with BACs or other libraries.

Screening a canine genomic BAC library. Six Ta1r1, seven Tas1r2, and twelve overgo probes (SEQ ID NOS:28-77) were used in screening a canine genomic BAC library. Probes were radioactively labeled by the random hexa-nucleotide method (Feinberg & Vogelstein, *Analytical Biochemistry*, 132:6-13 (1983)). Hybridization and washing of membranes followed standard protocols (Church & Gilbert, *PNAS U.S.A.*, 81:1991-1995 (1984)). One positive BAC clone was identified for dog Ta1r1 (clone 181F20). Two positive BAC clones were identified for each of canine Tas1r2 (clone 24F22 and 189L1) and canine Tas1R3 (clones 205J13 and 245K17).

Production of a shotgun library for BACs containing canine Tas1rs and identification of small insert clones containing canine T1Rs. All positive BACs containing canine Ta1r1, Tas1r2, and Tas1r3 were selected to prepare BAC DNAs using Qiagen Large Construct Kit. BAC DNA was digested by the restriction enzyme Sau3A1 and subcloned into pGEM+3Z (Promega) vector. After transformants were arrayed to a nylon membrane, two separate hybridizations were performed using pooled six Ta1r1 (SEQ ID NOs:28-39), seven Tas1r2 (SEQ ID NOs:40-53), and twelve Tas1r3 overgo probes (SEQ ID NOS:54-77). Sequencing of positive clones and chromosome walking yielded the partial coding regions of canine Ta1r1, Tas1r2, and Tas1r3.

Identification of full-length coding regions of canine Tas1rs. A BLAST search of a dog genome database using known Tas1r sequences was performed and yielded partial canine Tas1r sequences. This sequence information was combined with the sequence information yielded from the BAC library screening to generate the following primers for screening of the positive BAC clones:

| Name | Sequence | ID |
|------|----------|-----|
| dgR2ex3fa: | 5'CTACAACAGCCAGCTGCTCA3' | (SEQ ID NO:78) |
| dgR2ex3fb: | 5'CTTCAGCGAGTTCCGCATAC3' | (SEQ ID NO:79) |
| dogR1Ex4-5f1: | 5'GGTTCTGCTCTGGGAGTGAG3' | (SEQ ID NO:80) |
| dogR1Ex4-5f2: | 5'TTGGCCATGTGGTTACAGAA3' | (SEQ ID NO:81) |
| dogR1Ex1ra: | 5'GAGGTCCTTCTAGGCACAGG3' | (SEQ ID NO:82) |
| dogR1Ex1rb: | 5'CAGAAGTGCCAGGGAAGGT3' | (SEQ ID NO:83) |
| dgex4f1: | 5'ACATAATTGCCTGGGACTGG3' | (SEQ ID NO:84) |
| dgex4f2: | 5'ACCAAAATCCRGTGGCACGG3' | (SEQ ID NO:85) |
| dgex4r1: | 5'CCGTGCCACYGGATTTTGGT3' | (SEQ ID NO:86) |
| dgex4r2: | 5'TCCAGTCCCAGGCAATTATG3' | (SEQ ID NO:87) |
| dgex5f1: | 5'TCCAGTCCCAGGCAATTATGT3' | (SEQ ID NO:88) |
| dgex5f2: | 5'CTYGAAGGGCACCAGCGAGTG3' | (SEQ ID NO:89) |

```
dgex5r1:
5'ACAGGGCACACACTCAAAGC3'          (SEQ ID NO:90)

dgex5r2:
5'CACTCGCTGGTGCCCTTCRA3'          (SEQ ID NO:91)

dgex1r3:
5'GAGTGCAGAGGGAACAGACC3'          (SEQ ID NO:92)

dgex1r4:
5'TCACCTGTCACAGAGGGTCA3'          (SEQ ID NO:93)

dgex3f7:
5'GGACCCTCTCAGTGGCTATG3'          (SEQ ID NO:94)

dgex3f8:
5'ACGGAGAGGACAACCAGGTA3'          (SEQ ID NO:95)

dgR1Ex1f1:
5'CAGCTGCCACAACACAGAGT3'          (SEQ ID NO:96)

dgR1Ex1f2:
5'ATGTCACTCGTGGCAGCTC3'           (SEQ ID NO:97)

dgR1Ex3f1:
5'TACAGCAGATGCCCACACTC3'          (SEQ ID NO:98)

dgR1Ex3f2:
5'GAAACAGGGTGCTTTCCTGA3'          (SEQ ID NO:99)

dgR1Ex6r1:
5'AGGGCTAGTGGAGCAGTTCA3'          (SEQ ID NO:100)

dgR1Ex6r2:
5'AGGCCATGTGTTTCCTCAAG3'          (SEQ ID NO:101)

dogEx1f1:
5'CRCCTGGTCGGCCTGCAGCT3'          (SEQ ID NO:102)

dogEx1f2:
5'GATTACCTCCTSGCAGGYCT3'          (SEQ ID NO:103)

dogEx1r1:
5'CCTGTCACASAGGGTCACC3'           (SEQ ID NO:104)

dogEx1r2:
5'AGRCCTGCSAGGAGGTAATC3'          (SEQ ID NO:105)

dogEx3f1:
5'TCCCCAGCGATAAGTACCAG3'          (SEQ ID NO:106)

dogEx3f2:
5'GGGTCTGGATCTCATTGGTGGG3'        (SEQ ID NO:107)

dogEx6r1:
5'CGCAAGCCAAGTTACACAGATG3'        (SEQ ID NO:108)

dogEx6r2:
5'GGCGGAAAACTTGAAGATGAAG3'        (SEQ ID NO:109)

dogX4r1:
5'GTGTGCCAGGAGATGTTGTG3'          (SEQ ID NO:110)

dogX4r2:
5'GGGTAGTAGGAGGCGATGCT3'          (SEQ ID NO:111)

dogR2X4f1:
5'GAGCGTCGCCTCCTACTRCC3'          (SEQ ID NO:112)

dogR2X4F2:
5'ATCTGGAAGGTCAACTTCAC3'          (SEQ ID NO:113)

dogR2X4F3:
5'TGGGACCKGAGCCAGAACC3'           (SEQ ID NO:114)

dogR2x6R3:
5'CAGAGGGAGAGAAGGCATTG3'          (SEQ ID NO:115)

dogR2x6R4:
5'CCCGGCGTTTGTGATCTAT3'           (SEQ ID NO:116)

dogR3ex2f1:
5'AGCTTCTTCCTCATGCCTCA3'          (SEQ ID NO:117)

dogR3ex2f2:
5'GGGCTACGACCTCTTTGACA3'          (SEQ ID NO:118)

dogR3ex6r1:
5'AGTTGGCCTTTGAGTCAGGA3'          (SEQ ID NO:119)

dogR3ex6r2:
5'GGACCACTGGTTCTGGTCAC3'          (SEQ ID NO:120)

dogR3ex6f1:
5'TGACAGACTGGTGGGTGCTA3'          (SEQ ID NO:121)

dogR3ex6f2:
5'CCATGCTGGCCTACTTCATC3'          (SEQ ID NO:122)

dogR2ex6r1:
5'AGCAGGAGGTGTCGTTCCTA3'          (SEQ ID NO:123)

dogR2ex6r2:
5'CCCAGGATGGTCAGCATAAC3'          (SEQ ID NO:124)

dogR2ex3f1:
5'CTACAACAGCCAGCTGCTCA3'          (SEQ ID NO:125)

dogR2ex3r1:
5'CGGAAGAAGTTGTGCAGGAT3'          (SEQ ID NO:126)

dogR2ex3r2:
5'CTATCATGCGCTTCCTGACA3'          (SEQ ID NO:127)

dogR2ex3r3:
5'TGTGTGCCAAGTCTTCTTGC3'          (SEQ ID NO:128)

dogR2ex1r1:
5'GCAATGGATGAGGAGCATTT3'          (SEQ ID NO:129)

dogR2ex1r2:
5'ACCACATCCAGCCTCACACT3'          (SEQ ID NO:130)

dogR2ex2f1:
5'TTCCTCCTTCCACAGGTGAG3'          (SEQ ID NO:131)

dogR2ex2f2:
5'AAGCCAGGTCAGGATGTCAG3'          (SEQ ID NO:132)
```

Results

Approximately 8 kb of genomic sequence containing the open reading frame (ORF) for canine Ta1r1, approximately 9 kb of genomic sequence containing the ORF for canine Tas1r2, and approximately 4.4 kb of genomic sequence containing the ORF for canine Tas1r3 were obtained. The genomic sequences of canine T1R1, T1R2, and T1R3 are shown in provided in SEQ ID NOs:1, 4, and 7, respectively. The letter "N" denotes gaps between exons or unknown sequences.

A multiple sequence alignment of the T1R receptors of domestic dog (T1R1, SEQ ID NO:2; T1R2, SEQ ID NO:5; and T1R3, SEQ ID NO:8) with known nucleotide sequences of receptors of the T1R family from human (T1R1, SEQ ID NO:15; T1R2, SEQ ID NO:12; T1R3, SEQ ID NO:18), cat (T1R1, SEQ ID NO:133; T1R2, SEQ ID NO:135; T1R3, SEQ ID NO:137), mouse (T1R1, SEQ ID NO:13; T1R2, SEQ ID NO:10; T1R3, SEQ ID NO:16), and rat (T1R1, SEQ ID NO:14; T1R2, SEQ ID NO:11; T1R3, SEQ ID NO:17) is provided in FIGS. 1A-L. An asterisk (*) indicates a conserved nucleotide position among the sequences.

FIGS. 2A-D show the deduced amino acid sequences of the canine T1R taste receptors (T1R1, SEQ ID NO:3; T1R2, SEQ ID NO:6; and T1R3, SEQ ID NO:9) aligned with the amino acid sequences of members of the T1R receptor family from human (T1R1, SEQ ID NO:24; T1R2, SEQ ID NO:21; T1R3, SEQ ID NO:27), cat (T1R1, SEQ ID NO:134; T1R2, SEQ ID NO:136; and T1R3, SEQ ID NO:138), rat (T1R1, SEQ ID NO:23; T1R2, SEQ ID NO:20; T1R3, SEQ ID NO:26), and mouse (T1R1, SEQ ID NO:22; T1R2, SEQ ID NO:19; T1R3, SEQ ID NO:25). An asterisk (*) indicates a conserved nucleotide position among the sequences. A colon (:) indicates an observed conserved amino acid substitution. A period (.) indicates an observed semi-conserved amino acid substitution.

The relatedness of canine T1R receptor family to the T1R family of receptors including human, cat, rat, and mouse T1R1, T1R2, and T1R3 is shown in the phylogenetic tree of FIG. 3. The T1R receptors of the rat and mouse are closely related, while the T1R receptors of human and dog diverge from rat and mouse. Interestingly, the sweet stimuli to which the rat and mouse respond are very similar, whereas those that stimulate human and those that stimulate dog differ from one another and from those for rat and mouse. For example, humans are unique in their ability to taste most high-intensity sweeteners, while dogs apparently find saccharin bitter.

Figure 4A:
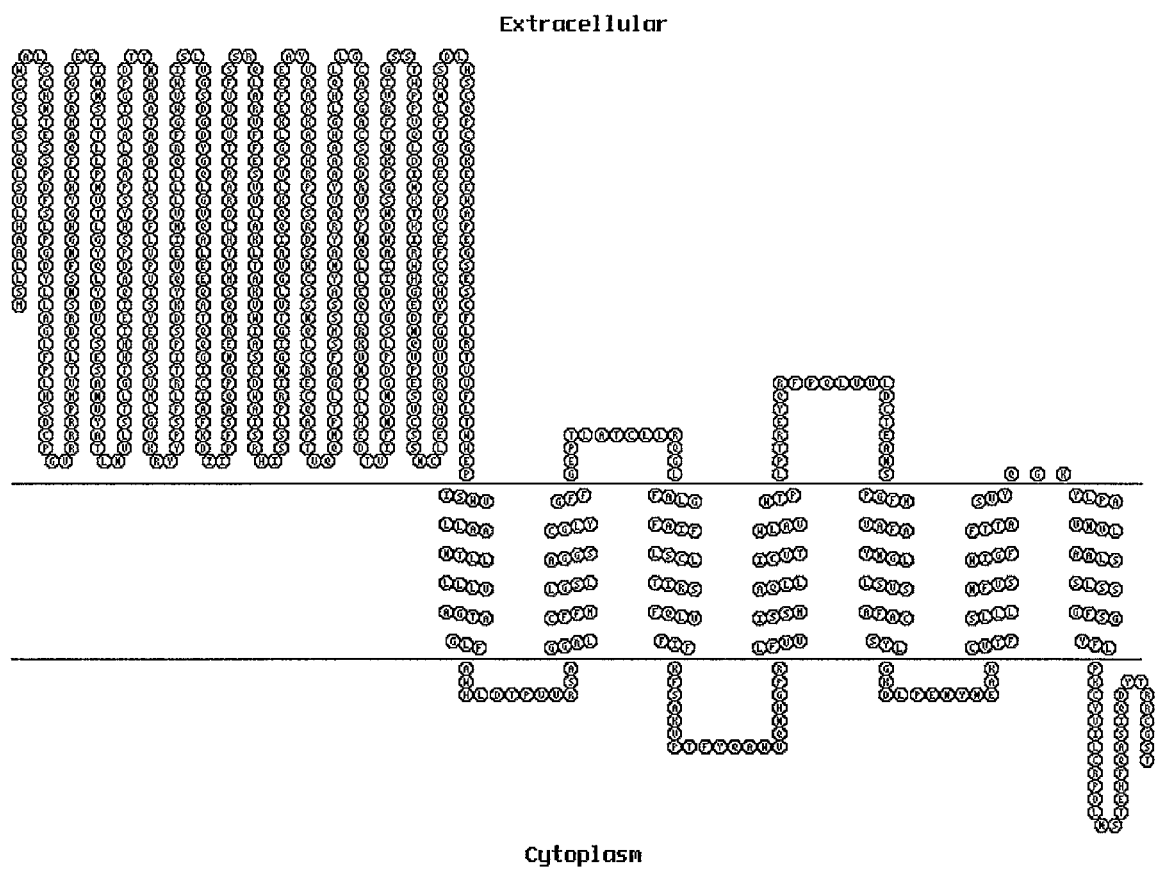
FIGS. 4A-C illustrate the predicted conformation of dog T1R receptors.
Figure 4B:
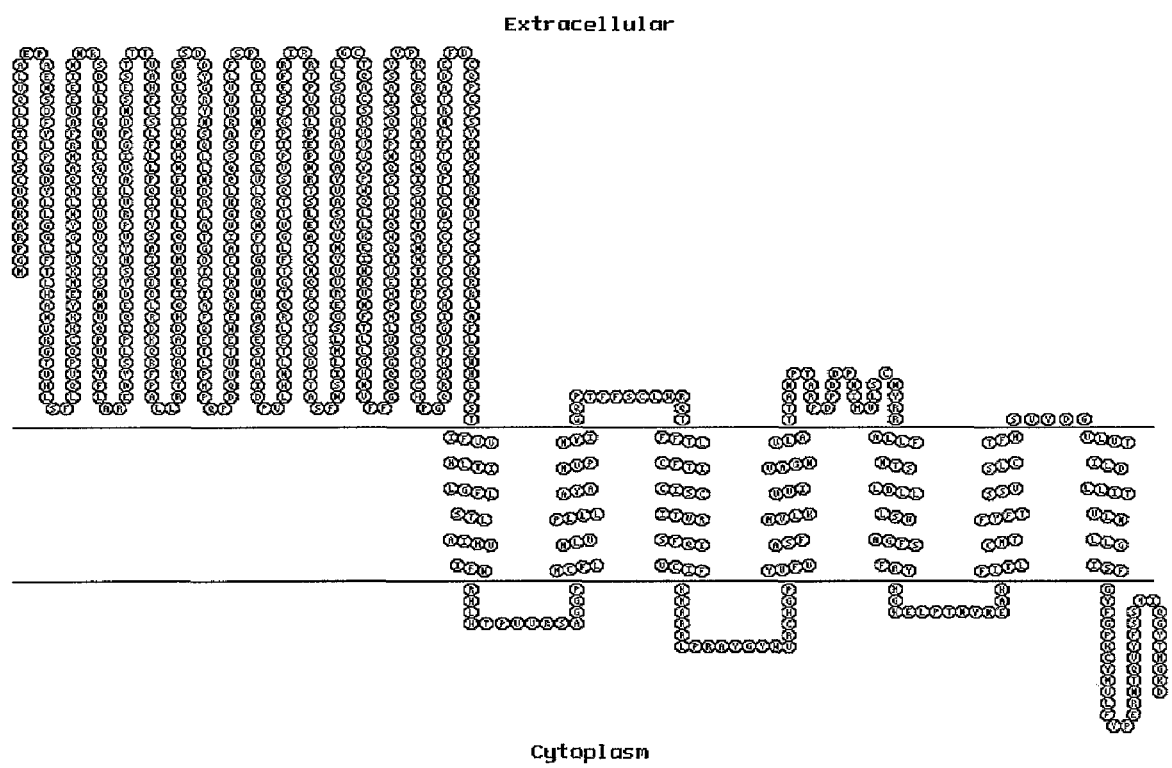
Figure 4C:
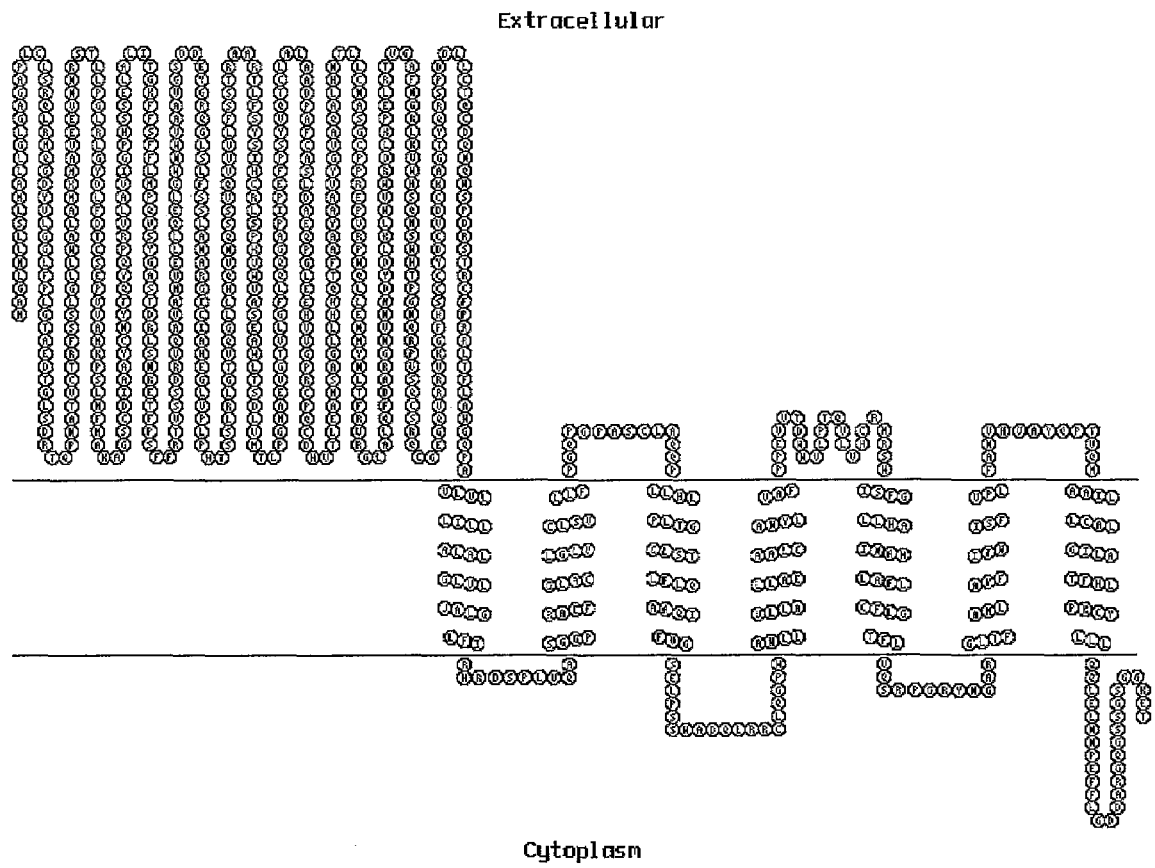

FIGS. 4A-C illustrate the predicted conformation of dog T1R receptors. FIG. 4A shows that the canine T1R1 receptor (SEQ ID NO:3) is a seven-transmembrane domain receptor. The structure of the canine T1R1 receptor was generated through use of the protein modeling programs available online through the European Bioinformatics Institute and the Sequence Analysis and Consulting Service of the University of California, San Francisco. FIG. 4B illustrates the predicted conformation of dog T1R2 receptor (SEQ ID NO:6) as a seven-transmembrane-domain receptor. FIG. 4C illustrates the predicted conformation of canine T1R3 receptor (SEQ ID NO:9), a seven-transmembrane domain structure. The dog T1R receptors T1R1, T1R2, and T1R3 are each predicted to have a seven transmembrane domain-structure, which is typical structure for G protein-coupled receptors involved in taste transduction.

Table 4 shows the percent homology among the members of the T1R family in relation to the dog T1R taste receptors. The portion of Table 4 to the left of the diagonal (in bold type) shows the percent homology based on the open reading frame of the nucleotide sequences obtained from FIG. 1 for the T1R family among human, dog, rat, and mouse. The upper portion to the right of the diagonal (in italic type) shows the percent homology of the T1R members based on the amino acid sequences of FIG. 2. Dog Ta1r1 shows 84% nucleotide sequence homology with human Ta1r1, 91% nucleotide homology with feline Ta1r1, and 78% nucleotide sequence homology with rat and mouse Ta1r1. At the amino acid level, dog T1R1 shows 80% homology with human T1R1, 91% homology with feline T1R1, 73% homology with rat T1R1, and 74% homology with mouse T1R1. Dog T1R1 shows generally low homology with the other known members of the T1R family, T1R2 and T1R3, from human, cat, rat and mouse. The same range of relatively low homology is present among the human, cat, rat, and mouse T1R1, T1R2 and T1R3 receptors from the same species. Dog Tas1r2 shows 83% nucleotide sequence homology with human Tas1r2, 71% nucleotide sequence homology with cat Tas1r2, and 79% nucleotide sequence homology with rat and mouse Tas1r2. At the amino acid level, dog T1R2 shows 76% homology with human T1R2, 62% homology with cat T1R2, and 71% with rat and mouse T1R2. Dog T1R2 shows generally low homology with the other members of the T1R family, T1R1 and T1R3, from human, cat, rat, and mouse. The same range of relatively low homology is present among the human, cat, rat, and mouse T1R2 and the T1R1 and T1R3 receptors from the same species. Dog Tas1r3 shows 78% nucleotide sequence homology with human Tas1r3, 87% homology with cat Tas1r3, 75% homology with rat, and 74% homology with mouse Tas1r3. At the amino acid sequence level, dog T1R3 shows 75% homology with human T1R3, 85% homology with cat T1R3, and 73% homology with rodent both rat and mouse T1R3.

SEQ ID NO: 1 Genomic sequence of canine Ta1r1 obtained from BAC sequencing and PCR:

AGGGTGGGGGGGCTCCCTTTCTGAGC-
CAGGTGAAGAAGCCMCAGGCACCAGAGCAAGA
ACTGAAGCCACAACCATGCAGAG-
GAAGGGTCAGTGGCTGCCACCTGGTTTG-
CATCTGTTC TTTCCCCCTGCTGAGTTCCTGAGCAG-
GACCACAGGCCCAGAAGGCCACGGCAAGCAGCC
AGGTTCCTACAACTGGATTTCAGC-
CCCACCCCTGGCACAAGCATGAAGTTGG-
GAAGCATC TGGGCAGCTGCCATCTATTCTATT-
TAAACGGCCAACCTGGTCAGAGGGCTCTGCTCGG-
CCATGCCAGGCACAGGACTGTGT
GGCCAGCATGTCACTCCTGGCAGCTCAC-
CTGGTCAGCTT GCAGCTCTCCCTCTCCTGCT-
GCTGGGCCCTCAGCTGCCACAACACA-
GAGTCATCTCCTGA
TTTCAGCCTCCCTGGGGATTACCTACT-
TGCAGGTCTGTTCCCTCTGCACTCTGACTGTCCC
GGGGTGAGACGCAGGCCCATGGTGAC-
CCTCTGTGACAGGTGAGTGAGGGGCCTGTGCCT
AGAAGGACCTCTGCCTGCCCTTTCTGC-
CTCTGGGGCCGCCTCCTGAACTATCTCCAGTCCC
TCCCCCTCCTAGGTCACTACCTTCAAGC-
CCTGGCTGGACCTTCCCTGGCACTTCTGCTCAG
GTTCCACTTTATAATATGT-
TATTTTGTCTTCACTATTAGAGT-
GCTTTGTATTGTAATCCCAT TCCAGTTGATCCAG-
GATTTGTGACATAAGTAGGCAGCAAAGGTTAAGCA-
ATCATGGCTTT TCCCTGCTTCCGTGTCCTCCCTAT-
TCCTCTCTGGGTCTCCCGATGGTGAGT-
GTGGTTTTCC ATGCAGGGTAAATGGAAGGCACA-
CAGCAGTAGATGCTTTAGCTTAGTAAAGATTCTTTA
GATTGGGTGCCTTGCCTTCATCAAGTC-
GACAGTCTTGGTAGAGAAAAGCATCTGCTTTTC
TCCTAAAGAAGACAAGTGGTGGGGCAGC-
CCCGGTGGTGCCGGGGTTWAGCGYCTGCCTG
CAGCCCAGGGTGTGAT-
NNNNNNNNNNNNNNNNNNNNNNNNNNNNNNNN-
NNNNNNNNNNNN NNNNNTGGGTTGCTTGGGTG-
GCTCAGCAGTTGAGTGTCTGCCTTTG-
GCTCAGGGAGTGAT CCTCGAGTCCCAGGATC-
GAGTCCCACATTGGACTCTCTTCATGGAGCCTGCT-
TCTCCCTCT TCCTGTGTCTCTGC-
CTCTCTCTCTCTCTCTCTCTCTCT-
GTGTCTCTCATGAATAAATA AATTAAGTCTTTT-
TAAAAAATTAATAAACCATAAAGAAACCAAAAAGC-
ATGTTGTGAAA CACATATTTGTAAAGCATTTGG-
GAATCCTATGAAGCTTTGTGTTTA-
CAAAACCATGCAAT GCTTGGTAAATGGTCAAA-
CACTTAGAAATGAGAATTTTTAAAAAAGAGAGAGG-
GAG GGATAGCTCAGCGGTGGCTGAGCGGTG-
TAGCGCCGCCTTTGGTCCAGGGCGTGATCCTG
GAGACCCAGGATCGAGTC-
CCACGTCGGGCTCCCTGCTTGGAGCCT-
GCTTCTCCCTCTGCC TGTGTCTCTGC-
CTCTCTCTTTCTCTCTTTCTCTCTCTCAATCTGTGT-
ATCTAATAAATAAAA TCTT-

TAAAAAAATAAATAAATCGATGGGTGAG-
TAAAGCAGATTGCCTTCCATTGTGTGGG TGGGCCT-
CATCCAATCAGTTGAAGACCTTAAAAGACTGAGGT-
CCCCTAAAAAGGAAGGA ATTCTGCCTTCAGACT-
CAAGACTGCAGCATCTACCATTAAGG-
GAATTTCTAACCTGCCCT GCAAACATCAGACTTGC-
CAGCCCCATAATCATACGAGCTAATTCCTTAAAATA-
ACCTTTC TCTCTACATATATGTCCAGTTGGTTCT-
GTTTCTCTAGAGAACCCTGATTAATACAGCACGT
GTCTCTGATACAGGACTTCATCAGC-
CTTTCAATGCTAATATGCTTATCTGGGGAGGCATG
GTATGGGTTCCTCCAACTTGTTCCCCAC-
CCCAAACCCCTGCAAAGGCCTATTAACACAAC TGT-
GTGTATGGTACAGGGCCCACATTGAG-
GTCCTGGTTGTAGGGGACTGGACAGATGAC
CTCAGAGTTTCCTCTCTACCCCCAAA-
GAGGGTTTCGGCAAGGCCTTGCCCTTCTCGGCTC
TCAGCTTGGCTTTCTCTACAGGCCCAA-
CAGCTTCAATGGCCATGGCTACCACCTCTTTCAG
GCCATGCGGTTTGGCATTGAGGAGAT-
CAACAACTCCACAACACTGCTGCCTAATGTCACC
CTGGGGTACCAGCTGTATGACGTGTGCT-
CAGAGTCAGCCAATGTGTACCACACTCAAC
GTACTCTCCACGCTGGGGACACATCA-
CATAGAGATCCAAGCAGACCCTTCCCACTATTCC
CCGGCCGCCCTGGCGGTGATTGGACCT-
GACACCACCAACCATGCTGCCACCGCTGCAGCC
CTGCTGAGCCCGTTTCTGGTGCCTGTGG-
TAAGCTGGTGCCCTGACAGGGTGTCCGTCTCC CCT-
TCTGTCAAGTCCAGT-
GTGGGCTAGGGGTGGTGGGCAGGAGCTGCTGGGC-
CCCCAGG CCAGTCTGAGCCCCTGGATCTCCTGGGT-
GATCACTGCTCATTAGTCACATTGCAGGAGGC CCT-
GCCCCATCGCAATCTGCACTCCAG-
CATTTCTTCCCCCAGGTGCTGCATCCAGACCCC
TGGCCTCAATGCTCCTGAGAAAACCCAT-
TCTATTGAAACTGCTGCCGTTTACTCCTNNNN
NNNNNNNNNNNNNNNNNNNNNNNNNNNNN-
NNNNNNNNTTCCTATTGAAATGAGAGATA CACTC-
CTAAAACACAAGTCTGAATATATCACT-
TCTCTGCCTAAATATTTAGGGGCTCCCA ATGGCCTA-
CAGATAAAGACCAAGTATCTTAGCCTGACAGTTAA-
GGCCCCCTTGGCCTAAC CACACTACCTACTTTTGT-
GCTCCTTCTTCTGGCATCCAACCTCT-
TGGGTCATTTCACTCACT GTGTGCAGCTTTTGTTC-
CCTTCCTTTTCTTCTCTCAGAACTCCCTCCTTGGGT-
TTCTGCCTC TTTTCCGCATGTAACTCGTCAGCCTC-
CTATGTCCACTAGAGCTCTCCTTGAGAACCAGGG
CAGGGACCATGTGTCCGCATC-
CCTGGGTCCGGTGCCCAGAACAGGGC-
CAGCACTTGG GGGCCCTGATTGAGACTGATGC-
CACTGAACTTGCTGAACTGAACCCCCGCAGATCAG-
CTA CGAGGCCAGCAGTGTGATGCTTGGAGT-
GAAGCGGTATTACCCCTCGTTTCTGCGCACTAT
CCCCAGCGATAAGTACCAGGTGGAGAT-
CATGGTGCTACTGCTGCAGAGGTTTGGGTGGG
TCTGGATCTCATTGGTGGGCAGCGACG-
GCGACTATGGGCAGCTGGGGGTGCAGGCACTG
GAGGAGCAGGCCACCCAGCAGGGCATCT-
GCATTGCCTTCAAGGACATCATACCCTTCTCT
GCCCAGCCGGGTAATGAGAGGATGCA-
GAGCATGATGTACCACCTGGACCGAGCAAGGAC
CACTGTTGGGTCGTTTTCTCCAGCAG-
GCAGCTGGCCAGGGTGTTCTTCGAGTCCGTGGT
CCTGGCCAAGCTGACTGCCAAGGTGTG-
GATCGCTTCAGAAGACTGGGCCATCTCCAGAC
ATATTAGCAGCCTGCCCAG-
GATCTGGGGCATTGGCACAGTGT-
TGGGCGTGGCCATCCAGC AGAAGCTTGTCCCTG-
GTCTGAAGGAGTTTGAAGAGGCCTACGTCCGGGC-
AAAGAAGGCA GCCCATAGGCCTTGCTCCAGG-
GACTCCTGGTGCAGCAGCAACCAACTCT-
GCAGAGAGTG CCAAGCTTTCACAGTACAGCAGAT-
GCCCACACTCGGAGCATTCTCCATGAGCTCTGCCTA
CAATGCCTACCGGGCTGTCTACGCAG-
CAGCCCATGGCCTCCACCAGCTCCTGGGCTGTGC
CTCTGGAGCCTGTTCCAGGGACCGAGTC-
TACCCCTGGCAGGTAAGGTGGCCCTACCCCTG
GCACCCTGAAACAGGGTGCTTTCCTGAG-
GAAACCAGAGTGATCACTCTCTGCCCAACTAA
GTGTTGGGGGCAGAGGACAAAGGCCAT-
TGACCAGAGGGCTGATCCCCTCTCTTAGGCTT
CAATTCTCTGAACCTCAGCCCCTC-
CCACTCACCATGCTTCATATCCAGGACTAAAAATCA
CTGTAAAGGGGTCCTTTGTTAGAAACT-
TCCTCTCAGAAGCCTGGTTGGGAGGGTTGAGGG
GTTTCCTTGGAGGGGAAGGAGGGCTCT-
GAATTTCCAGATGGCCTGAAACCACCCAAATA
GAAGCATAAGGCCCCAGGCACTTGATTC-
CTGATCCTTCCAGGTCTGGGTGGGTTGAGGAG
GAGCAACATTTGCCATCTACGGCAGCTC-
CCTGATCCCTGTGTATTTCAGCTTCTAGAGCA GATC-
CGCAAGGTGAATTTCCTTCTACACGAG-
GACACTGTGATATTTAATGACAACGGGGA
CCCTCTCAGTGGCTATGACATAATTGC-
CTGGGACTGGAGTGGTCCCAAGTGGACCTTCAG
GGTCATCGGCTCCTCCACGTGGCCTC-
CAGTTCAGCTGGACATAAATAAAACCAAAATCCG
GTGGCACGGAGAGGACAACCAGGTAATA-
GAGACATGGTCACTTACCAGATGACTGCTTT
ATGGGCAGCCTGCAGCCCAAGGATACT-
GTTGACATAGATTACACAGAGCAGGAGGGAGA
TCCCAGGTACCAGGCCAACATGCCTC-
TATCCAGCCCTGCTGGGGAAGCCCCACAGGCAG
CACCCAGATGGCCTGCTGCGCTGGTT-
TATAAAACCAGGGGTTCTGCTCTGGGAGTGAGCT
GTGAAGGCAGATGCACAGAGACTATTTC-
CCATTCCACCTGTGAGTATTCCTTGACTTGGC CAT-
GTGGTTACAGAACACCTGTGGCTTCTTG-
CAGGTGCCTGAGTCTGTGTGCTCCAGCAA
CTGTCTTGAAGGGCACCAGCGAGTAGT-
TGTGGGTTTCTACCACTGTTGCTTTGAGTGTGT
GCCCTGTGAGGCCGGCACCTTCCTCAA-
CAAGAGTGGTGAGTGATCAAGTGAGTGGGTGA
AGGACTGGGCACTCCTAGGGTCTGTA-
CAGCAGAAGAGGGGCTCTCCCTCAGGCCACACA
TGCACAGAACCAGGGCCTTGCTCGCT-
TCACTGCTAGTTAGGTATAGGCTGAAGAATACCT
GTCACCAGACTGAATTCTGAGGAAGCA-
GAAAGAAACAACCTGTTAAAATCCTCAGACCC ACT-
ATGTCTTTACTAGAGAGCTCCCAGC-
CCCATTCCTACAGGCACAATTTTATCCTAAAT
TCAACCTCTTTATGCAAGCAGAGGTAGC-
TACGTTCCCTTGTACCCTTCCCTGCTATCTGTG
TGAAGTCCCTTCTATTGCCCATGCTG-
TAGCTAGCACCTGAACAGCTTGGCCTGAATGAAG
AAACTGTATCTGCAGCTGAAAAAACAG-
CATACTATACCCAGTGATGCAAGGCCAAGATC
AGAGACAAATTAAGGCAACTAAGGGCT-
CAGCCCAGAGTTGGACGCCATGAGCCACATT
CTTTTCCTTTTATGATCTC-
TATGGGCATGGGAACGCATCTCTTCTGT-
TCTCAGAGTCAGAG AAACCACAGAGTGGCAGCA-
CAGGAAGGCGGATTTGGCTAGGTGGATTTAGCAC-

GGAAG TGCTGGGGAGAGAAGAAAATGCCCTTC-
CTTTGGGGCTGGCTGCTCCNNNNNNNNNNNNNNN
NNNNNNNNNNNNNNNNNNNNNNNNNNNNNNNN-
NNNNNCTATTGCCCATGCTGTAGCTAGCA CCTGAA-
CAGCTTGGCCTGAATGAAGAAACTG-
TATCTGCAGCTGAAAAAACAGCATACTA TAC-
CCAGTGATGCAAGGCCAAGATCAGAGAGCAAATTA-
AGGCAACTAAGGGCTCAGCCC AGAGTTGGACGC-
CATGAGCCACATTCTTTTCCTTTTAT-
GATCTCTATGGGCATGGGAACG CATCTCTTCTGT-
TCTCAGAGTCAGAGAAACCACAGAGTGGCAGCAC-
AGGAAGGCGGATT TGGCTAGGTGGATTTTAGCACG-
GAAGTGCTGGGGAGAGAAGAAAATGC-
CCTTCCTTTGG GGCTGGCTGCTCCTATTGGATCAT-
AGCCTCACTGGCAGGTGGGCAGAGCAACCAGAGTA
AAGCCCTCCCTAGGGACCTCTTGGTTTG-
CAAGCCCCTTCTGGGATCACGAGCCATACATA
ACCTACCCAAGGGTCTCCAGAATCTAAT-
TCACACAGGCATCTTGAGGAAACACATGGCCT
CAGGACCCCACTCAGGGCTAC-
CCCCATCTCCAGCTCCTGTGGTATCTC-
CCTCGCAGCACT TTGCAGATCAATGTGGTCTCCCT-
TCCTCATTCCTGAACTGCTCCACTAGCCCTTAGGAC-
TC CCCTCCGCCTTTCCTTCCAGACCTCCA-
CAGCTGCCAGCCTTGTGGGAAAGAAGAGTGGGC
ACCTGAGGGAAGTGAATCCTGCTTC-
CTACGCACTGTGGTGTTTTTGACTTGGCATGAGCC
TATCTCTTGGGTGCTGCTG-
GCAGCTAATACGCTGCTGTTGCTGCTG-
GTGGCTGGGACTGC TGGCCTGTTTGCCTGGCACT-
TAGACACCCCGGTGGTGAGGTCAGCTGGGGCAG-
GCTGTG CTTCTTTATGCTGGGCTCCCTG-
GCAGGGGGCAGCTGTGGGCTCTATG-
GCTTTTTTGGGGA GCCCACCCTGGCCACATGCT-
TGTTGCGCCAAGGCCTCTTTGCCCTCGGCTTTGCC-
ATCTTC CTGTCCTGCCTGACAATCCGCTCCTTC-
CAACTGGTCTTCATCTTCAAGTTTTCCGCCAAGG
TACCCACCTTCTACCAGGCCTGGGTC-
CAAAACCATGGTCCCCGCCTCTTTGTGGTGATCA
GCTCCATGGCCCAGCTGCTCATCTGTG-
TAACTTGGCTTGCGGTGTGGACCCCGTTGCCCA
CCAGGGAGTACCAGCGCTTCCCT-
CAGCTGGTGGTGCTTGACTGCACGGAG-
GCCAACTCCC CGGGCTTCATGGTGGCCTTTGCCTA-
CAATGGCCTGCTGTCCGTCAGCGCCTTTGCCTGCA
GCTACCTGGGTAAGGACCTGCCG-
GAGAACTACAACGAGGCCAAATGCGT-
CACCTTCAGT CTGCTCCTCAACTTCGTGTCCTG-
GATTGGCTTTTTCACCACAGCCAGCGTCTACCAGG-
GCA AATACCTGCCCGCGGTCAACGTGCTG-
GCGGCGCTGAGCAGCCTGAGCAGCGGCTTCAGC
GGTTACTTCCTCCCCAAGTGCTATGT-
GATCCTGTGCCGCCCAGATCTCAACAGCACCGAG
CACTTCCAGGCCTCCATCCAGGACTA-
CACGAGGCGCTGCGGCTCCACCTGACCCCGCCTC
CCCTGTCCCGAGGGCCGAGGGTCAAGC-
GAGGCGCGCACGCCCTGCGCTGTCCCGGAGGC
CTTTGGACTCTTCAGTTTGGGCTCGGG-
GAGTGTAAGCTCGCCGGAGGCCGCCCCGGGCTC
CCAGGCTCTGCCAATAAAGCGCTGAAAT-
GTGCGTCCTGGCTGCGCTTGCTGTCTGGGCC
AGGGGTGGGGCGCGGCCTCCAGCAGGCT-
GAGGGCGCCGCGGGGGCCCACCGCAGCCGG AAC-
CCGGGACCCAGCCCCAGCCGCGCAAC-
CAGCCGTCGCCCAGCTTGGCGTTGCTAAGC
AACATCGAGAGCCGAGCCAACCGC-
CGAGCGCCCAGGGCCTGGACCCCTCTCCCCATTCC
ATTGGCCGTTCTCTGCCTGGCCACGC-
CCTCGAGGGCGGAGCCAGAAGCCCGGCACCTCCC
AGGCTTTCGCCCCTTCCGGCGCGCCCT-
GACGTCACGTCCGGCGGCGGCGGCGGCGGCGG
CGGAGACGGCTGCGTCTCCGTACGGTCG-
GCGGGGCACGTACGGCCCGGGCAGTTGAGCA
GGGGGGCTGTGGCGACGACGAGGTC-
CAGGGTCGGTGGGGCCGGCACCGGGAGCACAGG

SEQ ID NO:4 Genomic sequence of canine Tas1r2 obtained from BAC sequencing and PCR:

TGCAACCTGGGGTGGGGGGTGGGGATTA-
GACTCTGCGTGCCTCCATTTCCTCATC-
CGTGAAATGGGTC TGGCACCATCCGTGCTTATCAT-
GAGCATTAAACGAGATGGTGAACGGCAAGCACGC-
AGCGTGATGCCT GGTTCTTACTGCCAGTGGCTGCT-
GCTCCTGGAACACCTGCTATGGGGC-
CAATGCTACCTATGAATTAT TGTGTGCCAGGCT-
CAGCTTGGGCTCCATTTGCCAGACTACTCTGCCCC-
CTTGGATGAGTACCTGGGTC CTTTGCTCCCAAAT-
GTTGGCTACGTCAGGGGCATGAGACCT-
GTCCTCAATCGAGTGGCAGAAGGCTAT AGGGAGT-
GTCCAAGTGAGCAGGACATGCTTTCTCTACTTCCA-
GGTGGGATTCTCCTAGACCACCCAGG TCCCACCAT-
ACCCTAGGAAGGGACCATCCTAGTTCCG-
GCCCCTTCCTTTCCCCCAGAGTTCGCAAAT
CTCTCCACCTGTGCCAGGTGCTTTC-
CCCGCCCCACGGGCCACGGCGGGGCCAC-
CATTATGTAAATGTC TGTGCAAATCCCCTGATGT-
CAAGCTGCCAGCTCTCTGATGAGGCAGGGCCACCT-
CTGGGGACCCCCAC TTCCCAGCCATGGGAC-
CCCGGGCCAAGGCGGTCTGCTCCCTAT-
TCATCCTGCTGCAGGTCCTGGCTGA ACCGGCT-
GAGAACTCAGACTTCTACCTGCCTGGAGATTACCT-
CCTGGGTGGCCTCTTCACCCTCCATG CCAACGT-
GAAGGGCACCGTCCACCTCAGCTTCCTG-
CAGGTGCCCCAGTGCAAGAAGTGAGTCTCCAGT
GTGAGGCTGGATGTGGT-
GATGGGGGTGGGGTGGGAAGCCT-
GCGCTGGTCCCGTGGTCCTCACGGACCA AGTC-
CCGGACCAAGGGCTTGAAATGCTCCTCATCCATTG-
CAAAACCCCTCATCCTGGGTTATCCCAC TGGC-
CCCCAGGGAGAACCCACACAGTTCATGT-
CACTAAGATCTTCGGCAATTGTGTTCTGAAACATGG
AGACCTGGTAGGCCCAAAGTCA-
CATCTCTTAATAAAGAGTTACAA-
GATATTTGAGCCTGGAGGGGTTG TAGAGACCGT-
CAAAATCACCCCCACCTACTTTGGCAACTGAGTCC-
ATGTCAAGGCCTGGTCTAGAAAC CAAGGGT-
TACGCCTTTGGAAGGCAGAAACGTG-
GTTTTTCTGTAGCAGGTTCTCAGACCG-
GAGGGGAAT GTTTGCCTTTCTCTAGGGCTGTGGTTAG-
GTGGGTGGCGGTGCTTCCAGGACGG-
GAAGGATTTCCTTCA CCCGTCTCACGGGGTGGTG-
GCATCACTCAAGATTAGGTGGACCATCTTCATGCA-
AGCAAGGGATTATG AATTAAAGACCTAGTGCA-
GAGAGGGAAGGCATTCTGAGAGAGAAG-
GAAAAAGGAAGGGATAAAGGTGA TAAAGGGC-
CAACTGTAAGAAATGCATGCTTTTTGTGATGTTGG-
GGAAGATCATGTGCTGATTTGAGAA TGGTGAGGGT-
GATGGTGCCGTGATGGTACCAGGCACAT-
TGTTGAATGTTCTGATGCCTGTGATAGTGG TGGG-
GAGACCAGTGAAGTAACGGTGGTGATGGTGGTGA-
TGTTGATAACATTGATAGCAGTCATACTGG
TGATAATGCAAATGGTGAAGAGTATGGT-
GATGATGATGGTGGTGGTGATGGTGGT-

GATGACGGCGATG ATGGTGATGATGATGATGGTGG-
TAATGATGGGGATGGTAATGGTGGTGAGGATCGTT-
GTGGTGGTGGT GATGGTGATGAAGATGATGATGGT-
GATGAAGATGATGGTGATGAGGGGGATG-
GTGGTGATGGTGGTGA TGAGGATCATGATGGTGAT-
GAAGATGATGGTGCTGGTGTGATGGTGCTGGCAGT-
ATTGGTAGTGGTGG GCACAGACATGTGGTCACAGT-
GATGGCAGTGATGATGATATTGTTCAT-
AGGGAATAGTAGGTGCATGA TGTGACAGTGATGAT-
AGCGATGGCAGACATTGTAGTGGGTAATGGTGATT-
GTATCCGTGGACATTGGT AAAGTGGTGGTAGAT-
CATAGGGATGGTGGTAGTGGTGACAATG-
GTAGTGATTGATGGTAGCCACAAGG ATCATAATGC-
CAGAGGTGGTCATAGGGATGATGGTGAACCTAGAG-
ATGTGGTATGGCATGGTGACCAC GATGTGAT-
GATAAAAATACCAGAATATCCTGGAATG-
GCGCTTTCTTGGATAACTCCTGGGCTTTCCTC TGG-
TAGGCAGAGGAAACAAGCAGGCTCTCCAGGAAAC-
AATCCTGCCCCTTCCCACTCTGGACCTGCTT
CCTACCCCACCCTCCATGGCTTCCCCAG-
GTATGAAATGAAGGTGTTGGGCTACAAC-
CTGATGCAGGCC ATGCGCTTTGCGGTGGAAGAGAT-
TAACAACGCAGCGACCTGCTGCCCGGCGTGCTG-
CTGGGCTATGA GATAGTGGATGTCTGCTACATCTC-
CAACAACGTCCAGCCCGTGCTCTACT-
TCTTGGCACGGGAGGACT ACTCCCTGCCCATCCAG-
GAGGACTACAGCCACTACGTGCCCCGTGTGTTGGC-
GGTCATTGGCCCTGAC AACTCCGAGTCCACTAC-
TACTGTGGCCCATTTCCTCTCACTCTTC-
CTCCTTCCACAGGTGAGGCCCTG GCTCCTGGGG-
GAAGGAGCTGGGGAGGGGGCAGAGGAGGGGTTG-
TCTAGAGGGCTCGCTTCCCCCCACT GGTCAT-
GAGGGGAGAAGGAGGTGGGAAGCCAGGT-
CAGGATGTCAGCCCCAACCCTGGGAGGGAAGCCT
GGCCTATTCATGAGAAGCCTAGGCTTTG-
GAGACAGACAGACCTGGGCGTGCATCT-
TGGCTCTGAGTCT TGGCCATTTTGAGTCACGGAG-
CAAATCTCTTAACTCTTCTGAGCTTCAGCTTCCCCA-
CCTATAAAATG GGATGATGAGAGTTCCATCCTAG-
GACTGTCTGAGGCTTAAAGGATTTAAC-
CTCTGCAGACATTTATAG GATACAGTAGCTGGT-
CAATTATGTAATGGTCGTTATCTAAGGCACCTTCCT-
TGCACAGAAATGAAAAC CCAGAAAATGCTCAATAT-
TATCCTGTACAGTTGCCTAGTA-
CAGGGTCTGCCACATAGTAGGTCCTCAG AAAAAT-
GCCACTAGTATTAGTACTATTATTGTAAGCGTCATCA-
TCATCATGATCGAAAATGCCTCAAC CAGTTTTAGT-
TGGTCTAAAACTTCAACACATTAAAGAG-
CAGCTAGCGCAAGAAGACTTGGCACACAGT AGG-
TAGCTGCAAATACTGTATTTTTGCTGACATTTTTATT-
ATGCAAAGCACCAAGGGTCTGACACACA GTAGGT-
GCCTAGTAAATGTTAATGTACTTAGGT-
GAGGCGTCTCTTTCAGGACTAAACTCATTCTTTCA
TTCCCTTAACAAATATTTATTGAGCT-
CACCCTCCAGTGGGAGAGACAGGCCAT-
GTCAGGAAGCGCATG ATAGGGCTGCTGGAAAGT-
GAGAAGTGCCGTGCACAAAGGTAAAAGGCAAACA-
GGGTGAGGGGGCTGG ACGGGTCGGTGGACA-
GATGGAACGGGGAGAGGGAGGCTG-
CAACTGCAAGCAGGGTGGTCGGGTGAGCC
TCGCTGGCAATTGGACAAAGGCTTGAGG-
GAGGTGAAGGGGTGAGGGAGGTACGGAG-
GTGTCTGGGAGA AGAGCCTTCAGGAA-
GAGGGGGCAGCGAATGCAGAGGCCGGCAGGTGCC-
TGGATTCGCTTATGGAACCA GGGAGCAGAACTGG-
GACCCGGGAGAGACTAGGAGGAGAT-
GAAGTCAGGGAGGTGAGGGCCGGGGTCAG TGATG-
GAGCCCCTTGGGGGGCCCCTGAAGGACTCTGACTG-
TCCCTGCATGACTTTCGGAGCTATTGAAG
GGTTTTCAAGTGCCTGCCGGGTCACCTG-
GCCGCCGCCACGTTCAGCGGAGACTG-
TAGGAGGAAGGGTG GGGGGATGCTTTGGTAGC-
CTGGCGAGGCCCTAGCTCATGTGCCGGCAGGGGT-
CCCCTCCCGCAGATCA CCTACAGCGCCATCAGT-
GACGATCTGCGGGACAAGCAGCGCTTC-
CCGGCCCTGCTGCGCACAGTGGCG GGCGCGGAC-
CACCAGATCGAGGCCATGGTGCAGCTCCTGCTCCA-
CTTCAACTGGAACTGGATCATCGT GCTAGTGAG-
CAGCGACGACTACGGCCGCTACAACAGC-
CAGCTGCTCAACGATCGCCTGGCCACCGGCG
ACATCTGCATCGCCTTCCAGGAGACGCT-
GCCCATGCCGCAGCCCGACCAGGTGGT-
GACGGAGTGGGAG CGCCAGCGCCTGGAGGC-
CATCGTGGGCAAGCTGCAGCAGAGCTCGGCGCGC-
GTCGTGGTGCTGTTCTC GCCAGACCTGATCCTGCA-
CAACTTCTTCCGCGAGGTGCTCCGCCA-
GAACTTCACGGGCGCCGTGTGGA TCGCCTC-
CGAGTCCTGGGCCATCGACCCGGTTCTGCACAACC-
TCACCGAGCTGCGCCAAACCGGCACC TTC-
CTGGGCGTCACCACCCAGAGTGTGC-
CCATCCCGGGCTTCAGCGAGTTCCGCAT-
ACGCCGCACCCC
GGTCAGGCTGCCTGAGCCCAACAGGAC-
CAGCCTGGAGGCCACCTGCAACCAG-
GAGTGCGACACCTGCC AGGACACCACCGCGTCCT-
TCAACAGCATCCTCATGCTCTCCGGCGAGCGCGTG-
GTCTACAACGTGTAC TCGGCTGTCTACGCCGTGGC-
CCATGCATTACACAGCCTTCTGGGCTG-
CACCCAGGCCTGCTCCAAGGA GGTGGTCTAC-
CCCTGGCAGGTGAGGCCCACCCCGTGGAAGGGCA-
GGCATAGAGTGGTTGTCATGGAGA CGCTGGGTG-
CACCTGCTGGGCTCTAGCCTTCCCATCT-
CATGCTGGGTTCTGGGCAAACTGGCGGGAGA GGT-
CATGGGACATGCCCTGCCCTCCAGACACATAGAAC-
CAGAAATCCTTCATGGTGACAAAACTCCTT
TTTTTTTTTTTTTAAATGTAATCATCGC-
CATCCAAGGTGGCCTGTCCTGGTAG-
GAGATTTGGGTGAAA TTCCCTGGAAGGGAGCCTG-
GCAGGCCGTGGGGGCCCCAGGTCCCCTGCCATTT-
CTCTGGATAAGAGGC CTCGGGGGCCCACTTGTG-
TACTCCCTCCTCTCTCTGAGGCCCTACT-
TGAGGTTTACGCACCTCCTCTC GTTCCAGGTTTGT-
GTTGTCTGGATTCCAAGCTGGAATTTAAAACTGTG-
TTTTTCTGACTTGCACTTAT ACACACGCACAC-
CCAATCAGGAAACCCTCATGGGGGT-
GAGAGGTTTTACTGAGGAGCAGAGGAGCAGA GGG-
GATTCACATCAGAGACGCACACCTCATACCTAATAA-
CCCGGCATCTCTGTGCTTGAATGGCTCCT
TGGCTTTTTCGTGGTTTAAGGTTCAG-
GCACTCCTCCAACCCTTGCCTATATTCT-
GTCTTTATTCTCTG CTTCCTCCCTTTTTCTGGATC-
CCCGATCCCCAAATACCTGTACACTTCCTTCCCAG-
AGCAACCTAGC TCTTTAAAAAAAAAAAAAAAAAAC-
CCTCCTTCCNNNNNNNNNNNNNNNNNNNNNN-
NNNNNNNNNNNNNN NNTGAATGTTTATTGAAT-
GAATTAATGAACAGAGGAGCACTTACT-
GTGTGCTAACCCCTTATGTGATT TGCCATCTACCCG-
CAGACACGCTGTGAGTAGACACTGTTGCTTGATGA-
TTGTTCTCCCACATTAGGTC TAGAGAAGTGACGAT-
CACCCAGCTGGGAGTGGC-
CAGGGCAGTGTGGGGGGGGGGCGTGGGGTGGT
AATGAGGCACAAGGGCAGGGGCAGTGGG-
GATGGAGAGGCCTCAGGTGACTAG-
GATACTTGAGGATGGA GGTTGGGAGGTCACACT-

GCCCGTGGTGTTGGGGGGCTGGGGATGCACTCGG-
GGGCACGCTCGGGAAAT CCAGGCTGGCA-
GAGGGCAGAGGGCTTTGGCGGTCCCAGG-
GAAACTGTTCATCAGGTTATGGAATCATA
GAGGGTGGAAGTTGCAAGGTCTTA-
GAATCTCCAGGTCCAATATTTTTGTTT-
TACAAATGGGGGTGGGG ATGGCGCCCTTGTG-
GCATTTGCCACGTGCTTGCCATCTCGGCATCTCAG-
GTACAGTCCCTCTGTCCGT CAGTCGGGGG-
GAGAGCTTGGTACTTAGGTTTGAATC-
CCAGCTTTGCCACCACTAGCTCTGCAACCTTG
GGCAGGTTATTTAATGCATCCGGGCCT-
TGGGTTTCTCATGTGCTAAGCAGAAG-
GAACGCTAAGCACCG TGCTGAGCTCTGGAGGG-
GACTGACCGCGCTGTGTGTCCATGACCCGGTGCA-
GATAGAAGCTCCGTGTC TTCCTCCCCCCCTCTTC-
CATGTCTGACACCAGTGTCTGGACAGT-
GATAATCCAGGCCTCCTCCCCGT CAGGAGAGTTG-
CAGGGAGGATCCTTTCTGACCCCTCTGTCAGAGCC-
CTGGAATCTGGGGTTGCTGAGC CCAGCCTGGC-
CAGGTCAGTGCGGGGATGGGCCTGGC-
CACCAGGACCTGGCTCCTTAAGGCCTCCACCA
TCCTCACCCCTGCCAGGGCCAACCAC-
CTGCGAGGAGCCTTCCTCCTCTCAGCTC-
CCGAGACCATTGC CCCCAGTCGCAGCATCATGTG-
CAAATTCCAGAGACTTCCAGAGCCTGACTCTGTGG-
TCAGGGTGGGAA AAGGCGAGAGCCCAAATCCCT-
TGGCTAACTGTGTGTCGGTCCCTGAAGG-
GAGGTCCCCCAAGATACA GCCCAATAGACTCTCT-
CATTTATGGTGGGAAAATCTAGGAGCTAGATTGATG-
AAATATCTAAGTTGGA AGTTCCCTCAAGGGGTCAG-
CACAGAGGTTCAGTGACTTACCCAAAGT-
CACACAGCAAATTGAGGAAAG AGCTCAGATTG-
GAATTCAGGCCAGAGGATGCCCAGTCCAAAGCAT-
GTTCCAGTTTGTACCAGCCTCTG CATGCTCAGAG-
CAACAGGGGACGATGACATGGG-
GAGAGACTGGAGACTGGC-
CTCTAACTGGGGGGAGG
CAGGAAGCCCCCAGAGGGACAGGGGCAG-
GTGCAGCTGACCAGGGCAGGTGAGGGAG-
GCAGTGGACTCG AGCTCAGCTATGGGTC-
CCCGAGGGGTGGCCGAGTGACTTCCAGGGAGAAG-
GAATAAGATCAACACTTC GGCGGGAGGTGAGTACT-
TACTCGTGTTGAGGCACCGTGCTAAGT-
TCCCAACATAGGTAAACTCTCATT TGTTGCCTC-
CGAGCCCAGGAGACAGGGTTTTTGTTGTCCTGCTT-
TGCTGAAGAGGAAACTGGGGCTCA CAGAGGTCAG-
GCGACAGGTGCAAGGCCTCATAGCAG-
GTGGCAGAGCTGGTGTCTAAACCCAGAGTATC
CGACCCCGGAGCTGGAGCTCTCAGC-
CCCCACCTCCCGGGTAGCCCCCTTCT-
CAGTCCTCTTGCCCCCT TGTCCCCATGTGGAAGT-
CAGGCTAGGGGGATGGGAAAATTTCCCCGGGTCT-
GGCCCCAGCTCTGATG CCAGCCTTTCCCTTTGGC-
CCTTCTAGCTCCTTAAGGAAATCTG-
GAAGGTCAACTTCACCCTTCTGGGC CACAAT-
GTCTTTTTTGGGCAGCAAGGGGACGTGCTCATGCC-
CATGGAGGTCATCCAGTGGCAGTGGGA CCTGAGC-
CAGAACCCTTTCCAGAGCATCGCCTC-
CTACTACCCCAAGCTGCGGCAGCTCAAGGCCATCC
ACAACATCCTGGCACACCGCCAACAA-
CACGGTCAGCTCTCT-
GAGGGCTGGGGCTGGGCCCCGGCTC
ACCCTGGGGTGGCGAGGGCCCTCTGGAC-
CCGAGATCCGTCACTGA-
CAGCGGGTGGGGGGGTGTCTGT
GCAGTGGGGGGGGGCGTCTAGGCCCT-
GTCCCTCCCGTTGATAAGGC-
CTAGGGTTTCTGGCTCCCCGA GACCCAGGGGCT-
CAGGGGCTGTGCCCAGTGAACGTGTGCTGGACAC-
GCGTGTGCTGAGGACTCAGCTC TCACGTCAACCAT-
TGCTGGTGCTCCCCGTACGGTAGCTG-
TACCCTCAACTGCGTCTGGCACCTGTCAT
TCCAAAGCTCCTCTGTTTTACCCTCTTA-
GATGCATAACAAGCTGTCGGAGTGGTG-
GTGGTGGTGTGTG GGGACAGACAGGGACCCAGC-
CTCGTAGGAGGGGAGGGGGAGGGGGAGGGGATAC-
AGAAGCTCCAAGAG CCTTCCTCATCTGGATC-
CTCTCCCCGCCCCATCCCCCTTTATCCT-
CANNNNNNNNNNNNNNNNNNNNN
NNNNNNNNNNNNNNNNNNNNNNC-
CGAGATCTCCAGGATCACGCCCTGGGC-
CAAAGGCAGGCGCCAAAC TGCTGCGCCACCCAGG-
GATCCCCCAGACGTCCAGTTCTAATGGCAACTCCT-
GCTCCTTCCCCATCCCA GATGGGGGCCAGGCTTC-
CCTCCCCAGAGCATCCTGCTGGTTG-
GTCTCAGGGGCTCTTGTCCTCCTCCC TCCAGATC-
CCCGTGTCCATGTGTTCCAAGGACTGCCATCCTGG-
CCAAAGGAAGAAGCCTGTGGGCATC CACTCCT-
GCTGCTTCGAGTGTATTGACTGCCTTC-
CTGGCACCTTCCTCAACCGAACTGCAGGTGGGAC
TTGCAGACCCGCACCCCTGCTCCCCAC-
CCTCAGCCCTGCCCTGCTCTGAGAG-
CAGGGTCTCTGGAGTC TCCCCCACAGGATGTAAGT-
GTCCAAAGGCCAGGGTCCATGCCTGATTCCAGTGT-
ATCTCCCTAGGAAT TGGTGTAGAGAAAAATCT-
TCAATGCTCGCTGCTAGGGAGGGTGG-
GAGAAGGAACAGCCCTCCACCAGG CAAGGCTGT-
CACTGGTCCCCACTCCACGCACATGTAGCTGAGGG-
CTCAGGGGTGTCAGACCAGAGAAT GTCCATTG-
GATGGATGGCTGGATGGATGGAT-
GAGTGGGTGAATGAATGAATAAATGAAT-
GTCTCTGTC
CATAGAAGAAATGTTTCTGGCAGACGGG-
GACAGGATCTGGTTTATCTCTCTGAC-
CTCCCAGTGCCTAA TGTAGTGCAGAGCGTAT-
CACGTTTGCTCAGTGAATTTTGATTGAGTGACATC-
CTTGATCAGAAGAGCT CATACCTCCCCCTATAGAT-
CACAAACGCCGGGAAGGTGCGGACAAT-
GCCTTCTCTCCCTCTGTTTTAG TGTTGAGCACCGT-
TCACAGCTGGGGCTTAAATTATTTTTTTTCGTGACT-
TCCTCATCAGAGTACTTAC CGTGGGCCCAGCAT-
AGCCCAGAGCCCAGAGTAGGTGCCCAA-
CAAAAATTTGTTGCATGATTTCACAGG CTGTTC-
CCCTACCCAGTTGGTCGGTTCCTGACGGCAGGGG-
GCTGGCTAGGTTTCGCCCACGTCTCTGT CCTC-
CCACCTCAGGTGCCCATCACCCACTGTG-
GAGGGTGTTTGAAAAAAAAAATGTGT-
TGAAGGAATT
CTTTGGACCAATGTGTGAGTGTCTATGC-
CACCAGAGGGTAAGGTCTCGGGAGCAAG-
GAATTACAGTTG TTAGGATCCGAGTCAAGGGAAC-
CTCGGTTCAAACCCTGCCTCTGTAACGACCACCTG-
GCTGAGCCTCG GGTTACTCATCTGTGAAATGGGGT-
TGCAGGGAGGAGCTGATGGGC-
CAGTGGGTGTAAGAGGGCAGTG AGTGGTGGTG-
GCTAGGCCGGTAGGCGTTGCCCTCAGCTCGCCCCC-
CACCCCCGAGGCCTGGCCCGGGG CGGGTGCAGAG-
GATGGGGGTGCTGCCAAGTGGGCGAG-
GCTGACGGGAGCTGCCGTGGGCTCTTGCAGA
CGAATTTGACTGCCAGCCTTGCCCAAGT-
TACGAGTGGTCCCATAGGAACGACAC-
CTCCTGCTTCAAGC GGCGGCTGGCCTTCCTC-
GAATGGCACGAGCCCTCCACCATCTTTGTGGTTAT-

GCTGACCATCCTGGGC TTCCTCAGCACCCTGGC-
CATCATGGTGATCTTCTGGAGGCACCTC-
CACACGCCCGTGGTTCGCTCGGC CGGGGGC-
CCCATGTGCTTCCTGATGCTGGTGCCGCTGCTGCT-
GGCGTACGCCATGGTCCCCATGTACA TAGGGCAGC-
CCACGTTCTTCTCGTGCCTCTGGCGCCA-
GACCTTCTTCACCCTCTGCTTCACCATCTGC ATCTC-
CTGCATCACCGTGCGCTCTTTCCAGATCGTCTGCAT-
CTTCAAGATGGCCAGGCGCCTCCCGCG CGC-
CTACGGCTACTGGGTGCGCTGC-
CACGGGCCCTACGTCTTCGTGGCGTCCT-
TCATGGTGCTCAAGG
TGGTCATCGTGGCAGGCAACGTGCTGGC-
CACGACCGCCAACCCTACTGCCCGC-
CCCGACCCCGATGAC CCCAATATCATGGTCCTGTC-
CTGCAACTACCGCAGGGCGCTGCTGTTCAACACCA-
GCCTGGACCTGCT CCTGTCCGTGGCGGGCT-
TCAGCTTCGCCTACATGGGCAAGGAGCT-
GCCCACCAACTACAACGAGGCCA AGTTCATCAC-
CCTCTGCATGACCTTCTACTTCACCTCCTCCGTCTC-
CCTCTGCACCTTCATGTCCGTC TATGATGGGGTC-
CTGGTCACCATCCTGGACCTCTTGAT-
CACCGTGCTCAACCTTCTGGGCATCAGCTT TGGC-
TACTTTGGTCCCAAATGCTACATGGTCCTCTTCTAC-
CCAGAGCGCAACACGCAGGTCTACTTCA GCAGCAT-
GATTCAGGGCTACACCATGGGGAAGGAC-
TAGCACCGCCCACTAGGGCTGCCCAGGGGGCCC
AAGGGCTCAGCTGGGGCGGGGG-
GAGACGCAGACGGGATGGGGAGGTG-
GAGCTGGGTGCAGGTCGCAG TTTCCCGGTAGCT-
GTTTGGCTTGCTAGGCCCTGCCGCCCATTCTAGGA-
AAACCTGCCCAGGGTGGGGA CCCTACTGGTGTC-
CCCGACAGAGATGGATTTGAGCAGCCTA-
CAGTCTCCATCGGTGGTCACAGCGGA TGCAG-
GCTCGTTCCCCTCCCTCCTGTTCGCGGGGAGCGAA-
GGCTGGGCTGCAGGGGCTGGGGCTGGGA
CGGGCTGGTGT

SEQ ID NO:7 Genomic sequence of canine Tas1r3 obtained from BAC sequencing and PCR:

TACCTACTCCTCAGGTCACTTGCACCTC-
CCTCAGGCAGCTGGAGACCCCAGGAC-
CCTCTGGCAGAGAA GTCCTGAGTGTCCTTCCTC-
CTTTCCAGGAGTGGGGTGGGGCTTGGGCACAGGC-
ATGTAACAAGATGTG GTCAGTGGTCAGTCAGAGC-
CCGACTGCCCAGGTCACTGTCAATCA-
GAGAGCCTCGTGGTGGCATCAGG ATAAACGAGTC-
CGGGATCCCTGGGTGGTACAGTGGTTTGGCGCCTG-
CCTTTGGCCCGGGGCACGATCC TGGAGACCCGG-
GATCAAATCCCACATCGGGCTCTCGGTG-
CATGGAGCCTGCTTCTCCCTCTGCCTGTG TCTCT-
GCCTCTCTCTGTGTGACTATCATAAATAAATAAA-
AATTTTAAAAATGTTTAAAAAAAAAAA
AGGATAAACGAGTCCAAGAAGCGCAGAC-
CTGCAAGGCCTAGGAAAGTGAGGGTGTC-
CCCAGGGGCCCC TGGACATGACTGGTAAGGACAG-
GTGATAATTTTGCTAAGCAAATCCTCTGCCCTCCCC-
TGCCCCCACT CATCATATTGGGGGCCCCACTCG-
GTTCTCTCATTTGCCGTCCCTGCTG-
GAAGCTGCCACCTGCCATG GCAGGCCTGATGCTC-
CTGAGCCTCATGGCTCTCTTGGGCCTTGGAGCAGG-
CGCCCCATTGTGCTTATC CCGGCAGCTCAGGATG-
CAAGGGGACTATGTGCTGGGCGGGCTCT-
TCCCCCTGGGCACAGTCTGAGGACA CAGGTCT-
CAGTGACAGGACACAGCCCAATGCCACTGTGTGC-
ACCAGGTAGGGATGCCGGGGCTGGGAA
GCAAAGGGTGACGGGGTGGGGGGCT-
CAGCTCTGGGGTGCTCCCAAGGGAG-
GACGTGGGGTCAGCCCCC CACAACCCTTGTGGC-
CCAGGTTCTCGTCCCTCGGCCTGCTCTGGGCGCTG-
GCCATGAAGATGGCGGTG GAGGAGGTCAACAA-
CAGGTCCACGCTGCTGCCAGGACTGCGC-
CTGGGCTACGACCTCTTTGACACATG TTCGGAGC-
CTGTGGTGGCCATGAAGCCCAGCCTCATGTTCATG-
GCCAAAGCGGGCAGCTGCGACATCG CCGCCTACT-
GCAACTACACGCAGTACCAGCCCCGTGT-
GCTGGCAGTCATTGGGCCACACTCATCTGAG
CTCGCCCTCATCACCGGCAAGTTCT-
TCAGCTTCTTCCTCATGCCTCAGGTGT-
GCTCCCCCTCCTCTCC TGGGTCCCCTGC-
CCCCACTGGCCCTGCCCACAGGAGCCCCCACATCA-
GGAGGTGCCTCCCGGCTGCCA CAGGTCAGC-
TACGGGCCAGCACCGACCGGCTGAG-
CAACCGGGAGACGTTCCCATCCTTCTTCCGCAC
GGTGTCCAGCGACCGCGTACAGGCAGTG-
GCCATGGTGGAGCTGCTGCAGGAGCTTG-
GCTGGAACTGGG TGGCTGCAGTGGGCAGCGAT-
GACGAGTATGGCCGGCAGGGCCTGAGCCTCTTCTC-
CAGCCTGGCCAAT GCCAGGGGCATCTGTATTGCG-
CATGAGGGCTGGTGCCATTGCCGCA-
CACGGATAGCCTGCGGCTGGG CACTGTCCAGGGC-
CTACTGCACCAGGTAAACCAGAGCAGCGTGCAGGT-
GGTGGTGCTTTTCTCTTCCA CTCGTGCTGCCCG-
CACCCTCTTCAGCTACAGCATCCACTG-
CAGGCTCTCGCCCAAGGTTTGGGTGGCC AGTGAG-
GCCTGGCTGACCTCGGACCTGGTCATGACGCTGCC-
TGGCATGGCTGAGGTGGGCACCGTGCT
TGGCTTTCTGCAGCAGGGCGC-
CCCAATACCCGAGTTCCCATCCTATGTG-
CAGACCTGCCTGGCCCTGG CTGCTGACCCTGC-
CTTTTGCGCCTCACTGGATGCAGAGCAGCCGGGCC-
TGGAAGAGCACGTGGTGGGG CCCCGCTGTC-
CCCAGTGTGACCACGTCACTCTGGAGGC-
TATGTCTGCAGGGCTGCTGCACCACCAGAC
CTTCGCGGCCTACGCAGCCGTGTATG-
GCGTGGCCCAGGCCCTCCACAACACACT-
GCTCTGCAATGCCT CAGGCTGCCCCCCACGG-
GAGCCAGTGCGGCCCTGGCAGGTAAGGCCAGGAG-
GCCCCGCACTTCTGAGG AGCAGTGTCAGTGGG-
GAGTCTGGGCCGGGGACAGCTACTGGC-
CTGGCCCCACCCACCTGCTCCAATCT GCCTAC-
CAGCTCCTAGAAAACATGTACAACTTGACCTTCCG-
TGTGCGCGGCTTAGCACTGCAGTTCGA TGC-
CAGGGGGAACGTGAATATGGATTATGAC-
CTGAAACTGTGGGTGTGGCGGGACCT-
GAAGCCCGAGT
TGCGCACCGTAGGTGCCTTCAACGGC-
CGCCTGAAGGTCTGGCACTCCCAGAT-
GTCCTGGCACACACCT GGGAACCAGGTGAGCAC-
CAGGTGGCACGGCCCTAACTGCACAGCAGCTTCC-
CTTCAGCCCCATACGA GCTCTGGCTCT-
GCTGGGGGGGGGGGTGAGGTGGGGGAG-
CACCCCAAAGACTGGGCGGGCGCACTCAG CACAG-
CACAGCCTGAGCCCCAAGGCCTTTGTGGCAGCGG-
CCCGTGTCCCAGTGCTCCGGCAGTGCGG
GGAGGGCCAGGTGCGCCGTGT-
GAAGGGCTTCCACTCCTGCTGCTAT-
GACTGCGTGGACTGCAAGGCGG GCACCTAT-
CAGCGCAGCCCAGGTGAGCACCTCTCCAAGGCCC-
ATACACACGGGACAGGTGGGGGCAGG GAC-
CCCCAGGTCTCATGTCCTGACTCAAAG-
GCCAACTTTGAGGCCAGAG-
CAAGTGGGTGGGAGCCTGA
ACTCTCCCCCAAGTGCCCCATCTTCCTC-

CCACATGACAGATGACCTCCTCTGCAC-
CCAGTGTGACCAG AACCAGTGGTCCCCAGACCG-
GAGCACACGCTGCTTCCCCCGCAGGCTCACTTTCC-
TGGCATGGGGGCA GCCGGCTGTGCTGGTGCTGCT-
TATACTGCTGGCTCTGGCGCTGGGCCTG-
GTGCTGGTGGCCCTGGGGC TCTTTATTAGGCAC-
CGGGACAGCCCACTGGTTCAGGCCTCAGGGGGGC-
CACGG-
GCCTGCTTTGGCTTG GCCTGCCTGGGCCTTGTCT-
GCCTCAGTGTCCTTCTGTTCCCTGGC-
CAGCCGGGCCCTGCCAGCTGCCT GGCCCAGCAGC-
CACTGCTTCACCTTCCACTCACTGGCTGTCTGAGC-
ACACTTTT-
CCTGCAAGCGGCCC AGATATTTGTGGGTTCA-
GAGCTGCCATCAAGCTGGGCAGAT-
CAGCTGCGTAGGTGCCTGCAGGGGCCC TGGGC-
CTGGTTGCTGGTGCTGCTTGCTTTGCTGGCGGAAG-
CGGCATTATGTGCCTGGTACCTGGTGGC CTTTC-
CACCAGAGGTGGTGACAGACTGGTGGGT-
GCTACCCACGCAAGTGCTGGTGCACTGCCGAATGC
GCTCCTGGATCAGCTTTGGCCTAtTG-
CATGCCATCAATGCCATGCTGGCCTTC-
CTCTGCTTCCTGGGC ACGTTCTTGGTGCAgAgCCG-
GCCAGGCCGCTACAATGGCGCCCGGGGTCTCACTT-
TTGCCATGCTGGC CTACTTCATCACCTGGATCTC-
CTTTGTCCCTCTCTTTGCCAATGTGCAT-
GTGGCCTACCAGCCCACTG TGCAGATGGCCGC-
CATCCTCCTCTGTGCCCTGGGCATCCTGGCCACCT-
TCCACCTGCCCAAGTGCTAC CTGCTGCTGCAG-
CAGCTGGAGCTCAACAACCCGGAGTTCT-
TCCTAGGAGATGATGCCAGAGGACAGGG CAG-
CAGTGGTAGTGGGGGGAAGGAGACTTAGGGCAAA-
AACAAGTGACCCCTGACCCAGTGACCCCAGA
CCTAGCTGAGATACCCACAAATCA-
CATTTCTATGAAGCAACCACCAACCTG-
GACCCCAGCTGCTGAGA CCACCCCTTTCTAGATC-
CTAACTGTAGGCTAACTAGCTGACCTTGATGGAAC-
AGTGACCGTTAGGCCT GTAGCATCCATGAAGGGCT-
TCAGCACCCACCTGAGGCCCCA-
GAAAAGCTTTGTCCCTGTCCTAGCCAA GGCCTG-
GCCAAGGCCTACCCATGTGATCCAGCCCTACTGAA-
CAAAAGGTCCACGAAAAGGATCCTTGA GGCTC-
CTGGCGTTCATGCCAAGAGCTCAAGA-
CACCTACCAGCCAGGTCACTTAAAGGC-
CAAACTGGGC
ATTACTTGCCTGGCCAGGCCCAGCCTG-
GAGCCTCCAGCCAGCACCCTCTCCAAG-
CATCACAGGGATGG GAGATTGGTAAGAGGGCTG-
GAGATGTCGTGACCCCTCTGCAGGGGTCTATGACT-
GACCACAGGACCAG ATGGGGCAGGAATGGTGAG-
CAGGGAAGAGGGCTAGTGGGAGGGTA-
CATACCCAACCTCCTTCT

TABLE 4

Percent Homology Among Diverse Species for T1Rs

| Species | Mouse T1R1 | Mouse T1R2 | Mouse T1R3 | Rat T1R1 | Rat T1R2 | Rat T1R3 | Human T1R1 | Human T1R2 | Human T1R3 | Cat T1R1 | Cat T1R2 | Cat T1R3 | Dog T1R1 | Dog T1R2 | Dog T1R3 |
|---|---|---|---|---|---|---|---|---|---|---|---|---|---|---|---|
| Mouse T1R1 |  | *36* | *30* | *90* | *36* | *30* | *73* | *37* | *30* | *74* | *30* | *30* | *74* | *36* | *29* |
| Mouse T1R2 | 55 |  | *28* | *36* | *91* | *28* | *34* | *69* | *28* | *36* | *53* | *28* | *35* | *71* | *28* |
| Mouse T1R3 | 33 | 15 |  | *31* | *28* | *92* | *30* | *27* | *72* | *30* | *25* | *72* | *30* | *27* | *73* |
| Rat T1R1 | 91 | 55 | 33 |  | *37* | *31* | *73* | *37* | *31* | *74* | *26* | *31* | *73* | *38* | *31* |
| Rat T1R2 | 55 | 91 | 15 | 57 |  | *28* | *34* | *71* | *29* | *36* | *52* | *28* | *36* | *71* | *29* |
| Rat T1R3 | 33 | 21 | 93 | 32 | 15 |  | *31* | *27* | *73* | *30* | *26* | *72* | *30* | *27* | *73* |
| Human T1R1 | 79 | 56 | 35 | 79 | 56 | 35 |  | *35* | *31* | *81* | *29* | *31* | *80* | *37* | *31* |
| Human T1R2 | 57 | 78 | 17 | 56 | 78 | 17 | 57 |  | *28* | *36* | *58* | *28* | *36* | *76* | *27* |
| Human T1R3 | 41 | 39 | 73 | 39 | 36 | 75 | 40 | 38 |  | *29* | *23* | *73* | *30* | *28* | *75* |
| Cat T1R1 | 79 | 54 | 35 | 78 | 56 | 35 | 84 | 56 | 53 |  | *28* | *30* | *91* | *38* | *30* |
| Cat T1R2 | 42 | 64 | 22 | 41 | 61 | 22 | 44 | 72 | 48 | 44 |  | *29* | *30* | *62* | *25* |
| Cat T1R3 | 33 | 34 | 74 | 36 | 36 | 75 | 53 | 39 | 79 | 53 | 39 |  | *30* | *28* | *85* |
| Dog T1R1 | 78 | 54 | 36 | 78 | 56 | 35 | 84 | 57 | 50 | 91 | 41 | 54 |  | *38* | *30* |
| Dog T1R2 | 56 | 79 | 35 | 56 | 79 | 37 | 59 | 83 | 51 | 58 | 71 | 40 | 57 |  | *28* |
| Dog T1R3 | 34 | 34 | 74 | 34 | 36 | 75 | 49 | 39 | 78 | 53 | 35 | 87 | 54 | 39 |  |

Note:
Upper right cells (*italics*) contain deduced amino acid homology; lower left cells (bold) contain nucleotide homology

What is claimed is:

1. An isolated and purified polynucleotide encoding a T1R receptor, said T1R receptor comprising the amino acid sequence of SEQ ID NO:3.

2. The polynucleotide of claim 1, wherein said polynucleotide is DNA.

3. The polynucleotide of claim 1, wherein said polynucleotide is RNA.

4. An expression vector comprising the polynucleotide of claim 1 operably linked to a promoter.

5. A host cell comprising the expression vector of claim 4.

6. The host cell of claim 5 wherein said cell is mammalian.

7. The host cell of claim 6 wherein said cell is a human, murine, or canine cell.

8. The host cell of claim 5 wherein said cell is bacterial.

9. A cell culture comprising at least one cell of claim 5.

10. A method of producing a canine T1R receptor comprising culturing the host cell of claim 5 and recovering said receptor from said host cell.

11. The canine T1R receptor produced according to the method of claim 10.

12. An isolated and purified T1R receptor polypeptide comprising an amino acid sequence having 95% identity with SEQ ID NO:3.

13. An isolated and purified T1R1 receptor polypeptide comprising the amino acid sequence of SEQ ID NO:3.

14. An isolated and purified polynucleotide encoding a T1R receptor, said polynucleotide comprising a nucleic acid sequence having at least 95% identity to SEQ ID NO:1 or SEQ ID NO:2.

15. An isolated and purified T1R receptor comprising a T1R1 polypeptide comprising the amino acid sequence of SEQ ID NO:3 and a T1R3 polypeptide comprising the amino acid sequence of SEQ ID NO:9.

16. A method for identifying compounds that interact with a canine T1R receptor comprising:

contacting a canine T1R receptor comprising a T1R1 polypeptide comprising the amino acid sequence of SEQ ID NO:3 and a T1R3 polypeptide comprising the amino acid sequence of SEQ ID NO:9 with a test compound, and detecting interaction between said T1R receptor and said compound.

17. A method for identifying an agonist of a canine T1R receptor comprising:

contacting a T1R receptor comprising a T1R1 polypeptide comprising the amino acid sequence of SEQ ID NO:3 and a T1R3 polypeptide comprising the amino acid sequence of SEQ ID NO:9 with a test compound, and detecting an increase in biological activity of said T1R receptor in the presence of said compound relative to biological activity of said T1R receptor in the absence of said compound.

18. A method for identifying an antagonist of a canine T1R receptor comprising:

contacting a T1R receptor comprising a T1R1 polypeptide comprising the amino acid sequence of SEQ ID NO:3 and a T1R3 polypeptide comprising the amino acid sequence of SEQ ID NO:9 with a test compound with a test compound, and detecting a decrease in biological activity of said T1R receptor in the presence of said compound relative to biological activity of said T1R receptor in the absence of said compound.

* * * * *

SEQUENCE LISTING

<160> NUMBER OF SEQ ID NOS: 138

<210> SEQ ID NO 1
<211> LENGTH: 7951
<212> TYPE: DNA
<213> ORGANISM: canine
<220> FEATURE:
<221> NAME/KEY: misc_feature
<222> LOCATION: (1037)..(1082)
<223> OTHER INFORMATION: n is a, c, g, or t
<220> FEATURE:
<221> NAME/KEY: misc_feature
<222> LOCATION: (2757)..(2797)
<223> OTHER INFORMATION: n is a, c, g, or t
<220> FEATURE:
<221> NAME/KEY: misc_feature
<222> LOCATION: (5733)..(5779)
<223> OTHER INFORMATION: n is a, c, g, or t

<400> SEQUENCE: 1

| | | | | | | |
|---|---|---|---|---|---|---|
| agggtgggg | ggctcccttt | ctgagccagg | tgaagaagcc | mcaggcacca | gagcaagaac | 60 |
| tgaagccaca | accatgcaga | ggaagggtca | gtggctgcca | cctggtttgc | atctgttctt | 120 |
| tccccctgct | gagttcctga | gcaggaccac | aggcccagaa | ggccacggca | agcagccagg | 180 |
| ttcctacaac | tggatttcag | ccccaccct | ggcacaagca | tgaagttggg | aagcatctgg | 240 |
| gcagctgcca | tctattctat | ttaaacggcc | aacctggtca | gagggctctg | ctcggccatg | 300 |
| ccaggcacag | gactgtgtgg | ccagcatgtc | actcctggca | gctcacctgg | tcagcttgca | 360 |
| gctctccctc | tcctgctgct | gggccctcag | ctgccacaac | acagagtcat | ctcctgattt | 420 |
| cagcctccct | ggggattacc | tacttgcagg | tctgttccct | ctgcactctg | actgtcccgg | 480 |
| ggtgagacgc | aggcccatgg | tgaccctctg | tgacaggtga | gtgaggggcc | tgtgcctaga | 540 |
| aggacctctg | cctgcccttt | ctgcctctgg | ggccgcctcc | tgaactatct | ccagtccctc | 600 |
| cccctcctag | gtcactacct | tcaagccctg | gctggacctt | ccctggcact | tctgctcagg | 660 |
| ttccacttta | taatatgtta | ttttgtcttc | actattagag | tgctttgtat | tgtaatccca | 720 |
| ttccagttga | tccaggattt | gtgacataag | taggcagcaa | aggttaagca | atcatggctt | 780 |
| ttccctgctt | ccgtgtcctc | cctattcctc | tctgggtctc | ccgatggtga | gtgtggtttt | 840 |
| ccatgcaggg | taaatggaag | gcacacagca | gtagatgctt | tagcttagta | aagattcttt | 900 |
| agattgggtg | ccttgccttc | atcaagtcga | cagtcttggt | agagaaaagc | atctgctttt | 960 |
| ctcctaaaga | agacaagtgg | tggggcagcc | ccggtggtgc | cggggttwag | cgyctgcctg | 1020 |
| cagcccaggg | tgtgatnnnn | nnnnnnnnn | nnnnnnnnn | nnnnnnnnn | nnnnnnnnn | 1080 |
| nntgggttgc | ttgggtggct | cagcagttga | gtgtctgcct | ttggctcagg | gagtgatcct | 1140 |
| cgagtcccag | gatcgagtcc | cacattggac | tctcttcatg | gagcctgctt | ctccctcttc | 1200 |
| ctgtgtctct | gcctctctct | ctctctctct | ctctctctct | gtgtctctca | tgaataaata | 1260 |
| aattaagtct | ttttaaaaaa | ttaataaacc | ataagaaac | caaaaagcat | gttgtgaaac | 1320 |
| acatatttgt | aaagcatttg | ggaatcctat | gaagctttgt | gtttacaaaa | ccatgcaatg | 1380 |
| cttggtaaat | ggtcaaacac | ttagaaatga | gaatttttt | taaaaagag | agagggaggg | 1440 |
| atagctcagc | ggtggctgag | cggtgtagcg | ccgcctttgg | tccagggcgt | gatcctggag | 1500 |
| acccaggatc | gagtcccacg | tcgggctccc | tgcttggagc | ctgcttctcc | ctctgcctgt | 1560 |
| gtctctgcct | ctctctttct | ctctttctct | ctctcaatct | gtgtatctaa | taataaaat | 1620 |
| cttttaaaaaa | ataaataaat | cgatgggtga | gtaaagcaga | ttgccttcca | ttgtgtgggt | 1680 |

```
gggcctcatc caatcagttg aagaccttaa aagactgagg tcccctaaaa aggaaggaat   1740
tctgccttca gactcaagac tgcagcatct accattaagg gaatttctaa cctgccctgc   1800
aaacatcaga cttgccagcc ccataatcat acgagctaat tccttaaaat aacctttctc   1860
tctacatata tgtccagttg gttctgtttc tctagagaac cctgattaat acagcacgtg   1920
tctctgatac aggacttcat cagcctttca atgctaatat gcttatctgg ggaggcatgg   1980
tatgggttcc tccaacttgt tccccacccc aaaccctgc aaaggcctat aacacaact    2040
gtgtgtatgg tacagggccc acattgaggt cctggttgta ggggactgga cagatgacct   2100
cagagtttcc tctctacccc ccaaagaggg tttcggcaag gccttgccct tctcggctct   2160
cagcttggct ttctctacag gcccaacagc ttcaatggcc atggctacca cctcttcag    2220
gccatgcggt ttggcattga ggagatcaac aactccacaa cactgctgcc taatgtcacc   2280
ctggggtacc agctgtatga cgtgtgctca gagtcagcca atgtgtacgc cacactcaac   2340
gtactctcca cgctggggac acatcacata gagatccaag cagacccttc ccactattcc   2400
ccggccgccc tggcggtgat tggacctgac accaccaacc atgctgccac cgctgcagcc   2460
ctgctgagcc cgtttctggt gcctgtggta agctggtgcc ctgacagggt gtccgtctcc   2520
ccttctgtca gtccagtgt  gggctagggg tggtgggcag gagctgctgg gcccccaggc   2580
cagtctgagc ccctggatct cctgggtgat cactgctcat tagtcacatt gcaggaggcc   2640
ctgccccatc gcaatctgca ctccagcatt tcttcccccc aggtgctgca tccagacccc   2700
tggcctcaat gctcctgaga aaacccattc tattgaaact gctgccgttt actcctnnnn   2760
nnnnnnnnnn nnnnnnnnnn nnnnnnnnnn nnnnnnnttc ctattgaaat gagagataca   2820
ctcctaaaac acaagtctga atatatcact tctctgccta aatatttagg ggctcccaat   2880
ggcctacaga taaagaccaa gtatcttagc ctgacagtta aggccccctt ggcctaacca   2940
catacctact tttgtgctcc ttcttctggc atccaacctc ttgggtcatt tcactcactg   3000
tgtgcagctt ttgttcccctt ccttttcttc tctcagaact ccctccttgg gtttctgcct   3060
cttttccgca tgtaactcgt cagcctccta tgtccactag agctctcctt gagaaccagg   3120
gcagggacca tgtgtcccgc atccctgggt cccggtgccc agaacagggc cagcacttgg   3180
gggccctgat tgagactgat gccactgaac ttgctgaact gaaccccgc agatcagcta    3240
cgaggccagc agtgtgatgc ttggagtgaa gcggtattac ccctcgtttc tgcgcactat   3300
ccccagcgat aagtaccagg tggagatcat ggtgctactg ctgcagaggt ttgggtgggt   3360
ctggatctca ttggtgggca gcgacggcga ctatgggcag ctggggggtgc aggcactgga   3420
ggagcaggcc acccagcagg gcatctgcat tgccttcaag gacatcatac ccttctctgc   3480
ccagccgggt aatgagagga tgcagagcat gatgtaccac ctggaccgag caaggaccac   3540
tgttgtggtc gttttctcca gcaggcagct ggccagggtg ttcttcgagt ccgtggtcct   3600
ggccaagctg actgccaagg tgtggatcgc ttcagaagac tgggccatct ccagacatat   3660
tagcagcctg cccaggatct ggggcattgg cacagtgttg ggcgtggcca tccagcagaa   3720
gcttgtccct ggtctgaagg agtttgaaga ggcctacgtc cgggcaaaga aggcagccca   3780
taggccttgc tccagggact cctggtgcag cagcaaccaa ctctgcagag agtgccaagc   3840
tttcacagta cagcagatgc ccacactcgg agcattctcc atgagctctg cctacaatgc   3900
ctaccgggct gtctacgcag cagcccatgg cctccaccag ctcctgggct gtgcctctgg   3960
agcctgttcc agggaccgag tctacccctg gcaggtaagg tggccctacc cctggcaccc   4020
```

```
tgaaacaggg tgcttcctg aggaaaccag agtgatcact ctctgcccaa ctaagtgttg    4080
ggggcagagg acaaaggcca ttgaccagag ggctgatccc ctctcttagg cttcaattct   4140
ctgaacctca gccctccca ctcaccatgc ttcatatcca ggactaaaaa tcactgtaaa    4200
ggggtccttt gttagaaact tcctctcaga agcctggttg ggagggttga ggggtttcct   4260
tggaggggaa ggaggctct gaatttccag atggcctgaa accacccaaa tagaagcata    4320
aggccccagg cacttgattc ctgatccttc caggtctggg tgggttgagg aggagcaaca   4380
tttgccatct acggcagctc cctgatcct gtgtatttca gcttctagag cagatccgca    4440
aggtgaattt ccttctacac gaggacactg tgatatttaa tgacaacggg gaccctctca   4500
gtggctatga cataattgcc tgggactgga gtggtcccaa gtggaccttc agggtcatcg   4560
gctcctccac gtggcctcca gttcagctgg acataaataa aaccaaaatc cggtggcacg   4620
gagaggacaa ccaggtaata gagacatggt cacttaccag atgactgctt tatgggcagc   4680
ctgcagccca aggatactgt tgacatagat tacacagagc aggagggaga tcccaggtac   4740
caggccaaca tgcctctatc cagccctgct ggggaagccc cacaggcagc acccagatgg   4800
cctgctgcgc tggtttataa aaccagggg tctgctctgg gagtgagctg tgaaggcaga    4860
tgcacagaga ctatttccca ttccacctgt gagtattcct tgacttggcc atgtggttac   4920 agaacctg tggcttcttg caggtgcctg agtctgtgtg ctccagcaac tgtcttgaag     4980
ggcaccagcg agtagttgtg ggtttctacc actgttgctt tgagtgtgtg ccctgtgagg   5040
ccggcacctt cctcaacaag agtggtgagt gatcaagtga gtgggtgaag gactgggcac   5100
tcctagggtc tgtacagcag aagagggct ctccctcagg ccacacatgc acagaaccag    5160
ggccttgctc gcttcactgc tagttaggta taggctgaag aatacctgtc accagactga   5220
attctgagga agcagaaaga aacaacctgt taaaatcctc agacccacta tgtcttttac   5280
tagagagctc ccagcccat tcctacaggc acaattttat cctaaattca acctcttat    5340 gcaagcagag gtagctacgt tcccttgtac ccttccctgc tatctgtgtg aagtcccttc   5400
tattgcccat gctgtagcta gcacctgaac agcttggcct gaatgaagaa actgtatctg   5460
cagctgaaaa aacagcatac tatacccagt gatgcaaggc caagatcaga gagcaaatta   5520
aggcaactaa gggctcagcc cagagttgga cgccatgagc cacattcttt tcctttatg    5580 atctctatgg gcatgggaac gcatctcttc tgttctcaga gtcagagaaa ccacagagtg   5640
gcagcacagg aaggcggatt tggctaggtg gatttagca cggaagtgct ggggagagaa    5700
gaaaatgccc ttcctttggg gctggctgct ccnnnnnnnn nnnnnnnnnn nnnnnnnnnn    5760
nnnnnnnnnn nnnnnnnnc tattgcccat gctgtagcta gcacctgaac agcttggcct    5820
gaatgaagaa actgtatctg cagctgaaaa aacagcatac tatacccagt gatgcaaggc   5880
caagatcaga gagcaaatta aggcaactaa gggctcagcc cagagttgga cgccatgagc   5940
cacattcttt tcctttatg atctctatgg gcatgggaac gcatctcttc tgttctcaga    6000
gtcagagaaa ccacagagtg gcagcacagg aaggcggatt tggctaggtg gatttagca    6060 cggaagtgct ggggagagaa gaaaatgccc ttcctttggg gctggctgct cctattggat   6120
catagcctca ctggcaggtg ggcagagcaa ccagagtaaa gccctcccta gggacctctt   6180
ggtttgcaag cccttctgg gatcacgagc catacataac ctacccaagg gtctccagaa    6240
tctaattcac acaggcatct tgaggaaaca catggcctca ggaccccact cagggctacc   6300
cccatctcca gctcctgtgg tatctcccct gcagcacttt gcagatcaat gtggtctccc   6360
ttcctcattc ctgaactgct ccactagccc ttaggactcc cctccgcctt tccttccaga   6420
```

```
cctccacagc tgccagcctt gtgggaaaga agagtgggca cctgagggaa gtgaatcctg    6480
cttcctacgc actgtggtgt ttttgacttg gcatgagcct atctcttggg tgctgctggc    6540
agctaatacg ctgctgttgc tgctggtggc tgggactgct ggcctgtttg cctggcactt    6600 agacacccg gtggtgaggt cagctggggg caggctgtgc ttctttatgc tgggctccct     6660 ggcaggggc agctgtgggc tctatggctt ttttggggag cccaccctgg ccacatgctt     6720
gttgcgccaa ggcctctttg ccctcggctt tgccatcttc ctgtcctgcc tgacaatccg    6780
ctccttccaa ctggtcttca tcttcaagtt ttccgccaag gtacccacct tctaccaggc    6840
ctgggtccaa aaccatggtc cccgcctctt tgtggtgatc agctccatgg cccagctgct    6900
catctgtgta acttggcttg cggtgtggac cccgttgccc accagggagt accagcgctt    6960
ccctcagctg gtggtgcttg actgcacgga ggccaactcc ccgggcttca tggtggcctt    7020
tgcctacaat ggcctgctgt ccgtcagcgc ctttgcctgc agctacctgg gtaaggacct    7080
gccggagaac tacaacgagg ccaaatgcgt caccttcagt ctgctcctca acttcgtgtc    7140
ctggattggc ttttcacca cagccagcgt ctaccaggc aaatacctgc ccgcggtcaa     7200
cgtgctggcg gcgctgagca gcctgagcag cggcttcagc ggttacttcc tccccaagtg    7260
ctatgtgatc ctgtgccgcc cagatctcaa cagcaccgag cacttccagg cctccatcca    7320
ggactacacg aggcgctgcg gctccacctg accccgcctc ccctgtcccg agggccgagg    7380
gtcaagcgag gcgcgcacgc cctgcgctgt cccggaggcc tttggactct tcagtttggg    7440
ctcggggagt gtaagctcgc cggaggccgc cccgggctcc caggctctgc caataaagcg    7500
ctgaaatgtg cgtcctggct gcgcttgctg tctgggccca ggggtggggc gcggcctcca    7560
gcaggctgag ggcgccgcgg gggcccaccg cagccggaac ccgggaccca gcccagccg    7620 cgcaaccagc cgtcgcccag cttggcgttg ctaagcaaca tcgagagccg agccaaccgc    7680
cgagcgccca gggcctggac ccctctcccc attccattgg ccgttctctg cctgccacg    7740 ccctcgaggg cggagccaga agcccggcac ctcccaggct ttcgccccttc cggcgcgcc    7800 ctgacgtcac gtccggcggc ggcggcggcg gggcggaga cggctgcgtc tccgtacggt     7860
cggcggggca cgtacggccc gggcagttga gcagggggc tgtggcgacg acgaggtcca    7920
gggtcggtgg ggccggcacc gggagcacag g                                   7951
```

<210> SEQ ID NO 2
<211> LENGTH: 2526
<212> TYPE: DNA
<213> ORGANISM: dog

<400> SEQUENCE: 2

```
atgtcactcc tggcagctca cctggtcagc ttgcagctct ccctctcctg ctgctgggcc      60
ctcagctgcc acaacacaga gtcatctcct gatttcagcc tccctgggga ttacctactt     120
gcaggtctgt tccctctgca ctctgactgt cccggggtga gacgcaggcc catggtgacc     180
ctctgtgaca ggtccaacag cttcaatggc catggctacc acctcttttca ggccatgcgg    240 tttggcattg aggagatcaa caactccaca acactgctgc taatgtcac cctggggtac     300 cagctgtatg acgtgtgctc agagtcagcc aatgtgtacg ccacactcaa cgtactctcc    360
acgctgggga cacatcacat agagatccaa gcagaccctt cccactattc cccggccgcc    420
ctggcggtga ttggacctga caccaccaac catgctgcca ccgctgcagc cctgctgagc    480
ccgtttctgg tgcctgtgat cagctacgag gccagcagtg tgatgcttgg agtgaagcgg    540
```

```
tattacccct cgtttctgcg cactatcccc agcgataagt accaggtgga gatcatggtg      600
ctactgctgc agaggtttgg gtgggtctgg atctcattgg tgggcagcga cggcgactat      660
gggcagctgg gggtgcaggc actggaggag caggccaccc agcagggcat ctgcattgcc      720
ttcaaggaca tcatacccett ctctgcccag ccgggtaatg agaggatgca gagcatgatg      780
taccacctgg accgagcaag gaccactgtt gtggtcgttt tctccagcag gcagctggcc      840
agggtgttct tcgagtccgt ggtcctggcc aagctgactg ccaaggtgtg gatcgcttca      900
gaagactggg ccatctccag acatattagc agcctgccca ggatctgggg cattggcaca      960
gtgttgggcg tggccatcca gcagaagctt gtccctggtc tgaaggagtt tgaagaggcc     1020
tacgtccggg caaagaaggc agcccatagg ccttgctcca gggactcctg gtgcagcagc     1080
aaccaactct gcagagagtg ccaagctttc acagtacagc agatgcccac actcggagca     1140
ttctccatga gctctgccta caatgcctac cgggctgtct acgcagcagc ccatggcctc     1200
caccagctcc tgggctgtgc ctctggagcc tgttccaggg accgagtcta cccctggcag     1260
cttctagagc agatccgcaa ggtgaatttc cttctacacg aggacactgt gatatttaat     1320
gacaacgggg accctctcag tggctatgac ataattgcct gggactggag tggtcccaag     1380
tggaccttca gggtcatcgg ctcctccacg tggcctccag ttcagctgga cataaataaa     1440
accaaaatcc ggtggcacgg agaggacaac caggtgcctg agtctgtgtg ctccagcaac     1500
tgtcttgaag gcaccagcg agtagttgtg ggtttctacc actgttgctt tgagtgtgtg     1560
ccctgtgagg ccggcacctt cctcaacaag agtgacctcc acagctgcca gccttgtggg     1620
aaagaagagt gggcacctga gggaagtgaa tcctgcttcc tacgcactgt ggtgtttttg     1680
acttggcatg agcctatctc ttgggtgctg ctggcagcta atacgctgct gttgctgctg     1740
gtggctggga ctgctggcct gtttgcctgg cacttagaca ccccggtggt gaggtcagct     1800
gggggcaggc tgtgcttctt tatgctgggc tccctggcag ggggcagctg tgggctctat     1860
ggcttttttg gggagcccac cctggccaca tgcttgttgc gccaaggcct cttttgccctc     1920 ggctttgcca tcttcctgtc ctgcctgaca atccgctcct tccaactggt cttcatcttc     1980
aagttttccg ccaaggtacc caccttctac caggcctggg tccaaaacca tggtccccgc     2040
ctctttgtgg tgatcagctc catggcccag ctgctcatct gtgtaacttg gcttgcggtg     2100 tggacccccgt tgcccaccag ggagtaccag cgcttccctc agctggtggt gcttgactgc     2160
acggaggcca actccccggg cttcatggtg gcctttgcct acaatggcct gctgtccgtc     2220
agcgcctttg cctgcagcta cctgggtaag gacctgccgg agaactacaa cgaggccaaa     2280
tgcgtcacct tcagtctgct cctcaacttc gtgtcctgga ttggctttttt caccacagcc     2340 agcgtctacc agggcaaata cctgcccgcg gtcaacgtgc tggcggcgct gagcagcctg     2400
agcagcggct tcagcggtta cttcctcccc aagtgctatg tgatcctgtg ccgcccagat     2460
ctcaacagca ccgagcactt ccaggcctcc atccaggact acacgaggcg ctgcggctcc     2520
acctga                                                                 2526
```

<210> SEQ ID NO 3
<211> LENGTH: 841
<212> TYPE: PRT
<213> ORGANISM: dog

<400> SEQUENCE: 3

Met Ser Leu Leu Ala Ala His Leu Val Ser Leu Gln Leu Ser Leu Ser
1               5                   10                  15

-continued

```
Cys Cys Trp Ala Leu Ser Cys His Asn Thr Glu Ser Ser Pro Asp Phe
             20                  25                  30

Ser Leu Pro Gly Asp Tyr Leu Leu Ala Gly Leu Phe Pro Leu His Ser
             35                  40                  45

Asp Cys Pro Gly Val Arg Arg Pro Met Val Thr Leu Cys Asp Arg
 50                  55                  60

Ser Asn Ser Phe Asn Gly His Gly Tyr His Leu Phe Gln Ala Met Arg
 65                  70                  75                  80

Phe Gly Ile Glu Glu Ile Asn Asn Ser Thr Thr Leu Leu Pro Asn Val
                 85                  90                  95

Thr Leu Gly Tyr Gln Leu Tyr Asp Val Cys Ser Glu Ser Ala Asn Val
             100                 105                 110

Tyr Ala Thr Leu Asn Val Leu Ser Thr Leu Gly Thr His His Ile Glu
             115                 120                 125

Ile Gln Ala Asp Pro Ser His Tyr Ser Pro Ala Ala Leu Ala Val Ile
130                 135                 140

Gly Pro Asp Thr Thr Asn His Ala Ala Thr Ala Ala Leu Leu Ser
145                 150                 155                 160

Pro Phe Leu Val Pro Val Ile Ser Tyr Glu Ala Ser Ser Val Met Leu
                 165                 170                 175

Gly Val Lys Arg Tyr Tyr Pro Ser Phe Leu Arg Thr Ile Pro Ser Asp
             180                 185                 190

Lys Tyr Gln Val Glu Ile Met Val Leu Leu Leu Gln Arg Phe Gly Trp
             195                 200                 205

Val Trp Ile Ser Leu Val Gly Ser Asp Gly Asp Tyr Gly Gln Leu Gly
             210                 215                 220

Val Gln Ala Leu Glu Glu Gln Ala Thr Gln Gln Gly Ile Cys Ile Ala
225                 230                 235                 240

Phe Lys Asp Ile Ile Pro Phe Ser Ala Gln Pro Gly Asn Glu Arg Met
                 245                 250                 255

Gln Ser Met Met Tyr His Leu Asp Arg Ala Arg Thr Val Val Val
             260                 265                 270

Val Phe Ser Ser Arg Gln Leu Ala Arg Val Phe Phe Glu Ser Val Val
             275                 280                 285

Leu Ala Lys Leu Thr Ala Lys Val Trp Ile Ala Ser Glu Asp Trp Ala
             290                 295                 300

Ile Ser Arg His Ile Ser Ser Leu Pro Arg Ile Trp Gly Ile Gly Thr
305                 310                 315                 320

Val Leu Gly Val Ala Ile Gln Gln Lys Leu Val Pro Gly Leu Lys Glu
                 325                 330                 335

Phe Glu Glu Ala Tyr Val Arg Ala Lys Lys Ala Ala His Arg Pro Cys
             340                 345                 350

Ser Arg Asp Ser Trp Cys Ser Ser Asn Gln Leu Cys Arg Glu Cys Gln
             355                 360                 365

Ala Phe Thr Val Gln Gln Met Pro Thr Leu Gly Ala Phe Ser Met Ser
370                 375                 380

Ser Ala Tyr Asn Ala Tyr Arg Ala Val Tyr Ala Ala His Gly Leu
385                 390                 395                 400

His Gln Leu Leu Gly Cys Ala Ser Gly Ala Cys Ser Arg Asp Arg Val
                 405                 410                 415

Tyr Pro Trp Gln Leu Leu Glu Gln Ile Arg Lys Val Asn Phe Leu Leu
             420                 425                 430

His Glu Asp Thr Val Ile Phe Asn Asp Asn Gly Asp Pro Leu Ser Gly
```

-continued

```
                435                 440                 445
Tyr Asp Ile Ile Ala Trp Asp Trp Ser Gly Pro Lys Trp Thr Phe Arg
450                 455                 460
Val Ile Gly Ser Ser Thr Trp Pro Pro Val Gln Leu Asp Ile Asn Lys
465                 470                 475                 480
Thr Lys Ile Arg Trp His Gly Glu Asp Asn Gln Val Pro Glu Ser Val
                485                 490                 495
Cys Ser Ser Asn Cys Leu Glu Gly His Gln Arg Val Val Gly Phe
            500                 505                 510
Tyr His Cys Cys Phe Glu Cys Val Pro Cys Glu Ala Gly Thr Phe Leu
        515                 520                 525
Asn Lys Ser Asp Leu His Ser Cys Gln Pro Cys Gly Lys Glu Glu Trp
530                 535                 540
Ala Pro Glu Gly Ser Glu Ser Cys Phe Leu Arg Thr Val Val Phe Leu
545                 550                 555                 560
Thr Trp His Glu Pro Ile Ser Trp Val Leu Leu Ala Ala Asn Thr Leu
                565                 570                 575
Leu Leu Leu Leu Val Ala Gly Thr Ala Gly Leu Phe Ala Trp His Leu
            580                 585                 590
Asp Thr Pro Val Val Arg Ser Ala Gly Gly Arg Leu Cys Phe Phe Met
            595                 600                 605
Leu Gly Ser Leu Ala Gly Gly Ser Cys Gly Leu Tyr Gly Phe Phe Gly
        610                 615                 620
Glu Pro Thr Leu Ala Thr Cys Leu Leu Arg Gln Gly Leu Phe Ala Leu
625                 630                 635                 640
Gly Phe Ala Ile Phe Leu Ser Cys Leu Thr Ile Arg Ser Phe Gln Leu
                645                 650                 655
Val Phe Ile Phe Lys Phe Ser Ala Lys Val Pro Thr Phe Tyr Gln Ala
                660                 665                 670
Trp Val Gln Asn His Gly Pro Arg Leu Phe Val Val Ile Ser Ser Met
            675                 680                 685
Ala Gln Leu Leu Ile Cys Val Thr Trp Leu Ala Val Trp Thr Pro Leu
690                 695                 700
Pro Thr Arg Glu Tyr Gln Arg Phe Pro Gln Leu Val Val Leu Asp Cys
705                 710                 715                 720
Thr Glu Ala Asn Ser Pro Gly Phe Met Val Ala Phe Ala Tyr Asn Gly
                725                 730                 735
Leu Leu Ser Val Ser Ala Phe Ala Cys Ser Tyr Leu Gly Lys Asp Leu
            740                 745                 750
Pro Glu Asn Tyr Asn Glu Ala Lys Cys Val Thr Phe Ser Leu Leu Leu
        755                 760                 765
Asn Phe Val Ser Trp Ile Gly Phe Phe Thr Thr Ala Ser Val Tyr Gln
770                 775                 780
Gly Lys Tyr Leu Pro Ala Val Asn Val Leu Ala Ala Leu Ser Ser Leu
785                 790                 795                 800
Ser Ser Gly Phe Ser Gly Tyr Phe Leu Pro Lys Cys Tyr Val Ile Leu
                805                 810                 815
Cys Arg Pro Asp Leu Asn Ser Thr Glu His Phe Gln Ala Ser Ile Gln
            820                 825                 830
Asp Tyr Thr Arg Arg Cys Gly Ser Thr
        835                 840
```

<210> SEQ ID NO 4

```
<211> LENGTH: 10959
<212> TYPE: DNA
<213> ORGANISM: canine
<220> FEATURE:
<221> NAME/KEY: misc_feature
<222> LOCATION: (5540)..(5578)
<223> OTHER INFORMATION: n is a, c, g, or t
<220> FEATURE:
<221> NAME/KEY: misc_feature
<222> LOCATION: (8208)..(8250)
<223> OTHER INFORMATION: n is a, c, g, or t

<400> SEQUENCE: 4
```

| | | | | | |
|---|---|---|---|---|---|
| tgcaacctgg | ggtgggggt | ggggattaga | ctctgcgtgc | ctccatttcc | tcatccgtga | 60 |
| aatgggtctg | gcaccatccg | tgcttatcat | gagcattaaa | cgagatggtg | aacggcaagc | 120 |
| acgcagcgtg | atgcctggtt | cttactgcca | gtggctgctg | ctcctggaac | acctgctatg | 180 |
| gggccaatgc | tacctatgaa | ttattgtgtg | ccaggctcag | cttgggctcc | atttgccaga | 240 |
| ctactctgcc | cccttggatg | agtacctggg | tcctttgctc | ccaaatgttg | gctacgtcag | 300 |
| gggcatgaga | cctgtcctca | atcgagtggc | agaaggctat | agggagtgtc | caagtgagca | 360 |
| ggacatgctt | tctctacttc | caggtgggat | tctcctagac | cacccaggtc | ccaccatacc | 420 |
| ctaggaaggg | accatcctag | ttccggcccc | ttcctttccc | cccagagttc | gcaaatctct | 480 |
| ccacctgtgc | caggtgcttt | ccccgcccca | cgggccacgg | cggggccacc | attatgtaaa | 540 |
| tgtctgtgca | aatcccctga | tgtcaagctg | ccagctctct | gatgaggcag | ggccacctct | 600 |
| ggggaccccc | acttcccagc | catgggaccc | cgggccaagg | cggtctgctc | cctattcatc | 660 |
| ctgctgcagg | tcctggctga | accggctgag | aactcagact | tctacctgcc | tggagattac | 720 |
| ctcctgggtg | gcctcttcac | cctccatgcc | aacgtgaagg | gcaccgtcca | cctcagcttc | 780 |
| ctgcaggtgc | cccagtgcaa | gaagtgagtc | tccagtgtga | ggctggatgt | ggtgatgggg | 840 |
| gtggggtggg | aagcctgcgc | tggtcccgtg | gtcctcacgg | accaagtccc | ggaccaaggg | 900 |
| cttgaaatgc | tcctcatcca | ttgcaaaacc | cctcatcctg | ggttatcccc | actggccccc | 960 |
| agggagaacc | cacacagttc | atgtcactaa | gatcttcggc | aattgtgttc | tgaaacatgg | 1020 |
| agacctggta | ggcccaaagt | cacatctctt | aataaagagt | tacaagatat | ttgagcctgg | 1080 |
| aggggttgta | gagaccgtca | aaatcaccc | cacctacttt | ggcaactgag | tccatgtcaa | 1140 |
| ggcctggtct | agaaaccaag | ggttacgcct | ttggaaggca | gaaacgtggt | ttttctgtag | 1200 |
| caggttctca | gaccggaggg | gaatgtttgc | ctttctctag | ggctgtggtt | aggtgggtgg | 1260 |
| cggtgcttcc | aggacgggaa | ggatttcctt | cacccgtctc | acgggtggt | ggcatcactc | 1320 |
| aagattaggt | ggaccatctt | catgcaagca | agggattatg | aattaaagac | ctagtgcaga | 1380 |
| gagggaaggc | attctgagag | agaaggaaaa | aggaagggat | aaaggtgata | aagggccaac | 1440 |
| tgtaagaaat | gcatgctttt | tgtgatgttg | gggaagatca | tgtgctgatt | tgagaatggt | 1500 |
| gagggtgatg | gtgccgtgat | ggtaccaggc | acattgttga | atgttctgat | gcctgtgata | 1560 |
| gtggtgggga | gaccagtgaa | gtaacggtgg | tgatggtggt | gatgttgata | acattgatag | 1620 |
| cagtcatact | ggtgataatg | caaatggtga | agagtatggt | gatgatgatg | gtggtggtga | 1680 |
| tggtggtgat | gacggcgatg | atggtgatga | tgatgatggt | ggtaatgatg | gggatggtaa | 1740 |
| tggtggtgag | gatcgttgtg | gtggtggtga | tggtgatgaa | gatgatgatg | gtgatgaaga | 1800 |
| tgatggtgat | gaggggatg | gtggtgatgg | tggtgatgag | gatcatgatg | gtgatgaaga | 1860 |
| tgatggtgct | ggtgtgatgg | tgctggcagt | attggtagtg | gtgggcacag | acatgtggtc | 1920 |
| acagtgatgg | cagtgatgat | gatattgttc | ataggaaata | gtaggtgcat | gatgtgacag | 1980 |

```
tgatgatagc gatggcagac attgtagtgg gtaatggtga ttgtatccgt ggacattggt    2040
aaagtggtgg tagatcatag ggatggtggt agtggtgaca atggtagtga ttgatggtag    2100
ccacaaggat cataatgcca gaggtggtca tagggatgat ggtgaaccta gagatgtggt    2160
atggcatggt gaccacgatg tgatgataaa ataccagaa tatcctggaa tggcgctttc     2220
ttggataact cctgggcttt cctctggtag gcagaggaaa caagcaggct ctccaggaaa    2280
caatcctgcc ccttcccact ctggacctgc ttcctacccc accctccatg gcttccccag    2340
gtatgaaatg aaggtgttgg gctacaacct gatgcaggcc atgcgctttg cggtggaaga    2400
gattaacaac cgcagcgacc tgctgcccgg cgtgctgctg ggctatgaga tagtggatgt    2460
ctgctacatc tccaacaacg tccagcccgt gctctacttc ttggcacggg aggactactc    2520
cctgcccatc caggaggact acagccacta cgtgcccgt gtgttggcgg tcattggccc     2580
tgacaactcc gagtccacta ctactgtggc ccatttcctc tcactcttcc tccttccaca    2640
ggtgaggccc tggctcctgg gggaaggagc tggggagggg gcagaggagg ggttgtctag    2700
agggctcgct tcccccact ggtcatgagg ggagaaggag gtgggaagcc aggtcaggat     2760
gtcagcccca accctgggag ggaagcctgg cctattcatg agaagcctag gctttggaga    2820
cagacagacc tgggcgtgca tcttggctct gagtcttggc cattttgagt cacggagcaa    2880
atctcttaac tcttctgagc ttcagcttcc ccacctataa aatgggatga tgagagttcc    2940
atcctaggac tgtctgaggc ttaaaggatt taacctctgc agacatttat aggatacagt    3000
agctggtcaa ttatgtaatg gtcgttatct aaggcacctt ccttgcacag aaatgaaaac    3060
ccagaaaatg ctcaatatta tcctgtacag ttgcctagta cagggtctgc cacatagtag    3120
gtcctcagaa aaatgccact agtattagta ctattattgt aagcgtcatc atcatcatga    3180
tcgaaaatgc ctcaaccagt tttagttggt ctaaaacttc aacacattaa agagcagcta    3240
gcgcaagaag acttggcaca cagtaggtag ctgcaaatac tgtattttg ctgacatttt      3300 tattatgcaa agcaccaagg gtctgacaca cagtaggtgc ctagtaaatg ttaatgtact    3360
taggtgaggc gtctctttca ggactaaact cattctttca ttcccttaac aaatatttat    3420
tgagctcacc ctccagtggg agagacaggc catgtcagga agcgcatgat agggctgctg    3480
gaaagtgaga agtgccgtgc acaaaggtaa aaggcaaaca gggtgagggg ggctggacgg    3540
gtcggtggac agatggaacg gggagaggga ggctgcaact gcaagcaggg tggtcgggtg    3600
agcctcgctg gcaattggac aaaaggcttga gggaggtgaa ggggtgaggg aggtacggag   3660
gtgtctggga gaagagcctt caggaagagg gggcagcgaa tgcagaggcc ggcaggtgcc    3720
tggattcgct tatggaacca gggagcagaa ctgggacccg ggagagacta ggaggagatg    3780
aagtcaggga ggtgagggcc ggggtcagtg atggagcccc ttgggggccc ctgaaggact    3840
ctgactgtcc ctgcatgact ttcggagcta ttgaagggtt ttcaagtgcc tgccgggtca    3900
cctggccgcc gccacgttca gcggagactg taggaggaag ggtgggggga tgctttggta    3960
gcctggcgag gccctagctc atgtgccggc agggtcccc tccgcagat cacctacagc       4020 gccatcagtg acgatctgcg ggacaagcag cgcttccgg ccctgctgcg cacagtggcg      4080
ggcgcggacc accagatcga ggccatggtg cagctcctgc tccacttcaa ctggaactgg    4140
atcatcgtgc tagtgagcag cgacgactac ggccgctaca cagccagct gctcaacgat     4200 cgcctggcca ccggcgacat ctgcatcgcc ttccaggaga cgctgcccat gccgcagccc    4260
gaccaggtgg tgacggagtg ggagcgccag cgcctggagg ccatcgtggg caagctgcag    4320
```

```
cagagctcgg cgcgcgtcgt ggtgctgttc tcgccagacc tgatcctgca caacttcttc      4380
cgcgaggtgc tccgccagaa cttcacgggc gccgtgtgga tcgcctccga gtcctgggcc      4440
atcgacccgg ttctgcacaa cctcaccgag ctgcgccaaa ccggcacctt cctgggcgtc      4500
accacccaga gtgtgcccat cccgggcttc agcgagttcc gcatacgccg cacccggtc       4560 aggctgcctg agcccaacag gaccagcctg gaggccacct gcaaccagga gtgcgacacc      4620
tgccaggaca ccaccgcgtc cttcaacagc atcctcatgc tctccggcga gcgcgtggtc      4680
tacaacgtgt actcggctgt ctacgccgtg gcccatgcat tacacagcct tctgggctgc     4740
acccaggcct gctccaagga ggtggtctac ccctggcagg tgaggcccac cccgtggaag      4800
ggcaggcata gagtggttgt catggagacg ctgggtgcac ctgctgggct ctagccttcc      4860
catctcatgc tgggttctgg gcaaactggg gggagaggtc atgggacatg ccctgccctc      4920
cagacacata gaaccagaaa tccttcatgg tgacaaaact cctttttttt ttttttttaaa     4980 tgtaatcatc gccatccaag gtggcctgtc tggtaggag atttgggtga aattccctgg       5040
aagggagcct ggcaggccgt gggggcccca gtccctgc catttctctg ataagaggc         5100 ctcgggggcc cacttgtgta ctccctcctc tctctgaggc cctacttgag gtttacgcac      5160
ctcctctcgt tccaggtttg tgttgtctgg attccaagct ggaatttaaa actgtgtttt      5220
tctgacttgc acttatacac acgcacaccc aatcaggaaa ccctcatggg ggtgagaggt      5280
tttactgagg agcagaggag cagaggggat tcacatcaga gacgcacacc tcatacctaa      5340
taacccggca tctctgtgct tgaatggctc cttggctttt tcgtggttta aggttcaggc      5400
actcctccaa cccttgccta tattctgtct ttattctctg cttcctcccc tttttctgga      5460
tccccgatcc ccaaatacct gtacacttcc ttcccagagc aacctagctc tttaaaaaaa      5520
aaaaaaaaac cctccttccn nnnnnnnnnn nnnnnnnnnn nnnnnnnnnn nnnnnnnntg      5580
aatgtttatt gaatgaatta atgaacagag gagcacttac tgtgtgctaa cccccttatgt     5640 gatttgccat ctacccgcag acacgctgtg agtagacact gttgcttgat gattgttctc      5700
ccacattagg tctagagaag tgacgatcac ccagctgggg agtggccagg gcagtggtgg      5760
ggggggggcg tgggggtggt aatgaggcac aaggcaggg gcagtgggga tggagaggcc      5820
tcaggtgact aggatacttg aggatggagg ttgggaggtc acactgcccg tggtgttggg      5880
gggctgggga tgcactcggg ggcacgctcg ggaaatccag gctggcagag ggcagagggc      5940
tttggcggtc ccagggaaac tgttcatcag gttatggaat catagagggt ggaagttgca      6000
aggtcttaga atctccaggt ccaatatttt tgttttacaa atggggtgg ggatggcgcc       6060 cttgtggcat ttgccacgtg cttgccatct cggcatctca ggtacagtcc ctctgtccgt      6120
cagtcggggg gagagcttgg tacttaggtt tgaatcccag ctttgccacc actagctctg      6180
caaccttggg caggttattt aatgcatccg ggccttgggt ttctcatgtg ctaagcagaa      6240
ggaacgctaa gcaccgtgct gagctctgga ggggactgac cgcgctgtgt gtccatgacc      6300
cggtgcagat agaagctccg tgtcttcctc cccccctct tccatgtctg acaccagtgt       6360
ctggacagtg ataatccagg cctcctcccc gtcaggagag ttgcagggag gatcctttct      6420 gaccctctg tcagagccct ggaatctggg gttgctgagc ccagcctggc caggtcagtg       6480
cggggatggg cctggccacc aggacctggc tccttaaggc ctccaccatc ctcacccctg      6540
ccagaggcca accacctgcg aggagccttc ctcctctcag ctcccgagac cattgcccc      6600 agtcgcagca tcatgtgcaa attccagaga cttccagagc ctgactctgt ggtcagggtg     6660
ggaagaaggc gagagcccaa atcccttggc taactgtgtg tcggtccctg aagggaggtc     6720
```

```
ccccaagata cagcccaata gactctctca tttatggtgg gaaaatctag gagctagatt    6780
gatgaaatat ctaagttgga agttccctca aggggtcagc acagaggttc agtgacttac    6840
ccaaagtcac acagcaaatt gaggaaagag ctcagattgg aattcaggcc agaggatgcc    6900
cagtccaaag catgttccag tttgtaccag cctctgcatg ctcagagcaa caggggacga    6960
tgacatgggg agagactgga gactggcctc taactggggg gaggcaggaa gcccccagag    7020
ggacaggggc aggtgcagct gaccagggca ggtgagggag gcagtggact cgagctcagc    7080
tatgggtccc cgaggggtgg ccgagtgact tccaggagaa aggaataaga tcaacacttc    7140
ggcgggaggt gagtacttac tcgtgttgag gcaccgtgct aagttcccaa cataggtaaa    7200
ctctcatttg ttgcctccga gcccaggaga cagggttttt gttgtcctgc tttgctgaag    7260
aggaaactgg ggctcacaga ggtcaggcga caggtgcaag gcctcatagc aggtggcaga    7320
gctggtgtct aaacccagag tatccgaccc cggagctgga gctctcagcc cccacctccc    7380
gggtagcccc cttctcagtc ctcttgcccc cttgtcccca tgtggaagtc aggctagggg    7440
gatgggaaaa tttcccccgg gtctggcccc agctctgatg ccagcctttc cctttggccc    7500
ttctagctcc ttaaggaaat ctggaaggtc aacttcaccc ttctgggcca caatgtcttt    7560
tttgggcagc aaggggacgt gctcatgccc atggaggtca tccagtggca gtgggacctg    7620
agccagaacc ctttccagag catcgcctcc tactacccca agctgcggca gctcaaggcc    7680
atccacaaca tctcctggca caccgccaac aacacggtca gctctctgag ggctggggct    7740
gggccccggc tcaccctggg gtggcgaggg ccctctggac ccgagatccg tcactgacag    7800
cgggtggggg gggtgtctgt gcagtggggg ggggcgtct aggccctgtc cctcccgttg    7860
ataaggccta gggtttctgg ctccccgaga cccaggggc caggggctgt gcccagtgaa    7920
cgtgtgctgg acacgcgtgt gctgaggact cagctctcac gtcaaccatt gctggtgctc    7980
cccgtacggt agctgtaccc tcaactgcgt ctggcacctg tcattccaaa gctcctctgt    8040
tttaccctct tagatgcata acaagctgtc ggagtggtgg tggtggtgtg tggggacaga    8100
cagggaccca gcctcgtagg aggggagggg gaggggagg ggatacagaa gctccaagag    8160
ccttcctcat ctggatcctc tccccgcccc atccccettt atcctcannn nnnnnnnnn    8220
nnnnnnnnnn nnnnnnnnnn nnnnnnnnnn ccgagatctc caggatcacg ccctgggcca    8280
aaggcaggcg ccaaactgct gcgccaccca gggatccccc agacgtccag ttctaatggc    8340
aactcctgct ccttccccat cccagatggg ggccaggctt ccctcccag agcatcctgc     8400
tggttggtct cagggctct tgtcctcctc cctccagatc cccgtgtcca tgtgttccaa     8460
ggactgccat cctggccaaa ggaagaagcc tgtgggcatc cactcctgct gcttcgagtg    8520
tattgactgc cttcctggca ccttcctcaa ccgaactgca ggtgggactt gcagacccgc    8580
acccctgctc cccacccctca gccctgccct gctctgagag cagggtctct ggagtctccc    8640
ccacaggatg taagtgtcca aaggccaggg tccatgcctg attccagtgt atctccctag    8700
gaattggtgt agagaaaaat cttcaatgct cgctgctagg gagggtggga aaggaacag    8760
ccctccacca ggcaaggctg tcactggtcc ccactccacg cacatgtagc tgagggctca    8820
ggggtgtcag accagagaat gtccattgga tggatggctg gatggatgga tgagtgggtg    8880
aatgaatgaa taaatgaatg tctctgtcca tagaagaaat gtttctggca gacggggaca    8940
ggatctggtt tatctctctg acctcccagt gcctaatgta gtgcagagcg tatcacgttt    9000
gctcagtgaa ttttgattga gtgacatcct tgatcagaag agctcatacc tcccctata    9060
```

| | | |
|---|---|---|
| gatcacaaac gccgggaagg tgcggacaat gccttctctc cctctgtttt agtgttgagc | 9120 |
| accgttcaca gctggggctt aaattatttt ttttcgtgac ttcctcatca gagtacttac | 9180 |
| cgtgggccca gcatagccca gagcccagag taggtgccca acaaaaattt gttgcatgat | 9240 |
| ttcacaggct gttcccctac ccagttggtc ggttcctgac ggcagggggc tggctaggtt | 9300 |
| tcgcccacgt ctctgtcctc ccacctcagg tgcccatcac ccactgtgga gggtgtttga | 9360 |
| aaaaaaaaat gtgttgaagg aattctttgg accaatgtgt gagtgtctat gccaccagag | 9420 |
| ggtaaggtct cgggagcaag gaattacagt tgttaggatc cgagtcaagg gaacctcggt | 9480 |
| tcaaaccctg cctctgtaac gaccacctgg ctgagcctcg ggttactcat ctgtgaaatg | 9540 |
| gggttgcagg gaggagctga tgggccagtg ggtgtaagag gggcagtgag tggtggtggc | 9600 |
| taggccggta ggcgttgccc tcagctcgcc ccccacccccc gaggcctggc ccggggcggg | 9660 |
| tgcagaggat gggggtgctg ccaagtgggc gaggctgacg ggagctgccg tgggctcttg | 9720 |
| cagacgaatt tgactgccag ccttgcccaa gttacgagtg gtcccatagg aacgacacct | 9780 |
| cctgcttcaa gcggcggctg gccttcctcg aatggcacga gccctccacc atctttgtgg | 9840 |
| ttatgctgac catcctgggc ttcctcagca ccctggccat catggtgatc ttctggaggc | 9900 |
| acctccacac gcccgtggtt cgctcggccg ggggccccat gtgcttcctg atgctggtgc | 9960 |
| cgctgctgct ggcgtacgcc atggtcccca tgtacatagg gcagcccacg ttcttctcgt | 10020 |
| gcctctggcg ccagaccttc ttcaccctct gcttcaccat ctgcatctcc tgcatcaccg | 10080 |
| tgcgctcttt ccagatcgtc tgcatcttca agatggccag gcgcctcccg cgcgcctacg | 10140 |
| gctactgggt gcgctgccac gggccctacg tcttcgtggc gtccttcatg gtgctcaagg | 10200 |
| tggtcatcgt ggcaggcaac gtgctggcca cgaccgccaa ccctactgcc cgccccgacc | 10260 |
| ccgatgaccc caatatcatg gtcctgtcct gcaactaccg cagggcgctg ctgttcaaca | 10320 |
| ccagcctgga cctgctcctg tccgtggcgg gcttcagctt cgcctacatg ggcaaggagc | 10380 |
| tgcccaccaa ctacaacgag gccaagttca tcaccctctg catgaccttc tacttcacct | 10440 |
| cctccgtctc cctctgcacc ttcatgtccg tctatgatgg ggtcctggtc accatcctgg | 10500 |
| acctcttgat caccgtgctc aaccttctgg gcatcagctt tggctacttt ggtcccaaat | 10560 |
| gctacatggt cctcttctac ccagagcgca cacgcaggt ctacttcagc agcatgattc | 10620 |
| agggctacac catggggaag gactagcacc gcccactagg gctgcccagg gggcccaagg | 10680 |
| gctcagctgg gggcgggggg agacgcagac gggatgggga ggtggagctg ggtgcaggtc | 10740 |
| gcagtttccc ggtagctgtt tggcttgcta ggccctgccg cccattctag gaaaacctgc | 10800 |
| ccagggtggg gaccctactg gtgtccccga cagagatgga tttgagcagc ctacagtctc | 10860 |
| catctggtgg tcacagcgga tgcaggctcg ttcccctccc tcctgttcgc ggggagcgaa | 10920 |
| ggctgggctg caggggctgg ggctgggacg ggctggtgt | 10959 |

<210> SEQ ID NO 5
<211> LENGTH: 2510
<212> TYPE: DNA
<213> ORGANISM: dog
<400> SEQUENCE: 5

| | | |
|---|---|---|
| atgggacccc gggccaaggc ggtctgctcc ctattcatcc tgctgcaggt cctggctgaa | 60 |
| ccggctgaga actcagactt ctacctgcct ggagattacc tcctgggtgg cctcttcacc | 120 |
| ctccatgcca acgtgaaggg caccgtccac ctcagcttcc tgcaggtgcc ccagtgcaag | 180 |
| aagtatgaaa tgaaggtgtt gggctacaac ctgatgcagg ccatgcgctt tgcggtggaa | 240 |

```
gagattaaca accgcagcga cctgctgccc ggcgtgctgc tgggctatga gatagtggat      300
gtctgctaca tctccaacaa cgtccagccc gtgctctact tcttggcacg ggaggactac      360
tccctgccca tccaggagga ctacagccac tacgtgcccc gtgtgttggc ggtcattggc      420
cctgacaact ccgagtccac tactactgtg gcccatttcc tctcactctt cctccttcca      480
cagatcacct acagcgccat cagtgacgat ctgcgggaca gcagcacttt ccggccctg       540
ctgcgcacag tggcgggcgc ggaccaccag atcgaggcca tggtgcagct cctgctccac      600
ttcaactgga actggatcat cgtgctagtg agcagcgacg actacggccg ctacaacagc      660
cagctgctca acgatcgcct ggccaccggc gacatctgca tcgccttcca ggagacgctg      720
cccatgccgc agcccgacca ggtggtgacg gagtgggagc ccagcgcct ggaggccatc       780
gtgggcaagc tgcagcagag ctcggcgcgc gtcgtggtgc tgttctcgcc agacctgatc      840
ctgcacaact tcttccgcga ggtgctccgc agaacttca cgggcgccgt gtggatcgcc       900
tccgagtcct gggccatcga cccggttctg cacaacctca ccgagctgcg ccaaaccggc      960
accttcctgg cgtcaccac ccagagtgtg cccatcccgg gcttcagcga gttccgcata      1020
cgccgcaccc cggtcaggct gcctgagccc aacaggacca gcctggaggc cacctgcaac     1080
caggagtgcg acacctgcca ggacaccacc gcgtccttca acagcatcct catgctctcc     1140
ggcgagcgcg tggtctacaa cgtgtactcg gctgtctacg ccgtgcccca tgcattacac     1200
agccttctgg gctgcaccca ggcctgctcc aaggaggtgg tctaccctg gcagctcctt     1260
aaggaaatct ggaaggtcaa cttcacccctt ctgggccaca atgtcttttt tgggcagcaa    1320
ggggacgtgc tcatgcccat ggaggtcatc cagtggcagt gggacctgag ccagaaccct     1380
ttccagagca tcgcctccta ctaccccaag ctgcggcagc tcaaggccat ccacaacatc     1440
tcctggcaca ccgccaacaa cacgatcccc gtgtccatgt gttccaagga ctgccatcct     1500
ggccaaagga gaagcctgt gggcatccac tcctgctgct cgagtgtat tgactgcctt       1560
cctggcacct tcctcaaccg aactgaagac gaatttgact gccagccttg cccaagttac     1620
gagtggtccc ataggaacga cacctcctgc ttcaagcggc ggctggcctt cctcgaatgg     1680
cacgagccct ccaccatctt tgtggttatg ctgaccatcc tgggcttcct cagcaccctg     1740
gccatcatgg tgatcttctg gaggcacctc cacacgcccg tggttcgctc ggccgggggc     1800
cccatgtgct tcctgatgct ggtgccgctg ctgctggcgt acgccatggt ccccatgtac     1860
atagggcagc ccacgttctt ctcgtgcctc tggcgccaga ccttcttcac cctctgcttc     1920
accatctgca tctcctgcat caccgtgcgc tctttccaga tcgtctgcat cttcaagatg     1980
gccaggcgcc tcccgcgcgc ctacggctac tgggtgcgct gccacggggcc ctacgtcttc    2040
gtggcgtcct tcatggtgct caaggtggtc atcgtggcag gcaacgtgct ggccacgacc     2100
gccaacccta ctgcccgccc cgaccccgat gaccccaata tcatggtcct gtcctgcaac     2160
taccgcaggg cgctgctgtt caacaccgcc tggacctgct cctgtccgtg gcgggcttca    2220
gcttcgccta catgggcaag gagctgccca ccaactacaa cgaggccaag ttcatcaccc     2280
tctgcatgac cttctacttc acctcctccg tctccctctg caccttcatg tccgtctatg     2340
atggggtcct ggtcaccatc ctggaccctct tgatacccgt gctcaaccctt ctgggcatca    2400
gctttggcta ctttggtccc aaatgctaca tggtcctctt ctacccagag cgcaacacgc     2460
aggtctactt cagcagcatg attcagggct acaccatggg gaaggactag                2510
```

<210> SEQ ID NO 6

```
<211> LENGTH: 836
<212> TYPE: PRT
<213> ORGANISM: dog

<400> SEQUENCE: 6

Met Gly Pro Arg Ala Lys Ala Val Cys Ser Leu Phe Ile Leu Leu Gln
1               5                   10                  15

Val Leu Ala Glu Pro Ala Glu Asn Ser Asp Phe Tyr Leu Pro Gly Asp
            20                  25                  30

Tyr Leu Gly Gly Leu Phe Thr Leu His Ala Asn Val Lys Gly Thr
        35                  40                  45

Val His Leu Ser Phe Leu Gln Val Pro Gln Cys Lys Lys Tyr Glu Met
    50                  55                  60

Lys Val Leu Gly Tyr Asn Leu Met Gln Ala Met Arg Phe Ala Val Glu
65                  70                  75                  80

Glu Ile Asn Asn Arg Ser Asp Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala Arg Glu Asp Tyr Ser Leu Pro Ile Gln Glu Asp Tyr
        115                 120                 125

Ser His Tyr Val Pro Arg Val Leu Ala Val Ile Gly Pro Asp Asn Ser
    130                 135                 140

Glu Ser Thr Thr Thr Val Ala His Phe Leu Ser Leu Phe Leu Leu Pro
145                 150                 155                 160

Gln Ile Thr Tyr Ser Ala Ile Ser Asp Asp Leu Arg Asp Lys Gln His
                165                 170                 175

Phe Pro Ala Leu Leu Arg Thr Val Ala Gly Ala Asp His Gln Ile Glu
            180                 185                 190

Ala Met Val Gln Leu Leu Leu His Phe Asn Trp Asn Trp Ile Ile Val
        195                 200                 205

Leu Val Ser Ser Asp Asp Tyr Gly Arg Tyr Asn Ser Gln Leu Leu Asn
210                 215                 220

Asp Arg Leu Ala Thr Gly Asp Ile Cys Ile Ala Phe Gln Glu Thr Leu
225                 230                 235                 240

Pro Met Pro Gln Pro Asp Gln Val Val Thr Glu Trp Glu Arg Gln Arg
                245                 250                 255

Leu Glu Ala Ile Val Gly Lys Leu Gln Gln Ser Ser Ala Arg Val Val
            260                 265                 270

Val Leu Phe Ser Pro Asp Leu Ile Leu His Asn Phe Arg Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Arg Gln Thr Gly
305                 310                 315                 320

Thr Phe Leu Gly Val Thr Thr Gln Ser Val Pro Ile Pro Gly Phe Ser
                325                 330                 335

Glu Phe Arg Ile Arg Arg Thr Pro Val Arg Leu Pro Glu Pro Asn Arg
            340                 345                 350

Thr Ser Leu Glu Ala Thr Cys Asn Gln Glu Cys Asp Thr Cys Gln Asp
        355                 360                 365

Thr Thr Ala Ser Phe Asn Ser Ile Leu Met Leu Ser Gly Glu Arg Val
    370                 375                 380

Val Tyr Asn Val Tyr Ser Ala Val Tyr Ala Val Ala His Ala Leu His
```

```
            385                 390                 395                 400
Ser Leu Leu Gly Cys Thr Gln Ala Cys Ser Lys Glu Val Val Tyr Pro
                405                 410                 415

Trp Gln Leu Leu Lys Glu Ile Trp Lys Val Asn Phe Thr Leu Leu Gly
                420                 425                 430

His Asn Val Phe Phe Gly Gln Gln Gly Asp Val Leu Met Pro Met Glu
                435                 440                 445

Val Ile Gln Trp Gln Trp Asp Leu Ser Gln Asn Pro Phe Gln Ser Ile
        450                 455                 460

Ala Ser Tyr Tyr Pro Lys Leu Arg Gln Leu Lys Ala Ile His Asn Ile
465                 470                 475                 480

Ser Trp His Thr Ala Asn Asn Thr Ile Pro Val Ser Met Cys Ser Lys
                485                 490                 495

Asp Cys His Pro Gly Gln Arg Lys Lys Pro Val Gly Ile His Ser Cys
                500                 505                 510

Cys Phe Glu Cys Ile Asp Cys Leu Pro Gly Thr Phe Leu Asn Arg Thr
            515                 520                 525

Ala Asp Glu Phe Asp Cys Gln Pro Cys Pro Ser Tyr Glu Trp Ser His
        530                 535                 540

Arg Asn Asp Thr Ser Cys Phe Lys Arg Leu Ala Phe Leu Glu Trp
545                 550                 555                 560

His Glu Pro Ser Thr Ile Phe Val Val Met Leu Thr Ile Leu Gly Phe
                565                 570                 575

Leu Ser Thr Leu Ala Ile Met Val Ile Phe Trp Arg His Leu His Thr
                580                 585                 590

Pro Val Val Arg Ser Ala Gly Gly Pro Met Cys Phe Leu Met Leu Val
                595                 600                 605

Pro Leu Leu Leu Ala Tyr Ala Met Val Pro Met Tyr Ile Gly Gln Pro
        610                 615                 620

Thr Phe Phe Ser Cys Leu Trp Arg Gln Thr Phe Phe Thr Leu Cys Phe
625                 630                 635                 640

Thr Ile Cys Ile Ser Cys Ile Thr Val Arg Ser Phe Gln Ile Val Cys
                645                 650                 655

Ile Phe Lys Met Ala Arg Arg Leu Pro Arg Ala Tyr Gly Tyr Trp Val
                660                 665                 670

Arg Cys His Gly Pro Tyr Val Phe Val Ala Ser Phe Met Val Leu Lys
            675                 680                 685

Val Val Ile Val Ala Gly Asn Val Leu Ala Thr Thr Ala Asn Pro Thr
        690                 695                 700

Ala Arg Pro Asp Pro Asp Asp Pro Asn Ile Met Val Leu Ser Cys Asn
705                 710                 715                 720

Tyr Arg Arg Ala Leu Leu Phe Asn Thr Ser Leu Asp Leu Leu Leu Ser
                725                 730                 735

Val Ala Gly Phe Ser Phe Ala Tyr Met Gly Lys Glu Leu Pro Thr Asn
                740                 745                 750

Tyr Asn Glu Ala Lys Phe Ile Thr Leu Cys Met Thr Phe Tyr Phe Thr
                755                 760                 765

Ser Ser Val Ser Leu Cys Thr Phe Met Ser Val Tyr Asp Gly Val Leu
            770                 775                 780

Val Thr Ile Leu Asp Leu Leu Ile Thr Val Leu Asn Leu Leu Gly Ile
785                 790                 795                 800

Ser Phe Gly Tyr Phe Gly Pro Lys Cys Tyr Met Val Leu Phe Tyr Pro
                805                 810                 815
```

Glu Arg Asn Thr Gln Val Tyr Phe Ser Ser Met Ile Gln Gly Tyr Thr
            820                 825                 830

Met Gly Lys Asp
        835

<210> SEQ ID NO 7
<211> LENGTH: 4347
<212> TYPE: DNA
<213> ORGANISM: canine

<400> SEQUENCE: 7

| | | | | | |
|---|---|---|---|---|---|
| tacctactcc | tcaggtcact | tgcacctccc | tcaggcagct | ggagacccca | ggaccctctg | 60 |
| gcagagaagt | cctgagtgtc | cttcctcctt | tccaggagtg | gggtggggct | tgggcacagg | 120 |
| catgtaacaa | gatgtggtca | gtggtcagtc | agagcccgac | tgcccaggtc | actgtcaatc | 180 |
| agagagcctc | gtggtggcat | caggataaac | gagtccggga | tccctgggtg | gtacagtggt | 240 |
| ttggcgcctg | cctttggccc | ggggcacgat | cctggagacc | cgggatcaaa | tcccacatcg | 300 |
| ggctctcggt | gcatggagcc | tgcttctccc | tctgcctgtg | tctctgcctc | tctctctgtg | 360 |
| tgactatcat | aaataaataa | aaattttaaa | aatgtttaaa | aaaaaaaaag | gataaacgag | 420 |
| tccaagaagc | gcagacctgc | aaggcctagg | aaagtgaggg | tgtccccagg | gcccctgga | 480 |
| catgactggt | aaggacaggt | gataattttg | ctaagcaaat | cctctgccct | ccctgcccc | 540 |
| cactcatcat | attggggggcc | ccactcggt | tctctcattt | gccgtccctg | ctggaagctg | 600 |
| ccacctgcca | tggcaggcct | gatgctcctg | agcctcatgg | ctctcttggg | ccttggagca | 660 |
| ggcgccccat | tgtgcttatc | ccggcagctc | aggatgcaag | gggactatgt | gctgggcggg | 720 |
| ctcttccccc | tgggcacagc | tgaggacaca | ggtctcagtg | acaggacaca | gcccaatgcc | 780 |
| actgtgtgca | ccaggtaggg | atgccggggc | tgggaagcaa | agggtgacgg | ggtgggggc | 840 |
| tcagctctgg | ggtgctccca | agggaggacg | tggggtcagc | cccccacaac | ccttgtggcc | 900 |
| caggttctcg | tccctcggcc | tgctctgggc | gctggccatg | aagatggcgg | tggaggaggt | 960 |
| caacaacagg | tccacgctgc | tgccaggact | gcgcctgggc | tacgacctct | ttgacacatg | 1020 |
| ttcggagcct | gtggtggcca | tgaagcccag | cctcatgttc | atggccaaag | cgggcagctg | 1080 |
| cgacatcgcc | gcctactgca | actacacgca | gtaccagccc | cgtgtgctgg | cagtcattgg | 1140 |
| gccacactca | tctgagctcg | ccctcatcac | cggcaagttc | ttcagcttct | tcctcatgcc | 1200 |
| tcaggtgtgc | tcccctcct | ctcctgggtc | ccctgcccc | actggccctg | cccacaggag | 1260 |
| ccccacatc | aggaggtgcc | tcccggctgc | acaggtcag | ctacggggcc | agcaccgacc | 1320 |
| ggctgagcaa | ccgggagacg | ttcccatcct | tcttccgcac | ggtgtccagc | gaccgcgtac | 1380 |
| aggcagtggc | catggtggag | ctgctgcagg | agcttggctg | gaactgggtg | gctgcagtgg | 1440 |
| gcagcgatga | cgagtatggc | cggcagggcc | tgagcctctt | ctccagcctg | ccaatgcca | 1500 |
| ggggcatctg | tattgcgcat | gagggcctgg | tgccattgcc | gcacacgagt | agcctgcggc | 1560 |
| tgggcactgt | ccagggccta | ctgcaccagg | taaaccagag | cagcgtgcag | gtggtggtgc | 1620 |
| ttttctcttc | cactcgtgct | gcccgcaccc | tcttcagcta | cagcatccac | tgcaggctct | 1680 |
| cgcccaaggt | ttgggtggcc | agtgaggcct | ggctgaccte | ggacctggtc | atgacgctgc | 1740 |
| ctggcatggc | tgaggtgggc | accgtgcttg | gcttctgca | gcagggcgcc | ccaatacccg | 1800 |
| agttcccatc | ctatgtgcag | acctgcctgg | ccctggctgc | tgaccctgcc | ttttgcgcct | 1860 |
| cactggatgc | agagcagccg | ggcctggaag | agcacgtggt | ggggccccgc | tgtccccagt | 1920 |

```
gtgaccacgt cactctggag gctatgtctg cagggctgct gcaccaccag accttcgcgg    1980
cctacgcagc cgtgtatggc gtggcccagg ccctccacaa cacactgctc tgcaatgcct    2040
caggctgccc cccacgggag ccagtgcggc cctggcaggt aaggccagga ggccccgcac    2100
ttctgaggag cagtgtcagt ggggagtctg ggccggggac agctactggc ctggcccac     2160 ccacctgctc caatctgcct accagctcct agaaaacatg tacaacttga ccttccgtgt    2220
gcgcggctta gcactgcagt tcgatgccag ggggaacgtg aatatggatt atgacctgaa    2280
actgtgggtg tggcgggacc tgaagcccga gttgcgcacc gtaggtgcct tcaacggccg    2340
cctgaaggtc tggcactccc agatgtcctg gcacacacct gggaaccagg tgagcaccag    2400
gtggcacggc cctaactgca cagcagcttt cccttcagcc ccatacgagc tctggctctg    2460 ctggggggggg ggggtgaggt gggggagcac cccaaagact gggcgggcgc actcagcaca   2520
gcacagcctg agcccccaagg cctttgtggc agcggcccgt gtcccagtgc tcccggcagt   2580
gcggggaggg ccaggtgcgc cgtgtgaagg gcttccactc ctgctgctat gactgcgtgg    2640
actgcaaggc gggcacctat cagcgcagcc caggtgagca cctctccaag gcccatacac    2700
acgggacagg tgggggcagg gacccccagg tctcatgtcc tgactcaaag gccaactttg    2760
aggccagagc aagtgggtgg gagcctgaac tctcccccaa gtgccccatc ttcctcccac    2820
atgacagatg acctcctctg cacccagtgt gaccagaacc agtggtcccc agaccggagc    2880
acacgctgct tcccccgcag gctcactttc ctggcatggg ggcagccggc tgtgctggtg    2940
ctgcttatac tgctggctct ggcgctgggc ctggtgctgg tggccctggg gctctttatt    3000
aggcaccggg acagcccact ggttcaggcc tcaggggggc cacgggcctg ctttggcttg    3060
gcctgcctgg gccttgtctg cctcagtgtc cttctgttcc ctggccagcc gggccctgcc    3120
agctgcctgg cccagcagcc actgcttcac cttccactca ctggctgtct gagcacactt    3180
ttcctgcaag cggcccagat atttgtgggt tcagagctgc catcaagctg gcagatcag    3240 ctgcgtaggt gcctgcaggg gccctgggcc tggttgctgg tgctgcttgc tttgctggcg    3300
gaagcggcat tatgtgcctg gtacctggtg gcctttccac cagaggtggt gacagactgg    3360
tgggtgctac ccacgcaagt gctggtgcac tgccgaatgc gctcctggat cagctttggc    3420
ctattgcatg ccatcaatgc catgctggcc ttcctctgct tcctgggcac gttcttggtg    3480
cagagccggc caggccgcta caatggcgcc cggggtctca cttttgccat gctggcctac    3540
ttcatcacct ggatctcctt tgtccctctc tttgccaatg tgcatgtggc ctaccagccc    3600
actgtgcaga tggccgccat cctcctctgt gccctgggca tcctggccac cttccacctg    3660
cccaagtgct acctgctgct gcagcagctg gagctcaaca acccggagtt cttcctagga    3720
gatgatgcca gaggacaggg cagcagtggt agtggggggga aggagactta gggcaaaaac    3780
aagtgacccc tgacccagtg accccagacc tagctgagat ccccacaaat cacatttcta    3840
tgaagcaacc accaacctgg accccagctg ctgagaccac ccctttctag atcctaactg    3900
taggctaact agctgacctt gatggaacag tgaccgttag gcctgtagca tccatgaagg    3960
gcttcagcac ccacctgagg ccccagaaaa gctttgtccc tgtcctagcc aaggcctggc    4020
caaggcctac ccatgtgatc cagccctact gaacaaaagg tccacgaaaa ggatccttga    4080
ggctcctggc gttcatgcca agagctcaag acacctacca gccaggtcac ttaaaggcca    4140
aactgggcat tacttgcctg gccaggccca gcctggagcc tccagccagc accctctcca    4200
agcatcacag ggatgggaga ttggtaagag ggctggagat gtcgtgaccc ctctgcaggg    4260
gtctatgact gaccacagga ccagatgggg caggaatggt gagcagggaa gagggctagt    4320
```

```
gggagggtac atacccaacc tccttct                                        4347

<210> SEQ ID NO 8
<211> LENGTH: 2496
<212> TYPE: DNA
<213> ORGANISM: dog

<400> SEQUENCE: 8
atggcaggcc tgatgctcct gagcctcatg gctctcttgg ccttggagc aggcgcccca      60
ttgtgcttat cccggcagct caggatgcaa ggggactatg tgctgggcgg gctcttcccc    120
ctgggcacag ctgaggacac aggtctcagt gacaggacac agcccaatgc cactgtgtgc    180
accaggttct cgtccctcgg cctgctctgg gcgctggcca tgaagatggc ggtggaggag    240
gtcaacaaca ggtccacgct gctgccagga ctgcgcctgg gctacgacct ctttgacaca    300
tgttcggagc ctgtggtggc catgaagccc agcctcatgt tcatggccaa agcgggcagc    360
tgcgacatcg ccgcctactg caactacacg cagtaccagc ccgtgtgct ggcagtcatt     420
gggccacact catctgagct cgccctcatc accggcaagt tcttcagctt cttcctcatg    480
cctcaggtca gctacggggc cagcaccgac cggctgagca accgggagac gttcccatcc    540
ttcttccgca cggtgtccag cgaccgcgta caggcagtgg ccatggtgga gctgctgcag    600
gagcttggct ggaactgggt ggctgcagtg gcagcgatg acgagtatgg ccggcagggc     660
ctgagcctct tctccagcct ggccaatgcc aggggcatct gtattgcgca tgagggcctg    720
gtgccattgc cgcacacgag tagcctgcgg ctgggcactg tccagggcct actgcaccag    780
gtaaaccaga gcagcgtgca ggtggtggtg ctttttctctt ccactcgtgc tgcccgcacc   840
ctcttcagct acagcatcca ctgcaggctc tcgcccaagg tttgggtggc cagtgaggcc    900
tggctgacct cggacctggt catgacgctg cctggcatgg ctgaggtggg caccgtgctt    960
ggctttctgc agcagggcgc cccaataccc gagttcccat cctatgtgca gacctgcctg   1020
gccctggctg ctgaccctgc cttttgcgcc tcactggatg cagagcagcc gggcctggaa   1080
gagcacgtgg tggggcccg ctgtccccag tgtgaccacg tcactctgga gctatgtctg    1140
cagggctgct gcaccaccag accttcgcgg cctacgcagc cgtgtatggc gtggcccagg   1200
ccctccacaa cacactgctc tgcaatgcct caggctgccc ccacgggag ccagtgcggc    1260
cctggcagct cctagaaaac atgtacaact tgaccttccg tgtgcgcggc ttagcactgc   1320
agttcgatgc caggggaaac gtgaatatgg attatgacct gaaactgtgg gtgtggcggg   1380
acctgaagcc cgagttgcgc accgtaggtg ccttcaacgg ccgcctgaag gtctggcact   1440
cccagatgtc ctggcacaca cctgggaacc agcggcccgt gtcccagtgc tcccggcagt   1500
gcggggaggg ccaggtgcgc cgtgtgaagg cttccactc ctgctgctat gactgcgtgg    1560
actgcaaggc gggcacctat agcgcagcc cagatgacct cctctgcacc cagtgtgacc   1620
agaaccagtg gtccccagac cggagcacac gctgcttccc ccgcaggctc actttcctgg   1680
catgggggca gccggctgtg ctggtgctgc ttatactgct ggctctggcg ctgggcctgg   1740
tgctggtggc cctggggctc tttattaggc accgggacag cccactggtt caggcctcag   1800
gggggccacg ggcctgcttt ggcttggcct gctgggcct tgtctgcctc agtgtccttc    1860
tgttccctgg ccagccgggc cctgccagct gcctggccca gcagccactg cttcaccttc   1920
cactcactgg ctgtctgagc acactttttcc tgcaagcggc ccagatattt gtgggttcag   1980
agctgccatc aagctgggca gatcagctgc gtaggtgcct gcaggggccc tgggcctggt   2040
```

```
tgctggtgct gcttgctttg ctggcggaag cggcattatg tgcctggtac ctggtggcct      2100
ttccaccaga ggtggtgaca gactggtggg tgctacccac gcaagtgctg gtgcactgcc      2160
gaatgcgctc ctggatcagc tttggcctag tgcatgccat caatgccatg ctggccttcc      2220
tctgcttcct gggcacgttc ttggtgcaga gccggccagg ccgctacaat ggcgcccggg      2280
gtctcacttt tgccatgctg gcctacttca tcacctggat ctcctttgtc cctctctttg      2340
ccaatgtgca tgtggcctac cagcccactg tgcagatggc cgccatcctc ctctgtgccc      2400
tgggcatcct ggccaccttc cacctgccca agtgctacct gctgctgcag cagctggagc      2460
tcaacaaccc ggagttcttc ctaggagatg atgcca                                2496
```

```
<210> SEQ ID NO 9
<211> LENGTH: 845
<212> TYPE: PRT
<213> ORGANISM: dog

<400> SEQUENCE: 9
```

```
Met Ala Gly Leu Met Leu Leu Ser Leu Met Ala Leu Leu Gly Leu Gly
1               5                   10                  15

Ala Gly Ala Pro Leu Cys Leu Ser Arg Gln Leu Arg Met Gln Gly Asp
            20                  25                  30

Tyr Val Leu Gly Gly Leu Phe Pro Leu Gly Thr Ala Glu Asp Thr Gly
        35                  40                  45

Leu Ser Asp Arg Thr Gln Pro Asn Ala Thr Val Cys Thr Arg Phe Ser
    50                  55                  60

Ser Leu Gly Leu Leu Trp Ala Leu Ala Met Lys Met Ala Val Glu Glu
65                  70                  75                  80

Val Asn Asn Arg Ser Thr Leu Leu Pro Gly Leu Arg Leu Gly Tyr Asp
                85                  90                  95

Leu Phe Asp Thr Cys Ser Glu Pro Val Val Ala Met Lys Pro Ser Leu
            100                 105                 110

Met Phe Met Ala Lys Ala Gly Ser Cys Asp Ile Ala Ala Tyr Cys Asn
        115                 120                 125

Tyr Thr Gln Tyr Gln Pro Arg Val Leu Ala Val Ile Gly Pro His Ser
    130                 135                 140

Ser Glu Leu Ala Leu Ile Thr Gly Lys Phe Phe Ser Phe Phe Leu Met
145                 150                 155                 160

Pro Gln Val Ser Tyr Gly Ala Ser Thr Asp Arg Leu Ser Asn Arg Glu
                165                 170                 175

Thr Phe Pro Ser Phe Phe Arg Thr Val Ser Ser Asp Arg Val Gln Ala
            180                 185                 190

Val Ala Met Val Glu Leu Leu Gln Glu Leu Gly Trp Asn Trp Val Ala
        195                 200                 205

Ala Val Gly Ser Asp Asp Glu Tyr Gly Arg Gln Gly Leu Ser Leu Phe
    210                 215                 220

Ser Ser Leu Ala Asn Ala Arg Gly Ile Cys Ile Ala His Glu Gly Leu
225                 230                 235                 240

Val Pro Leu Pro His Thr Ser Ser Leu Arg Leu Gly Thr Val Gln Gly
                245                 250                 255

Leu Leu His Gln Val Asn Gln Ser Ser Val Gln Val Val Leu Phe
            260                 265                 270

Ser Ser Thr Arg Ala Ala Arg Thr Leu Phe Ser Tyr Ser Ile His Cys
        275                 280                 285

Arg Leu Ser Pro Lys Val Trp Val Ala Ser Glu Ala Trp Leu Thr Ser
```

-continued

```
            290                 295                 300
Asp Leu Val Met Thr Leu Pro Gly Met Ala Glu Val Gly Thr Val Leu
305                 310                 315                 320
Gly Phe Leu Gln Gln Gly Ala Pro Ile Pro Glu Phe Pro Ser Tyr Val
                    325                 330                 335
Gln Thr Cys Leu Ala Leu Ala Ala Asp Pro Ala Phe Cys Ala Ser Leu
                340                 345                 350
Asp Ala Glu Gln Pro Gly Leu Glu Glu His Val Val Gly Pro Arg Cys
                355                 360                 365
Pro Gln Cys Asp His Val Thr Leu Glu Ala Met Ser Ala Gly Leu Leu
370                 375                 380
His His Gln Thr Phe Ala Ala Tyr Ala Ala Val Tyr Gly Val Ala Gln
385                 390                 395                 400
Ala Leu His Asn Thr Leu Leu Cys Asn Ala Ser Gly Cys Pro Pro Arg
                    405                 410                 415
Glu Pro Val Arg Pro Trp Gln Leu Leu Glu Asn Met Tyr Asn Leu Thr
                420                 425                 430
Phe Arg Val Arg Gly Leu Ala Leu Gln Phe Asp Ala Arg Gly Asn Val
                435                 440                 445
Asn Met Asp Tyr Asp Leu Lys Leu Trp Val Trp Arg Asp Leu Lys Pro
450                 455                 460
Glu Leu Arg Thr Val Gly Ala Phe Asn Gly Arg Leu Lys Val Trp His
465                 470                 475                 480
Ser Gln Met Ser Trp His Thr Pro Gly Asn Gln Arg Pro Val Ser Gln
                    485                 490                 495
Cys Ser Arg Gln Cys Gly Glu Gly Gln Val Arg Arg Val Lys Gly Phe
                500                 505                 510
His Ser Cys Cys Tyr Asp Cys Val Asp Cys Lys Ala Gly Thr Tyr Gln
                515                 520                 525
Arg Ser Pro Asp Asp Leu Leu Cys Thr Gln Cys Asp Gln Asn Gln Trp
530                 535                 540
Ser Pro Asp Arg Ser Thr Arg Cys Phe Pro Arg Arg Leu Thr Phe Leu
545                 550                 555                 560
Ala Trp Gly Gln Pro Ala Val Leu Val Leu Leu Ile Leu Leu Ala Leu
                    565                 570                 575
Ala Leu Gly Leu Val Leu Val Ala Leu Gly Leu Phe Ile Arg His Arg
                580                 585                 590
Asp Ser Pro Leu Val Gln Ala Ser Gly Gly Pro Arg Ala Cys Phe Gly
                595                 600                 605
Leu Ala Cys Leu Gly Leu Val Cys Leu Ser Val Leu Leu Phe Pro Gly
610                 615                 620
Gln Pro Gly Pro Ala Ser Cys Leu Ala Gln Gln Pro Leu Leu His Leu
625                 630                 635                 640
Pro Leu Thr Gly Cys Leu Ser Thr Leu Phe Leu Gln Ala Ala Gln Ile
                    645                 650                 655
Phe Val Gly Ser Glu Leu Pro Ser Ser Trp Ala Asp Gln Leu Arg Arg
                660                 665                 670
Cys Leu Gln Gly Pro Trp Ala Trp Leu Leu Val Leu Leu Ala Leu Leu
                675                 680                 685
Ala Glu Ala Ala Leu Cys Ala Trp Tyr Leu Val Ala Phe Pro Pro Glu
690                 695                 700
Val Val Thr Asp Trp Trp Val Leu Pro Thr Gln Val Leu Val His Cys
705                 710                 715                 720
```

```
Arg Met Arg Ser Trp Ile Ser Phe Gly Leu Val His Ala Ile Asn Ala
            725                 730                 735
Met Leu Ala Phe Leu Cys Phe Leu Gly Thr Phe Leu Val Gln Ser Arg
            740                 745                 750
Pro Gly Arg Tyr Asn Gly Ala Arg Gly Leu Thr Phe Ala Met Leu Ala
            755                 760                 765
Tyr Phe Ile Thr Trp Ile Ser Phe Val Pro Leu Phe Ala Asn Val His
            770                 775                 780
Val Ala Tyr Gln Pro Thr Val Gln Met Ala Ala Ile Leu Leu Cys Ala
785                 790                 795                 800
Leu Gly Ile Leu Ala Thr Phe His Leu Pro Lys Cys Tyr Leu Leu Leu
                805                 810                 815
Gln Gln Leu Glu Leu Asn Asn Pro Glu Phe Phe Leu Gly Asp Asp Ala
            820                 825                 830
Arg Gly Gln Gly Ser Ser Gly Ser Gly Gly Lys Glu Thr
            835                 840                 845

<210> SEQ ID NO 10
<211> LENGTH: 2532
<212> TYPE: DNA
<213> ORGANISM: mouse

<400> SEQUENCE: 10
atgggacccc aggcgaggac actccatttg ctgtttctcc tgctgcatgc tctgcctaag    60
ccagtcatgc tggtagggaa ctccgacttt cacctggctg ggactacct cctgggtggc   120
ctctttaccc tccatgccaa cgtgaagagc gtctctcacc tcagctacct gcaggtgccc   180
aagtgcaatg agtacaacat gaaggtcttg ggctacaacc tcatgcaggc catgcgattc   240
gccgtggagg aaatcaacaa ctgtagctct ctgctgcccg cgtgctgct cggctacgag   300
atggtggatg tctgctacct ctccaacaat atccagcctg gctctactt cctgtcacag   360
atagatgact tcctgcccat cctcaaagac tacagccagt acaggcccca gtggtggcc   420
gtcattggcc agacaactc tgagtccgcc atcaccgtgt ccaacattct tcctacttc   480
ctcgtgccac aggtcacata tagcgccatc accgacaagc tgcgagacaa gcggcgcttc   540
cctgccatgc tgcgcactgt gcccagcgcc acccaccaca tcgaggccat ggtgcaactg   600
atggttcact tccagtggaa ctggatcgtg gtgctggtga gcgatgacga ttatggccga   660
gagaacagcc acctgctgag ccagcgtctg accaacactg gcgatatctg cattgccttc   720
caggaggttc tgcctgtacc agaacccaac caggccgtga ggcctgagga gcaggaccaa   780
ctggacaaca tcctggacaa gctgcggcgg acctcggcgc gtgtggtggt gatattctcg   840
ccagagctga gcctgcacaa cttcttccgc gaggtgctgc gctggaactt cacaggcttt   900
gtgtggattg cctctgagtc ctgggccatc gaccctgttc tacacaacct cacagagctg   960
cgccacacgg gcactttcct gggcgtcacc atccagaggg tgtccatccc tggcttcagc  1020
cagttccgag tgcgccacga caagccgaga tatcccatgc taacgagac cagcctgagg  1080
actacctgta accaggactg tgacgcctgc atgaacatca ccgagtcctt taacaacgtt  1140
ctcatgcttt cggggagcg tgtggtctac agtgtgtact cggccgtcta cgcggtagcc  1200
cacacccctcc acagactcct ccactgcaac caggtccgct gcaccaagca aatcgtctat  1260
ccatggcagc tactcaggga gatctggcat gtcaacttca cgctcctggg caaccagctc  1320
ttcttcgacg aacaagggga catgccgatg ctcctggaca tcatccagtg gcaatggggc  1380
```

-continued

```
ctgagccaga accccttcca aagcatcgcc tcctactccc ccaccgagac gaggctgacc    1440
tacattagca atgtgtcctg gtacaccccc aacaacacgg tccccatatc catgtgttct    1500
aagagttgcc agcctgggca atgaaaaaaa cccataggcc tccacccgtg ctgcttcgag    1560
tgtgtggact gtccgccggg cacctacctc aaccgatcag tagatgagtt taactgtctg    1620
tcctgcccgg gttccatgtg gtcttacaag aacaacatcg cttgcttcaa gcggcggctg    1680
gccttcctgg agtggcacga agtgccccact atcgtggtga ccatcctggc cgccctgggc    1740
ttcatcagta cgctggccat tctgctcatc ttctggagac atttccagac gcccatggtg    1800
cgctcggcgg gcggcccccat gtgcttcctg atgctggtgc cctgctgct ggcgttcggg     1860 atggtccccg tgtatgtggg cccccccacg gtcttctcct gtttctgccg ccaggctttc    1920
ttcaccgttt gcttctccgt ctgcctctcc tgcatcacgg tgcgctcctt ccagattgtg    1980
tgcgtcttca agatggccag acgcctgcca agcgcctacg gtttctggat gcgttaccac    2040
gggccctacg tctttgtggc cttcatcacg gccgtcaagg tggccctggt ggcaggcaac    2100
atgctggcca ccaccatcaa ccccattggc cggaccgacc ccgatgaccc caatatcata    2160
atcctctcct gccacccta actaccgcaac gggctactct tcaacaccag catggacttg    2220
ctgctgtccg tgctgggttt cagcttcgcg tacgtgggca aggaactgcc caccaactac    2280
aacgaagcca agttcatcac cctcagcatg accttctcct tcacctcctc catctccctc    2340
tgcacgttca tgtctgtcca cgatggcgtg ctggtcacca tcatggatct cctggtcact    2400
gtgctcaact ttctggccat cggcttgggg tactttggcc ccaagtgtta catgatcctt    2460
ttctacccgg agcgcaacac ttcagcttat ttcaatagca tgattcaggg ctacacgatg    2520
aggaagagct ag                                                        2532
```

<210> SEQ ID NO 11
<211> LENGTH: 2529
<212> TYPE: DNA
<213> ORGANISM: rat

<400> SEQUENCE: 11

```
atgggtcccc aggcaaggac actctgcttg ctgtctctcc tgctgcatgt tctgcctaag     60
ccaggcaagc tggtagagaa ctctgacttc cacctggccg gggactacct cctgggtggc    120
ctctttaccc tccatgccaa cgtgaagagc atctcccacc tcagctacct gcaggtgccc    180
aagtgcaatg agttcaccat gaaggtgttg ggctacaacc tcatgcaggc catgcgtttc    240
gctgtggagg agatcaacaa ctgtagctcc ctgctacccg gcgtgctgct cggctacgag    300
atggtggatg tctgttacct ctccaacaat atccaccctg gctctactt cctggcacag     360 gacgacgacc tcctgcccat cctcaaagac tacagccagt acatgcccca cgtggtggct    420
gtcattggcc ccgacaactc tgagtccgcc attaccgtgt ccaacattct ctctcatttc    480
ctcatcccac agatcacata cagcgccatc tccgacaagc tgcgggacaa gcggcacttc    540
cctagcatgc tacgcacagt gcccagcgcc acccaccaca tcgaggccat ggtgcagctg    600
atggttcact tccaatggaa ctggattgtg gtgctggtga cgacgacga ttacggccgc    660 gagaacagcc acctgttgag ccagcgtctg accaaaacga gcgacatctg cattgccttc    720
caggaggttc tgcccatacc tgagtccagc caggtcatga ggtccgagga gcagagacaa    780
ctggacaaca tcctggacaa gctgcggcgg acctcggcgc gcgtcgtggt ggtgttctcg    840
cccgagctga gcctgtatag cttctttcac gaggtgctcc gctggaactt cacgggtttt    900
gtgtggatcg cctctgagtc ctgggctatc gacccagttc tgcataacct cacggagctg    960
```

-continued

| | |
|---|---|
| cgccacacgg gtacttttct gggcgtcacc atccagaggg tgtccatccc tggcttcagt | 1020 |
| cagttccgag tgcgccgtga caagccaggg tatcccgtgc ctaacacgac caacctgcgg | 1080 |
| acgacctgca accaggactg tgacgcctgc ttgaacacca ccaagtcctt caacaacatc | 1140 |
| cttatacttt cgggggagcg cgtggtctac agcgtgtact cggcagttta cgcggtggcc | 1200 |
| catgccctcc acagactcct cggctgtaac cgggtccgct gcaccaagca aaaggtctac | 1260 |
| ccgtggcagc tactcaggga gatctggcac gtcaacttca cgctcctggg taaccggctc | 1320 |
| ttctttgacc aacaagggga catgccgatg ctccttggaca tcatccagtg gcagtgggac | 1380 |
| ctgagccaga atcccttcca aagcatcgcc tcctattctc ccaccagcaa gaggctaacc | 1440 |
| tacattaaca atgtgtcctg gtacaccccc aacaacacgg tccctgtctc catgtgttcc | 1500 |
| aagagctgcc agccagggca aatgaaaaag tctgtgggcc tccaccccttg ttgcttcgag | 1560 |
| tgcttggatt gtatgccagg cacctacctc aaccgctcag cagatgagtt taactgtctg | 1620 |
| tcctgcccgg gttccatgtg gtcctacaag aacgacatca cttgcttcca gcggcggcct | 1680 |
| accttcctgg agtggcacga agtgcccacc atcgtggtgg ccatactggc tgccctgggc | 1740 |
| ttcttcagta cactggccat tctttttcatc ttctggagac atttccagac acccatggtg | 1800 |
| cgctcggccg gtggccccat gtgcttcctg atgctcgtgc ccctgctgct ggcgtttggg | 1860 |
| atggtgcccg tgtatgtggg gccccccacg gtcttctcat gcttctgccg acaggctttc | 1920 |
| ttccgtgtct gcttctccat ctgcctatcc tgcatcaccg tgcgctcctt ccagatcgtg | 1980 |
| tgtgtcttca agatggccag acgcctgcca agtgcctaca gttttggat gcgttaccac | 2040 |
| gggccctatg tcttcgtggc cttcatcacg gccatcaagg tggccctggt ggtgggcaac | 2100 |
| atgctggcca ccaccatcaa ccccattggc cggaccgacc cggatgaccc caacatcatg | 2160 |
| atcctctcgt gccacccta ctaccgcaac gggctactgt tcaacaccag catggacttg | 2220 |
| ctgctgtctg tgctgggttt cagcttcgct tacatgggca aggagctgcc caccaactac | 2280 |
| aacgaagcca agttcatcac tctcagcatg accttctcct tcacctcctc catctccctc | 2340 |
| tgcaccttca tgtctgtgca cgacggcgtg ctggtcacca tcatggacct cctggtcact | 2400 |
| gtgctcaact tcctggccat cggcttggga tactttggcc ccaagtgtta catgatcctt | 2460 |
| ttctacccgg agcgcaacac ctcagcctat ttcaatagca tgatccaggg ctacaccatg | 2520 |
| aggaagagc | 2529 |

<210> SEQ ID NO 12
<211> LENGTH: 2520
<212> TYPE: DNA
<213> ORGANISM: human

<400> SEQUENCE: 12

| | |
|---|---|
| atggggccca gggcaaagac catctgctcc ctgttcttcc tcctatgggt cctggctgag | 60 |
| ccggctgaga actcggactt ctacctgcct ggggattacc tctgggtgg cctcttctcc | 120 |
| ctccatgcca acatgaaggg cattgttcac cttaacttcc tgcaggtgcc catgtgcaag | 180 |
| gagtatgaag tgaaggtgat aggctacaac ctcatgcagg ccatgcgctt cgcggtggag | 240 |
| gagatcaaca atgacagcag cctgctgcct ggtgtgctgc tgggctatga gatcgtggat | 300 |
| gtgtgctaca tctccaacaa tgtccagccg gtgctctact tcctggcaca cgaggacaac | 360 |
| ctccttccca tccaagagga ctacagtaac tacatttccc cgtgtggtgc tgtcattggc | 420 |
| cctgacaact ccgagtctgt catgactgtg gccaacttcc tctccctatt tctccttcca | 480 |

```
cagatcacct acagcgccat cagcgatgag ctgcgagaca aggtgcgctt cccggctttg    540
ctgcgtacca cacccagcgc cgaccaccac gtcgaggcca tggtgcagct gatgctgcac    600
ttccgctgga actggatcat tgtgctggtg agcagcgaca cctatggccg cgacaatggc    660
cagctgcttg gcgagcgcgt ggcccggcgc gacatctgca tcgccttcca ggagacgctg    720
cccacactgc agcccaacca gaacatgacg tcagaggagc gccagcgcct ggtgaccatt    780
gtggacaagc tgcagcagag cacagcgcgc gtcgtggtcg tgttctcgcc cgacctgacc    840
ctgtaccact tcttcaatga ggtgctgcgc cagaacttca cgggcgccgt gtggatcgcc    900
tccgagtcct gggccatcga cccggtcctg cacaacctca cggagctggg ccacttgggc    960
accttcctgg gcatcaccat ccagagcgtg cccatcccgg gcttcagtga gttccgcgag   1020
tggggcccac aggctgggcc gccaccectc agcaggacca gccagagcta tacctgcaac   1080
caggagtgcg acaactgcct gaacgccacc ttgtccttca acaccattct caggctctct   1140
ggggagcgtg tcgtctacag cgtgtactct gcggtctatg ctgtggccca tgccctgcac   1200
agcctcctcg gctgtgacaa agcacctgc accaagaggg tggtctaccc ctggcagctg   1260
cttgaggaga tctggaaggt caacttcact ctcctggacc accaaatctt cttcgacccg   1320
caaggggacg tggctctgca cttggagatt gtccagtggc aatgggaccg gagccagaat   1380
cccttccaga gcgtcgcctc ctactacccc ctgcagcgac agctgaagaa catccaagac   1440
atctcctggc acaccgtcaa caacacgatc cctatgtcca tgtgttccaa gaggtgccag   1500
tcagggcaaa agaagaagcc tgtgggcatc cacgtctgct gcttcgagtg catcgactgc   1560
cttcccggca ccttcctcaa ccacactgaa gatgaatatg aatgccaggc tgcccgaat   1620 aacgagtggt cctaccagag tgagacctcc tgcttcaagc ggcagctggt cttcctggaa   1680
tggcatgagg cacccaccat cgctgtggcc ctgctggccg ccctgggctt cctcagcacc   1740
ctggccatcc tggtgatatt ctggaggcac ttccagacac ccatagttcg ctcggctggg   1800
ggccccatgt gcttcctgat gctgacactg ctgctggtgg catacatggt ggtcccggtg   1860
tacgtggggc cgcccaaggt ctccacctgc ctctgccgcc aggccctctt tcccctctgc   1920
ttcacaattt gcatctcctg tatcgccgtg cgttctttcc agatcgtctg cgccttcaag   1980
atggccagcc gcttcccacg cgcctacagc tactgggtcc gctaccaggg ccctacgtc    2040 tctatggcat ttatcacggt actcaaaatg gtcattgtgg taattggcat gctggccacg   2100
ggcctcagtc ccaccaccccg tactgacccc gatgaccca agatcacaat tgtctcctgt   2160
aaccccaact accgcaacag cctgctgttc aacaccagcc tggaccctgct gctctcagtg   2220 gtgggtttca gcttcgccta catgggcaaa gagctgccca ccaactacaa cgaggccaag   2280
ttcatcaccc tcagcatgac cttctatttc acctcatccg tctcccctctg cacccttcatg   2340 tctgcctaca gcggggtgct ggtcaccatc gtggacctct tggtcactgt gctcaacctc   2400
ctggccatca gcctgggcta cttcggcccc aagtgctaca tgatcctctt ctacccggag   2460
cgcaacacgc ccgcctactt caacagcatg atccagggct acaccatgag gagggactag   2520
```

```
<210> SEQ ID NO 13
<211> LENGTH: 2529
<212> TYPE: DNA
<213> ORGANISM: mouse

<400> SEQUENCE: 13 atgctttct gggcagctca cctgctgctc agcctgcagc tggccgttgc ttactgctgg     60
gctttcagct gccaaaggac agaatcctct ccaggtttca gcctccctgg ggacttcctc    120
```

```
ctggcaggcc tgttctccct ccatgctgac tgtctgcagg tgagacacag acctctggtg      180
acaagttgtg acaggtctga cagcttcaac ggccatggct atcacctctt ccaagccatg      240
cggttcaccg ttgaggagat aaacaactcc acagctctgc ttcccaacat cacccctgggg     300 tatgaactgt atgacgtgtg ctcagagtct ccaatgtct atgccaccct gagggtgctc       360
gcccagcaag ggacaggcca cctagagatg cagagagatc ttcgcaacca ctcctccaag      420
gtggtggcac tcattgggcc tgataacact gaccacgctg tcaccactgc tgccctgctg      480
agcccttttc tgatgcccct ggtcagctat gaggcgagca gcgtgatcct cagtgggaag      540
cgcaagttcc cgtccttctt gcgcaccatc cccagcgata agtaccaggt ggaagtcata      600
gtgcggctgc tgcagagctt cggctgggtc tggatctcgc tcgttggcag ctatggtgac      660
tacgggcagc tgggcgtaca ggcgctggag gagctggcca ctccacgggg catctgcgtc      720
gccttcaagg acgtggtgcc tctctccgcc caggcgggtg acccaaggat gcagcgcatg      780
atgctgcgtc tggctcgagc caggaccacc gtggtcgtgg tcttctctaa ccggcacctg      840
gctggagtgt tcttcaggtc tgtggtgctg gccaacctga ctggcaaagt gtggatcgcc      900
tccgaagact gggccatctc cacgtacatc accaatgtgc ccgggatcca gggcattggg      960
acggtgctgg gggtggccat ccagcagaga caagtccctg gcctgaagga gtttgaagag     1020
tcctatgtcc aggcagtgat gggtgctccc agaacttgcc cagaggggtc ctggtgcggc     1080
actaaccagc tgtgcaggga gtgtcacgct tcacgacat ggaacatgcc cgagcttgga     1140
gccttctcca tgagcgctgc ctacaatgtg tatgaggctg tgtatgctgt ggcccacggc     1200
ctccaccagc tcctgggatg tacctctggg acctgtgcca gaggcccagt ctaccccctgg    1260 cagcttcttc agcagatcta caaggtgaat ttccttctac ataagaagac tgtagcattc     1320
gatgacaagg gggaccctct aggttattat gacatcatcg cctgggactg gaatggacct     1380
gaatggacct ttgaggtcat tggttctgcc tcactgtctc cagttcatct agacataaat     1440
aagacaaaaa tccagtggca cgggaagaac aatcaggtgc ctgtgtcagt gtgtaccagg     1500
gactgtctcg aagggcacca caggttggtc atgggttccc accactgctg cttcgagtgc     1560
atgccctgtg aagctgggac atttctcaac acgagtgagc ttcacacctg ccagccttgt     1620
ggaacagaag aatgggcccc tgaggggagc tcagcctgct tctcacgcac cgtggagttc     1680
ttggggtggc atgaacccat ctctttggtg ctattagcag ctaacacgct attgctgctg     1740
ctgctgattg ggactgctgg cctgtttgcc tggcgtcttc acacgcctgt tgtgaggtca     1800
gctgggggta ggctgtgctt cctcatgctg ggttccttgg tagctgggag ttgcagcctc     1860
tacagcttct cgggaagcc cacggtgccc gcgtgcttgc tgcgtcagcc cctcttttct     1920
ctcgggtttg ccatttttcct ctcctgtctg acaatccgct ccttccaact ggtcatcatc     1980
ttcaagtttt ctaccaaggt acccacattc taccacactt gggcccaaaa ccatggtgcc     2040
ggaatattcg tcattgtcag ctccacggtc catttgttcc tctgtctcac gtggcttgca     2100
atgtggaccc cacggcccac cagggagtac cagcgcttcc cccatctggt gattcttgag     2160
tgcacagagg tcaactctgt gggcttcctg gtggctttcg cacacaacat cctcctctcc     2220
atcagcacct ttgtctgcag ctacctgggt aaggaactgc cggagaacta taacgaagcc     2280
aaatgtgtca ccttcagcct gctcctccac ttcgtatcct ggatcgcttt cttcaccatg     2340
tccagcattt accagggcag ctacctaccc gcggtcaatg tgctggcagg ctggccact     2400 ctgagtggcg gcttcagcgg ctatttcctc cctaaatgct acgtgattct ctgccgtcca     2460
```

```
gaactcaaca acacagaaca ctttcaggcc tccatccagg actacacgag gcgctgcggc    2520
actacctga                                                             2529

<210> SEQ ID NO 14
<211> LENGTH: 2520
<212> TYPE: DNA
<213> ORGANISM: rat

<400> SEQUENCE: 14
atgctcttct gggctgctca cctgctgctc agcctgcagt tggtctactg ctgggctttc     60
agctgccaaa ggacagagtc ctctccaggc ttcagccttc tggggacttc cctccttgca    120
ggtctgttct ccctccatgg tgactgtctg caggtgagac acagacctct ggtgacaagt    180
tgtgacaggc ccgacagctt caacggccat ggctaccacc tcttccaagc catgcggttc    240
actgttgagg agataaacaa ctcctcggcc ctgcttccca acatcaccct ggggtatgag    300
ctgtacgacg tgtgctcaga atctgccaat gtgtatgcca ccctgagggt gcttgccctg    360
caagggcccc gccacataga gatacagaaa gaccttcgca accactcctc aaggtggtg    420 gccttcatcg ggcctgacaa cactgaccac gctgtcacta ccgctgcctt gctgggtcct    480
ttcctgatgc cctggtcag ctatgaggca agcagcgtgg tactcagtgc caagcgcaag    540
ttcccgtctt ccttcgtac cgtccccagt gaccggcacc aggtggaggt catggtgcag    600
ctgctgcaga gttttgggtg ggtgtggatc tcgctcattg gcagctacgg tgattacggg    660
cagctggggt tgcaggcgct ggaggagctg gccgtgcccc ggggcatctg cgtcgccttc    720
aaggacatcg tgccttttctc tgcccgggtg ggtgacccga ggatgcagag catgatgcag    780
catctggctc aggccaggac caccgtggtt gtggtcttct ctaaccggca cctggctaga    840
gtgttcttca ggtccgtggt gctggccaac ctgactggca aagtgtgggt cgcctcagaa    900
gactgggcca tctccacgta catcaccagc gtgactggga tccaaggcat gggacggtg    960 ctcggtgtgg ccgtccagca gagacaagtc cctgggctga aggagtttga ggagtcttat   1020
gtcagggctg taacagctgc tcccagcgct tgcccggagg ggtcctggtg cagcactaac   1080
cagctgtgcc gggagtgcca cacgttcacg actcgtaaca tgcccacgct ggagccttc    1140 tccatgagtg ccgcctacag agtgtatgag gctgtgtacg ctgtggccca cggcctccac   1200
cagctcctgg gatgtacttc tgagatctgt tccagaggcc cagtctaccc ctggcagctt   1260
cttcagcaga tctacaaggt gaattttctt ctacatgaga atactgtggc atttgatgac   1320
aacggggaca ctctaggtta ctacgacatc atcgcctggg actggaatgg acctgaatgg   1380
acctttgaga tcattggctc tgcctcactg tctccagttc atctggacat aaataagaca   1440
aaaatccagt ggcacgggaa gaacaatcag gtgcctgtgt cagtgtgtac cacggactgt   1500
ctggcagggc accacagggt ggttgtgggt tcccaccact gctgcttcga gtgcatgccc   1560
tgtgaagctg gacatttct caacacgagt gagcttcaca tctgccagcc ttgtggaaca   1620
gaagaatggg cacccaagga gagcactact tgcttcccac gcacggtgga gttcttggct   1680
tggcatgaac ccatctcttt ggtgctaata gcagctaaca cgctattgct gctgctgctg   1740
gttgggactg ctggcctgtt tgcctggcat ttcacacac ctgtagtgag gtcagctggg   1800
ggtaggctgt gcttcctcat gctggggtcc ctggtggccg aagttgcag cttctatagc    1860 ttcttcgggg agcccacggt gcccgcgtgc ttgctgcgtc agcccctctt ttctctcggg   1920
tttgccatct tcctctcctg cctgacaatc cgctccttcc aactggtcat catcttcaag   1980
ttttctacca aggtgcccac attctaccgt acctgggccc aaaaccatgg tgcaggtcta   2040
```

| | | | |
|---|---|---|---|
| ttcgtcattg | tcagctccac | ggtccatttg ctcatctgtc tcacatggct tgtaatgtgg | 2100 |
| accccacgac | ccaccaggga | ataccagcgc ttcccccatc tggtgattct cgagtgcaca | 2160 |
| gaggtcaact | ctgtaggctt | cctgttggct ttcacccaca acattctcct ctccatcagt | 2220 |
| accttcgtct | gcagctacct | gggtaaggaa ctgccagaga actataatga agccaaatgt | 2280 |
| gtcaccttca | gcctgctcct | caacttcgta tcctggatcg ccttcttcac catggccagc | 2340 |
| atttaccagg | gcagctacct | gcctgcggtc aatgtgctgg cagggctgac cacactgagc | 2400 |
| ggcggcttca | gcggttactt | cctccccaag tgctatgtga ttctctgccg tccagaactc | 2460 |
| aacaatacag | aacactttca | ggcctccatc caggactaca cgaggcgctg cggcactacc | 2520 |

<210> SEQ ID NO 15
<211> LENGTH: 2526
<212> TYPE: DNA
<213> ORGANISM: human

<400> SEQUENCE: 15

| | | | |
|---|---|---|---|
| atgctgctct | gcacggctcg | cctggtcggc ctgcagcttc tcatttcctg ctgctgggcc | 60 |
| tttgcctgcc | atagcacgga | gtcttctcct gacttcaccc tccccggaga ttacctcctg | 120 |
| gcaggcctgt | tccctctcca | ttctggctgt ctgcaggtga ggcacagacc cgaggtgacc | 180 |
| ctgtgtgaca | ggtcttgtag | cttcaatgag catggctacc acctcttcca ggctatgcgg | 240 |
| cttggggttg | aggagataaa | caactccacg gccctgctgc ccaacatcac cctggggtac | 300 |
| cagctgtatg | atgtgtgttc | tgactctgcc aatgtgtatg ccacgctgag agtgctctcc | 360 |
| ctgccagggc | aacaccacat | agagctccaa ggagaccttc tccactattc ccctacggtg | 420 |
| ctggcagtga | ttgggcctga | cagcaccaac cgtgctgcca ccacagccgc cctgctgagc | 480 |
| cctttcctgg | tgcccatgat | tagctatgcg ccagcagcg agacgctcag cgtgaagcgg | 540 |
| cagtatccct | ctttcctgcg | caccatcccc aatgacaagt accaggtgga gaccatggtg | 600 |
| ctgctgctgc | agaagttcgg | gtggacctgg atctctctgg ttggcagcag tgacgactat | 660 |
| gggcagctag | gggtgcaggc | actggagaac caggccactg tcaggggat ctgcattgct | 720 |
| ttcaaggaca | tcatgccctt | ctctgcccag gtgggcgatg agaggatgca gtgcctcatg | 780 |
| cgccacctgg | cccaggccgg | ggccaccgtc gtggttgttt tttccagccg gcagttggcc | 840 |
| agggtgtttt | tcgagtccgt | ggtgctgacc aacctgactg gcaaggtgtg ggtcgcctca | 900 |
| gaagcctggg | ccctctccag | gcacatcact ggggtgcccg ggatccagcg cattgggatg | 960 |
| gtgctgggcg | tggccatcca | agagagggct gtccctggcc tgaaggcgtt tgaagaagcc | 1020 |
| tatgcccggg | cagacaagaa | ggcccctagg ccttgccaca gggctcctg gtgcagcagc | 1080 |
| aatcagctct | gcagagaatg | ccaagctttc atggcacaca cgatgcccaa gctcaaagcc | 1140 |
| ttctccatga | gttctgccta | caacgcatac cgggctgtgt atgcggtggc ccatggcctc | 1200 |
| caccagctcc | tgggctgtgc | ctctggagct tgttccaggg gccgagtcta cccctggcag | 1260 |
| cttttggagc | agatccacaa | ggtgcatttc cttctacaca aggacactgt ggcgtttaat | 1320 |
| gacaacagag | atccctcag | tagctataac ataattgcct gggactggaa tggacccaag | 1380 |
| tggaccttca | cggtcctcgg | ttcctccaca tggtctccag ttcagctaaa cataaatgag | 1440 |
| accaaaatcc | agtggcacgg | aaaggacaac caggtgccta gtctgtgtg ttccagcgac | 1500 |
| tgtcttgaag | gcaccagcg | agtggttacg ggtttccatc actgctgctt tgagtgtgtg | 1560 |
| ccctgtgggg | ctgggaccct | cctcaacaag agtgacctct acagatgcca gccttgtggg | 1620 |

-continued

```
aaagaagagt gggcacctga gggaagccag acctgcttcc cgcgcactgt ggtgttttttg    1680
gctttgcgtg agcacacctc ttgggtgctg ctggcagcta acacgctgct gctgctgctg    1740
ctgcttggga ctgctggcct gtttgcctgg cacctagaca ccctgtggt gaggtcagca     1800
gggggccgcc tgtgctttct tatgctgggc tccctggcag caggtagtgg cagcctctat    1860
ggcttctttg gggaacccac aaggcctgcg tgcttgctac gccaggccct ctttgccctt    1920
ggtttcacca tcttcctgtc ctgcctgaca gttcgctcat ccaactaat catcatcttc     1980
aagttttcca ccaaggtacc tacattctac cacgcctggg tccaaaacca cggtgctggc    2040
ctgtttgtga tgatcagctc agcggcccag ctgcttatct gtctaacttg gctggtggtg    2100
tggaccccac tgcctgctag ggaataccag cgcttccccc atctggtgat gcttgagtgc    2160
acagagacca actccctggg cttcatactg gccttcctct acaatggcct cctctccatc    2220
agtgcctttg cctgcagcta cctgggtaag gacttgccag agaactacaa cgaggccaaa    2280
tgtgtcacct tcagcctgct cttcaacttc gtgtcctgga tcgccttctt caccacggcc    2340
agcgtctacg acggcaagta cctgcctgcg gccaacatga tggctgggct gagcagcctg    2400
agcagcggct tcgtgtggta ttttctgcct aagtgctacg tgatcctctg ccgcccagac    2460
ctcaacagca cagagcactt ccaggcctcc attcaggact cacgaggcg ctgcggctcc     2520
acctga                                                               2526
```

<210> SEQ ID NO 16
<211> LENGTH: 2577
<212> TYPE: DNA
<213> ORGANISM: mouse

<400> SEQUENCE: 16

```
atgccagctt tggctatcat gggtctcagc ctggctgctt cctggagct tgggatgggg    60
gcctctttgt gtctgtcaca gcaattcaag gcacaagggg actacatact gggcgggcta    120
tttcccctgg gctcaaccga ggaggccact ctcaaccaga gaacacaacc caacagcatc    180
ccgtgcaaca ggttctcacc ccttggtttg ttcctggcca tggccatgtg ctttgcaggg    240
gaggagatca atagccagag cagcctgctg cctggcgtgc tgctgggcta tgacctattt    300
gacacatgct ccgagccagt ggtcaccatg aaatccagtc tcatgttcct ggccaaggtg    360
ggcagtcaaa gcattgctgc ctactgcaac tacacacagt accaaccccg tgtgctggct    420
gtcatcggcc cccactcatc agagcttgcc ctcattacag gcaagttctt cagcttcttc    480
ctcatgccac aggtcagcta tagtgccagc atggatcggc taagtgaccg ggaaacgttt    540
ccatccttct ccgcacagt gcccagtgac cgggtgcagc tgcaggcagt tgtgactctg    600
ttgcagaact tcagctggaa ctgggtgcc gccttaggga gtgatgatga ctatggccgg    660
gaaggtctga gcatcttttc tagtctggcc aatgcacgag gtatctgcat cgcacatgag    720
ggcctggtgc acaacatga cactagtggc aacagttgg gcaaggtgct ggatgtacta    780
cgccaagtga accaaagtaa agtacaagtg gtggtgctgt ttgcctctgc ccgtgctgtc    840
tactcccttt ttagttacag catccatcat ggcctctcac ccaaggtatg ggtggccagt    900
gagtcttggc tgacatctga cctggtcatg acacttccca atattgcccg tgtgggcact    960
gtgcttgggt ttttgcagcg gggtgcccta ctgcctgaat tttcccatta tgtggagact    1020
cacctttgccc tggccgctga cccagcattc tgtgcctcac tgaatgcgga gttggatctg    1080
gaggaacatg tgatggggca acgctgtcca cggtgtgacg acatcatgct gcagaaccta    1140
tcatctgggc tgttgcagaa cctatcagct gggcaattgc accaccaaat atttgcaacc    1200
```

```
tatgcagctg tgtacagtgt ggctcaagcc cttcacaaca ccctacagtg caatgtctca   1260
cattgccacg tatcagaaca tgttctaccc tggcagctcc tggagaacat gtacaatatg   1320
agtttccatg ctcgagactt gacactacag tttgatgctg aagggaatgt agacatggaa   1380
tatgacctga agatgtgggt gtggcagagc cctacacctg tattacatac tgtgggcacc   1440
ttcaacggca cccttcagct gcagcagtct aaaatgtact ggccaggcaa ccaggtgcca   1500
gtctcccagt gttcccgcca gtgcaaagat ggccaggttc gccgagtaaa gggctttcat   1560
tcctgctgct atgactgcgt ggactgcaag gcgggcagct accggaagca tccagatgac   1620
ttcacctgta ctccatgtaa ccaggaccag tggtccccag agaaaagcac agcctgctta   1680
cctcgcaggc ccaagtttct ggcttggggg gagccagttg tgctgtcact cctcctgctg   1740
ctttgcctgg tgctgggtct agcactggct gctctggggc tctctgtcca ccactgggac   1800
agccctcttg tccaggcctc aggtggctca cagttctgct ttggcctgat ctgcctaggc   1860
ctcttctgcc tcagtgtcct tctgttccca gggcggccaa gctctgccag ctgccttgca   1920
caacaaccaa tggctcacct ccctctcaca ggctgcctga gcacactctt cctgcaagca   1980
gctgagacct ttgtggagtc tgagctgcca ctgagctggg caaactggct atgcagctac   2040
cttcggggac tctgggcctg gctagtggta ctgttggcca cttttgtgga ggcagcacta   2100
tgtgcctggt atttgatcgc tttcccacca gaggtggtga cagactggtc agtgctgccc   2160
acagaggtac tggagcactg ccacgtgcgt tcctgggtca gcctgggctt ggtgcacatc   2220
accaatgcaa tgttagcttt cctctgcttt ctgggcactt tcctggtaca gagccagcct   2280
ggccgctaca accgtgcccg tggtctcacc ttcgccatgc tagcttattt catcacctgg   2340
gtctcttttg tgcccctcct ggccaatgtg caggtggcct accagccagc tgtgcagatg   2400
ggtgctatcc tagtctgtgc cctgggcatc ctggtcacct tccacctgcc caagtgctat   2460
gtgcttcttt ggctgccaaa gctcaacacc caggagttcc tctgggaag gaatgccaag   2520 aaagcagcag atgagaacag tggcggtggt gaggcagctc agggacacaa tgaatga     2577
```

<210> SEQ ID NO 17
<211> LENGTH: 2577
<212> TYPE: DNA
<213> ORGANISM: rat

<400> SEQUENCE: 17

```
atgccgggtt tggctatctt gggcctcagt ctggctgctt tcctggagct tgggatgggg    60
tcctctttgt gtctgtcaca gcaattcaag gcacaagggg actatatatt gggtggacta   120
tttcccctgg gcacaactga ggaggccact ctcaaccaga gaacacagcc caacggcatc   180
ctatgtacca ggttctcgcc ccttggtttg ttcctggcca tggctatgaa gatggctgta   240
gaggagatca caatggatc tgccttgctc cctgggctgc gactgggcta tgacctgttt   300
gacacatgct cagagccagt ggtcaccatg aagcccagcc tcatgttcat ggccaaggtg   360
ggaagtcaaa gcattgctgc ctactgcaac tacacacagt accaaccccg tgtgctggct   420
gtcattggtc cccactcatc agagcttgcc ctcattacag gcaagttctt cagcttcttc   480
ctcatgccac aggtcagcta tagtgccagc atggatcggc taagtgaccg ggaaacattt   540
ccatccttct tccgcacagt gcccagtgac cgggtgcagc tgcaggccgt tgtgacactg   600
ttgcagaatt tcagctggaa ctgggtggct gccttaggta gtgatgatga ctatggccgg   660
gaaggtctga gcatctttc tggtctggcc aactcacgag gtatctgcat tgcacacgag   720
```

| | |
|---|---:|
| ggcctggtgc cacaacatga cactagtggc caacaattgg gcaaggtggt ggatgtgcta | 780 |
| cgccaagtga accaaagcaa agtacaggtg gtggtgctgt ttgcatctgc ccgtgctgtc | 840 |
| tactcccttt ttagctacag catccttcat gacctctcac ccaaggtatg ggtggccagt | 900 |
| gagtcctggc tgacctctga cctggtcatg acacttccca atattgcccg tgtgggcact | 960 |
| gttcttgggt ttctgcagcg cggtgcccta ctgcctgaat tttcccatta tgtggagact | 1020 |
| cgccttgccc tagctgctga cccaacattc tgtgcctccc tgaaagctga gttggatctg | 1080 |
| gaggagcgcg tgatggggcc acgctgttca caatgtgact acatcatgct acagaacctg | 1140 |
| tcatctgggc tgatgcagaa cctatcagct gggcagttgc accaccaaat atttgcaacc | 1200 |
| tatgcagctg tgtacagtgt ggctcaggcc cttcacaaca ccctgcagtg caatgtctca | 1260 |
| cattgccaca catcagagcc tgttcaaccc tggcagctcc tggagaacat gtacaatatg | 1320 |
| agtttccgtg ctcgagactt gacactgcag tttgatgcca agggagtgt agacatggaa | 1380 |
| tatgacctga agatgtgggt gtggcagagc cctacacctg tactacatac tgtaggcacc | 1440 |
| ttcaacggca cccttcagct gcagcactcg aaaatgtatt ggccaggcaa ccaggtgcca | 1500 |
| gtctcccagt gctcccggca gtgcaaagat ggccaggtgc gcagagtaaa gggcttttcat | 1560 |
| tcctgctgct atgactgtgt ggactgcaag gcagggagct accggaagca tccagatgac | 1620 |
| ttcacctgta ctccatgtgg caaggatcag tggtccccag aaaaaagcac aacctgctta | 1680 |
| cctcgcaggc ccaagtttct ggcttggggg agccagctg tgctgtcact tctcctgctg | 1740 |
| cttttgcctgg tgctgggcct gacactggct gccctgggc tctttgtcca ctactgggac | 1800 |
| agccctcttg ttcaggcctc aggtgggtca ctgttctgct ttggcctgat ctgcctaggc | 1860 |
| ctcttctgcc tcagtgtcct tctgttccca ggacgaccac gctctgccag ctgccttgcc | 1920 |
| caacaaccaa tggctcacct ccctctcaca ggctgcctga gcacactctt cctgcaagca | 1980 |
| gccgagatct ttgtggagtc tgagctgcca ctgagttggg caaactggct ctgcagctac | 2040 |
| cttcggggcc cctgggcttg gctggtggta ctgctggcca ctcttgtgga ggctgcacta | 2100 |
| tgtgcctggt acttgatggc tttccctcca gaggtggtga cagattggca ggtgctgccc | 2160 |
| acggaggtac tggaacactg ccgcatgcgt tcctgggtca gcctgggctt ggtgcacatc | 2220 |
| accaatgcag tgttagcttt cctctgcttt ctgggcactt tcctggtaca gagccagcct | 2280 |
| ggtcgctata accgtgcccg tggcctcacc ttcgccatgc tagcttattt catcatctgg | 2340 |
| gtctcttttg tgcccctcct ggctaatgtg caggtggcct accagccagc tgtgcagatg | 2400 |
| ggtgctatct tattctgtgc cctgggcatc ctggccacct tccacctgcc caatgctat | 2460 |
| gtacttctgt ggctgccaga gctcaacacc caggagttct tcctgggaag gagccccaag | 2520 |
| gaagcatcag atgggaatag tggtagtagt gaggcaactc ggggacacag tgaatga | 2577 |

<210> SEQ ID NO 18
<211> LENGTH: 2559
<212> TYPE: DNA
<213> ORGANISM: human

<400> SEQUENCE: 18

| | |
|---|---:|
| atgctgggcc tgctgtcct gggcctcagc ctctgggctc tcctgcaccc tgggacgggg | 60 |
| gccccattgt gcctgtcaca gcaacttagg atgaagggg actacgtgct gggggggctg | 120 |
| ttccccctgg gcgaggccga ggaggctggc ctccgcagcc ggacacggcc cagcagccct | 180 |
| gtgtgcacca ggttctcctc aaacggcctg ctctgggcac tggccatgaa atgccgtg | 240 |
| gaggagatca acaacaagtc ggatctgctg cccgggctgc gcctgggcta cgacctcttt | 300 |

-continued

```
gatacgtgct cggagcctgt ggtggccatg aagcccagcc tcatgttcct ggccaaggca    360
ggcagccgcg acatcgccgc ctactgcaac tacacgcagt accagccccg tgtgctggct    420
gtcatcgggc cccactcgtc agagctcgcc atggtcaccg gcaagttctt cagcttcttc    480
ctcatgcccc aggtcagcta cggtgctagc atggagctgc tgagcgcccg ggagaccttc    540
ccctccttct tccgcaccgt gcccagcgac cgtgtgcagc tgacgccgcc gcggagctg    600
ctgcaggagt tcggctggaa ctgggtggcc gccctgggca gcgacgacga gtacggccgg    660
cagggcctga gcatcttctc ggccctgccc gcggcacgcg catctgcat cgcgcacgag    720
ggcctggtgc cgctgccccg tgccgatgac tcgcggctgg ggaaggtgca ggacgtcctg    780
caccaggtga accagagcag cgtgcaggtg gtgctgctgt tcgcctccgt gcacgccgcc    840
cacgccctct tcaactacag catcagcagc aggctctcgc ccaaggtgtg ggtggccagc    900
gaggcctggc tgacctctga cctggtcatg gggctgcccg gcatggccca gatgggcacg    960
gtgcttggct tcctccagag gggtgcccag ctgcacgagt ccccccagta cgtgaagacg   1020
cacctggccc tggccaccga cccggccttc tgctctgccc tgggcgagag ggagcagggt   1080
ctggaggagg acgtggtggg ccagcgctgc ccgcagtgtg actgcatcac gctgcagaac   1140
gtgagcgcag gctaaaatca ccaccagacg ttctctgtct acgcagctgt gtatagcgtg   1200
gcccaggccc tgcacaacac tcttcagtgc aacgcctcag gctgccccgc gcaggacccc   1260
gtgaagccct gcagctcct ggagaacatg tacaacctga ccttccacgt gggcgggctg   1320
ccgctgcggt tcgacagcag cggaaacgtg gacatggagt acgacctgaa gctgtgggtg   1380
tggcagggct cagtgcccag gctccacgac gtgggcaggt tcaacggcag cctcaggaca   1440
gagcgcctga gatccgctg gcacacgtct gacaaccaga agcccgtgtc ccggtgctcg   1500
cggcagtgcc aggagggcca ggtgcgccgg gtcaaggggt tccactcctg ctgctacgac   1560
tgtgtggact cgaggcggg cagctaccgg caaaacccag acgacatcgc ctgcaccttt   1620
tgtggccagg atgagtggtc cccggagcga agcacacgct gcttccgccg caggtctcgg   1680
ttcctggcat ggggcgagcc ggctgtgctg ctgctgctcc tgctgctgag cctggcgctg   1740
ggccttgtgc tggctgcttt ggggctgttc gttcaccatc gggacagccc actggttcag   1800
gcctcggggg ggcccctggc ctgctttggc ctggtgtgcc tgggcctggt ctgcctcagc   1860
gtcctcctgt tccctggcca gcccagccct gcccgatgcc tggcccagca gcccttgtcc   1920
cacctcccgc tcacgggctg cctgagcaca ctcttcctgc aggcggccga gatcttcgtg   1980
gagtcagaac tgcctctgag ctgggcagac cggctgagtg gctgcctgcg ggggccctgg   2040
gcctggctgg tggtgctgct ggccatgctg gtggaggtcg cactgtgcac ctggtacctg   2100
gtggccttcc cgccggaggt ggtgacggac tggcacatgc tgcccacgga ggcgctggtg   2160
cactgccgca cacgctcctg ggtcagcttc ggcctagcgc acgccaccaa tgccacgctg   2220
gcctttctct gcttcctggg cactttcctg gtgcggagcc agccgggccg ctacaaccgt   2280
gcccgtggcc tcacctttgc catgctggcc tacttcatca cctgggtctc ctttgtgccc   2340
ctcctggcca atgtgcaggt ggtcctcagg cccgccgtgc agatgggcgc cctcctgctc   2400
tgtgtcctgg gcatcctggc tgccttccac ctgcccaggt gttacctgct catgcggcag   2460
ccagggctca acaccccga gttcttcctg ggaggggcc ctggggatgc caaggccag    2520
aatgacggga acacaggaaa tcaggggaaa catgagtga                        2559
```

<210> SEQ ID NO 19

<211> LENGTH: 843
<212> TYPE: PRT
<213> ORGANISM: mouse

<400> SEQUENCE: 19

```
Met Gly Pro Gln Ala Arg Thr Leu His Leu Phe Leu Leu Leu His
1               5                   10                  15

Ala Leu Pro Lys Pro Val Met Leu Val Gly Asn Ser Asp Phe His Leu
            20                  25                  30

Ala Gly Asp Tyr Leu Leu Gly Gly Leu Phe Thr Leu His Ala Asn Val
        35                  40                  45

Lys Ser Val Ser His Leu Ser Tyr Leu Gln Val Pro Lys Cys Asn Glu
    50                  55                  60

Tyr Asn Met Lys Val Leu Gly Tyr Asn Leu Met Gln Ala Met Arg Phe
65                  70                  75                  80

Ala Val Glu Glu Ile Asn Asn Cys Ser Ser Leu Leu Pro Gly Val Leu
                85                  90                  95

Leu Gly Tyr Glu Met Val Asp Val Cys Tyr Leu Ser Asn Asn Ile Gln
            100                 105                 110

Pro Gly Leu Tyr Phe Leu Ser Gln Ile Asp Asp Phe Leu Pro Ile Leu
        115                 120                 125

Lys Asp Tyr Ser Gln Tyr Arg Pro Gln Val Val Ala Val Ile Gly Pro
    130                 135                 140

Asp Asn Ser Glu Ser Ala Ile Thr Val Ser Asn Ile Leu Ser Tyr Phe
145                 150                 155                 160

Leu Val Pro Gln Val Thr Tyr Ser Ala Ile Thr Asp Lys Leu Arg Asp
                165                 170                 175

Lys Arg Arg Phe Pro Ala Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Tyr Gly Arg Glu Asn Ser His
    210                 215                 220

Leu Leu Ser Gln Arg Leu Thr Asn Thr Gly Asp Ile Cys Ile Ala Phe
225                 230                 235                 240

Gln Glu Val Leu Pro Val Pro Glu Pro Asn Gln Ala Val Arg Pro Glu
                245                 250                 255

Glu Gln Asp Gln Leu Asp Asn Ile Leu Asp Lys Leu Arg Arg Thr Ser
            260                 265                 270

Ala Arg Val Val Val Ile Phe Ser Pro Glu Leu Ser Leu His Asn Phe
        275                 280                 285

Phe Arg Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg His Asp Lys Pro Glu Tyr Pro
            340                 345                 350

Met Pro Asn Glu Thr Ser Leu Arg Thr Thr Cys Asn Gln Asp Cys Asp
        355                 360                 365

Ala Cys Met Asn Ile Thr Glu Ser Phe Asn Asn Val Leu Met Leu Ser
    370                 375                 380

Gly Glu Arg Val Val Tyr Ser Val Tyr Ser Ala Val Tyr Ala Val Ala
```

-continued

```
            385                 390                 395                 400
His Thr Leu His Arg Leu Leu His Cys Asn Gln Val Arg Cys Thr Lys
                405                 410                 415
Gln Ile Val Tyr Pro Trp Gln Leu Leu Arg Glu Ile Trp His Val Asn
                420                 425                 430
Phe Thr Leu Leu Gly Asn Gln Leu Phe Phe Asp Glu Gln Gly Asp Met
                435                 440                 445
Pro Met Leu Leu Asp Ile Ile Gln Trp Gln Trp Gly Leu Ser Gln Asn
                450                 455                 460
Pro Phe Gln Ser Ile Ala Ser Tyr Ser Pro Thr Glu Thr Arg Leu Thr
465                 470                 475                 480
Tyr Ile Ser Asn Val Ser Trp Tyr Thr Pro Asn Asn Thr Val Pro Ile
                485                 490                 495
Ser Met Cys Ser Lys Ser Cys Gln Pro Gly Gln Met Lys Lys Pro Ile
                500                 505                 510
Gly Leu His Pro Cys Cys Phe Glu Cys Val Asp Cys Pro Pro Gly Thr
                515                 520                 525
Tyr Leu Asn Arg Ser Val Asp Glu Phe Asn Cys Leu Ser Cys Pro Gly
                530                 535                 540
Ser Met Trp Ser Tyr Lys Asn Asn Ile Ala Cys Phe Lys Arg Arg Leu
545                 550                 555                 560
Ala Phe Leu Glu Trp His Glu Val Pro Thr Ile Val Thr Ile Leu
                565                 570                 575
Ala Ala Leu Gly Phe Ile Ser Thr Leu Ala Ile Leu Ile Phe Trp
                580                 585                 590
Arg His Phe Gln Thr Pro Met Val Arg Ser Ala Gly Gly Pro Met Cys
                595                 600                 605
Phe Leu Met Leu Val Pro Leu Leu Ala Phe Gly Met Val Pro Val
                610                 615                 620
Tyr Val Gly Pro Pro Thr Val Phe Ser Cys Phe Cys Arg Gln Ala Phe
625                 630                 635                 640
Phe Thr Val Cys Phe Ser Val Cys Leu Ser Cys Ile Thr Val Arg Ser
                645                 650                 655
Phe Gln Ile Val Cys Val Phe Lys Met Ala Arg Arg Leu Pro Ser Ala
                660                 665                 670
Tyr Gly Phe Trp Met Arg Tyr His Gly Pro Tyr Val Phe Val Ala Phe
                675                 680                 685
Ile Thr Ala Val Lys Val Ala Leu Val Ala Gly Asn Met Leu Ala Thr
                690                 695                 700
Thr Ile Asn Pro Ile Gly Arg Thr Asp Pro Asp Asp Pro Asn Ile Ile
705                 710                 715                 720
Ile Leu Ser Cys His Pro Asn Tyr Arg Asn Gly Leu Leu Phe Asn Thr
                725                 730                 735
Ser Met Asp Leu Leu Leu Ser Val Leu Gly Phe Ser Phe Ala Tyr Val
                740                 745                 750
Gly Lys Glu Leu Pro Thr Asn Tyr Asn Glu Ala Lys Phe Ile Thr Leu
                755                 760                 765
Ser Met Thr Phe Ser Phe Thr Ser Ser Ile Ser Leu Cys Thr Phe Met
                770                 775                 780
Ser Val His Asp Gly Val Leu Val Thr Ile Met Asp Leu Leu Val Thr
785                 790                 795                 800
Val Leu Asn Phe Leu Ala Ile Gly Leu Gly Tyr Phe Gly Pro Lys Cys
                805                 810                 815
```

```
Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840

<210> SEQ ID NO 20
<211> LENGTH: 843
<212> TYPE: PRT
<213> ORGANISM: rat

<400> SEQUENCE: 20

Met Gly Pro Gln Ala Arg Thr Leu Cys Leu Leu Ser Leu Leu Leu His
1               5                   10                  15

Val Leu Pro Lys Pro Gly Lys Leu Val Glu Asn Ser Asp Phe His Leu
            20                  25                  30

Ala Gly Asp Tyr Leu Leu Gly Gly Leu Phe Thr Leu His Ala Asn Val
        35                  40                  45

Lys Ser Ile Ser His Leu Ser Tyr Leu Gln Val Pro Lys Cys Asn Glu
    50                  55                  60

Phe Thr Met Lys Val Leu Gly Tyr Asn Leu Met Gln Ala Met Arg Phe
65                  70                  75                  80

Ala Val Glu Glu Ile Asn Asn Cys Ser Ser Leu Leu Pro Gly Val Leu
                85                  90                  95

Leu Gly Tyr Glu Met Val Asp Val Cys Tyr Leu Ser Asn Asn Ile His
            100                 105                 110

Pro Gly Leu Tyr Phe Leu Ala Gln Asp Asp Leu Leu Pro Ile Leu
        115                 120                 125

Lys Asp Tyr Ser Gln Tyr Met Pro His Val Val Ala Val Ile Gly Pro
    130                 135                 140

Asp Asn Ser Glu Ser Ala Ile Thr Val Ser Asn Ile Leu Ser His Phe
145                 150                 155                 160

Leu Ile Pro Gln Ile Thr Tyr Ser Ala Ile Ser Asp Lys Leu Arg Asp
                165                 170                 175

Lys Arg His Phe Pro Ser Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Tyr Gly Arg Glu Asn Ser His
    210                 215                 220

Leu Leu Ser Gln Arg Leu Thr Lys Thr Ser Asp Ile Cys Ile Ala Phe
225                 230                 235                 240

Gln Glu Val Leu Pro Ile Pro Glu Ser Ser Gln Val Met Arg Ser Glu
                245                 250                 255

Glu Gln Arg Gln Leu Asp Asn Ile Leu Asp Lys Leu Arg Arg Thr Ser
            260                 265                 270

Ala Arg Val Val Val Phe Ser Pro Glu Leu Ser Leu Tyr Ser Phe
        275                 280                 285

Phe His Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg Arg Asp Lys Pro Gly Tyr Pro
```

-continued

```
                     340                 345                 350
    Val Pro Asn Thr Thr Asn Leu Arg Thr Thr Cys Asn Gln Asp Cys Asp
            355                 360                 365
    Ala Cys Leu Asn Thr Thr Lys Ser Phe Asn Asn Ile Leu Ile Leu Ser
        370                 375                 380
    Gly Glu Arg Val Val Tyr Ser Val Tyr Ser Ala Val Tyr Ala Val Ala
    385                 390                 395                 400
    His Ala Leu His Arg Leu Leu Gly Cys Asn Arg Val Arg Cys Thr Lys
                    405                 410                 415
    Gln Lys Val Tyr Pro Trp Gln Leu Leu Arg Glu Ile Trp His Val Asn
                420                 425                 430
    Phe Thr Leu Leu Gly Asn Arg Leu Phe Phe Asp Gln Gln Gly Asp Met
            435                 440                 445
    Pro Met Leu Leu Asp Ile Ile Gln Trp Gln Trp Asp Leu Ser Gln Asn
        450                 455                 460
    Pro Phe Gln Ser Ile Ala Ser Tyr Ser Pro Thr Ser Lys Arg Leu Thr
    465                 470                 475                 480
    Tyr Ile Asn Asn Val Ser Trp Tyr Thr Pro Asn Asn Thr Val Pro Val
                    485                 490                 495
    Ser Met Cys Ser Lys Ser Cys Gln Pro Gly Gln Met Lys Lys Ser Val
                500                 505                 510
    Gly Leu His Pro Cys Cys Phe Glu Cys Leu Asp Cys Met Pro Gly Thr
            515                 520                 525
    Tyr Leu Asn Arg Ser Ala Asp Glu Phe Asn Cys Leu Ser Cys Pro Gly
        530                 535                 540
    Ser Met Trp Ser Tyr Lys Asn Asp Ile Thr Cys Phe Gln Arg Arg Pro
    545                 550                 555                 560
    Thr Phe Leu Glu Trp His Glu Val Pro Thr Ile Val Val Ala Ile Leu
                    565                 570                 575
    Ala Ala Leu Gly Phe Phe Ser Thr Leu Ala Ile Leu Phe Ile Phe Trp
                580                 585                 590
    Arg His Phe Gln Thr Pro Met Val Arg Ser Ala Gly Gly Pro Met Cys
            595                 600                 605
    Phe Leu Met Leu Val Pro Leu Leu Ala Phe Gly Met Val Pro Val
        610                 615                 620
    Tyr Val Gly Pro Pro Thr Val Phe Ser Cys Phe Cys Arg Gln Ala Phe
    625                 630                 635                 640
    Phe Thr Val Cys Phe Ser Ile Cys Leu Ser Cys Ile Thr Val Arg Ser
                    645                 650                 655
    Phe Gln Ile Val Cys Val Phe Lys Met Ala Arg Arg Leu Pro Ser Ala
                660                 665                 670
    Tyr Ser Phe Trp Met Arg Tyr His Gly Pro Tyr Val Phe Val Ala Phe
            675                 680                 685
    Ile Thr Ala Ile Lys Val Ala Leu Val Val Gly Asn Met Leu Ala Thr
        690                 695                 700
    Thr Ile Asn Pro Ile Gly Arg Thr Asp Pro Asp Asp Pro Asn Ile Met
    705                 710                 715                 720
    Ile Leu Ser Cys His Pro Asn Tyr Arg Asn Gly Leu Leu Phe Asn Thr
                    725                 730                 735
    Ser Met Asp Leu Leu Leu Ser Val Leu Gly Phe Ser Phe Ala Tyr Met
                740                 745                 750
    Gly Lys Glu Leu Pro Thr Asn Tyr Asn Glu Ala Lys Phe Ile Thr Leu
            755                 760                 765
```

Ser Met Thr Phe Ser Phe Thr Ser Ser Ile Ser Leu Cys Thr Phe Met
    770             775                 780

Ser Val His Asp Gly Val Leu Val Thr Ile Met Asp Leu Leu Val Thr
785             790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
            835                 840

<210> SEQ ID NO 21
<211> LENGTH: 839
<212> TYPE: PRT
<213> ORGANISM: human

<400> SEQUENCE: 21

Met Gly Pro Arg Ala Lys Thr Ile Cys Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp

-continued

```
              290                 295                 300
Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
            340                 345                 350

Thr Ser Gln Ser Tyr Thr Cys Asn Gln Glu Cys Asp Asn Cys Leu Asn
                355                 360                 365

Ala Thr Leu Ser Phe Asn Thr Ile Leu Arg Leu Ser Gly Glu Arg Val
370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Lys Pro Val Gly Ile His Val
            500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
        595                 600                 605

Thr Leu Leu Leu Val Ala Tyr Met Val Val Pro Val Tyr Val Gly Pro
    610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670

Val Arg Tyr Gln Gly Pro Tyr Val Ser Met Ala Phe Ile Thr Val Leu
        675                 680                 685

Lys Met Val Ile Val Val Ile Gly Met Leu Ala Thr Gly Leu Ser Pro
    690                 695                 700

Thr Thr Arg Thr Asp Pro Asp Pro Lys Ile Thr Ile Val Ser Cys
705                 710                 715                 720
```

-continued

Asn Pro Asn Tyr Arg Asn Ser Leu Leu Phe Asn Thr Ser Leu Asp Leu
            725                 730                 735

Leu Leu Ser Val Val Gly Phe Ser Phe Ala Tyr Met Gly Lys Glu Leu
        740                 745                 750

Pro Thr Asn Tyr Asn Glu Ala Lys Phe Ile Thr Leu Ser Met Thr Phe
            755                 760                 765

Tyr Phe Thr Ser Ser Val Ser Leu Cys Thr Phe Met Ser Ala Tyr Ser
    770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
                820                 825                 830

Gly Tyr Thr Met Arg Arg Asp
            835

<210> SEQ ID NO 22
<211> LENGTH: 842
<212> TYPE: PRT
<213> ORGANISM: mouse

<400> SEQUENCE: 22

Met Leu Phe Trp Ala Ala His Leu Leu Leu Ser Leu Gln Leu Ala Val
1               5                   10                  15

Ala Tyr Cys Trp Ala Phe Ser Cys Gln Arg Thr Glu Ser Ser Pro Gly
            20                  25                  30

Phe Ser Leu Pro Gly Asp Phe Leu Leu Ala Gly Leu Phe Ser Leu His
        35                  40                  45

Ala Asp Cys Leu Gln Val Arg His Arg Pro Leu Val Thr Ser Cys Asp
    50                  55                  60

Arg Ser Asp Ser Phe Asn Gly His Gly Tyr His Leu Phe Gln Ala Met
65                  70                  75                  80

Arg Phe Thr Val Glu Glu Ile Asn Asn Ser Thr Ala Leu Leu Pro Asn
                85                  90                  95

Ile Thr Leu Gly Tyr Glu Leu Tyr Asp Val Cys Ser Glu Ser Ser Asn
            100                 105                 110

Val Tyr Ala Thr Leu Arg Val Leu Ala Gln Gln Gly Thr Gly His Leu
        115                 120                 125

Glu Met Gln Arg Asp Leu Arg Asn His Ser Ser Lys Val Val Ala Leu
    130                 135                 140

Ile Gly Pro Asp Asn Thr Asp His Ala Val Thr Thr Ala Ala Leu Leu
145                 150                 155                 160

Ser Pro Phe Leu Met Pro Leu Val Ser Tyr Glu Ala Ser Ser Val Ile
                165                 170                 175

Leu Ser Gly Lys Arg Lys Phe Pro Ser Phe Leu Arg Thr Ile Pro Ser
            180                 185                 190

Asp Lys Tyr Gln Val Glu Val Ile Val Arg Leu Leu Gln Ser Phe Gly
        195                 200                 205

Trp Val Trp Ile Ser Leu Val Gly Ser Tyr Gly Asp Tyr Gly Gln Leu
    210                 215                 220

Gly Val Gln Ala Leu Glu Glu Leu Ala Thr Pro Arg Gly Ile Cys Val
225                 230                 235                 240

Ala Phe Lys Asp Val Val Pro Leu Ser Ala Gln Ala Gly Asp Pro Arg

```
                245                 250                 255
Met Gln Arg Met Met Leu Arg Leu Ala Arg Ala Arg Thr Thr Val Val
            260                 265                 270
Val Val Phe Ser Asn Arg His Leu Ala Gly Val Phe Phe Arg Ser Val
            275                 280                 285
Val Leu Ala Asn Leu Thr Gly Lys Val Trp Ile Ala Ser Glu Asp Trp
            290                 295                 300
Ala Ile Ser Thr Tyr Ile Thr Asn Val Pro Gly Ile Gln Gly Ile Gly
305                 310                 315                 320
Thr Val Leu Gly Val Ala Ile Gln Gln Arg Gln Val Pro Gly Leu Lys
            325                 330                 335
Glu Phe Glu Glu Ser Tyr Val Gln Ala Val Met Gly Ala Pro Arg Thr
            340                 345                 350
Cys Pro Glu Gly Ser Trp Cys Gly Thr Asn Gln Leu Cys Arg Glu Cys
            355                 360                 365
His Ala Phe Thr Thr Trp Asn Met Pro Glu Leu Gly Ala Phe Ser Met
            370                 375                 380
Ser Ala Ala Tyr Asn Val Tyr Glu Ala Val Tyr Ala Val Ala His Gly
385                 390                 395                 400
Leu His Gln Leu Leu Gly Cys Thr Ser Gly Thr Cys Ala Arg Gly Pro
            405                 410                 415
Val Tyr Pro Trp Gln Leu Leu Gln Gln Ile Tyr Lys Val Asn Phe Leu
            420                 425                 430
Leu His Lys Lys Thr Val Ala Phe Asp Asp Lys Gly Asp Pro Leu Gly
            435                 440                 445
Tyr Tyr Asp Ile Ile Ala Trp Asp Trp Asn Gly Pro Glu Trp Thr Phe
            450                 455                 460
Glu Val Ile Gly Ser Ala Ser Leu Ser Pro Val His Leu Asp Ile Asn
465                 470                 475                 480
Lys Thr Lys Ile Gln Trp His Gly Lys Asn Asn Gln Val Pro Val Ser
            485                 490                 495
Val Cys Thr Arg Asp Cys Leu Glu Gly His His Arg Leu Val Met Gly
            500                 505                 510
Ser His His Cys Cys Phe Glu Cys Met Pro Cys Glu Ala Gly Thr Phe
            515                 520                 525
Leu Asn Thr Ser Glu Leu His Thr Cys Gln Pro Cys Gly Thr Glu Glu
            530                 535                 540
Trp Ala Pro Glu Gly Ser Ser Ala Cys Phe Ser Arg Thr Val Glu Phe
545                 550                 555                 560
Leu Gly Trp His Glu Pro Ile Ser Leu Val Leu Leu Ala Ala Asn Thr
            565                 570                 575
Leu Leu Leu Leu Leu Leu Ile Gly Thr Ala Gly Leu Phe Ala Trp Arg
            580                 585                 590
Leu His Thr Pro Val Val Arg Ser Ala Gly Gly Arg Leu Cys Phe Leu
            595                 600                 605
Met Leu Gly Ser Leu Val Ala Gly Ser Cys Ser Leu Tyr Ser Phe Phe
            610                 615                 620
Gly Lys Pro Thr Val Pro Ala Cys Leu Leu Arg Gln Pro Leu Phe Ser
625                 630                 635                 640
Leu Gly Phe Ala Ile Phe Leu Ser Cys Leu Thr Ile Arg Ser Phe Gln
            645                 650                 655
Leu Val Ile Ile Phe Lys Phe Ser Thr Lys Val Pro Thr Phe Tyr His
            660                 665                 670
```

```
Thr Trp Ala Gln Asn His Gly Ala Gly Ile Phe Val Ile Val Ser Ser
            675                 680                 685

Thr Val His Leu Phe Leu Cys Leu Thr Trp Leu Ala Met Trp Thr Pro
        690                 695                 700

Arg Pro Thr Arg Glu Tyr Gln Arg Phe Pro His Leu Val Ile Leu Glu
705                 710                 715                 720

Cys Thr Glu Val Asn Ser Val Gly Phe Leu Val Ala Phe Ala His Asn
                725                 730                 735

Ile Leu Leu Ser Ile Ser Thr Phe Val Cys Ser Tyr Leu Gly Lys Glu
            740                 745                 750

Leu Pro Glu Asn Tyr Asn Glu Ala Lys Cys Val Thr Phe Ser Leu Leu
        755                 760                 765

Leu His Phe Val Ser Trp Ile Ala Phe Phe Thr Met Ser Ser Ile Tyr
    770                 775                 780

Gln Gly Ser Tyr Leu Pro Ala Val Asn Val Leu Ala Gly Leu Ala Thr
785                 790                 795                 800

Leu Ser Gly Gly Phe Ser Gly Tyr Phe Leu Pro Lys Cys Tyr Val Ile
                805                 810                 815

Leu Cys Arg Pro Glu Leu Asn Asn Thr Glu His Phe Gln Ala Ser Ile
            820                 825                 830

Gln Asp Tyr Thr Arg Arg Cys Gly Thr Thr
        835                 840

<210> SEQ ID NO 23
<211> LENGTH: 840
<212> TYPE: PRT
<213> ORGANISM: rat

<400> SEQUENCE: 23

Met Leu Phe Trp Ala His Leu Leu Ser Leu Gln Leu Val Tyr
1               5                   10                  15

Cys Trp Ala Phe Ser Cys Gln Arg Thr Glu Ser Ser Pro Gly Phe Ser
            20                  25                  30

Leu Pro Gly Asp Phe Leu Leu Ala Gly Leu Phe Ser Leu His Gly Asp
        35                  40                  45

Cys Leu Gln Val Arg His Arg Pro Leu Val Thr Ser Cys Asp Arg Pro
    50                  55                  60

Asp Ser Phe Asn Gly His Gly Tyr His Leu Phe Gln Ala Met Arg Phe
65                  70                  75                  80

Thr Val Glu Glu Ile Asn Asn Ser Ser Ala Leu Leu Pro Asn Ile Thr
                85                  90                  95

Leu Gly Tyr Glu Leu Tyr Asp Val Cys Ser Glu Ser Ala Asn Val Tyr
            100                 105                 110

Ala Thr Leu Arg Val Leu Ala Leu Gln Gly Pro Arg His Ile Glu Ile
        115                 120                 125

Gln Lys Asp Leu Arg Asn His Ser Ser Lys Val Val Ala Phe Ile Gly
    130                 135                 140

Pro Asp Asn Thr Asp His Ala Val Thr Thr Ala Ala Leu Leu Gly Pro
145                 150                 155                 160

Phe Leu Met Pro Leu Val Ser Tyr Glu Ala Ser Ser Val Val Leu Ser
                165                 170                 175

Ala Lys Arg Lys Phe Pro Ser Phe Leu Arg Thr Val Pro Ser Asp Arg
            180                 185                 190

His Gln Val Glu Val Met Val Gln Leu Leu Gln Ser Phe Gly Trp Val
```

```
                195                 200                 205
Trp Ile Ser Leu Ile Gly Ser Tyr Gly Asp Tyr Gly Gln Leu Gly Val
    210                 215                 220

Gln Ala Leu Glu Glu Leu Ala Val Pro Arg Gly Ile Cys Val Ala Phe
225                 230                 235                 240

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val Val
                260                 265                 270

Phe Ser Asn Arg His Leu Ala Arg Val Phe Phe Arg Ser Val Val Leu
            275                 280                 285

Ala Asn Leu Thr Gly Lys Val Trp Val Ala Ser Glu Asp Trp Ala Ile
            290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
                340                 345                 350

Glu Gly Ser Trp Cys Ser Thr Asn Gln Leu Cys Arg Glu Cys His Thr
            355                 360                 365

Phe Thr Thr Arg Asn Met Pro Thr Leu Gly Ala Phe Ser Met Ser Ala
    370                 375                 380

Ala Tyr Arg Val Tyr Glu Ala Val Tyr Ala Val Ala His Gly Leu His
385                 390                 395                 400

Gln Leu Leu Gly Cys Thr Ser Glu Ile Cys Ser Arg Gly Pro Val Tyr
                405                 410                 415

Pro Trp Gln Leu Leu Gln Gln Ile Tyr Lys Val Asn Phe Leu Leu His
                420                 425                 430

Glu Asn Thr Val Ala Phe Asp Asp Asn Gly Asp Thr Leu Gly Tyr Tyr
            435                 440                 445

Asp Ile Ile Ala Trp Asp Trp Asn Gly Pro Glu Trp Thr Phe Glu Ile
    450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Gly Ser His
            500                 505                 510       His

His Cys Cys Phe Glu Cys Val Pro Cys Glu Ala Gly Thr Phe Leu Asn
            515                 520                 525

Met Ser Glu Leu His Ile Cys Gln Pro Cys Gly Thr Glu Glu Trp Ala
            530                 535                 540

Pro Lys Glu Ser Thr Thr Cys Phe Pro Arg Thr Val Glu Phe Leu Ala
545                 550                 555                 560

Trp His Glu Pro Ile Ser Leu Val Leu Ile Ala Ala Asn Thr Leu Leu
                565                 570                 575

Leu Leu Leu Leu Val Gly Thr Ala Gly Leu Phe Ala Trp His Phe His
            580                 585                 590

Thr Pro Val Val Arg Ser Ala Gly Gly Arg Leu Cys Phe Leu Met Leu
        595                 600                 605

Gly Ser Leu Val Ala Gly Ser Cys Ser Phe Tyr Ser Phe Phe Gly Glu
610                 615                 620
```

Pro Thr Val Pro Ala Cys Leu Arg Gln Pro Leu Phe Ser Leu Gly
625                 630                 635                 640

Phe Ala Ile Phe Leu Ser Cys Leu Thr Ile Arg Ser Phe Gln Leu Val
            645                 650                 655

Ile Ile Phe Lys Phe Ser Thr Lys Val Pro Thr Phe Tyr Arg Thr Trp
            660                 665                 670

Ala Gln Asn His Gly Ala Gly Leu Phe Val Ile Val Ser Ser Thr Val
            675                 680                 685

His Leu Leu Ile Cys Leu Thr Trp Leu Val Met Trp Thr Pro Arg Pro
690                 695                 700

Thr Arg Glu Tyr Gln Arg Phe Pro His Leu Val Ile Leu Glu Cys Thr
705                 710                 715                 720

Glu Val Asn Ser Val Gly Phe Leu Leu Ala Phe Thr His Asn Ile Leu
            725                 730                 735

Leu Ser Ile Ser Thr Phe Val Cys Ser Tyr Leu Gly Lys Glu Leu Pro
            740                 745                 750

Glu Asn Tyr Asn Glu Ala Lys Cys Val Thr Phe Ser Leu Leu Leu Asn
            755                 760                 765

Phe Val Ser Trp Ile Ala Phe Phe Thr Met Ala Ser Ile Tyr Gln Gly
770                 775                 780

Ser Tyr Leu Pro Ala Val Asn Val Leu Ala Gly Leu Thr Thr Leu Ser
785                 790                 795                 800

Gly Gly Phe Ser Gly Tyr Phe Leu Pro Lys Cys Tyr Val Ile Leu Cys
            805                 810                 815

Arg Pro Glu Leu Asn Asn Thr Glu His Phe Gln Ala Ser Ile Gln Asp
            820                 825                 830

Tyr Thr Arg Arg Cys Gly Thr Thr
835                 840

<210> SEQ ID NO 24
<211> LENGTH: 841
<212> TYPE: PRT
<213> ORGANISM: human

<400> SEQUENCE: 24

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser

-continued

```
                145                 150                 155                 160
        Pro Phe Leu Val Pro Met Ile Ser Tyr Ala Ala Ser Ser Glu Thr Leu
                        165                 170                 175

Ser Val Lys Arg Gln Tyr Pro Ser Phe Leu Arg Thr Ile Pro Asn Asp
                        180                 185                 190

Lys Tyr Gln Val Glu Thr Met Val Leu Leu Gln Lys Phe Gly Trp
                        195                 200                 205

Thr Trp Ile Ser Leu Val Gly Ser Ser Asp Asp Tyr Gly Gln Leu Gly
                        210                 215                 220

Val Gln Ala Leu Glu Asn Gln Ala Thr Gly Gln Gly Ile Cys Ile Ala
        225                 230                 235                 240

Phe Lys Asp Ile Met Pro Phe Ser Ala Gln Val Gly Asp Glu Arg Met
                        245                 250                 255

Gln Cys Leu Met Arg His Leu Ala Gln Ala Gly Ala Thr Val Val Val
                        260                 265                 270

Val Phe Ser Ser Arg Gln Leu Ala Arg Val Phe Phe Glu Ser Val Val
                        275                 280                 285

Leu Thr Asn Leu Thr Gly Lys Val Trp Val Ala Ser Glu Ala Trp Ala
                        290                 295                 300

Leu Ser Arg His Ile Thr Gly Val Pro Gly Ile Gln Arg Ile Gly Met
        305                 310                 315                 320

Val Leu Gly Val Ala Ile Gln Lys Arg Ala Val Pro Gly Leu Lys Ala
                        325                 330                 335

Phe Glu Glu Ala Tyr Ala Arg Ala Asp Lys Lys Ala Pro Arg Pro Cys
                        340                 345                 350

His Lys Gly Ser Trp Cys Ser Ser Asn Gln Leu Cys Arg Glu Cys Gln
                        355                 360                 365

Ala Phe Met Ala His Thr Met Pro Lys Leu Lys Ala Phe Ser Met Ser
                        370                 375                 380

Ser Ala Tyr Asn Ala Tyr Arg Ala Val Tyr Ala Val Ala His Gly Leu
        385                 390                 395                 400

His Gln Leu Leu Gly Cys Ala Ser Gly Ala Cys Ser Arg Gly Arg Val
                        405                 410                 415

Tyr Pro Trp Gln Leu Leu Glu Gln Ile His Lys Val His Phe Leu Leu
                        420                 425                 430

His Lys Asp Thr Val Ala Phe Asn Asp Asn Arg Asp Pro Leu Ser Ser
                        435                 440                 445

Tyr Asn Ile Ile Ala Trp Asp Trp Asn Gly Pro Lys Trp Thr Phe Thr
                        450                 455                 460

Val Leu Gly Ser Ser Thr Trp Ser Pro Val Gln Leu Asn Ile Asn Glu
        465                 470                 475                 480

Thr Lys Ile Gln Trp His Gly Lys Asp Asn Gln Val Pro Lys Ser Val
                        485                 490                 495

Cys Ser Ser Asp Cys Leu Glu Gly His Gln Arg Val Val Thr Gly Phe
                        500                 505                 510

His His Cys Cys Phe Glu Cys Val Pro Cys Gly Ala Gly Thr Phe Leu
                        515                 520                 525

Asn Lys Ser Asp Leu Tyr Arg Cys Gln Pro Cys Gly Lys Glu Glu Trp
                        530                 535                 540

Ala Pro Glu Gly Ser Gln Thr Cys Phe Pro Arg Thr Val Val Phe Leu
        545                 550                 555                 560

Ala Leu Arg Glu His Thr Ser Trp Val Leu Leu Ala Ala Asn Thr Leu
                        565                 570                 575
```

```
Leu Leu Leu Leu Leu Leu Gly Thr Ala Gly Leu Phe Ala Trp His Leu
                580                 585                 590

Asp Thr Pro Val Val Arg Ser Ala Gly Gly Arg Leu Cys Phe Leu Met
            595                 600                 605

Leu Gly Ser Leu Ala Ala Gly Ser Gly Ser Leu Tyr Gly Phe Phe Gly
        610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
                660                 665                 670

Trp Val Gln Asn His Gly Ala Gly Leu Phe Val Met Ile Ser Ser Ala
            675                 680                 685

Ala Gln Leu Leu Ile Cys Leu Thr Trp Leu Val Val Trp Thr Pro Leu
        690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
                725                 730                 735

Leu Leu Ser Ile Ser Ala Phe Ala Cys Ser Tyr Leu Gly Lys Asp Leu
                740                 745                 750

Pro Glu Asn Tyr Asn Glu Ala Lys Cys Val Thr Phe Ser Leu Leu Phe
            755                 760                 765

Asn Phe Val Ser Trp Ile Ala Phe Phe Thr Thr Ala Ser Val Tyr Asp
770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
            835                 840

<210> SEQ ID NO 25
<211> LENGTH: 858
<212> TYPE: PRT
<213> ORGANISM: mouse

<400> SEQUENCE: 25

Met Pro Ala Leu Ala Ile Met Gly Leu Ser Leu Ala Ala Phe Leu Glu
1               5                   10                  15

Leu Gly Met Gly Ala Ser Leu Cys Leu Ser Gln Gln Phe Lys Ala Gln
                20                  25                  30

Gly Asp Tyr Ile Leu Gly Gly Leu Phe Pro Leu Gly Ser Thr Glu Glu
            35                  40                  45

Ala Thr Leu Asn Gln Arg Thr Gln Pro Asn Ser Ile Pro Cys Asn Arg
        50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Ser
```

-continued

```
                100                 105                 110
Ser Leu Met Phe Leu Ala Lys Val Gly Ser Gln Ser Ile Ala Ala Tyr
            115                 120                 125
Cys Asn Tyr Thr Gln Tyr Gln Pro Arg Val Leu Ala Val Ile Gly Pro
            130                 135                 140
His Ser Ser Glu Leu Ala Leu Ile Thr Gly Lys Phe Phe Ser Phe Phe
145                 150                 155                 160
Leu Met Pro Gln Val Ser Tyr Ser Ala Ser Met Asp Arg Leu Ser Asp
                165                 170                 175
Arg Glu Thr Phe Pro Ser Phe Phe Arg Thr Val Pro Ser Asp Arg Val
                180                 185                 190
Gln Leu Gln Ala Val Val Thr Leu Leu Gln Asn Phe Ser Trp Asn Trp
            195                 200                 205
Val Ala Ala Leu Gly Ser Asp Asp Tyr Gly Arg Glu Gly Leu Ser
            210                 215                 220
Ile Phe Ser Ser Leu Ala Asn Ala Arg Gly Ile Cys Ile Ala His Glu
225                 230                 235                 240
Gly Leu Val Pro Gln His Asp Thr Ser Gly Gln Gln Leu Gly Lys Val
                245                 250                 255
Leu Asp Val Leu Arg Gln Val Asn Gln Ser Lys Val Gln Val Val
                260                 265                 270
Leu Phe Ala Ser Ala Arg Ala Val Tyr Ser Leu Phe Ser Tyr Ser Ile
            275                 280                 285
His His Gly Leu Ser Pro Lys Val Trp Val Ala Ser Glu Ser Trp Leu
            290                 295                 300
Thr Ser Asp Leu Val Met Thr Leu Pro Asn Ile Ala Arg Val Gly Thr
305                 310                 315                 320
Val Leu Gly Phe Leu Gln Arg Gly Ala Leu Leu Pro Glu Phe Ser His
                325                 330                 335
Tyr Val Glu Thr His Leu Ala Leu Ala Ala Asp Pro Ala Phe Cys Ala
                340                 345                 350
Ser Leu Asn Ala Glu Leu Asp Leu Glu Glu His Val Met Gly Gln Arg
            355                 360                 365
Cys Pro Arg Cys Asp Asp Ile Met Leu Gln Asn Leu Ser Ser Gly Leu
            370                 375                 380
Leu Gln Asn Leu Ser Ala Gly Gln Leu His His Gln Ile Phe Ala Thr
385                 390                 395                 400
Tyr Ala Ala Val Tyr Ser Val Ala Gln Ala Leu His Asn Thr Leu Gln
                405                 410                 415
Cys Asn Val Ser His Cys His Val Ser Glu His Val Leu Pro Trp Gln
                420                 425                 430
Leu Leu Glu Asn Met Tyr Asn Met Ser Phe His Ala Arg Asp Leu Thr
            435                 440                 445
Leu Gln Phe Asp Ala Glu Gly Asn Val Asp Met Glu Tyr Asp Leu Lys
            450                 455                 460
Met Trp Val Trp Gln Ser Pro Thr Pro Val Leu His Thr Val Gly Thr
465                 470                 475                 480
Phe Asn Gly Thr Leu Gln Leu Gln Gln Ser Lys Met Tyr Trp Pro Gly
                485                 490                 495
Asn Gln Val Pro Val Ser Gln Cys Ser Arg Gln Cys Lys Asp Gly Gln
                500                 505                 510
Val Arg Arg Val Lys Gly Phe His Ser Cys Cys Tyr Asp Cys Val Asp
            515                 520                 525
```

```
Cys Lys Ala Gly Ser Tyr Arg Lys His Pro Asp Asp Phe Thr Cys Thr
            530                 535                 540

Pro Cys Asn Gln Asp Gln Trp Ser Pro Glu Lys Ser Thr Ala Cys Leu
545                 550                 555                 560

Pro Arg Arg Pro Lys Phe Leu Ala Trp Gly Glu Pro Val Val Leu Ser
                    565                 570                 575

Leu Leu Leu Leu Leu Cys Leu Val Leu Gly Leu Ala Leu Ala Ala Leu
                580                 585                 590

Gly Leu Ser Val His His Trp Asp Ser Pro Leu Val Gln Ala Ser Gly
            595                 600                 605

Gly Ser Gln Phe Cys Phe Gly Leu Ile Cys Leu Gly Leu Phe Cys Leu
        610                 615                 620

Ser Val Leu Leu Phe Pro Gly Arg Pro Ser Ala Ser Cys Leu Ala
625                 630                 635                 640

Gln Gln Pro Met Ala His Leu Pro Leu Thr Gly Cys Leu Ser Thr Leu
                    645                 650                 655

Phe Leu Gln Ala Ala Glu Thr Phe Val Glu Ser Glu Leu Pro Leu Ser
                660                 665                 670

Trp Ala Asn Trp Leu Cys Ser Tyr Leu Arg Gly Leu Trp Ala Trp Leu
            675                 680                 685

Val Val Leu Leu Ala Thr Phe Val Glu Ala Ala Leu Cys Ala Trp Tyr
        690                 695                 700

Leu Ile Ala Phe Pro Pro Glu Val Val Thr Asp Trp Ser Val Leu Pro
705                 710                 715                 720

Thr Glu Val Leu Glu His Cys His Val Arg Ser Trp Val Ser Leu Gly
                    725                 730                 735

Leu Val His Ile Thr Asn Ala Met Leu Ala Phe Leu Cys Phe Leu Gly
                740                 745                 750

Thr Phe Leu Val Gln Ser Gln Pro Gly Arg Tyr Asn Arg Ala Arg Gly
            755                 760                 765

Leu Thr Phe Ala Met Leu Ala Tyr Phe Ile Thr Trp Val Ser Phe Val
        770                 775                 780

Pro Leu Leu Ala Asn Val Gln Val Ala Tyr Gln Pro Ala Val Gln Met
785                 790                 795                 800

Gly Ala Ile Leu Val Cys Ala Leu Gly Ile Leu Val Thr Phe His Leu
                    805                 810                 815

Pro Lys Cys Tyr Val Leu Leu Trp Leu Pro Lys Leu Asn Thr Gln Glu
                820                 825                 830

Phe Phe Leu Gly Arg Asn Ala Lys Lys Ala Ala Asp Glu Asn Ser Gly
            835                 840                 845

Gly Gly Glu Ala Ala Gln Gly His Asn Glu
    850                 855

<210> SEQ ID NO 26
<211> LENGTH: 858
<212> TYPE: PRT
<213> ORGANISM: rat

<400> SEQUENCE: 26

Met Pro Gly Leu Ala Ile Leu Gly Leu Ser Leu Ala Ala Phe Leu Glu
1               5                   10                  15

Leu Gly Met Gly Ser Ser Leu Cys Leu Ser Gln Gln Phe Lys Ala Gln
                20                  25                  30

Gly Asp Tyr Ile Leu Gly Gly Leu Phe Pro Leu Gly Thr Thr Glu Glu
```

-continued

```
                35                  40                  45
Ala Thr Leu Asn Gln Arg Thr Gln Pro Asn Gly Ile Leu Cys Thr Arg
             50                  55                  60
Phe Ser Pro Leu Gly Leu Phe Leu Ala Met Ala Met Lys Met Ala Val
 65                  70                  75                  80
Glu Glu Ile Asn Asn Gly Ser Ala Leu Leu Pro Gly Leu Arg Leu Gly
                 85                  90                  95
Tyr Asp Leu Phe Asp Thr Cys Ser Glu Pro Val Val Thr Met Lys Pro
            100                 105                 110
Ser Leu Met Phe Met Ala Lys Val Gly Ser Gln Ser Ile Ala Ala Tyr
            115                 120                 125
Cys Asn Tyr Thr Gln Tyr Gln Pro Arg Val Leu Ala Val Ile Gly Pro
        130                 135                 140
His Ser Ser Glu Leu Ala Leu Ile Thr Gly Lys Phe Phe Ser Phe Phe
145                 150                 155                 160
Leu Met Pro Gln Val Ser Tyr Ser Ala Ser Met Asp Arg Leu Ser Asp
            165                 170                 175
Arg Glu Thr Phe Pro Ser Phe Phe Arg Thr Val Pro Ser Asp Arg Val
            180                 185                 190
Gln Leu Gln Ala Val Val Thr Leu Leu Gln Asn Phe Ser Trp Asn Trp
        195                 200                 205
Val Ala Ala Leu Gly Ser Asp Asp Tyr Gly Arg Glu Gly Leu Ser
        210                 215                 220
Ile Phe Ser Gly Leu Ala Asn Ser Arg Gly Ile Cys Ile Ala His Glu
225                 230                 235                 240
Gly Leu Val Pro Gln His Asp Thr Ser Gly Gln Gln Leu Gly Lys Val
            245                 250                 255
Val Asp Val Leu Arg Gln Val Asn Gln Ser Lys Val Gln Val Val Val
            260                 265                 270
Leu Phe Ala Ser Ala Arg Ala Val Tyr Ser Leu Phe Ser Tyr Ser Ile
        275                 280                 285
Leu His Asp Leu Ser Pro Lys Val Trp Val Ala Ser Glu Ser Trp Leu
        290                 295                 300
Thr Ser Asp Leu Val Met Thr Leu Pro Asn Ile Ala Arg Val Gly Thr
305                 310                 315                 320
Val Leu Gly Phe Leu Gln Arg Gly Ala Leu Leu Pro Glu Phe Ser His
            325                 330                 335
Tyr Val Glu Thr Arg Leu Ala Leu Ala Ala Asp Pro Thr Phe Cys Ala
            340                 345                 350
Ser Leu Lys Ala Glu Leu Asp Leu Glu Glu Arg Val Met Gly Pro Arg
        355                 360                 365
Cys Ser Gln Cys Asp Tyr Ile Met Leu Gln Asn Leu Ser Ser Gly Leu
        370                 375                 380
Met Gln Asn Leu Ser Ala Gly Gln Leu His His Gln Ile Phe Ala Thr
385                 390                 395                 400
Tyr Ala Ala Val Tyr Ser Val Ala Gln Ala Leu His Asn Thr Leu Gln
            405                 410                 415
Cys Asn Val Ser His Cys His Thr Ser Glu Pro Val Gln Pro Trp Gln
        420                 425                 430
Leu Leu Glu Asn Met Tyr Asn Met Ser Phe Arg Ala Arg Asp Leu Thr
        435                 440                 445
Leu Gln Phe Asp Ala Lys Gly Ser Val Asp Met Glu Tyr Asp Leu Lys
    450                 455                 460
```

```
Met Trp Val Trp Gln Ser Pro Thr Pro Val Leu His Thr Val Gly Thr
465                 470                 475                 480

Phe Asn Gly Thr Leu Gln Leu Gln His Ser Lys Met Tyr Trp Pro Gly
            485                 490                 495

Asn Gln Val Pro Val Ser Gln Cys Ser Arg Gln Cys Lys Asp Gly Gln
            500                 505                 510

Val Arg Val Lys Gly Phe His Ser Cys Cys Tyr Asp Cys Val Asp
            515                 520                 525

Cys Lys Ala Gly Ser Tyr Arg Lys His Pro Asp Asp Phe Thr Cys Thr
530                 535                 540

Pro Cys Gly Lys Asp Gln Trp Ser Pro Glu Lys Ser Thr Thr Cys Leu
545                 550                 555                 560

Pro Arg Arg Pro Lys Phe Leu Ala Trp Gly Glu Pro Ala Val Leu Ser
                565                 570                 575

Leu Leu Leu Leu Leu Cys Leu Val Leu Gly Leu Thr Leu Ala Ala Leu
                580                 585                 590

Gly Leu Phe Val His Tyr Trp Asp Ser Pro Leu Val Gln Ala Ser Gly
            595                 600                 605

Gly Ser Leu Phe Cys Phe Gly Leu Ile Cys Leu Gly Leu Phe Cys Leu
            610                 615                 620

Ser Val Leu Leu Phe Pro Gly Arg Pro Arg Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Ile Phe Val Glu Ser Glu Leu Pro Leu Ser
                660                 665                 670

Trp Ala Asn Trp Leu Cys Ser Tyr Leu Arg Gly Pro Trp Ala Trp Leu
                675                 680                 685

Val Val Leu Leu Ala Thr Leu Val Glu Ala Ala Leu Cys Ala Trp Tyr
690                 695                 700

Leu Met Ala Phe Pro Pro Glu Val Val Thr Asp Trp Gln Val Leu Pro
705                 710                 715                 720

Thr Glu Val Leu Glu His Cys Arg Met Arg Ser Trp Val Ser Leu Gly
                725                 730                 735

Leu Val His Ile Thr Asn Ala Val Leu Ala Phe Leu Cys Phe Leu Gly
            740                 745                 750

Thr Phe Leu Val Gln Ser Gln Pro Gly Arg Tyr Asn Arg Ala Arg Gly
            755                 760                 765

Leu Thr Phe Ala Met Leu Ala Tyr Phe Ile Ile Trp Val Ser Phe Val
770                 775                 780

Pro Leu Leu Ala Asn Val Gln Val Ala Tyr Gln Pro Ala Val Gln Met
785                 790                 795                 800

Gly Ala Ile Leu Phe Cys Ala Leu Gly Ile Leu Ala Thr Phe His Leu
                805                 810                 815

Pro Lys Cys Tyr Val Leu Leu Trp Leu Pro Glu Leu Asn Thr Gln Glu
            820                 825                 830

Phe Phe Leu Gly Arg Ser Pro Lys Glu Ala Ser Asp Gly Asn Ser Gly
            835                 840                 845

Ser Ser Glu Ala Thr Arg Gly His Ser Glu
            850                 855

<210> SEQ ID NO 27
<211> LENGTH: 852
```

```
<212> TYPE: PRT
<213> ORGANISM: human

<400> SEQUENCE: 27

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
370                 375                 380

Leu Asn His His Gln Thr Phe Ser Val Tyr Ala Ala Val Tyr Ser Val
385                 390                 395                 400
```

-continued

```
Ala Gln Ala Leu His Asn Thr Leu Gln Cys Asn Ala Ser Gly Cys Pro
                405                 410                 415
Ala Gln Asp Pro Val Lys Pro Trp Gln Leu Glu Asn Met Tyr Asn
            420                 425                 430
Leu Thr Phe His Val Gly Gly Leu Pro Leu Arg Phe Asp Ser Ser Gly
            435                 440                 445
Asn Val Asp Met Glu Tyr Asp Leu Lys Leu Trp Val Trp Gln Gly Ser
        450                 455                 460
Val Pro Arg Leu His Asp Val Gly Arg Phe Asn Gly Ser Leu Arg Thr
465                 470                 475                 480
Glu Arg Leu Lys Ile Arg Trp His Thr Ser Asp Asn Gln Lys Pro Val
                485                 490                 495
Ser Arg Cys Ser Arg Gln Cys Gln Glu Gly Gln Val Arg Arg Val Lys
                500                 505                 510
Gly Phe His Ser Cys Cys Tyr Asp Cys Val Asp Cys Glu Ala Gly Ser
            515                 520                 525
Tyr Arg Gln Asn Pro Asp Asp Ile Ala Cys Thr Phe Cys Gly Gln Asp
        530                 535                 540
Glu Trp Ser Pro Glu Arg Ser Thr Arg Cys Phe Arg Arg Ser Arg
545                 550                 555                 560
Phe Leu Ala Trp Gly Glu Pro Ala Val Leu Leu Leu Leu Leu Leu Leu
                565                 570                 575
Ser Leu Ala Leu Gly Leu Val Leu Ala Ala Leu Gly Leu Phe Val His
            580                 585                 590
His Arg Asp Ser Pro Leu Val Gln Ala Ser Gly Gly Pro Leu Ala Cys
        595                 600                 605
Phe Gly Leu Val Cys Leu Gly Leu Val Cys Leu Ser Val Leu Leu Phe
610                 615                 620
Pro Gly Gln Pro Ser Pro Ala Arg Cys Leu Ala Gln Gln Pro Leu Ser
625                 630                 635                 640
His Leu Pro Leu Thr Gly Cys Leu Ser Thr Leu Phe Leu Gln Ala Ala
                645                 650                 655
Glu Ile Phe Val Glu Ser Glu Leu Pro Leu Ser Trp Ala Asp Arg Leu
                660                 665                 670
Ser Gly Cys Leu Arg Gly Pro Trp Ala Trp Leu Val Val Leu Leu Ala
            675                 680                 685
Met Leu Val Glu Val Ala Leu Cys Thr Trp Tyr Leu Val Ala Phe Pro
        690                 695                 700
Pro Glu Val Val Thr Asp Trp His Met Leu Pro Thr Glu Ala Leu Val
705                 710                 715                 720
His Cys Arg Thr Arg Ser Trp Val Ser Phe Gly Leu Ala His Ala Thr
                725                 730                 735
Asn Ala Thr Leu Ala Phe Leu Cys Phe Leu Gly Thr Phe Leu Val Arg
                740                 745                 750
Ser Gln Pro Gly Arg Tyr Asn Arg Ala Arg Gly Leu Thr Phe Ala Met
            755                 760                 765
Leu Ala Tyr Phe Ile Thr Trp Val Ser Phe Val Pro Leu Leu Ala Asn
        770                 775                 780
Val Gln Val Val Leu Arg Pro Ala Val Gln Met Gly Ala Leu Leu Leu
785                 790                 795                 800
Cys Val Leu Gly Ile Leu Ala Ala Phe His Leu Pro Arg Cys Tyr Leu
                805                 810                 815
```

```
Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
            835                 840                 845

Gly Lys His Glu
        850

<210> SEQ ID NO 28
<211> LENGTH: 24
<212> TYPE: DNA
<213> ORGANISM: t1r1_1-OVa

<400> SEQUENCE: 28
taaacaactc cacggccctg ctgc                                          24

<210> SEQ ID NO 29
<211> LENGTH: 24
<212> TYPE: DNA
<213> ORGANISM: t1r1_1-OVb

<400> SEQUENCE: 29
cccagggtga tgttgggcag cagg                                          24

<210> SEQ ID NO 30
<211> LENGTH: 24
<212> TYPE: DNA
<213> ORGANISM: t1r1_2-OVa

<400> SEQUENCE: 30
gctgtgtatg cggtggccca tggc                                          24

<210> SEQ ID NO 31
<211> LENGTH: 24
<212> TYPE: DNA
<213> ORGANISM: t1r1_2-OVb

<400> SEQUENCE: 31
ccaggagctg gtggaggcca tggg                                          24

<210> SEQ ID NO 32
<211> LENGTH: 24
<212> TYPE: DNA
<213> ORGANISM: t1r1_3-OVa

<400> SEQUENCE: 32
tgctgaccaa cctgactggc aagg                                          24

<210> SEQ ID NO 33
<211> LENGTH: 24
<212> TYPE: DNA
<213> ORGANISM: t1r1_3-OVb

<400> SEQUENCE: 33
tctgaggcga cccacacctt gcca                                          24

<210> SEQ ID NO 34
<211> LENGTH: 24
<212> TYPE: DNA
<213> ORGANISM: t1r1_4-OVa

<400> SEQUENCE: 34
ccagttcagc taaacataaa tgag                                          24
```

<210> SEQ ID NO 35
<211> LENGTH: 24
<212> TYPE: DNA
<213> ORGANISM: t1r1_4-OVb

<400> SEQUENCE: 35
gccactggat tttggtctca ttta                                              24

<210> SEQ ID NO 36
<211> LENGTH: 24
<212> TYPE: DNA
<213> ORGANISM: t1r1_5-OVa

<400> SEQUENCE: 36
agctaacacg ctgctgctgc tgct                                              24

<210> SEQ ID NO 37
<211> LENGTH: 24
<212> TYPE: DNA
<213> ORGANISM: t1r1_5-OVb

<400> SEQUENCE: 37
agcagtccca agcagcagca gcag                                              24

<210> SEQ ID NO 38
<211> LENGTH: 24
<212> TYPE: DNA
<213> ORGANISM: t1r1_6-OVa

<400> SEQUENCE: 38
tgtgtcacct tcagcctgct cttc                                              24

<210> SEQ ID NO 39
<211> LENGTH: 24
<212> TYPE: DNA
<213> ORGANISM: t1r1_6-OVb

<400> SEQUENCE: 39
tccaggacac gaagttgaag agca                                              24

<210> SEQ ID NO 40
<211> LENGTH: 24
<212> TYPE: DNA
<213> ORGANISM: t1r2_1-OVa

<400> SEQUENCE: 40
tacttcggcc ccaagtgcta catg                                              24

<210> SEQ ID NO 41
<211> LENGTH: 24
<212> TYPE: DNA
<213> ORGANISM: t1r2_1-OVb

<400> SEQUENCE: 41
ccgggtagaa gaggatcatg tagc                                              24

<210> SEQ ID NO 42
<211> LENGTH: 24
<212> TYPE: DNA
<213> ORGANISM: t1r2_2-OVa

<400> SEQUENCE: 42
tggtcaccat cgtggacctc ttgg                                              24

<210> SEQ ID NO 43
<211> LENGTH: 24
<212> TYPE: DNA
<213> ORGANISM: t1r2_2-OVb

<400> SEQUENCE: 43
aggttgagca cagtgaccaa gagg                                            24

<210> SEQ ID NO 44
<211> LENGTH: 24
<212> TYPE: DNA
<213> ORGANISM: t1r2_3-OVa

<400> SEQUENCE: 44
accaactaca acgaggccaa gttc                                            24

<210> SEQ ID NO 45
<211> LENGTH: 24
<212> TYPE: DNA
<213> ORGANISM: t1r2_3-OVb

<400> SEQUENCE: 45
tcatgctgag ggtgatgaac ttgg                                            24

<210> SEQ ID NO 46
<211> LENGTH: 24
<212> TYPE: DNA
<213> ORGANISM: t1r2_4-OVa

<400> SEQUENCE: 46
tccgagtcct gggccatcga cccg                                            24

<210> SEQ ID NO 47
<211> LENGTH: 24
<212> TYPE: DNA
<213> ORGANISM: t1r2_4-OVb

<400> SEQUENCE: 47
tgaggttgtg caggaccggg tcga                                            24

<210> SEQ ID NO 48
<211> LENGTH: 24
<212> TYPE: DNA
<213> ORGANISM: t1r2_5-OVa

<400> SEQUENCE: 48
tacaacctca tgcaggccat gcgc                                            24

<210> SEQ ID NO 49
<211> LENGTH: 24
<212> TYPE: DNA
<213> ORGANISM: t1r2_5-OVb

<400> SEQUENCE: 49
tctcctccac cgcgaagcgc atgg                                            24

<210> SEQ ID NO 50
<211> LENGTH: 24
<212> TYPE: DNA
<213> ORGANISM: t1r2_6-OVa

<400> SEQUENCE: 50

```
atcaccatcc agagcgtgcc catc                                          24

<210> SEQ ID NO 51
<211> LENGTH: 24
<212> TYPE: DNA
<213> ORGANISM: t1r2_6-OVb

<400> SEQUENCE: 51
actcactgaa gcccgggatg ggca                                          24

<210> SEQ ID NO 52
<211> LENGTH: 24
<212> TYPE: DNA
<213> ORGANISM: t1r2_7-OVa

<400> SEQUENCE: 52
accaccacgt cgaggccatg gtgc                                          24

<210> SEQ ID NO 53
<211> LENGTH: 24
<212> TYPE: DNA
<213> ORGANISM: t1r2_7-OVb

<400> SEQUENCE: 53
aagtgcagca tcagctgcac catg                                          24

<210> SEQ ID NO 54
<211> LENGTH: 24
<212> TYPE: DNA
<213> ORGANISM: t1r3-OV1a

<400> SEQUENCE: 54
cttccactcc tgctgctacg actg                                          24

<210> SEQ ID NO 55
<211> LENGTH: 24
<212> TYPE: DNA
<213> ORGANISM: t1r3-OV1b

<400> SEQUENCE: 55
tgcctcgcag tccacgcagt cgta                                          24

<210> SEQ ID NO 56
<211> LENGTH: 24
<212> TYPE: DNA
<213> ORGANISM: t1r3-OV2a

<400> SEQUENCE: 56
aggtgcgccg cgtcaagggc ttcc                                          24

<210> SEQ ID NO 57
<211> LENGTH: 24
<212> TYPE: DNA
<213> ORGANISM: t1r3-OV2b

<400> SEQUENCE: 57
tcgtagcagc aggagtggaa gccc                                          24

<210> SEQ ID NO 58
<211> LENGTH: 24
<212> TYPE: DNA
<213> ORGANISM: t1r3-OV3a

<400> SEQUENCE: 58
```

```
gttcctggca tgggggagc cggc                                                 24

<210> SEQ ID NO 59
<211> LENGTH: 24
<212> TYPE: DNA
<213> ORGANISM: t1r3-OV3b

<400> SEQUENCE: 59
gagcagcaca agcacagccg gctc                                                24

<210> SEQ ID NO 60
<211> LENGTH: 24
<212> TYPE: DNA
<213> ORGANISM: t1r3-OV4a

<400> SEQUENCE: 60
acagcccact agttcaggcc gcag                                                24

<210> SEQ ID NO 61
<211> LENGTH: 24
<212> TYPE: DNA
<213> ORGANISM: t1r3-OV4b

<400> SEQUENCE: 61
caggcccggg gtccccctgc ggcc                                                24

<210> SEQ ID NO 62
<211> LENGTH: 24
<212> TYPE: DNA
<213> ORGANISM: t1r3-OV5a

<400> SEQUENCE: 62
cccactggtt caggcctcgg gggg                                                24

<210> SEQ ID NO 63
<211> LENGTH: 24
<212> TYPE: DNA
<213> ORGANISM: t1r3-OV5b

<400> SEQUENCE: 63
aaagcaggcc aggggccccc ccga                                                24

<210> SEQ ID NO 64
<211> LENGTH: 24
<212> TYPE: DNA
<213> ORGANISM: t1r3-OV6a

<400> SEQUENCE: 64
aggcgctggt gcactgccgc acac                                                24

<210> SEQ ID NO 65
<211> LENGTH: 24
<212> TYPE: DNA
<213> ORGANISM: t1r3-OV6b

<400> SEQUENCE: 65
aagctgaccc aggagcgtgt gcgg                                                24

<210> SEQ ID NO 66
<211> LENGTH: 24
<212> TYPE: DNA
<213> ORGANISM: t1r3-OV7a
```

```
<400> SEQUENCE: 66
acagaggcac tggtgcactg ccgc                                          24

<210> SEQ ID NO 67
<211> LENGTH: 24
<212> TYPE: DNA
<213> ORGANISM: t1r3-OV7b

<400> SEQUENCE: 67
tgatccagga gtgcacgcgg cagt                                          24

<210> SEQ ID NO 68
<211> LENGTH: 24
<212> TYPE: DNA
<213> ORGANISM: t1r3-OV8a

<400> SEQUENCE: 68
accaatgcca cgctggcctt tctc                                          24

<210> SEQ ID NO 69
<211> LENGTH: 24
<212> TYPE: DNA
<213> ORGANISM: t1r3-OV8b

<400> SEQUENCE: 69
aagtgcccag gaagcagaga aagg                                          24

<210> SEQ ID NO 70
<211> LENGTH: 24
<212> TYPE: DNA
<213> ORGANISM: t1r3-OV9a

<400> SEQUENCE: 70
tggtacatgc tgccaatgcc acgc                                          24

<210> SEQ ID NO 71
<211> LENGTH: 24
<212> TYPE: DNA
<213> ORGANISM: t1r3-OV9b

<400> SEQUENCE: 71
aagcagagga aagccagcgt ggca                                          24

<210> SEQ ID NO 72
<211> LENGTH: 24
<212> TYPE: DNA
<213> ORGANISM: t1r3-OV10a

<400> SEQUENCE: 72
tacaaccgtg cccgtggcct cacc                                          24

<210> SEQ ID NO 73
<211> LENGTH: 24
<212> TYPE: DNA
<213> ORGANISM: t1r3-OV10b

<400> SEQUENCE: 73
aggccagcat ggcgaaggtg aggc                                          24

<210> SEQ ID NO 74
<211> LENGTH: 24
<212> TYPE: DNA
<213> ORGANISM: t1r3-OV11a
```

<400> SEQUENCE: 74
tcatcacctg ggtctccttt gtgc                                          24

<210> SEQ ID NO 75
<211> LENGTH: 24
<212> TYPE: DNA
<213> ORGANISM: t1r3-OV11b

<400> SEQUENCE: 75
acattggcca ggagggcac aaag                                           24

<210> SEQ ID NO 76
<211> LENGTH: 24
<212> TYPE: DNA
<213> ORGANISM: t1r3-OV12a

<400> SEQUENCE: 76
tgcagatggg tgccctcctg ctct                                          24

<210> SEQ ID NO 77
<211> LENGTH: 24
<212> TYPE: DNA
<213> ORGANISM: t1r3-OV12b

<400> SEQUENCE: 77
aggatgccca gcacacagag cagg                                          24

<210> SEQ ID NO 78
<211> LENGTH: 20
<212> TYPE: DNA
<213> ORGANISM: dgR2ex3fa

<400> SEQUENCE: 78
ctacaacagc cagctgctca                                               20

<210> SEQ ID NO 79
<211> LENGTH: 20
<212> TYPE: DNA
<213> ORGANISM: dgR2ex3fb

<400> SEQUENCE: 79
cttcagcgag ttccgcatac                                               20

<210> SEQ ID NO 80
<211> LENGTH: 20
<212> TYPE: DNA
<213> ORGANISM: dogR1Ex4-5f1

<400> SEQUENCE: 80
ggttctgctc tgggagtgag                                               20

<210> SEQ ID NO 81
<211> LENGTH: 20
<212> TYPE: DNA
<213> ORGANISM: dogR1Ex4-5f2

<400> SEQUENCE: 81
ttggccatgt ggttacagaa                                               20

<210> SEQ ID NO 82
<211> LENGTH: 20
<212> TYPE: DNA

<213> ORGANISM: dogR1Ex1ra

<400> SEQUENCE: 82
gaggtccttc taggcacagg					20

<210> SEQ ID NO 83
<211> LENGTH: 19
<212> TYPE: DNA
<213> ORGANISM: dogR1Ex1rb

<400> SEQUENCE: 83
cagaagtgcc agggaaggt					19

<210> SEQ ID NO 84
<211> LENGTH: 20
<212> TYPE: DNA
<213> ORGANISM: dgex4f1

<400> SEQUENCE: 84
acataattgc ctgggactgg					20

<210> SEQ ID NO 85
<211> LENGTH: 20
<212> TYPE: DNA
<213> ORGANISM: dgex4f2

<400> SEQUENCE: 85
accaaaatcc rgtggcacgg					20

<210> SEQ ID NO 86
<211> LENGTH: 20
<212> TYPE: DNA
<213> ORGANISM: dgex4r1

<400> SEQUENCE: 86
ccgtgccacy ggattttggt					20

<210> SEQ ID NO 87
<211> LENGTH: 20
<212> TYPE: DNA
<213> ORGANISM: dgex4r2

<400> SEQUENCE: 87
tccagtccca ggcaattatg					20

<210> SEQ ID NO 88
<211> LENGTH: 21
<212> TYPE: DNA
<213> ORGANISM: dgex5f1

<400> SEQUENCE: 88
tccagtccca ggcaattatg t					21

<210> SEQ ID NO 89
<211> LENGTH: 21
<212> TYPE: DNA
<213> ORGANISM: dgex5f2

<400> SEQUENCE: 89
ctygaagggc accagcgagt g					21

<210> SEQ ID NO 90
<211> LENGTH: 20

<212> TYPE: DNA
<213> ORGANISM: dgex5r1

<400> SEQUENCE: 90
acagggcaca cactcaaagc                                               20

<210> SEQ ID NO 91
<211> LENGTH: 20
<212> TYPE: DNA
<213> ORGANISM: dgex5r2

<400> SEQUENCE: 91
cactcgctgg tgcccttcra                                               20

<210> SEQ ID NO 92
<211> LENGTH: 20
<212> TYPE: DNA
<213> ORGANISM: dgex1r3

<400> SEQUENCE: 92
gagtgcagag ggaacagacc                                               20

<210> SEQ ID NO 93
<211> LENGTH: 20
<212> TYPE: DNA
<213> ORGANISM: dgex1r4

<400> SEQUENCE: 93
tcacctgtca cagagggtca                                               20

<210> SEQ ID NO 94
<211> LENGTH: 20
<212> TYPE: DNA
<213> ORGANISM: dgex3f7

<400> SEQUENCE: 94
ggaccctctc agtggctatg                                               20

<210> SEQ ID NO 95
<211> LENGTH: 20
<212> TYPE: DNA
<213> ORGANISM: dgex3f8

<400> SEQUENCE: 95
acggagagga caaccaggta                                               20

<210> SEQ ID NO 96
<211> LENGTH: 20
<212> TYPE: DNA
<213> ORGANISM: dgR1Ex1f1

<400> SEQUENCE: 96
cagctgccac aacacagagt                                               20

<210> SEQ ID NO 97
<211> LENGTH: 19
<212> TYPE: DNA
<213> ORGANISM: dgR1Ex1f2

<400> SEQUENCE: 97
atgtcactcg tggcagctc                                                19

<210> SEQ ID NO 98

-continued

```
<211> LENGTH: 20
<212> TYPE: DNA
<213> ORGANISM: dgR1Ex3f1

<400> SEQUENCE: 98
tacagcagat gcccacactc                                              20

<210> SEQ ID NO 99
<211> LENGTH: 20
<212> TYPE: DNA
<213> ORGANISM: dgR1Ex3f2

<400> SEQUENCE: 99
gaaacagggt gctttcctga                                              20

<210> SEQ ID NO 100
<211> LENGTH: 20
<212> TYPE: DNA
<213> ORGANISM: dgR1Ex6r1

<400> SEQUENCE: 100
agggctagtg gagcagttca                                              20

<210> SEQ ID NO 101
<211> LENGTH: 20
<212> TYPE: DNA
<213> ORGANISM: dgR1Ex6r2

<400> SEQUENCE: 101
aggccatgtg tttcctcaag                                              20

<210> SEQ ID NO 102
<211> LENGTH: 20
<212> TYPE: DNA
<213> ORGANISM: dogEx1f1

<400> SEQUENCE: 102
crcctggtcg gcctgcagct                                              20

<210> SEQ ID NO 103
<211> LENGTH: 20
<212> TYPE: DNA
<213> ORGANISM: dogEx1f2

<400> SEQUENCE: 103
gattacctcc tsgcaggyct                                              20

<210> SEQ ID NO 104
<211> LENGTH: 19
<212> TYPE: DNA
<213> ORGANISM: dogEx1r1

<400> SEQUENCE: 104
cctgtcacas agggtcacc                                               19

<210> SEQ ID NO 105
<211> LENGTH: 20
<212> TYPE: DNA
<213> ORGANISM: dogEx1r2

<400> SEQUENCE: 105
agrcctgcsa ggaggtaatc                                              20
```

```
<210> SEQ ID NO 106
<211> LENGTH: 20
<212> TYPE: DNA
<213> ORGANISM: dogEx3f1

<400> SEQUENCE: 106
tccccagcga taagtaccag                                               20

<210> SEQ ID NO 107
<211> LENGTH: 22
<212> TYPE: DNA
<213> ORGANISM: dogEx3f2

<400> SEQUENCE: 107
gggtctggat ctcattggtg gg                                            22

<210> SEQ ID NO 108
<211> LENGTH: 22
<212> TYPE: DNA
<213> ORGANISM: dogEx6r1

<400> SEQUENCE: 108
cgcaagccaa gttacacaga tg                                            22

<210> SEQ ID NO 109
<211> LENGTH: 22
<212> TYPE: DNA
<213> ORGANISM: dogEx6r2

<400> SEQUENCE: 109
ggcggaaaac ttgaagatga ag                                            22

<210> SEQ ID NO 110
<211> LENGTH: 20
<212> TYPE: DNA
<213> ORGANISM: dogX4r1

<400> SEQUENCE: 110
gtgtgccagg agatgttgtg                                               20

<210> SEQ ID NO 111
<211> LENGTH: 20
<212> TYPE: DNA
<213> ORGANISM: dogX4r2

<400> SEQUENCE: 111
gggtagtagg aggcgatgct                                               20

<210> SEQ ID NO 112
<211> LENGTH: 20
<212> TYPE: DNA
<213> ORGANISM: dogR2X4f1

<400> SEQUENCE: 112
gagcgtcgcc tcctactrcc                                               20

<210> SEQ ID NO 113
<211> LENGTH: 20
<212> TYPE: DNA
<213> ORGANISM: dogR2X4F2

<400> SEQUENCE: 113
atctggaagg tcaacttcac                                               20
```

```
<210> SEQ ID NO 114
<211> LENGTH: 19
<212> TYPE: DNA
<213> ORGANISM: dogR2X4F3

<400> SEQUENCE: 114
tgggacckga gccagaacc                                                        19

<210> SEQ ID NO 115
<211> LENGTH: 20
<212> TYPE: DNA
<213> ORGANISM: dogR2x6R3

<400> SEQUENCE: 115
cagagggaga gaaggcattg                                                       20

<210> SEQ ID NO 116
<211> LENGTH: 19
<212> TYPE: DNA
<213> ORGANISM: dogR2x6R4

<400> SEQUENCE: 116
cccggcgttt gtgatctat                                                        19

<210> SEQ ID NO 117
<211> LENGTH: 20
<212> TYPE: DNA
<213> ORGANISM: dogR3ex2f1

<400> SEQUENCE: 117
agcttcttcc tcatgcctca                                                       20

<210> SEQ ID NO 118
<211> LENGTH: 20
<212> TYPE: DNA
<213> ORGANISM: dogR3ex2f2

<400> SEQUENCE: 118
gggctacgac ctctttgaca                                                       20

<210> SEQ ID NO 119
<211> LENGTH: 20
<212> TYPE: DNA
<213> ORGANISM: dogR3ex6r1

<400> SEQUENCE: 119
agttggcctt tgagtcagga                                                       20

<210> SEQ ID NO 120
<211> LENGTH: 20
<212> TYPE: DNA
<213> ORGANISM: dogR3ex6r2

<400> SEQUENCE: 120
ggaccactgg ttctggtcac                                                       20

<210> SEQ ID NO 121
<211> LENGTH: 20
<212> TYPE: DNA
<213> ORGANISM: dogR3ex6f1

<400> SEQUENCE: 121
tgacagactg gtgggtgcta                                                       20
```

<210> SEQ ID NO 122
<211> LENGTH: 20
<212> TYPE: DNA
<213> ORGANISM: dogR3ex6f2

<400> SEQUENCE: 122
ccatgctggc ctacttcatc                                                   20

<210> SEQ ID NO 123
<211> LENGTH: 20
<212> TYPE: DNA
<213> ORGANISM: dogR2ex6r1

<400> SEQUENCE: 123
agcaggaggt gtcgttccta                                                   20

<210> SEQ ID NO 124
<211> LENGTH: 20
<212> TYPE: DNA
<213> ORGANISM: dogR2ex6r2

<400> SEQUENCE: 124
cccaggatgg tcagcataac                                                   20

<210> SEQ ID NO 125
<211> LENGTH: 20
<212> TYPE: DNA
<213> ORGANISM: dogR2ex3f1

<400> SEQUENCE: 125
ctacaacagc cagctgctca                                                   20

<210> SEQ ID NO 126
<211> LENGTH: 20
<212> TYPE: DNA
<213> ORGANISM: dogR2ex3r1

<400> SEQUENCE: 126
cggaagaagt tgtgcaggat                                                   20

<210> SEQ ID NO 127
<211> LENGTH: 20
<212> TYPE: DNA
<213> ORGANISM: dogR2ex3r2

<400> SEQUENCE: 127
ctatcatgcg cttcctgaca                                                   20

<210> SEQ ID NO 128
<211> LENGTH: 20
<212> TYPE: DNA
<213> ORGANISM: dogR2ex3r3

<400> SEQUENCE: 128
tgtgtgccaa gtcttcttgc                                                   20

<210> SEQ ID NO 129
<211> LENGTH: 20
<212> TYPE: DNA
<213> ORGANISM: dogR2ex1r1

<400> SEQUENCE: 129
gcaatggatg aggagcattt    20

<210> SEQ ID NO 130
<211> LENGTH: 20
<212> TYPE: DNA
<213> ORGANISM: dogR2ex1r2

<400> SEQUENCE: 130
accacatcca gcctcacact    20

<210> SEQ ID NO 131
<211> LENGTH: 20
<212> TYPE: DNA
<213> ORGANISM: dogR2ex2f1

<400> SEQUENCE: 131
ttcctccttc cacaggtgag    20

<210> SEQ ID NO 132
<211> LENGTH: 20
<212> TYPE: DNA
<213> ORGANISM: dogR2ex2f2

<400> SEQUENCE: 132
aagccaggtc aggatgtcag    20

<210> SEQ ID NO 133
<211> LENGTH: 2526
<212> TYPE: DNA
<213> ORGANISM: cat

<400> SEQUENCE: 133
atgtcactcc cggcggctca cctggtcggc ctgcagctct ccctctcctg ctgctgggct    60
ctcagctgcc acagcacaga gacgtctgcc gacttcagcc tccctgggga ttacctcctc    120
gcaggtctgt tccctctgca ctctgactgt ccgggcgtga ggcaccggcc cacggtgacc    180
ctctgtgaca ggcccgacag cttcaacggt cacggctacc acctcttcca ggccatgcgg    240
tttggcatcg aggagataaa caactccacg gccctcctgc cgaacgtcac cctgggatac    300
cagctgtacg acgtgtgctc ggagtctgcc aacgtgtatg ccacactaaa cgtgctctcc    360
ctgctgggga cacatcacgt agagatccga gcagacccct tcccactatt cgcctgccgc    420
ctggctgtca ttgggcctga caccaccaac cacgcagcca ccactgcagc cctgctgagc    480
cccttcctgg tgccctgat cagctacgag gccagcagcg tgacgctcgg agtgaagcgg    540
cattaccccct cgtttctgcg caccatcccc agcgacaagc accaggtgga ggccatggtg    600
ctgctgctgc agagcttcgg gtgggtctgg atctcggtgg tcggcagcga cggcgactac    660
gggcagctgg gggtgcaggc gctggaggag caggccaccc agcagggcat ctgcgttgcc    720
ttcaaggaca tcatcccctt ctctgcccgg ccgggcgacg agaggatgca gagcatcatg    780
caccacctgg cccgagcgag gaccaccgtt gtggtcgttt ctccagcag gcagctggcc    840
agggtgttct tgagtcggt ggtgctggcc aacctgactg ccaaggtgtg gatcgcctca    900
gaagactggg ccatctctag acacatcagc aatgtgcccg ggatccaggg cattggcacg    960
gtgctgggtg tggccatcca gcagaggctt gtccctggcc tgaaggagtt tgaagaggcc    1020
tatgtccagg cagataaggg ggcccctggg ccttgctcca ggacctccga gtgcagcagc    1080
aaccagctct gtagagagtg tcgggctttc acgcagagc agatgcccac gctcgggca    1140
ttctccatga gctctgctta taacgcctac cgggcagtct acgcagtggc ccatggcctc    1200

```
caccagctcc tgggctgtgc ctctggagcc tgttccaggg accgagtcta cccctggcag    1260
cttctggagc agatccgcaa ggtgaatttc ctcctacaca aggacaccgt gaggtttaat    1320
gacaacgggg accctctcag tggctacgac ataattgcct gggactggag tggccccaag    1380
tggaacttca gggtcattgg ctcctccatg tggcctccag ttcagctgga cataaataaa    1440
accaaaatcc ggtggcacgg gaaggacaac caggtgccaa agtctgtgtg ctccagcgac    1500
tgcctcgaag ggcaccagcg agtgatttcg ggtttctacc actgttgctt tgagtgtgtg    1560
ccctgtgagg ccgggagctt cctcaacaag agcgacctcc acagctgcca gccttgtggg    1620
aaagaaaagt gggcacccgc gggaagtgaa acctgctttc cacgcaccgt ggtgtttttg    1680
acttggcacg agaccatctc ttgggtgctg ctggcagcta atacgttgct gctgctgctg    1740
gtgactggga ctgctggcct gtttgcctgg cacttagaca cccctgtggt gaagtccgct    1800
gggggccgac tgtgcttctt catgctaggc tccctggcag ggggcagctg tgggctctac    1860
ggcttttttg gggagcccac gctgcccaca tgcttgttgc gccaaagcct ccttgccctg    1920
ggttttgcca tcttcctgtc ctgcctgacc atccgctcct tccaactggt cttcatcttc    1980 aagtttttctg ccaaggtacc caccttctac cgtgcctggg tccaaaacca cggtcctggc    2040
ctatttgtgg tgatcagctc aatggcccag ctgctcatct gtctaacttg ctggcggtg     2100 tggaccccac tgcccaccag ggagtaccag cgcttccctc agctggtggt gcttgattgc    2160
acagaggcca actcaccggg cttcatgttg gctttcgcct acaatggcct cctgtccgtc    2220
agcgcctttg cctgcagcta cctgggcaag gacctgccag agaactacaa cgaggccaaa    2280
tgtgtcactt ttagtctgct gctcaacttc gtgtcctgga ttgccttctt caccacggcc    2340
agcgtctacc agggcaagta cttgcccgcg gtcaacgtgc tggcggcgct gagcagcctg    2400
agtggcggct tcagcggtta tttcctcccc aagtgctacg tgatcctgtg ccgcccaaaa    2460
tttaacagca cacagcactt ccaggcctcc atccaggagt acacgaggcg ctgcggctcc    2520
acctga                                                               2526
```

<210> SEQ ID NO 134
<211> LENGTH: 841
<212> TYPE: PRT
<213> ORGANISM: cat

<400> SEQUENCE: 134

```
Met Ser Leu Pro Ala Ala His Leu Val Gly Leu Gln Leu Ser Leu Ser
1               5                  10                  15

Cys Cys Trp Ala Leu Ser Cys His Ser Thr Glu Thr Ser Ala Asp Phe
            20                  25                  30

Ser Leu Pro Gly Asp Tyr Leu Leu Ala Gly Leu Phe Pro Leu His Ser
        35                  40                  45

Asp Cys Pro Gly Val Arg His Arg Pro Thr Val Thr Leu Cys Asp Arg
    50                  55                  60

Pro Asp Ser Phe Asn Gly His Gly Tyr His Leu Phe Gln Ala Met Arg
65                  70                  75                  80

Phe Gly Ile Glu Glu Ile Asn Asn Ser Thr Ala Leu Leu Pro Asn Val
                85                  90                  95

Thr Leu Gly Tyr Gln Leu Tyr Asp Val Cys Ser Glu Ser Ala Asn Val
            100                 105                 110

Tyr Ala Thr Leu Asn Val Leu Ser Leu Leu Gly Thr His His Val Glu
        115                 120                 125
```

```
Ile Arg Ala Asp Pro Ser His Tyr Ser Pro Ala Ala Leu Ala Val Ile
130                 135                 140
Gly Pro Asp Thr Thr Asn His Ala Ala Thr Thr Ala Ala Leu Leu Ser
145                 150                 155                 160
Pro Phe Leu Val Pro Leu Ile Ser Tyr Glu Ala Ser Ser Val Thr Leu
                165                 170                 175
Gly Val Lys Arg His Tyr Pro Ser Phe Leu Arg Thr Ile Pro Ser Asp
            180                 185                 190
Lys His Gln Val Glu Ala Met Val Leu Leu Gln Ser Phe Gly Trp
            195                 200                 205
Val Trp Ile Ser Val Val Gly Ser Asp Gly Asp Tyr Gly Gln Leu Gly
    210                 215                 220
Val Gln Ala Leu Glu Glu Gln Ala Thr Gln Gln Gly Ile Cys Val Ala
225                 230                 235                 240
Phe Lys Asp Ile Ile Pro Phe Ser Ala Arg Pro Gly Asp Glu Arg Met
                245                 250                 255
Gln Ser Ile Met His His Leu Ala Arg Ala Arg Thr Val Val Val
            260                 265                 270
Val Phe Ser Ser Arg Gln Leu Ala Arg Val Phe Phe Glu Ser Val Val
    275                 280                 285
Leu Ala Asn Leu Thr Ala Lys Val Trp Ile Ala Ser Glu Asp Trp Ala
290                 295                 300
Ile Ser Arg His Ile Ser Asn Val Pro Gly Ile Gln Gly Ile Gly Thr
305                 310                 315                 320
Val Leu Gly Val Ala Ile Gln Gln Arg Leu Val Pro Gly Leu Lys Glu
                325                 330                 335
Phe Glu Glu Ala Tyr Val Gln Ala Asp Lys Gly Ala Pro Gly Pro Cys
            340                 345                 350
Ser Arg Thr Ser Glu Cys Ser Ser Asn Gln Leu Cys Arg Glu Cys Arg
            355                 360                 365
Ala Phe Thr Ala Glu Gln Met Pro Thr Leu Gly Ala Phe Ser Met Ser
370                 375                 380
Ser Ala Tyr Asn Ala Tyr Arg Ala Val Tyr Ala Val Ala His Gly Leu
385                 390                 395                 400
His Gln Leu Leu Gly Cys Ala Ser Gly Ala Cys Ser Arg Asp Arg Val
                405                 410                 415
Tyr Pro Trp Gln Leu Leu Glu Gln Ile Arg Lys Val Asn Phe Leu Leu
            420                 425                 430
His Lys Asp Thr Val Arg Phe Asn Asp Asn Gly Asp Pro Leu Ser Gly
            435                 440                 445
Tyr Asp Ile Ile Ala Trp Asp Trp Ser Gly Pro Lys Trp Asn Phe Arg
450                 455                 460
Val Ile Gly Ser Ser Met Trp Pro Val Gln Leu Asp Ile Asn Lys
465                 470                 475                 480
Thr Lys Ile Arg Trp His Gly Lys Asp Asn Gln Val Pro Lys Ser Val
                485                 490                 495
Cys Ser Ser Asp Cys Leu Glu Gly His Gln Arg Val Ile Ser Gly Phe
            500                 505                 510
Tyr His Cys Cys Phe Glu Cys Val Pro Cys Glu Ala Gly Ser Phe Leu
            515                 520                 525
Asn Lys Ser Asp Leu His Ser Cys Gln Pro Cys Gly Lys Glu Lys Trp
530                 535                 540
Ala Pro Ala Gly Ser Glu Thr Cys Phe Pro Arg Thr Val Val Phe Leu
```

```
                545                 550                 555                 560
Thr Trp His Glu Thr Ile Ser Trp Val Leu Leu Ala Ala Asn Thr Leu
                565                 570                 575

Leu Leu Leu Leu Val Thr Gly Thr Ala Gly Leu Phe Ala Trp His Leu
            580                 585                 590

Asp Thr Pro Val Val Lys Ser Ala Gly Gly Arg Leu Cys Phe Phe Met
            595                 600                 605

Leu Gly Ser Leu Ala Gly Gly Ser Cys Gly Leu Tyr Gly Phe Phe Gly
        610                 615                 620

Glu Pro Thr Leu Pro Thr Cys Leu Leu Arg Gln Ser Leu Leu Ala Leu
625                 630                 635                 640

Gly Phe Ala Ile Phe Leu Ser Cys Leu Thr Ile Arg Ser Phe Gln Leu
                645                 650                 655

Val Phe Ile Phe Lys Phe Ser Ala Lys Val Pro Thr Phe Tyr Arg Ala
                660                 665                 670

Trp Val Gln Asn His Gly Pro Gly Leu Phe Val Val Ile Ser Ser Met
                675                 680                 685

Ala Gln Leu Leu Ile Cys Leu Thr Trp Leu Ala Val Trp Thr Pro Leu
            690                 695                 700

Pro Thr Arg Glu Tyr Gln Arg Phe Pro Gln Leu Val Val Leu Asp Cys
705                 710                 715                 720

Thr Glu Ala Asn Ser Pro Gly Phe Met Leu Ala Phe Ala Tyr Asn Gly
                725                 730                 735

Leu Leu Ser Val Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Leu
            755                 760                 765

Asn Phe Val Ser Trp Ile Ala Phe Phe Thr Thr Ala Ser Val Tyr Gln
            770                 775                 780

Gly Lys Tyr Leu Pro Ala Val Asn Val Leu Ala Ala Leu Ser Ser Leu
785                 790                 795                 800

Ser Gly Gly Phe Ser Gly Tyr Phe Leu Pro Lys Cys Tyr Val Ile Leu
                805                 810                 815

Cys Arg Pro Lys Phe Asn Ser Thr Gln His Phe Gln Ala Ser Ile Gln
            820                 825                 830

Glu Tyr Thr Arg Arg Cys Gly Ser Thr
            835                 840

<210> SEQ ID NO 135
<211> LENGTH: 1176
<212> TYPE: DNA
<213> ORGANISM: cat

<400> SEQUENCE: 135
atgggacccc gggccaggga agtctgctgc ttcatcatcc tgccgcggct cctggctgag    60
ccggctgaga actcagactt ctacttggct ggggattact ccctcggcgg cctcttcacc   120
ctccatgcca acgtgaaggg catcgtccac ctcaacctcc tgcaggtgcc ccagtgcaag   180
gagtatgaaa taaaggtgtt gggctacgat ctcatgcagg ccatgtgctt tgcagggag   240 gagatcaata gccagagcag cctgctgcct ggcgtgctgc tgggctacaa aatggtggat   300
gtcagctaca tctccaacaa tgtccagccc gtgctccact cccggcaaa ggaggactgt   360 tccttgccca tccaggagga ctacagccac tgtgtgcccc gtgtggtggc tgtcattggt   420
cctggcaact ctgagtccac tgtgactgtg gcccgcttcc tctctctctt cctccttcca   480
```

-continued

```
cagatcacct acagcgccat cagtgacgag ctacgggaca agcagcgctt cccggcccctt    540 ctgcccacag cgccgggcgc cgatcaccag atcgaggcca tggtgcagct gatgttgtac    600
ttccgccgga actggatcat cgcgctggtg agcagcggcg actgcggccg cgacgacagc    660
cagctgctca gcgatcgccc ggccggcggc gacacctgca tcgccttccg ggagacgctg    720
cccatgcccc agcccaacca ggcggtgacg cagtgggagc gccggcgcct gaaggccatc    780
gtggacgagc agcagcggca gagctctgcg cgcgtcgtgg tcctgctgtc gccaaagctg    840
gtcctgcaca acttcttccg cgaggtgctc cgccagaacc tcacgggcgt cgtgcggatc    900
gcctccgagt cctgggccat cgacccggtc ctgcacgaca ggcccacgcg ctgcacagcc    960
tcctgggctg cacccagacc agcagctccg ggtcgtctat ccctggcagg tgaggcccca   1020
cccacggaga gtcggggcca cacgcaggcgccgccaca gccctgagtg gttgccatgg   1080
agaccactgc cctgctctag cgtccccctc tctggccggg tcctgggcaa actggcggga   1140
gaggccaggg gacgtaccct gtccccagac acataa                              1176
```

<210> SEQ ID NO 136
<211> LENGTH: 391
<212> TYPE: PRT
<213> ORGANISM: cat

<400> SEQUENCE: 136

```
Met Gly Pro Arg Ala Arg Glu Val Cys Cys Phe Ile Ile Leu Pro Arg
1               5                   10                  15

Leu Leu Ala Glu Pro Ala Glu Asn Ser Asp Phe Tyr Leu Ala Gly Asp
            20                  25                  30

Tyr Phe Leu Gly Gly Leu Phe Thr Leu His Ala Asn Val Lys Gly Ile
        35                  40                  45

Val His Leu Asn Leu Leu Gln Val Pro Gln Cys Lys Glu Tyr Glu Ile
    50                  55                  60

Lys Val Leu Gly Tyr Asp Leu Met Gln Ala Met Cys Phe Ala Gly Glu
65                  70                  75                  80

Glu Ile Asn Ser Gln Ser Ser Leu Leu Pro Gly Val Leu Leu Gly Tyr
                85                  90                  95

Lys Met Val Asp Val Ser Tyr Ile Ser Asn Asn Val Gln Pro Val Leu
            100                 105                 110

His Phe Pro Ala Lys Glu Asp Cys Ser Leu Pro Ile Gln Glu Asp Tyr
        115                 120                 125

Ser His Cys Val Pro Arg Val Val Ala Val Ile Gly Pro Gly Asn Ser
    130                 135                 140

Glu Ser Thr Val Thr Val Ala Arg Phe Leu Ser Leu Phe Leu Leu Pro
145                 150                 155                 160

Gln Ile Thr Tyr Ser Ala Ile Ser Asp Glu Leu Arg Asp Lys Gln Arg
                165                 170                 175

Phe Pro Ala Leu Leu Pro Thr Ala Pro Gly Ala Asp His Gln Ile Glu
            180                 185                 190

Ala Met Val Gln Leu Met Leu Tyr Phe Arg Arg Asn Trp Ile Ile Ala
        195                 200                 205

Leu Val Ser Ser Gly Asp Cys Gly Arg Asp Asp Ser Gln Leu Leu Ser
    210                 215                 220

Asp Arg Pro Ala Gly Gly Asp Thr Cys Ile Ala Phe Arg Glu Thr Leu
225                 230                 235                 240

Pro Met Pro Gln Pro Asn Gln Ala Val Thr Gln Trp Glu Arg Arg Arg
```

```
                245                 250                 255
Leu Lys Ala Ile Val Asp Glu Gln Gln Arg Gln Ser Ser Ala Arg Val
            260                 265                 270

Val Val Leu Leu Ser Pro Lys Leu Val Leu His Asn Phe Phe Arg Glu
            275                 280                 285

Val Leu Arg Gln Asn Leu Thr Gly Val Val Arg Ile Ala Ser Glu Ser
            290                 295                 300

Trp Ala Ile Asp Pro Val Leu His Asp Arg Pro Thr Arg Cys Thr Ala
305                 310                 315                 320

Ser Trp Ala Ala Pro Arg Pro Ala Pro Gly Arg Leu Ser Leu Ala
                325                 330                 335

Gly Glu Ala Pro Pro Thr Glu Ser Arg Gly His Thr Arg Arg Arg
            340                 345                 350

His Ser Pro Glu Trp Leu Pro Trp Arg Pro Leu Pro Cys Ser Ser Val
            355                 360                 365

Pro Leu Ser Gly Arg Val Leu Gly Lys Leu Ala Gly Glu Ala Arg Gly
        370                 375                 380

Arg Thr Leu Ser Pro Asp Thr
385                 390

<210> SEQ ID NO 137
<211> LENGTH: 2569
<212> TYPE: DNA
<213> ORGANISM: cat

<400> SEQUENCE: 137
atgcccggcc tcgctctcct gggcctcacg gctctcctgg gcctcacggc tctcttggac      60
cacggggagg gcgcaacgtc ctgcttgtca cagcagctca ggatgcaggg ggactatgtg     120
ctgggtgggc tcttccctct gggctctgcc gagggtacag gtcttggcga cgggctgcag     180
cccaatgcca ccgtgtgcac caggttctcg tctctgggcc tgctctgggc gctggccgtg     240
aagatggcgg tggaggagat caacaacggg tcggccctgc tgcccgggct gcacctgggc     300
tatgacctct tgacacgtgt tcagagccca tggtggcca tgaagcccag cctcgtgttc     360
atggccaaag caggcagctg cagcattgcc gcctactgca attacacaca gtaccagccc     420
cgcgtgctgg ccgtcatcgg gcccactcg tctgagctcg ccctcgtcac cggcaagttc     480
ttcagcttct tccttgtgcc tcaggtcagc tacggcgcca gcaccgaccg gctgagcaac     540
cgggagacgt tccatccttt cttccgcacg gtgtccagcg accgcgtaca ggcagcggcc     600
atggtggagc tgctggagga gctcggctgg aactgggtgg cggcggtggg tagtgacgac     660
gagtatggcc ggcagggcct gagcctcttc tccggcctgg ccagcgccag ggcatctgc     720 atcgcgcatg agggcctggt gccactgccg ccaggcagcc tgcggctggg cgccctacag     780
ggcctgctgc gccaggtgaa ccagagcagc gtgcaggtgg tggtgctgtt ctcctccgcc     840
cacgcggccc gcaccctctt cagctacagc atccgctgca agctctcacc caaggtgtgg     900
gtggccagcg aggcctggct gacctcagac ctggtcatga cgctgcccgg catgcctggg     960
gtgggcaccg tgctgggctt cctgcagcag ggcgccccga tgccggagtt cccatcctac    1020
gtgcggaccc gctggccct ggccgctgac cctgccttct cgcctcgct ggacgctgaa    1080 cagccaggcc tggaggagca cgtggtgggg ccacgctgcc cccaatgtga ccacgtcacg    1140
ctagagaacc tatctgcggg gctgctgcac accagacct tcgctgccta cgcggctgtg    1200
tatggcgtgg cccaagccct tcacaacaca ctgcgctgca atgcctcggg ctgccccagg    1260
```

```
cgggagcctg tgcggccctg gcagctccta gagaacatgt acaacgtgag cttccgtgct    1320
cgcggcctgg cactgcagtt cgacgccagc gggaacgtga acgtggatta cgacctgaaa    1380
ctgtgggtgt ggcaggaccc gacgcccgag ctgcgcaccg taggcacctt caagggccgc    1440
ctggagctct ggcgctctca gatgtgctgg cacacgccgg ggaagcagca gcccgtgtcc    1500
cagtgctccc ggcagtgcaa ggaaggccag gtgcgccgcg tgaagggctt ccactcttgc    1560
tgttacaact gcgtggactg caaggcgggc agttatcagc gcaacccaga tgacctcctc    1620
tgcacccagt gtgaccagga ccagtggtcc ccagaccgga gcacgcgctg cttcgcccgc    1680
aagcccatgt tcctggcatg gggggagcca gctgtgctgc tactgctcgc gctgctggct    1740
ctggcgctgg gcctggcgct ggcagccctg gggctcttcc tctggcactc ggacagcccg    1800
ctggttcagg cctcaggtgg gccacgggcc tgctttggcc tggcttgcct gggcctggtc    1860
tgcctcagtg tcctcctgtt ccctggccag ccaggccctg ccagctgcct ggcccagcag    1920
ccactgttcc acctcccact cactggctgc ctgagcacgt ttttcctgca gcggccgag    1980 atatttgtgg ggtcggagct gccaccaagc tgggctgaga agatgcgtgg ccgcctgcgg    2040
gggccctggg cctggctggt ggtgctgctt gctatgctgg cagaagccgc attgtgtgcc    2100
tggtacctgg tagccttccc gccagaggtg gtgacggact ggcgggtact gcccacagag    2160
gcgctggtgc actgccacgt gcactcctgg atcagcttcg gcctggtgca tgccactaac    2220
gccatgctgg ccttcctctg cttcctgggc actttcctgg tgcagagccg gccaggccgc    2280
tacaatggtg cccgcggcct cacctttgcc atgctggcct acttcatcac ctggatctcc    2340
tttgtgcccc tctttgccaa tgtgcacgtg gcctaccagc ctgccgtgca gatgggcacc    2400
atcctcctct gtgccctggg tatcctagcc accttccacc tgcccaagtg ctacctgctg    2460
ctgcagcggc cggagctcaa caccctgag ttcttcctgg aagacaatgc cagagcacag    2520
ggcagcagtt gggggcaggg gaggggagaa tcggggcaaa acaagtga             2569
```

<210> SEQ ID NO 138
<211> LENGTH: 865
<212> TYPE: PRT
<213> ORGANISM: cat

<400> SEQUENCE: 138

```
Met Pro Gly Leu Ala Leu Leu Gly Leu Thr Ala Leu Leu Gly Leu Thr
  1               5                  10                  15

Ala Leu Leu Asp His Gly Glu Gly Ala Thr Ser Cys Leu Ser Gln Gln
             20                  25                  30

Leu Arg Met Gln Gly Asp Tyr Val Leu Gly Gly Leu Phe Pro Leu Gly
         35                  40                  45

Ser Ala Glu Gly Thr Gly Leu Gly Asp Gly Leu Gln Pro Asn Ala Thr
     50                  55                  60

Val Cys Thr Arg Phe Ser Ser Leu Gly Leu Leu Trp Ala Leu Ala Val
 65                  70                  75                  80

Lys Met Ala Val Glu Glu Ile Asn Asn Gly Ser Ala Leu Leu Pro Gly
                 85                  90                  95

Leu His Leu Gly Tyr Asp Leu Phe Asp Thr Cys Ser Glu Pro Met Val
            100                 105                 110

Ala Met Lys Pro Ser Leu Val Phe Met Ala Lys Ala Gly Ser Cys Ser
        115                 120                 125

Ile Ala Ala Tyr Cys Asn Tyr Thr Gln Tyr Gln Pro Arg Val Leu Ala
    130                 135                 140
```

```
Val Ile Gly Pro His Ser Ser Glu Leu Ala Leu Val Thr Gly Lys Phe
145                 150                 155                 160

Phe Ser Phe Phe Leu Val Pro Gln Val Ser Tyr Gly Ala Ser Thr Asp
            165                 170                 175

Arg Leu Ser Asn Arg Glu Ile Phe Pro Ser Phe Arg Thr Val Pro
            180                 185                 190

Ser Asp Gln Val Gln Val Ala Ala Met Val Glu Leu Leu Glu Glu Leu
            195                 200                 205

Gly Trp Asn Trp Val Ala Val Gly Ser Asp Asp Glu Tyr Gly Arg
            210                 215                 220

Gln Gly Leu Ser Leu Phe Ser Gly Leu Ala Ser Ala Arg Gly Ile Cys
225                 230                 235                 240

Ile Ala His Glu Gly Leu Val Pro Leu Pro Gly Ser Leu Arg Leu
            245                 250                 255

Gly Ala Leu Gln Gly Leu Leu Arg Gln Val Asn Gln Ser Ser Val Gln
            260                 265                 270

Val Val Val Leu Phe Ser Ser Ala His Ala Ala Arg Thr Leu Phe Ser
            275                 280                 285

Tyr Ser Ile Arg Cys Lys Leu Ser Pro Lys Val Trp Val Ala Ser Glu
290                 295                 300

Ala Trp Leu Thr Ser Asp Leu Val Met Thr Leu Pro Gly Met Pro Gly
305                 310                 315                 320

Val Gly Thr Val Leu Gly Phe Leu Gln Gln Gly Ala Pro Met Pro Glu
            325                 330                 335

Phe Pro Ser Tyr Val Arg Thr Arg Leu Ala Leu Ala Ala Asp Pro Ala
            340                 345                 350

Phe Cys Ala Ser Leu Asp Ala Glu Gln Pro Gly Leu Glu Glu His Val
            355                 360                 365

Val Gly Pro Arg Cys Pro Gln Cys Asp His Val Thr Leu Glu Asn Leu
            370                 375                 380

Ser Ala Gly Leu Leu His His Gln Thr Phe Ala Ala Tyr Ala Ala Val
385                 390                 395                 400

Tyr Gly Val Ala Gln Ala Leu His Asn Thr Leu Arg Cys Asn Ala Ser
            405                 410                 415

Gly Cys Pro Arg Arg Glu Pro Val Arg Pro Trp Gln Leu Leu Glu Asn
            420                 425                 430

Met Tyr Asn Val Ser Phe Arg Ala Arg Gly Leu Ala Leu Gln Phe Asp
            435                 440                 445

Ala Ser Gly Asn Val Asn Val Asp Tyr Asp Leu Lys Leu Trp Val Trp
            450                 455                 460

Gln Asp Pro Thr Pro Glu Leu Arg Thr Val Gly Thr Phe Lys Gly Arg
465                 470                 475                 480

Leu Glu Leu Trp Arg Ser Gln Met Cys Trp His Thr Pro Gly Lys Gln
            485                 490                 495

Gln Pro Val Ser Gln Cys Ser Arg Gln Cys Lys Glu Gly Gln Val Arg
            500                 505                 510

Arg Val Lys Gly Phe His Ser Cys Cys Tyr Asn Cys Val Asp Cys Lys
            515                 520                 525

Ala Gly Ser Tyr Gln Arg Asn Pro Asp Asp Leu Leu Cys Thr Gln Cys
            530                 535                 540

Asp Gln Asp Gln Trp Ser Pro Asp Arg Ser Thr Arg Cys Phe Ala Arg
545                 550                 555                 560

Lys Pro Met Phe Leu Ala Trp Gly Glu Pro Ala Val Leu Leu Leu Leu
```

-continued

```
                565                 570                 575
Ala Leu Leu Ala Leu Ala Leu Gly Leu Ala Leu Ala Ala Leu Gly Leu
            580                 585                 590
Phe Leu Trp His Ser Asp Ser Pro Leu Val Gln Ala Ser Gly Gly Pro
            595                 600                 605
Arg Ala Cys Phe Gly Leu Ala Cys Leu Gly Leu Val Cys Leu Ser Val
            610                 615                 620
Leu Leu Phe Pro Gly Gln Pro Gly Pro Ala Ser Cys Leu Ala Gln Gln
625                 630                 635                 640
Pro Leu Phe His Leu Pro Leu Thr Gly Cys Leu Ser Thr Phe Phe Leu
            645                 650                 655
Gln Ala Ala Glu Ile Phe Val Gly Ser Glu Leu Pro Pro Ser Trp Ala
            660                 665                 670
Glu Lys Met Arg Gly Arg Leu Arg Gly Pro Trp Ala Trp Leu Val Val
            675                 680                 685
Leu Leu Ala Met Leu Ala Glu Ala Ala Leu Cys Ala Trp Tyr Leu Val
            690                 695                 700
Ala Phe Pro Pro Glu Val Val Thr Asp Trp Arg Val Leu Pro Thr Glu
705                 710                 715                 720
Ala Leu Val His Cys His Val His Ser Trp Ile Ser Phe Gly Leu Val
            725                 730                 735
His Ala Thr Asn Ala Met Leu Ala Phe Leu Cys Phe Leu Gly Thr Phe
            740                 745                 750
Leu Val Gln Ser Arg Pro Gly Arg Tyr Asn Gly Ala Arg Gly Leu Thr
            755                 760                 765
Phe Ala Met Leu Ala Tyr Phe Ile Thr Trp Ile Ser Phe Val Pro Leu
            770                 775                 780
Phe Ala Asn Val His Val Ala Tyr Gln Pro Ala Val Gln Met Gly Thr
785                 790                 795                 800
Ile Leu Leu Cys Ala Leu Gly Ile Leu Ala Thr Phe His Leu Pro Lys
            805                 810                 815
Cys Tyr Leu Leu Leu Gln Arg Pro Glu Leu Asn Thr Pro Glu Phe Phe
            820                 825                 830
Leu Glu Asp Asn Ala Arg Ala Gln Gly Ser Ser Trp Gly Gln Gly Arg
            835                 840                 845
Gly Glu Ser Gly Gln Lys Gln Val Thr Pro Asp Pro Val Thr Ser Pro
            850                 855                 860
Gln
865
```